US012760299B2

(12) United States Patent
Karatt Vellatt et al.

(10) Patent No.: US 12,760,299 B2
(45) Date of Patent: Oct. 13, 2026

(54) BINDING MEMBERS WITH ALTERED DIVERSITY SCAFFOLD DOMAINS

(71) Applicant: MAXION THERAPEUTICS LIMITED, Cambridge (GB)

(72) Inventors: Aneesh Karatt Vellatt, Cambridge (GB); John McCafferty, Cambridge (GB); Sachin Surade, Cambridge (GB); Tim Luetkens, Salt Lake City, UT (US); Edward Masters, Cambridge (GB); Michael Dyson, Cambridge (GB)

(73) Assignee: MAXION THERAPEUTICS LIMITED, Cambridge (GB)

( * ) Notice: Subject to any disclaimer, the term of this patent is extended or adjusted under 35 U.S.C. 154(b) by 1144 days.

(21) Appl. No.: 16/066,638

(22) PCT Filed: Jan. 9, 2017

(86) PCT No.: PCT/EP2017/050337
§ 371 (c)(1),
(2) Date: Jun. 27, 2018

(87) PCT Pub. No.: WO2017/118761
PCT Pub. Date: Jul. 13, 2017

(65) Prior Publication Data

US 2019/0256840 A1 Aug. 22, 2019

(30) Foreign Application Priority Data

Jan. 8, 2016 (GB) ..................................... 1600341
Dec. 12, 2016 (GB) ..................................... 1621070

(51) Int. Cl.

| | |
|---|---|
| ***C07K 16/46*** | (2006.01) |
| ***C07K 16/42*** | (2006.01) |
| ***C12N 15/10*** | (2006.01) |
| ***C12N 15/62*** | (2006.01) |
| ***C12N 15/85*** | (2006.01) |
| ***C40B 30/04*** | (2006.01) |
| ***C40B 40/02*** | (2006.01) |
| ***C40B 40/10*** | (2006.01) |
| ***C40B 50/14*** | (2006.01) |

(52) U.S. Cl.
CPC ...... *C12N 15/1037* (2013.01); *C07K 16/4208* (2013.01); *C07K 16/46* (2013.01); *C12N 15/62* (2013.01); *C12N 15/85* (2013.01); *C40B 30/04* (2013.01); *C40B 40/02* (2013.01); *C40B 40/10* (2013.01); *C40B 50/14* (2013.01); *C07K 2317/565* (2013.01); *C07K 2317/567* (2013.01); *C07K 2318/20* (2013.01); *C12N 2015/8518* (2013.01)

(58) Field of Classification Search
CPC .... C12N 15/1037; C12N 15/62; C12N 15/85; C12N 2015/8518; C07K 16/4208; C07K 16/46; C07K 16/62; C07K 2317/565; C07K 2317/567; C07K 2318/20; C40B 30/04; C40B 40/02; C40B 40/10; C40B 50/14
See application file for complete search history.

(56) References Cited

U.S. PATENT DOCUMENTS

| | | | | |
|---|---|---|---|---|
| 6,740,747 | B2 | 5/2004 | Kaushik | |
| 7,258,986 | B2 | 8/2007 | Auf Der Maur et al. | |
| 2003/0170646 | A1 | 9/2003 | Kaushik et al. | |
| 2003/0232972 | A1 | 12/2003 | Bowdish et al. | |
| 2010/0004134 | A1* | 1/2010 | Horowitz ........... | C12N 15/1037 435/254.2 |
| 2014/0073518 | A1* | 3/2014 | Cochran ................ | C07K 14/81 435/255.1 |
| 2015/0119294 | A1 | 4/2015 | Fischer et al. | |
| 2015/0210756 | A1* | 7/2015 | Torres et al. ...... | C07K 16/1271 |
| 2016/0159928 | A1* | 6/2016 | Bazirgan ................ | C07K 16/00 435/69.6 |

FOREIGN PATENT DOCUMENTS

| | | | |
|---|---|---|---|
| EP | 1709972 | A1 | 10/2006 |
| WO | WO 94/18221 | A1 | 8/1994 |
| WO | WO 02/02773 | A2 | 1/2002 |
| WO | WO 02/46238 | A2 | 6/2002 |
| WO | WO 03/002609 | A2 | 1/2003 |
| WO | WO 2004/050017 | A2 | 6/2004 |
| WO | WO 2004/108078 | A2 | 12/2004 |
| WO | WO 2005/060642 | A2 | 7/2005 |
| WO | WO 2006/036834 | A2 | 4/2006 |
| WO | WO 2006/105954 | A2 | 10/2006 |

(Continued)

OTHER PUBLICATIONS

Miura et al. "Diversification of the Ig Variable Region Gene Repertoire of Synovial B Lymphocytes by Nucleotide Insertion and Deletion" Mol Med. May-Aug. 2003; 9(5-8): 166-174; doi: 10.2119/2003-00025.chiorazzi (Year: 2003).*

(Continued)

*Primary Examiner* — Christopher M Gross

(74) *Attorney, Agent, or Firm* — NIXON PEABODY LLP; David S. Resnick; Nicole D. Kling

(57) ABSTRACT

This invention relates to libraries of binding members that each comprise a fusion protein which contains a donor diversity scaffold domain, such as a cysteine rich protein, inserted within a recipient diversity scaffold domain, such as an antibody constant or variable domain. Libraries and methods of generating libraries are provided, along with screening methods, binding members and methods of using the binding members.

33 Claims, 28 Drawing Sheets

Specification includes a Sequence Listing.

(56) References Cited

FOREIGN PATENT DOCUMENTS

| | | | |
|---|---|---|---|
| WO | WO 2006/116156 | A2 | 11/2006 |
| WO | WO 2008/027236 | A2 | 3/2008 |
| WO | WO 2008/045252 | A2 | 4/2008 |
| WO | WO 2008/089073 | A2 | 7/2008 |
| WO | WO 2008/153745 | A2 | 12/2008 |
| WO | WO 2009/040550 | A1 | 4/2009 |
| WO | WO 2009/068649 | A2 | 6/2009 |
| WO | WO 2010/048588 | A2 | 4/2010 |
| WO | WO 2010/097589 | A1 | 9/2010 |
| WO | WO 2010/135558 | A1 | 11/2010 |
| WO | WO 2011/084255 | A2 | 7/2011 |
| WO | WO 2012/064658 | A1 | 5/2012 |
| WO | WO 2012/163520 | A1 | 12/2012 |
| WO | WO 2013/106485 | A2 | 7/2013 |
| WO | WO 2013/106489 | A1 | 7/2013 |
| WO | WO 2013/134880 | A1 | 9/2013 |
| WO | WO 2013/134881 | A1 | 9/2013 |
| WO | WO 2014/028502 | A1 | 2/2014 |
| WO | WO 2014/063012 | A1 | 4/2014 |
| WO | WO 2014/110368 | A1 | 7/2014 |
| WO | WO2014124677 | * | 8/2014 |
| WO | WO 2015/010100 | A2 | 1/2015 |
| WO | WO 2015/017146 | A2 | 2/2015 |
| WO | WO 2015/032916 | A1 | 3/2015 |
| WO | WO 2015/081440 | A1 | 6/2015 |
| WO | WO 2015/166272 | A2 | 11/2015 |
| WO | WO 2016/040856 | A2 | 3/2016 |
| WO | WO 2016/089829 | A1 | 6/2016 |
| WO | WO 2016/168755 | A1 | 10/2016 |

OTHER PUBLICATIONS

Kogelberg et al. Journal of Molecular Biology 382, 385-401 (2008) (Year: 2008).*

Mouhat et al. Current Pharmaceutical Design 14, 2503-2518 (2008), abstract only. (Year: 2008).*

Chou et al. "Prediction of Membrane Protein Types and Subcellular Locations" Proteins: Structure, Function, and Genetics 34: 137-153 (1999) (Year: 1999).*

Heitz et al. "Min-21 and Min-23, the Smallest Peptides That Fold Like a Cystine-Stabilized β-Sheet Motif: Design, Solution Structure , and Thermal Stability" Biochemistry 1999, 38, 32, 10615-10625, publ. Jul. 23, 1999; https://doi.org/10.1021/bi990821k (Year: 1999).*

Popov et al (JMB 325:325-35) (Year: 2003).*

Wang et al (Cell 153:1379-93) (Year: 2013).*

Reverdatto et al., "Peptide Aptamers: Development and Applications", Curr Top Med Chem., 2015, 15(12): 1082-1101.

Ackerman, et al., "Cystine-knot peptides: emerging tools for cancer imaging and therapy", Expert Rev Proteomics 11(5), 561-572 (2014).

Bell, et al., "Knotbodies: A New Generation of Ion Channel Therapeutic Biologics Created by Fusing Knottin Toxins Into Antibodies", Biophysical Journal 114 (3), Supplement 1, p. 203A (Feb. 2018).

Moore, et al., "Engineering Knottins as Novel Binding Agents", Methods in Enzymology 503, 223-251 (2012).

Patent Cooperation Treaty, International Searching Authority, Search Report and Written Opinion for PCT/EP2017/050337, 16 pages, Jun. 12, 2017.

Vazquez-Lombardi, et al., "Challenges and opportunities for non-antibody scafold drugs", Drug Discovery Today 20(10), 1271-1283 (2015).

Hosse et al., "A new generation of protein display scaffolds for molecular recognition", Protein Science, 2006, 15: 14-27.

Cheek et al., "Structural Classification of Small, Disulfide-rich Protein Domains", J. Mol. Biol., 2006, 359: 215-237.

Definition of "diverse" in Merriam-Webster's Collegiate Dictionary, 10th Edition, 1997.

Hegde et al., "The mechanisms of integral membrane protein biogenesis", Nature Reviews Molecular Cell Biology, Sep. 2021, 23: 107-124.

Kumari et al., "Cysteine-Rich Peptide Family with Unusual Disulfide Connectivity from Jasminum sambac", J. Nat. Prod., 2015, 78: 2791-2799.

Lavergne et al., "Cysteine-Rich Mini-Proteins in Human Biology", Current Topics in Medicinal Chemistry, 2012, 12: 1514-1533.

Mouhat et al., "Animal Toxins Acting on Voltage-Gated Potassium Channels", Current Pharmaceutical Design, 2008, 14: 2503-2518.

Ueberheide et al., "Rapid sensitive analysis of cysteine rich peptide venom components", PNAS, Apr. 2009, 106(17): 6910-6915.

Zhang et al. "An Antibody with a Variable-Region Coiled-Coil "Knob" Domain." Angewandte Chemie International Edition 53.1: 132-135 (2014).

* cited by examiner

```
A.
   NcoI
gccatggctgaagtccaactggtcgaaagcggtggtggtctggtgcgtccgggcggctcc
 A  M  A  E  V  Q  L  V  E  S  G  G  G  L  V  R  P  G  G  S
ctgcgtctgtcgtgtgcggcgtcgggttttacctttagctcttatgcgatgagctgggtt
 L  R  L  S  C  A  A  S  G  F  T  F  S  S  Y  A  M  S  W  V
cgtcaggctccgggtaaaggcctggaatgggtctccgcaattagtggttccggcggttcg
 R  Q  A  P  G  K  G  L  E  W  V  S  A  I  S  G  S  G  G  S
acgtattacgctgatagcgtgaaaggccgtttcaccatctctcgcgacaacacgaaaaat
 T  Y  Y  A  D  S  V  K  G  R  F  T  I  S  R  D  N  T  K  N
agtctgtacctgcaaatgacctctctgcgcgcagatgacacggcttttattactgcgtt
 S  L  Y  L  Q  M  T  S  L  R  A  D  D  T  A  F  Y  Y  C  V
gatttcggtccgggctatggtaccggctggtttgactactggggtccgggcaccctggtg
 D  F  G  P  G  Y  G  T  G  W  F  D  Y  W  G  P  G  T  L  V
      XhoI                                                  NheI
Accgtctcgagt    ggtggaggcggttcaggcggaggtggctctggcggtggcgctagc
 T  V  S  S      G  G  G  G  S  G  G  G  G  S  G  G  G  A  S
cagtctgtgctgactcagccaccctcggtgtctgaagccccaggcagagggtcaccatc
 Q  S  V  L  T  Q  P  P  S  V  S  E  A  P  R  Q  R  V  T  I

 PmlI                 <-------CDR1------------>
acgtgt tctggaagcagctccaacatcggaaataatgctgtaaactggtaccagcagctc
 T  C   S  G  S  S  S  N  I  G  N  N  A  V  N  W  Y  Q  Q  L

                                            PstI             NotI
Ccagggaaagcccctaagctcctgatctatgctgcaaggt gtgctgggt gcggccgc(SEQ ID NO: 352)
 P  G  K  A  P  K  L  L  I  Y  A  A  G                A  A   (SEQ ID NO: 353)
```

Figure 2A

```
   NcoI
gccatggctgaagtccaactggtcgaaagcggtggtggtctggtgcgtccgggcggctcc
 A  M  A  E  V  Q  L  V  E  S  G  G  G  L  V  R  P  G  G  S
ctgcgtctgtcgtgtgcggcgtcgggttttacctttagctcttatgcgatgagctgggtt
 L  R  L  S  C  A  A  S  G  F  T  F  S  S  Y  A  M  S  W  V
cgtcaggctccgggtaaaggcctggaatgggtctccgcaattagtggttccggcggttcg
 R  Q  A  P  G  K  G  L  E  W  V  S  A  I  S  G  S  G  G  S
acgtattacgctgatagcgtgaaaggccgtttcaccatctctcgcgacaacacgaaaaat
 T  Y  Y  A  D  S  V  K  G  R  F  T  I  S  R  D  N  T  K  N
agtctgtacctgcaaatgacctctctgcgcgcagatgacacggcttttattactgcgtt
 S  L  Y  L  Q  M  T  S  L  R  A  D  D  T  A  F  Y  Y  C  V
gatttcggtccgggctatggtaccggctggtttgactactggggtccgggcaccctggtg
 D  F  G  P  G  Y  G  T  G  W  F  D  Y  W  G  P  G  T  L  V

      XhoI                                                  NheI
Accgtctcgagt    ggtggaggcggttcaggcggaggtggctctggcggtggcgctagc
 T  V  S  S      G  G  G  G  S  G  G  G  G  S  G  G  G  A  S
gacatccagatgacccagtctccatcctccctgtctgcatctgtaggagacagagtcacc
 D  I  Q  M  T  Q  S  P  S  S  L  S  A  S  V  G  D  R  V  T

   PmlI              <--CDR1-------->
atcacgtgc cgggcaagtcagagcattagcagctatttaaattggtatcagcagaaacca
 I  T  C   R  A  S  Q  S  I  S  S  Y  L  N  W  Y  Q  Q  K  P
                                     PstI                NotI
Gggaaagcccctaagctcctgatctatgctgcaggt  gtgctgggt  gcggccgc(SEQ ID NO: 354)
 G  K  A  P  K  L  L  I  Y  A  A  G    V  L  G    A  A   (SEQ ID NO: 355)
```

Figure 2B

```
ggctgcccgcgtatcctgatgcgttgcaaacaggactcagactgcctggccggctgcgta
 G   C   P R I L   M   R   C   K   Q   D   S   D   C   L   A   G   C   V
tgcggtccgaacggcttctgcggg(SEQ ID NO: 356)
 C   G   P   N   G   F   C   G (SEQ ID NO: 357)
```

Figure 3A

```
i   RQRVTITCsgs          ssnignna           vNWYQQLP
ii  RQRVTITCxxx -CPRILMRCKQDSDCLAGCVCGPNGFCG X xNWYQQLP
iiiRQRVTITCgxx xCPRILMRCKQDSDCLAGCVCGPNGFCG X xNWYQQLP
iv  KAPKLLIY              ydd              llpSGVSDRFS
v   KAPKLLIY AAZ xCPRILMRCKQDSDCLAGCVCGPNGFCG ~XXSGVSDRFS
(SEQ ID NOS: 358-362)
```

Figure 3B

```
Nhe1
gctagccagtctgtgctgactcagccaccctcggtgtctgaagcccccaggcagagggtc
 A   S   Q   S   V   L   T   Q   P   P   S   V   S   E   A   P   R   Q   R   V
      ←-------------------------FW1-------------------------
      Pml1
accatcacgtgtvnsvnsvnstgcccgcgtatcctgatgcgttgcaaacaggactcagac
 T   I   T   C   X   X   X   C   P   R   I   L   M   R   C   K   Q   D   S   D
------------→           ←---------------EETI-II-----------------

                                                      Mfe1
tgcctggccggctgcgtatgcggtccgaacggcttctgcgggvnsvncaattggtaccag
 C   L   A   G   C   V   C   G   P   N   G   F   C   G   X   X   N   W   Y   Q
---------------------------------------------→         I-----FW2---

                                                           Not1
cagctcccagga ←-Vlambda library-> accgtcctaggtcagcccgcggccgca
 Q   L   P   G                    T   V   L   G   Q   P   A   A   A
-----FW2-----→                   <-----------FW4---------I

 (SEQ ID NOS: 319 & 320)
```

Figure 3C

```
NheI
gctagcgacatccagatgacccagtctccatcctccctgtctgcatctgtaggagacaga
 A  S  D  I  Q  M  T  Q  S  P  S  S  L  S  A  S  V  G  D  R
      <-------------------------FW1-------------------------
      PmlI
gtcaccatcacgtgtvnsvnsvnstgcccgcgtatcctgatgcgttgcaaacaggactca
 V  T  I  T  C  X  X  X  C  P  R  I  L  M  R  C  K  Q  D  S
--------------->         <-------EETI-II----------------

                                                  MfeI
gactgcctggccggctgcgtatgcggtccgaacggcttctgcgggvnsvncaattggtat
 D  C  L  A  G  C  V  C  G  P  N  G  F  C  G  X  X  N  W  Y
------------------------------------------------->  I----FW2--

                                                      NotI
cagcagaaaccagg <--V kappa library-->atcaaacgtaccgcggccgca
 Q  Q  K  P                          I  K  R  T  A  A  A
---FW2----->                        <----FW4---I

(SEQ ID NOS: 321 & 322)
```

Figure 3D

```
NheI
gctagccagtctgtgctgactcagccaccctcggtgtctgaagcccccaggcagagggtc
 A  S  Q  S  V  L  T  Q  P  P  S  V  S  E  A  P  R  Q  R  V
    <-----------------------------FW1--------------------------
    PmlI
accatcacgtgttctggaagcagctccaacatcggaaataatgctgtaaactggtaccag
 T  I  T  C  S  G  S  S  S  N  I  G  N  N  A  V  N  W  Y  Q
 ------------------><---------CDR1------------><------FW2------

                                            PstI
cagctcccaggaaaagcccctaagctcctgatctatgctgcagnsvnstgcccgcgtatc
 Q  L  P  G  K  A  P  K  L  L  I  Y  A  A  X  X  C  P  R  I
------------------------------------->              <-- EETI-II

ctgatgcgttgcaaacaggactcagactgcctggccggctgcgtatgcggtccgaacggc
 L  M  R  C  K  Q  D  S  D  C  L  A  G  C  V  C  G  P  N  G
--------------------------EETI-II---------------------------

                BspEI
ttctgcgggvnsvnstccggagtctctgaccgattctctggctcc<-Vlambda library->
 F  C  G  X  X  S  G  V  S  D  R  F  S  G  S
----->           I-------------FW3--------------->

                  NotI
accgtcctaggtcagcccgcggccgca (SEQ ID NOS: 323)
 T  V  L  G  Q  P  A  A  A  (SEQ ID NOS: 324)
<------FW4---------I
```

Figure 3E

```
Nhe1
gctagcgacatccagatgacccagtctccatcctccctgtctgcatctgtaggagacaga
 A  S  D  I  Q  M  T  Q  S  P  S  S  L  S  A  S  V  G  D  R
      <--------------------FW1---------------------------------
   Pml1
gtcaccatcacgtgccgggcaagtcagagcattagcagctatttaaattggtatcagcag
 V  T  I  T  C  R  A  S  Q  S  I  S  S  Y  L  N  W  Y  Q  Q
--------------------->|<------CDR1----->|<-------FW2-------

                                             Pst1
aaaccagggaaagcccctaagctcctgatctatgctgcagnsvnstgcccgcgtatcctg
 K  P  G  K  A  P  K  L  L  I  Y  A  A  X  X  C  P  R  I  L
--------------------------------->              <-- EETI-II

atgcgttgcaaacaggactcagactgcctggccggctgcgtatgcggtccgaacggcttc
 M  R  C  K  Q  D  S  D  C  L  A  G  C  V  C  G  P  N  G  F
------------------------EETI-II------------------------------

          BspE1
tgcgggvnsvnstccggagtcccatcaaggttcagtggcagt<~V kappa library~>
 C  G  X  X  S  G  V  P  S  R  F  S  G  S
---->      I----------FW3--------------->

              Not1
Atcaaacgtaccgcggccgca (SEQ ID NOS: 325)
 I  K  R  T  A  A  A  (SEQ ID NOS: 326)
<----FW4---I
```

Figure 3F

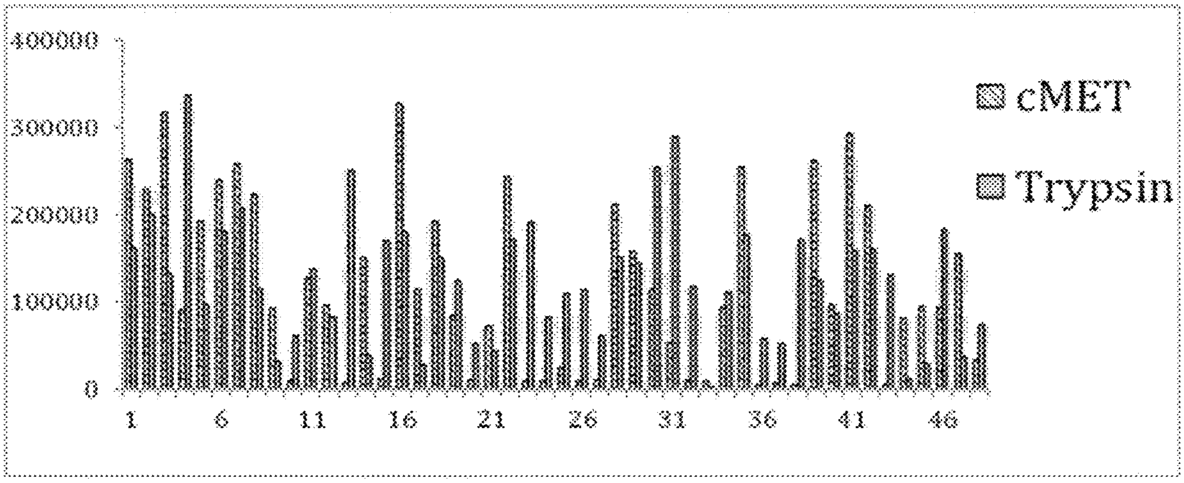
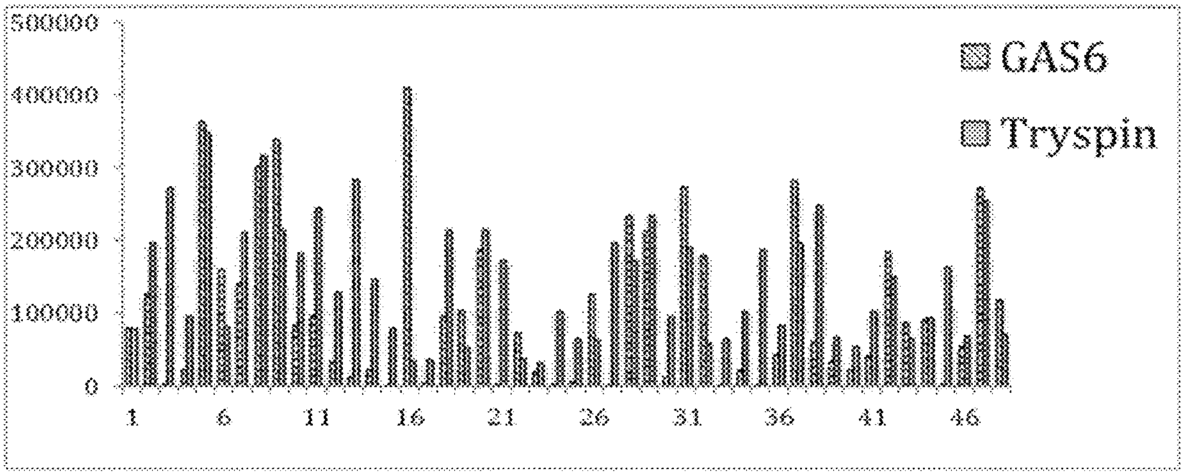
Figure 12

A

```
           10         20         30         40         50
RDLEVVAATPTSLLISwdapavtvrYYRITYGETGGNSPVQEFTVPgsks

           60         70         80         90
TATISGLKPGVDYTITVYAVtgrgdspasskpISINYRTEI (SEQID NO: 28)
```

B.

```
MSNVNTGSLSVDNKKFWATVEssehSFEVPIYAETLDEALELAEWQYvpa
               beta        beta        alpha

gfEVTRVRPCVAPK (SEQ ID NO: 29)
  beta
```

Ai CAASGFTFS syams WVRQAPGKG
(SEQ ID NO: 327)
Aii CAASGFTFS XX CPRILMRCKQDSDCLAGCVCGPNGFCG XX
WVRQAPGKG(SEQ ID NO: 328)

Bi PGKGLEWVS aisgsggstyyadsvkg RFTISRDNT
(SEQ ID NO: 329)
Bii PGKGLEWVS XX CPRILMRCKQDSDCLAGCVCGPNGFCG XX RFTISRDNT
(SEQ ID NO: 330)

Ci DTAFYYCVD fgpgygtgwfdy WGPGTLVTV
(SEQ ID NO: 331)
Cii DTAFYYCVD XX CPRILMRCKQDSDCLAGCVCGPNGFCG XX WGPGTLVTV
(SEQ ID NO: 332)

Di VGDRVTITC rasqsissyln WYQQKPGKA
(SEQ ID NO: 333)
Dii VGDRVTITC XX CPRILMRCKQDSDCLAGCVCGPNGFCG XX
WYQQKPGKA(SEQ ID NO: 334)

Ei KAPKLLIHD asslqs GVPSRFSGS
(SEQ ID NO: 335)
Eii KAPKLLIHD XX CPRILMRCKQDSDCLAGCVCGPNGFCG XX GVPSRFSGS
(SEQ ID NO: 336)

Fi PEDFATYYC qqsfsiplt FGGGTKMDI
(SEQ ID NO: 337)
Fii PEDFATYYC XX CPRILMRCKQDSDCLAGCVCGPNGFCG XX FGGGTKMDI
(SEQ ID NO: 338)

Gi APKLLIYAA GV CPRILMRCKQDSDCLAGCVCGPNGFCG SR SGVPSRFS
(SEQ ID NO: 339)
Gii APKLLIYAA XX CPRILMRCKQDSDCLAGCVCGPNGFCG XX SGVPSRFS
(SEQ ID NO: 340)

Figure 28

```
tgcggtccgaacggcttctgcggaagcggcagcgatggcggtgtgtgcccgcgtatcctg
 C   G   P   N   G   F   C   G   S   G   S   D   G   G   V   C   P   R   I   L
    ________LOOP5____>    <________LOOP6_______________>    <___LOOP1_____
atgcgttgcaaacaggactcagactgcctggccggctgc(SEQ ID NO: 341)
 M   R   C   K   Q   D   S   D   C   L   A   G   C(SEQ ID NO: 342)
______>    <____LOOP2_____>    <_LOOP3_>
```

Figure 29A

```
i  RVTITCsgs           ssnignna                      vNWYQQLP
(SEQ ID 343)
ii RVTITCxxx - CGPNGFCGSGSDGGVCPRILMRCKQDSDCLAGC X xNWYQQLP
iiiRVTITCgxx X CGPNGFCGSGSDGGVCPRILMRCKQDSDCLAGC X xNWYQQLP
(SEQ IDs 344 and 345)

iv KLLIY                  ydd                       llpSGVSDRFS
(SEQ ID NOS: 346)
v  KLLIY AAZ x CGPNGFCGSGSDGGVCPRILMRCKQDSDCLAGC gxxSGVSDRFS
(SEQ ID 347)
```

Figure 29B

```
NheI
gctagccagtctgtgctgactcagccaccctcggtgtctgaagccccaggcagagggtc
 A   S   Q   S   V   L   T   Q   P   P   S   V   S   E   A   P   R   Q   R   V
      <-------------------------------FW1---------------------------------

     PmlI
accatcacgtgtvnsvnsvnstgcggtccgaacggcttctgcggaagcggcagcgatggc
 T   I   T   C   X   X   X   C   G   P   N   G   F   C   G   S   G   S   D   G
------------>              <-----------EETI-II-------------------

ggtgtgtgcccgcgtatcctgatgcgttgcaaacaggactcagactgcctggccggctgc
 G   V   C   P   R   I   L   M   R   C   K   Q   D   S   D   C   L   A   G   C
------------------------------------------------------------------------------->
     Mfe 1                                                     Not1
vnsvncaattggtaccagcagctcccagga <-Vlambda library->
gcggccgc(SEQ ID NO: 348)
 X   X   N   W   Y   Q   Q   L   P   G   (SEQ ID NO: 349)
      I-----FW2--------------->
```

Figure 29C

```
Nhe1
gctagccagtctgtgctgactcagccaccctcggtgtctgaagccccaggcagagggtc
 A  S  Q  S  V  L  T  Q  P  P  S  V  S  E  A  P  R  Q  R  V
      <------------------------FW1------------------------
      Pml1
accatcacgtgttctggaagcagctccaacatcggaaataatgctgtaaactggtaccag
 T  I  T  C  S  G  S  S  S  N  I  G  N  N  A  V  N  W  Y  Q
------------------><---------CDR1-----------><------FW2-----

                                               Pst1
cagctcccagggaaagcccctaagctcctgatctatgctgcagnsvnstgcggtccgaac
 Q  L  P  G  K  A  P  K  L  L  I  Y  A  A  Z  X  C  G  P  N
---------------------------------------------->          <-- EETI-II

ggcttctgcggaagcggcagcgatggcggtgtgtgcccgcgtatcctgatgcgttgcaaa
 G  F  C  G  S  G  S  D  G  G  V  C  P  R  I  L  M  R  C  K
------------------------EETI-II-----------------------------

                                             BspE1
caggactcagactgcctggccggctgcgggvnsvnstccggagtctctgaccgattctct
 Q  D  S  D  C  L  A  G  C  G  X  X  S  G  V  S  D  R  F  S
-------------------------->                I----------FW3---------

                                                    Not1
ggctcc<-Vlambda library->accgtcctaggtcagcccgcggccgc(SEQ ID NO:
350)
 G  S                         T  V  L  G  Q  P    (SEQ ID NO: 351)
----->
```

Figure 29D

BINDING MEMBERS WITH ALTERED DIVERSITY SCAFFOLD DOMAINS

CROSS-REFERENCE TO RELATED APPLICATION(S)

This patent application is a 35 U.S.C. § 371 National Phase Entry of International Application No. PCT/EP2017/050337 filed Jan. 9, 2017, which designates the U.S. and claims the benefit of priority under 35 U.S.C. § 119 to Great Britain application serial No. 1600341.0, filed 8 Jan. 2016 and to Great Britain application serial No. 1621070.0, filed 12 Dec. 2016.

SEQUENCE LISTING

The instant application contains a Sequence Listing which has been submitted in ASCII format via EFS-Web and is hereby incorporated by reference in its entirety. Said ASCII copy, created on Jun. 25, 2018, is named 00130008US1.txt and is 230,898 bytes in size.

FIELD

This invention relates to binding members with altered diversity scaffold domains, the production of libraries of such binding members and the selection and screening of binding members from such libraries.

BACKGROUND

Antibody humanisation involves combining animal CDRs with human frameworks. CDR grafting is a well-established method used for antibody humanisation. Antibodies generated by immunisation of an animal are sequenced, CDR loops identified and a hybrid molecule is prepared consisting of a human framework with one or more CDRs derived for the animal antibody[1]. In CDR grafting, it is likely that the incoming peptide is required to adopt a particular structure to maintain the original binding specificity and it is often necessary to "fine-tune" the humanisation process by changing addition residues including supporting residues within the framework region.

Non-antibody peptides from other sources have also been transplanted into antibody frameworks. Barbas et al (1993) inserted a naturally-occurring integrin binding sequence in to the VH CDR3 region of a human antibody[2] and Frederickson et al (2006)[3] cloned a 14-mer peptide which was known to bind to the thrombopoietin (TPO) receptor into the several CDR regions of an anti-tetanus toxoid antibody. 2 amino acids at each end of the peptide were randomized and the resultant library selected by phage display. This same work was described in US 20100041012A1, along with insertion of an 18 amino acid peptide known to bind to the erythropoietin receptor[4]. The original erythropoietin receptor binding peptide sequence contained two cysteines which were removed due to anticipated problems with antibody disulphide bond formation. In these cases, 2-3 codons were randomised at the junction between the inserted peptide coding region and the recipient framework to select optimal junctional sequences from the resultant phage display libraries. Liu et al inserted a 14-16 amino acid peptide with binding activity to CXCR4 into 2 different CDRs (VH CDR3 and VH CDR2[5]). Kogelberg inserted an αVβ6 17 mer peptide which adopts a hairpin:alpha helix motif, into VH CDR3 of a murine antibody[6]. This peptide contained core RGDLxxL element known to direct binding to αVβ6.

This work led on to a library-based approach focussed on VH CDR3, which sought to mimic the hairpin:alpha helix structure[7] of the original insert. In all these cases, the antibody acted as a carrier for the incoming peptide without contributing to target binding.

Gallo et al have inserted peptides into a VH CDR3 using an alternative approach for diversification. Antibody diversification naturally occurs within in B cells and U.S. Pat. No. 8,012,714 describes a method replicating this diversification process within heterologous mammalian cells. In maturing B cells antibody genes are assembled by recombination of separate V, D and J segments through the activities of "recombination activating genes" (RAG1 and RAG2) resulting in deletion of large segments of intervening sequences. In U.S. Pat. No. 8,012,714, RAG1, and RAG2 were introduced into human embryonic kidney cells (HEK293) along with plasmids encompassing recombination substrates to replicate recombination V-D-J joining in non-B cells. This RAG1/2 recombination-based approach utilizes DNA repair and excision mechanisms of mammalian cells and has not been demonstrated in prokaryotic cells.

The same mammalian cell-based in vitro system was used in WO2013134881A1 with the D segment being effectively replaced by DNA which encodes peptide fragments derived from two other binding molecules. Since RAG1/RAG2 driven diversification only occurs in mammalian cells this system cannot be used directly in prokaryotic approaches such as phage display. WO2013134881A1 exemplifies the introduction into the heavy chain CDR3 of the same 14-mer peptide fragments used by Frederickson[3] and Bowdish (US20100041012 A1). The TPO receptor binding construct was introduced into the middle of CDR3 and so retained the CDR sequences as well as grafting in additional amino acids to create a total of 12 or more amino acids between the antibody framework and the incoming peptide. WO2013134881A1 also exemplifies antibody fusions with extendin-4 which were generated with combined linker length between the antibody framework and the incoming peptide ranging from 9-14 amino acids.

Saini et al[8, 9] reported the occurrence of ultra-long cysteine-rich CDR3s within the VH domain of bovine antibodies. These ultra-long VH CDRs of 40-67 amino acids which constitute 9% of the bovine antibody response were typically restricted to pairing with a specific Vλ1 light chains. Recently the structure of two such bovine antibodies has been determined through X ray crystallography[10] revealing an unusual stalk structure formed by an ascending and descending β strands which is topped by a "knob" comprising a peptide with multiple disulphide bonds formed from cysteine pairs. This stalk: knob structure is formed by CDR3 of the VH domain but the stalk is supported by interactions with VH CDR1, VH CDR2, as well as all CDRs of the partner Vλ1 chain. Thus the entire CDR diversity of these antibodies is devoted to the presentation of the "knob" structure which itself is presented at a distance of approximately 38 Angstroms from the supporting framework to the first cysteine of the "knob"[11]. The potential of the other CDRs to interact with the same epitope recognized by the knob is therefore abolished or severely limited.

In subsequent work, "the knob" was replaced by cytokines, such as granulocyte colony stimulating factor[12] and erythropoietin[13], which were linked to the stalk by a flexible Gly-Gly-Gly-Gly-Ser (SEQ ID NO: 1) sequence (Gly4Ser) at the N and C terminal junctions. It was subsequently shown that the rigid β sheet stalk structure could be replaced with a rigid anti-parallel coiled coil structure[11]. Flexible Gly4Ser and Gly-Gly-Ser-Gly (SEQ ID NO: 2) linkers were again placed at each end of the coiled: coil sequence to "optimize the folding and stability of the resulting antibody". This construction also allowed the presentation granulocyte colony stimulating factor. Liu et al have taken the same approach of using rigid stalk structures coupled with a flexible peptides at both junctions to fuse leptin and Growth Hormone into VH CDR3 and VH CDR2 and VL CDR3[14]. In this example, retained antibody binding was seen as a potential disadvantage and the suggestion was made of using a "null" antibody partner e.g. anti-RSV antibody to avoid contribution of binding of the host antibody.

Peng et al (2015) reports the insertion of two natural agonists (leptin and follicle stimulating hormone) as "guests" into an antibody VH CDR3 in a way which retained agonistic activity[15]. A library of fusions was created wherein flexible peptides of 5-15 amino acids were inserted between the domains at each of the N terminal and C terminal ends along with a random 3 amino acids at each end (i.e. total linker lengths of 16-36 amino acids). A library of $10^7$ fusion variants was expressed in HEK293 cells and fusions which retained agonist activity of the "guest" were identified through reporter gene activation in an autocrine-based screening approach. The beneficial half-life properties of the antibody are extended to the incoming guest.

The approach of Peng et al (2015) was carried out in mammalian cells using an autocrine reporter system wherein cells are grown in semi-solid medium and secreted antibody fusions are retained in the vicinity of the producing cell. Thus, relatively high concentrations of the secreted product accumulated in the immediate vicinity of the cell[16] making it difficult to distinguish clones within a library with altered expression/stability or binding properties. Thus, there is a limitation on stringency within the system described by Peng et al (2015). Furthermore the functional screening approach is also limited to screens for which a relevant receptor/reporter system is available. The proportion of clones which worked was low (despite the benefit of endogenous chaperone-assisted folding within mammalian cells).

Antibodies represent a commonly used binding scaffold. As an alternative, the generation of binding members based on non-antibody scaffolds has been demonstrated[38, 39]. These engineered proteins are derived from libraries of variants wherein exposed surface residues are diversified upon a core scaffold[38-40].

Betton et al (1997)[17] reports fusing β lactamase into several accommodating permissive sites in maltose binding proteins using 9-10 amino acid linkers (DPGG-insert-YPGDP (SEQ ID NOS: 3, 4) and PDPGG-insert-YPGGP (SEQ ID NOS: 5, 6). Collinet[18] reports inserting P lactamase or dihydrofolate reductase into permissive sites of phosphoglycerate kinase using amino acid residues SGG or GG at the N terminal insertion point and GAG at the C terminal insertion point. Studies of the enzyme β-lactamase, which confers bacterial resistance to ampicillin, have also revealed potential sites into which peptide insertions could be accommodated[19]. Vandevenne et al reports the insertion into one of these sites of a chitin binding domain protein of the human macrophage chitotriosidase[20], using a construct that introduced 6-7 amino acids each at the N and C termini of the insertion. Crasson et al[21] have demonstrated functionalization of a nanobody by inserting it into a permissive site of β lactamase joining two helices.

SUMMARY

The present inventors have found that the incorporation of an entire binding domain ("donor diversity scaffold domain") within a second binding domain ("a recipient scaffold domain") increases the diversity of populations of binding members and allows the selection and isolation of binding members with advantageous properties from these populations. This may be useful for example in selecting binding members which bind to target molecules, such as ion channels, that are difficult to target with conventional antibodies.

An aspect of the invention provides a method of screening comprising;

(i) providing a founder library of binding members, each binding member in the founder library comprising a fusion protein and optionally, a partner domain associated with the fusion protein, wherein the fusion protein comprises a donor diversity scaffold domain inserted within a recipient diversity scaffold domain, optionally wherein the N and C terminals of the donor diversity scaffold domain are each linked to the recipient diversity scaffold domain with linkers of 4 amino acids or fewer each, wherein the donor diversity scaffold domain comprises a donor scaffold and a donor interaction sequence and the recipient diversity scaffold domain comprises a recipient scaffold and a recipient interaction sequence, and one or more of the donor interaction sequence, recipient interaction sequence and the linkers are diverse in said founder library, (ii) screening the founder library for founder binding members which display binding activity, and (iii) identifying one or more founder binding members in the founder library which display the binding activity.

In some embodiments, the linkers are diverse in said founder library.

The method may further comprise;

(iv) introducing diverse amino acid residues at one or more positions in the amino acid sequence of one or more identified founder binding members to produce a modified library of binding members, (v) screening the modified library for modified binding members which display a binding activity and (vi) identifying one or more modified binding members in the modified library which display the binding activity.

In some embodiments, diverse amino acid residues may be introduced into the donor interaction sequence, recipient interaction sequence and/or partner domain of the one or more identified founder binding members.

The method may further comprise;

(vii) associating the fusion protein from the one or more identified binding members or modified binding members with a diverse population of partner binding domains (partner chains) to produce a shuffled library of binding members, (viii) screening the shuffled library for shuffled binding members which display a binding activity, (ix) identifying one or more shuffled binding members which display the binding activity.

Another aspect of the invention provides a method of producing a library of binding members comprising;

providing a population of nucleic acids encoding a diverse population of fusion proteins comprising a donor diversity scaffold domain inserted into a recipient diversity scaffold domain, optionally wherein the N and C terminals of the donor diversity scaffold domain are linked to the recipient diversity scaffold domain with linkers of 4 amino acids or fewer at each terminal, wherein the donor diversity scaffold domain comprises a donor scaffold and a donor interaction sequence and the recipient diversity scaffold domain comprises a recipient scaffold and a recipient interaction sequence, and one or more of the donor interaction sequence, recipient interaction sequence and linkers are diverse in said population, expressing said population of nucleic acids to produce the diverse population, and optionally associating the fusion proteins with a population of partner domains, thereby producing a library of binding members.

Another aspect of the invention provides a library of binding members comprising;

a diverse population of fusion proteins comprising a donor diversity scaffold domain inserted into a recipient diversity scaffold domain, wherein the donor diversity scaffold domain comprises a donor scaffold and a donor interaction sequence and the recipient diversity scaffold domain comprises a recipient scaffold and a recipient interaction sequence, optionally wherein the N and C terminals of the donor diversity scaffold domain are each linked to the recipient diversity scaffold domain with linkers of 4 amino acids or fewer, wherein the donor diversity scaffold domain comprises a donor scaffold and a donor interaction sequence and the recipient diversity scaffold domain comprises a recipient scaffold and a recipient interaction sequence, and one or more of the donor interaction sequence, recipient interaction sequence and linkers are diverse in said population, and optionally wherein the fusion proteins are associated with binding partners to form heterodimers.

Another aspect of the invention provides a fusion protein comprising a donor diversity scaffold domain inserted into a recipient diversity scaffold domain wherein the donor diversity scaffold domain comprises a donor scaffold and a donor interaction sequence and the recipient diversity scaffold domain comprises a recipient scaffold and a recipient interaction sequence, optionally wherein the N and C terminals of the donor diversity scaffold domain are linked to the recipient diversity scaffold domain with linkers of 4 amino acids or fewer.

Another aspect of the invention provides a binding member comprising a fusion protein described herein and a partner domain associated with the fusion protein.

Other aspects of the invention provide isolated donor diversity scaffold domains, recipient diversity scaffold domains or partner domains from binding members identified and/or isolated as described herein, for example isolated donor diversity scaffold domains engineered as described herein or isolated recipient diversity scaffold domains or partner domains which may be useful in heterologous binding members, for example binding members which do not include the original donor diversity scaffold domain.

BRIEF DESCRIPTION OF FIGURES

FIG. 2 shows the sequence of synthetic single chain Fv genes used in KnotBody construction. The VH of an existing antibody D12 was used within KnotBody constructs. FIG. 2A shows restriction sites Nco1 and Xho1 which flank the VH sequence as well as the flexible linker joining VH to VL. This is followed by a sequence encoding the Vlamda1a (IGLV1-36) germline. CDR1 of the VL is shown and is preceded by a Pml1 cloning site. A Ser to Thr mutation was introduced to enable the inclusion of a Pml1 site at the end of framework 1. This site allows cloning of the knottin into the CDR1 position of the VL. At the end of VL framework 2 of the synthetic gene is a Pst1 site allowing cloning of a knottin into the CDR2 position. FIG. 2B is as for FIG. 2A but showing the V kappa germline sequence IGKV1D-39

FIG. 3 shows the insertion of EETI-II donor knottin into VL recipient. FIG. 3A shows the sequence of knottin donor EETI-II with cysteine residues emboldened and core sequence involved in trypsin binding ("PRIL") underlined. FIG. 3B shows a representation of the insertion of EETI-II donor into CDR1 or CDR2 of the lambda germline gene IGLV1-36. Boundaries are defined according to the international ImMunoGeneTics information system (IMGT)[29]. Amino acids are represented by IUPAC single letter amino acids code. FIG. 3Bi shows the sequence of the V lambda recipient domain at CDR1 before insertion of the knottin. FIGS. 3*ii* and 3*iii* show the sequence after insertion of the donor EETI-II donor. (FIG. 3Biii is generated by a primer which introduced an extra Gly residue between donor and framework residues compared to 3B ii). FIG. 3B iv show the sequence of the V lambda recipient domain at CDR2 before donor insertion and 3B v shows after insertion of the EETI-II donor. Antibody framework residues are shown underlined and residues from the antibody recipient which are lost are shown in lower case. At the junctions, randomising residues are shown as x with those which replace framework or donor residues shown as x in lower case. Any "additional" residues within the linker between the domains are shown emboldened in upper case (A, Z or X). Z means any amino acid from Val, Ala, Asp or Gly. X represents the amino acids encoded by the codon VNC (encoding 12 amino acids) or VNS encoding 16 amino acids in total. (V=A, C or G and S=C or G). FIGS. 3C-F show the DNA and amino acid sequence of the construct arising from insertion of the EETI-II knottin donor into respectively C. CDR1 of IGLV1-36, D. CDR1 of IGKV1D-39, E. CDR2 of IGLV1-36 and F. CDR2 of IGKV1D-39. (IGLV1-36 is a V lambda germline gene and IGKV1D-39 is a V kappa germline gene). Restriction sites used in cloning are highlighted and the framework and CDR regions are identified.

FIG. 10A (ii) EETI-II as VL CDR2 fusion. FIG. 10A (iii) Superimposition of previously published EETI-II structure and EETI-II as VL CDR2 fusion.

FIG. 12 shows representative examples of monoclonal bi-specific KnotBodies (from cMET-Fc and GAS6-CD4 selections) binding to trypsin and cMET-Fc or trypsin and GAS6-CD4. Monoclonal phage binding to the antigens immobilised on Maxisorp™ plates were detected using a mouse anti-M13 antibody followed by europium conjugated anti-mouse antibody. X-axis shows the clone number and the Y-axis shows antigen binding in fluorescent units (FU).

FIG. 20 shows a representation secondary structure overlaid on primary sequence

FIG. 28 shows a representation of the insertion of EETI-II donor knottin into VH CDR1 (A), VH CDR2 (B), VH CDR3 (C), VL CDR1 (D), VL CDR2 (E) and VL CDR3 (F) of the anti-TACE antibody D1A12 scFv (Table 23, Tape, C. J., PNAS USA 108, 5578-5583 (2011)). In addition, a linker library was created for KB_A07 where the EETI-II donor knottin was inserted into VL CDR2 (G). Boundaries in this example were defined according to the V BASE database (MRC, Cambridge UK) according to criteria defined by Chothia (Chothia et al, J. Mol. Biol. 264, 220-232 (1996)). Amino acids are represented by IUPAC single letter amino acids code. FIG. 28Ai shows the sequence of the VH recipient domain at CDR1 before insertion of the knottin. FIG. 28Aii shows the sequence after insertion of the donor EETI-II donor. FIG. 28Bi shows the sequence of the VH recipient domain at CDR2 before insertion of the knottin. FIG. 28Bii shows the sequence after insertion of the donor EETI-II donor. FIG. 28Ci shows the sequence of the VH recipient domain at CDR3 before insertion of the knottin. FIG. 28Cii shows the sequence after insertion of the donor EETI-II donor. FIG. 28Di shows the sequence of the VL recipient domain at CDR1 before insertion of the knottin. FIG. 28Dii shows the sequence after insertion of the donor EETI-II donor. FIG. 28Ei shows the sequence of the VL recipient domain at CDR2 before insertion of the knottin. FIG. 28Eii shows the sequence after insertion of the donor EETI-II donor. FIG. 28Fi shows the sequence of the VL recipient domain at CDR3 before insertion of the knottin. FIG. 28Fii shows the sequence after insertion of the donor EETI-II donor. FIG. 28Gi shows the sequence of the "wild-type" KB_A07 VL recipient domain at CDR2 before linker randomisation. FIG. 28Gii shows the sequence after randomization of the linker residues. At the junctions, randomising residues are shown as X.

FIG. 29 shows the insertion of the alternatively framed 5-3 EETI-II knottin donor into VL recipient. Alternatively framed knottins were inserted into CDR1 or CDR2 of a V kappa (IGKV1 D-39) or V lambda (IGLV1-36) light chain. FIG. 29A shows the nucleic acid and amino acid sequence of the alternatively framed knottin construct EET 5-3 which is used as a donor into CDR1 and CDR2 of the VL recipient. Cysteine residues are emboldened and core sequence involved in trypsin binding ("PRIL") underlined. FIG. 29B shows a representation of the insertion of 5-3 EETI-II donor into CDR1 or CDR2 of the lambda germline gene IGLV1-36. Boundaries are defined according to the international ImMunoGeneTics information system (IMGT)[29]. Amino acids are represented by IUPAC single letter amino acids code. FIG. 29Bi shows the sequence of the V lambda recipient domain at CDR1 before insertion of the knottin.

FIGS. 29Bii and 29Biii show the sequence after insertion of the 5-3 EETI-II donor. (The sequence in FIG. 29Biii is generated by a primer which introduced an extra Gly residue between donor and framework residues compared to 29B ii). FIG. 29B iv show the sequence of the V lambda recipient domain at CDR2 before donor insertion and 29B v shows after insertion of the EETI-II donor. Antibody framework residues are shown underlined and residues from the antibody recipient which are lost are shown in lower case. At the junctions, randomising residues are shown as x with those which replace framework or donor residues shown as x in lower case. Any "additional" residues within the linker between the domains are shown emboldened in upper case (A, Z or X). Z means any amino acid from Val, Ala, Asp, Gly or Glu (encoded by GNS codon). X represents the amino acids encoded by the codon VNC (encoding 12 amino acids) or VNS encoding 16 amino acids in total. (V=A, C or G and S=C or G). FIGS. 29 C-D show the DNA and amino acid sequence of the construct arising from insertion of the 5-3 EETI-II knottin donor into either CDR1 (C) or CDR2 of IGLV1-36 (D). The same 5-3 EET format was also introduced into CDR1 and CDR2 of IGKV1 D-39 which is a V kappa germline gene and the depiction of this is shown in FIG. 3 using the native (1-5) orientation of EETI-II, but applying the same approach as described in example 16 and depicted in FIG. 29 for insertion of the 5-3 EETI-II format. Restriction sites used in cloning are highlighted and the framework and CDR regions are identified.

DETAILED DESCRIPTION

Figures 1A, 1B, 1C:
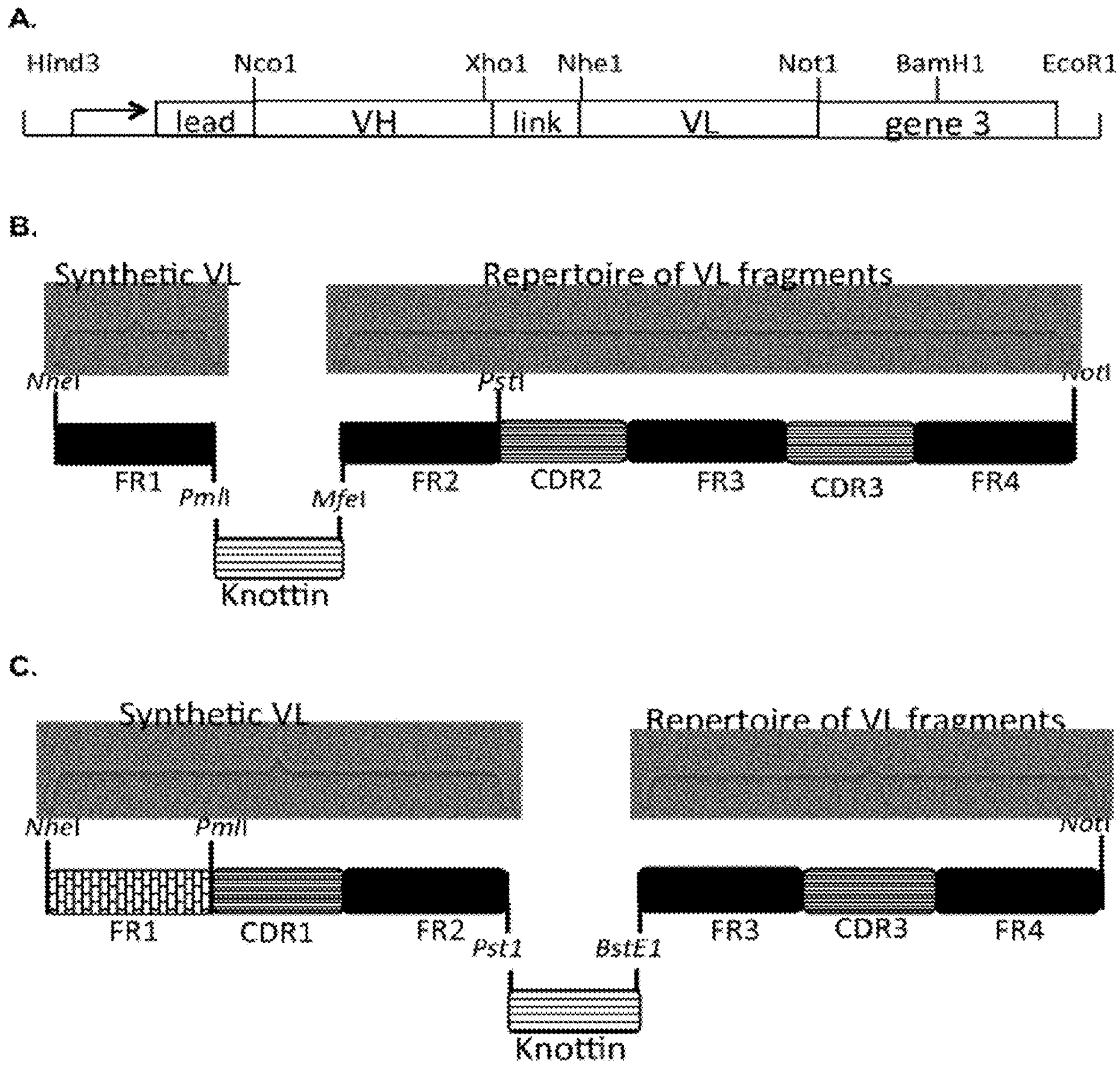
FIG. 1A shows a representation of pIONTAS1, showing the cassette encompassing the lacI promoter, M13 leader sequence scFv antibody gene-gene 3 (not to scale). This cassette is present within the Hind3/EcoR1 cloning sites of pUC119 which has an Ampicillin resistance gene and a coleE1 origin and an f1 bacteriophage origin of replication. The VH gene is flanked by an Nco1 and Xho1 restriction site and the VL gene is flanked by Nhe1 and Not 1 restriction sites allowing simple cloning into compatible vectors.
FIG. 1B shows a representation of the VL domain showing positions of framework regions (FW) and CDR regions. A knottin donor has been inserted at CDR1 position of the VL recipient. Pml1 and Mfe1 sites allow cloning of the knottin donor library. The region from FR2 to the end of FR4 is derived from a repertoire of light chains[28].
FIG. 1C is as described for FIG. 1B but with the knottin donor replacing CDR2 of the VL gene using Pst1 and BspE1 sites.

This invention relates to diverse populations and libraries of binding members that comprise a donor diversity scaffold domain inserted within a recipient diversity scaffold domain, and binding members isolated from such populations and libraries.

The present inventors have shown that an entire donor diversity scaffold domain is capable of folding correctly into a stable functional conformation following insertion into a recipient binding domain, with both domains remaining biologically active. The recipient binding domain is found to accommodate the incoming donor domain without its structure being compromised. Furthermore, donor and recipient domains with multiple cysteine residues each form the correct disulphide bond patterns within the fusion protein.

Combinations of donor and recipient diversity scaffold domains as described herein are useful in increasing the diversity of the populations and libraries of binding members. For example, antibodies are naturally-evolved diversity scaffolds but most of the diversity is focussed within the CDR3 region and in particular the CDR3 region of the antibody heavy chain. The introduction of a donor diversity scaffold domain into a recipient antibody VH and/or VL domain greatly increases the available diversity of the chimeric donor/antibody binding member.

Furthermore, if the donor diversity scaffold domain is predisposed to binding a particular class of target molecule, such as an ion channel, this predisposition may be conferred on the binding member comprising the donor diversity scaffold domain. Thus, the binding member may retain the binding activity of the donor diversity scaffold domain (for example, knottin binding to an ion channel) whilst also displaying the in vivo half-life of the recipient diversity scaffold domain (for example, an antibody).

Preferably, the donor and recipient diversity scaffold domains of the chimeric binding member of the invention are joined directly together or linked by short linkers to limit or constrain flexibility and relative movement between the domains, so that the binding member is relatively rigid. Longer, unstructured linkers are more liable to proteolytic degradation and may also facilitate the formation of incorrect disulphide bonds through increased conformational flexibility. In addition, the conformational flexibility of longer, relatively unstructured peptides compromises the affinity of interaction. In an interaction between 2 molecules, such as an antibody and an antigen, conformational entropy is lost upon complex formation. With longer linkers between donor and recipient diversity scaffold domains, there are potentially many more conformations available, making complex formation energetically unfavourable. In contrast, complex formation involving a more structured fusion protein with short or absent linkers will be entropically more favourable, potentially leading to a higher affinity interaction[30, 31, 32, 33].

Since conformational flexibility carries a thermodynamic "entropic penalty" for binding interactions, constraining the conformational relationship between the donor and recipient diversity scaffold domains as described herein minimises the entropic penalty of interactions, with a resultant benefit in affinity of the resulting interaction of the binding member.

Given the close proximity of the donor and recipient diversity scaffold domains, amino acids on the surface of both donor and recipient diversity scaffold domains may contribute to the paratope that binds to the target molecule or different target molecules within a complex. This may increase affinity or specificity of the binding member compared to either diversity scaffold domain alone. A partner domain of either the donor or recipient diversity scaffold domain may also contribute to binding of target molecule. Any of the donor, recipient or partner domains may contact closely apposed sites on a target molecule or complex.

A binding member described herein may comprise a fusion protein. The fusion protein is a chimeric molecule comprising two diversity scaffold domains; a donor diversity scaffold domain and a recipient diversity scaffold domain.

The donor diversity scaffold domain is located within the recipient diversity scaffold domain i.e. the donor diversity scaffold domain is flanked at both its N and C termini by the recipient diversity scaffold domain.

Preferably, both the donor and recipient diversity scaffold domains of the fusion protein contribute to the binding activity of the fusion protein, for example binding to the same or different target molecules.

In other embodiments, one of the donor and recipient diversity scaffold domains of the fusion protein, preferably the donor diversity scaffold domain is responsible for the binding activity of the fusion protein, for example the binding of the target molecule.

In some preferred embodiments, the fusion protein is suitable for display on the surface of a bacteriophage, for example for selection by phage display. A fusion protein for display may further comprise a phage coat protein, such as pIII, pVI, pVIII, pVII and pIX from Ff phage or the gene 10 capsid protein of T7 phage. The phage coat protein may be located at the N or the C terminal of the fusion protein, preferably at the C terminal of the fusion protein.

A diversity scaffold domain is an independently folding structural domain with a stable tertiary structure which is able to present diverse interaction sequences with potential to mediate binding to a target molecule. Diversity scaffold domains include domains represented within paralogous or orthologous groups which have been utilized in evolution for driving interactions of said scaffold with other molecules. Diversity scaffold domains also include natural domains which have been engineered to display diversity as well as entirely synthetic proteins evolved or designed to form a stable self-folding structure.

Examples of diversity scaffold domains known in the art include immunoglobulin domains[41], cysteine-rich peptides, such as knottins and venom toxin peptides, affibodies (engineered Z domain of Protein A domain)[42, 43], monobodies (i.e. engineered fibronectins)[44], designed ankyrin repeat proteins (DARPins)[45], adhirons[46], anticalins[47], thioredoxin[48], single domain antibodies[49, 50] and T7 phage gene 2 protein (Gp2)[51].

In some preferred embodiments, a diversity scaffold domain may comprise multiple disulphide bridges formed by cysteine residues within the scaffold domain.

Preferred diversity scaffold domains for use as described herein include the VH and VL domains of an antibody. The binding of T cell receptors to their targets is also directed by CDR loops present within variable Ig domains (a and (3) with greatest diversity present in CDR3 of the β chain. These have been used in vitro to present diverse sequences[34, 35]. Other Ig domains, such as the constant Ig domains in antibody heavy chains (e.g. CH1, CH2, and CH3) and light chains (C kappa, C lambda) may also be used as diversity scaffolds[36, 37]. Beyond antibodies and T cell receptors, the Ig domain has acted as a diversity scaffold expanding and evolving on an evolutionary timescale and Ig domains are found in many hundreds of different proteins involved in molecular recognition. Ig domains from such proteins may be used as diversity scaffold domains as described herein, The scaffold of the diversity scaffold domain is the framework which maintains the secondary structural elements which combine to form the stable core structure of the domain. The scaffold comprises multiple contiguous or non-contiguous scaffold residues which form covalent and non-covalent interactions with the side chains or the peptide backbone of other scaffold residues in the domain. Interactions may include hydrogen bonds, disulphide bonds, ionic interactions and hydrophobic interactions. The scaffold residues may form secondary structural elements of the domain, such as a helices, 1 strands, 1 sheets, and other structural motifs. Because they contribute to the core structure of the diversity scaffold domain, scaffold residues are conserved and substitution of scaffold residues within the diversity scaffold domain is constrained.

Examples of scaffolds include the framework regions of an antibody variable domain or the cysteine knot framework of knottins (e.g. the six or more cysteine residues which form the characteristic knot structure) together with the knottin beta sheets and $3_{10}$ helix motif.

The interaction sequence of a diversity scaffold domain is a contiguous or non-contiguous amino acid sequence which is presented by the stable core structure of the scaffold. The interaction sequence may interact with other molecules and mediate the binding activity of the domain, for example binding to a target molecule. In some embodiments, the interaction sequence of a domain may comprise one or more diverse residues, allowing selection of binding members with specific binding activity to be isolated from a library.

The residues of the interaction sequence may be entirely non-structural and may not support or contribute to the tertiary structure of the domain. For example, the interaction residues may be located at the loops or turns between secondary structural elements or motifs.

Because they do not contribute to the core structure of the diversity scaffold domain, the residues of the interaction sequence are less conserved and substitution of interaction residues within the diversity scaffold domain is less constrained. In some embodiments, the interaction sequence of a diversity scaffold domain may comprise residues in the non-loop faces of the protein[43,44,52].

Examples of interaction sequences include the CDRs of an antibody variable domain and the loops joining secondary structural elements of stable, self-folding protein domains e.g. the joining loops of a knottin, such as the PRIL motif of loop 1 of EETI-II. Other examples of interaction sequences within scaffold domains are known in the art[34-38, 41-48, 51, 53].

In some embodiments, a domain may contain residues which contribute to both binding and secondary structure. These residues may constitute both scaffold and interaction sequences. This is illustrated with affibodies (the engineered Z domain of protein A domain)[43, 52] and monobodies (engineered scaffolds based on a fibronectin domain)[44]. Residues which contribute to both secondary structure and binding may be diversified in the binding members described herein. Binding members which retain secondary structure may, for example, be identified in libraries using routine selection techniques. In some embodiments, residues which contribute to both secondary structure and binding may not be diversified.

Diversity scaffold domains may be used as either donor or recipient diversity scaffold domains in the fusion proteins and binding members described herein.

The donor diversity scaffold domain comprises a donor scaffold and a donor interaction sequence.

Preferably, donor diversity scaffold domains have N and C termini that are proximal to each other within the native structure of the domain. The distance between the termini of the donor may, for example, be within 20% of the distance between the ends of the insertion site in the recipient diversity scaffold domain, more preferably the same distance. Examples of donor domains with proximal termini include knottins[54], adhirons[46] and Gp2 scaffolds[51].

In other embodiments, donor diversity scaffold domains may have N and C termini that are not proximal in the native structure of the domain. Donor diversity scaffold domains with non-proximal N and C termini may be inserted into the recipient diversity scaffold domain as described herein using linkers that are sufficiently long to allow fusion of the termini of the donor domain with the loops of the recipient diversity scaffold domain, such that the linkers bridge the gap between the termini of donor and recipient domains. Alternatively, the donor diversity scaffold domain may be truncated to create a donor domain where the N and C termini are in proximity, or the recipient diversity scaffold domain may be truncated to create a recipient domain in which the termini of the insertion site are in proximity with the termini of the donor domain. The net result will be a loss of residues arising from the fusion of the donor and recipient structural domains. Linkers or truncations may reduce the distance between the termini of the donor domain to within 20% of the distance between the termini of the insertion site in the recipient scaffold or more preferably the same distance.

The donor diversity scaffold domain may consist of at least 15, at least 20, at least 25, at least 30 or at least 40 amino acids. The donor diversity scaffold domain may consist of 400 or fewer, 300 or fewer, 200 or fewer or 100 or fewer amino acids. For example, the donor diversity scaffold domain may consist of from 20 to 400 amino acids.

The donor diversity scaffold domain may comprise 2, 4, 6, 8, 10 or more cysteine residues which form disulphide bonds in the scaffold domain (i.e. the domain may contain 1, 2, 3, 4, 5 or more disulphide bonds).

In some embodiments, a donor diversity scaffolds may consist of at least 15 amino acids and contain 4 or more cysteine residues.

Examples of suitable donor diversity scaffold domains include an immunoglobulin, an immunoglobulin domain, a VH domain, a VL domain, an affibody, a cysteine-rich peptide, such as a venom toxin peptide or knottin, a "Designed ankyrin repeat protein" (DARPin), an adhiron, a fibronectin domain, an anticalin, a T7 phage gene 2 protein (Gp2) a monobody, a single domain antibody[49, 50] or an affibody.

Preferred donor diversity scaffold domains include cysteine-rich peptides, such as ion channel-modulating peptides, venom toxin peptides and knottins.

Cysteine-rich peptides comprise a network of disulphide bonds as a core structural element. The structural conformations of cysteine-rich peptides are well-known in the art[55, 6].

Ion channel-modulating peptides (both agonistic and antagonistic) comprising multiple disulphide bonds are well-known in the art. Examples include venom toxin peptides from venomous species, such as spiders, snakes, scorpions and venomous snails[26, 55].

The structural conformations and disulphide linkage patterns of venom toxin peptides are also well known in the art. For example, an analysis of venoms of spiders and other animals reveals a multitude of conformations and patterns of disulphide linkage[55, 65, 66, 67]. For example, spider toxin huwentoxin-II has a disulphide linkage pattern of I-III, II-V, IV-VI[68] and "Janus-faced atracotoxins" (J-ACTXs) has a disulphide linkage pattern of I-IV, II-VII, III-IV and V-VIII (including an unusual "vicinal" disulphide bond between 2 neighbouring cysteines)[56], where the pairs of roman numeral refer to the order where each cysteine appears in the sequence and the position of the partner cysteine with which it forms a disulphide bond.

Cysteine-rich peptides may have a "disulphide-directed beta hairpin" (DDH) structure comprising an anti-parallel beta hairpin stabilised by 2 disulphide bonds[56]. The DDH core structure is found in the widely studied "inhibitory cysteine knot" structure (hereafter referred to as cysteine-knot miniproteins or knottins).

Knottins are small cysteine rich proteins that have an interwoven disulphide bonded framework, triple-stranded 13-sheet fold, and one or more solvent exposed loops. Knottins typically comprise at least 3 disulphide bridges and are characterised by a disulphide knot which is achieved when a disulphide bridge between cysteines III and VI crosses the macrocycle formed by the two other disulphides (disulphides I-IV and II-V) and the interconnecting backbone. These bridges stabilise the common tertiary fold formed of antiparallel 13-sheets and in some cases a short 310 helix. (The pairs of Roman numeral refers to the order where each cysteine appears in the sequence and the position of the partner cysteine with which it forms a disulphide bond). Knottins are 20-60 residues long, usually 26-48 residues, and are found in diverse organisms ranging from arthropods, molluscs, and arachnids to plants[57]. Knottins arising from conus snails (conotoxins) in particular have been widely studied[54,58-60]. Many thousands of other knottins have been identified and their sequences and structures are publically available[57,61,62] for example from on-line databases (such as the Knottin on-line database[57], Centre de Biochimie Structural, CNRS, France).

In some embodiments, the overall correct secondary structure of the knottin may be conferred by the correct distribution and spacing of cysteines. In other embodiments one or more additional scaffold residues may be required to confer the correct secondary structure. For example, residues 11-15 and 22-25 of EETI-II direct the folding propensity towards the 11-15 $3_{10}$-helix region and a 22-25 β-turn region respectively in the absence of any disulphides[63].

Knottins display a high degree of sequence flexibility and can accommodate large amounts of non-native sequence. For example, EETI-II can accommodate over 50% non-native sequence (by randomising 2 of the loops)[24].

A suitable cysteine-rich peptide for use as a diversity scaffold as described herein may for example comprise the amino acid sequence of Huwentoxin-IV, ProTx-II, Ssm6a, Kaliotoxin, mokatoxin-1, Conotoxin-ω, MCoTI-II, Shk, PcTX1 or mambalgin (as shown in Table 8A; SEQ ID NOS: 7-25) or other sequence set out in the Knottin database or may be a fragment or variant of this sequence which retains the correct fold structure.

A knottin which is a variant of a reference knottin sequence, such as sequence shown in Table 8A (SEQ ID NOS: 7-25) or set out in the Knottin database, may comprise an amino acid sequence having at least 20%, at least 30%, at least 40%, at least 50%, at least 60%, at least 70%, at least 80%, at least 90%, at least 95%, or at least 98% sequence identity to the reference sequence. Particular amino acid sequence variants may differ from a knottin sequence of Table 8A (SEQ ID NOS: 7-25) by insertion, addition, substitution or deletion of 1 amino acid, 2, 3, 4, 5, 6, 7, 8, 9, or 10 or more than 10 amino acids.

Sequence similarity and identity are commonly defined with reference to the algorithm GAP (Wisconsin Package, Accelerys, San Diego USA). GAP uses the Needleman and Wunsch algorithm to align two complete sequences that maximizes the number of matches and minimizes the number of gaps. Generally, default parameters are used, with a gap creation penalty=12 and gap extension penalty=4. Use of GAP may be preferred but other algorithms may be used, e.g. BLAST (which uses the method of Altschul et al. (1990) *J. Mol. Biol.* 215: 405-410), FASTA (which uses the method of Pearson and Lipman (1988) *PNAS USA* 85: 2444-2448), or the Smith-Waterman algorithm (Smith and Waterman (1981) *J. Mol Biol.* 147: 195-197), or the TBLASTN program, of Altschul et al. (1990) supra, generally employing default parameters. In particular, the psi-Blast algorithm (*Nucl. Acids Res.* (1997) 25 3389-3402) may be used.

Sequence comparison may be made over the full-length of the relevant sequence described herein.

One or more residues within a loop of a knottin, for example, one or more residues within loop 1, 2, 3, 4 or 5 of a knottin may be diversified or randomised. In some embodiments, one or more within the target binding motif, such as the trypsin binding motif PRIL in loop 1 of EETI-II, or the corresponding residues in a different knottin, may be diversified. For example, 1, 2, 3, 4, 5, 6, 7, 8, 9, or 10 or more residues may be diversified.

The formation of native disulphide linkage patterns in the donor and recipient diversity together and the adoption of correct secondary structures within the scaffold domains of a fusion protein is exemplified below.

In other preferred embodiments, the donor diversity scaffold is an adhiron. Adhirons are peptides of about 80-100 amino acids based on plant-derived phytocystatins[46]. Suitable adhiron sequences are well-known in the art and described elsewhere herein. A suitable adhiron for use as a diversity scaffold as described herein may for example comprise an amino acid sequence shown in Table 12 (SEQ ID NOS: 26, 27) or may be a fragment or variant of this sequence.

An adhiron which is a variant of a reference adhiron sequence, such as sequence shown in Table 12 (SEQ ID NOS: 26 & 27) may comprise an amino acid sequence having at least 20%, at least 30%, at least 40%, at least 50%, at least 60%, at least 70%, at least 80%, at least 90%, at least 95%, or at least 98% sequence identity to the reference sequence. Particular amino acid sequence variants may differ from a sequence of Table 12 (SEQ ID NOS: 26 & 27) by insertion, addition, substitution or deletion of 1 amino acid, 2, 3, 4, 5, 6, 7, 8, 9, or 10 or more than 10 amino acids.

The methods described herein do not require knowledge of the structure of the donor diversity scaffold domain. Selection of binding members may be based on binding to the target molecule (if known) or the correct folding of the recipient domain. The donor diversity scaffold domain may be provided within a library from which clones with proper folding of the recipient scaffold can be selected or may be inserted into an existing recipient diversity scaffold which accommodates an incoming donor diversity scaffold.

The failure of one scaffold domain to fold will affect the overall expression and stability of the resultant fusion protein and so it will also be possible to introduce diversification in the absence of structural knowledge and screen for retained expression of a folded scaffold domain. However, where the structure of the donor diversity scaffold domain is known, sites for diversification in the construction of libraries may be guided by this structure.

The recipient diversity scaffold domain and the donor diversity scaffold domain are preferably heterologous i.e. they are associated by artificially by recombinant means and are not associated in nature. In some preferred embodiments, the donor and recipient diversity scaffold domains are from different scaffold classes e.g. they are not both immunoglobulins, both cysteine-rich proteins, both knottins or both adhirons.

The recipient diversity scaffold domain comprises a recipient scaffold and a recipient interaction sequence.

In some embodiments, the recipient diversity scaffold domain may lack cysteine residues which form disulphide bonds. For example, the scaffold domain may comprise 0 or 1 cysteine residue. In other embodiments, the recipient diversity scaffold domain may comprise 2, 4, 6, 8, 10 or more cysteine residues which form disulphide bonds in the scaffold domain (i.e. the domain may comprise 1, 2, 3, 4, 5 or more disulphide bonds).

Examples of suitable recipient diversity scaffold domains include an immunoglobulin domain, a VH domain, a VL domain, a knottin, a Protein A, cysteine-rich peptide, venom toxin, a Designed ankyrin repeat protein (DARPin), an adhiron, a fibronectin domain, an anticalin and a T7 phage gene 2 protein (Gp2).

Figures 19, 20A, 20B:
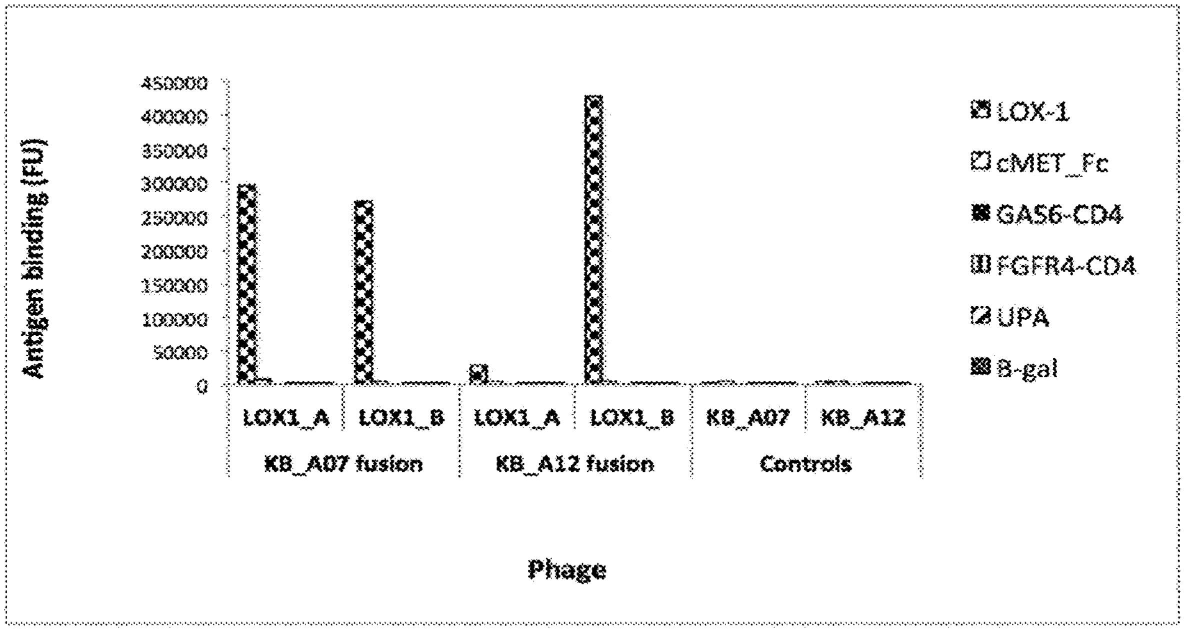
FIG. 19 show specific binding of two adhiron-antibody fusions to LOX-1 protein. In this assay, binding of phage displaying adhiron-antibody fusions to LOX1 was detected using a mouse anti-M13 antibody followed by europium conjugated anti-mouse antibody. Parent KnotBodies KB_A07 and KB_A12 (EETI-II fusions) were included as controls. Proteins cMET-FC, GAS6-CD4, FGFR4-CD4, UPA and B-gal were used to examine non-specific binding. All antigens were directly immobilised on Maxisorp™ plates.
FIG. 20A shows the sequence of $10^{th}$ type III cell adhesion domain of fibronectin. Secondary structural elements (beta sheets) are underlined. The residues which join the beta sheets on the upper face of the domain are shown lower case.
FIG. 20B shows the sequence of gp2 protein with beta sheets and alpha helical regions labelled. Potential sites for donor insertion or diversification are shown in lower case. N and C terminal residues removed without affecting structure are shown in italics and smaller font.

Selection of the insertion site for the donor diversity scaffold domain and linker sequences may be guided by the structure of the recipient domain, where the structure is known[64, 53, 23, 75, 39, 43]. For example, a suitable insertion site may be located in a region which joins secondary structural elements of the recipient diversity scaffold domain, such as beta strands or alpha helices. Suitable regions for the insertion site within the $10^{th}$ type III cell adhesion domain of fibronectin are shown in FIG. 20A (SEQ ID NO: 28) and regions for the insertion site within the T7 Gp2 protein are shown in FIG. 20B (SEQ ID NO: 29). The identification of suitable insertion sites is described in more detail in example 10 below. Structural knowledge may also be used to direct diversification in the construction of libraries.

Preferably, the recipient diversity scaffold domain is all or part of an immunoglobulin, most preferably, all or part of an antibody variable domain. For example, the recipient diversity scaffold domain may be an antibody light chain variable (VL) domain or an antibody heavy chain variable (VH) domain.

The incoming donor diversity scaffold domain separates the recipient diversity scaffold domain into N terminal and C terminal parts at the point of insertion into the recipient. The donor diversity scaffold domain is fused internally within the recipient diversity scaffold domain such that the N terminus and C terminus of the donor diversity scaffold domain are connected either directly or via a linker to the N and C terminal parts respectively of the recipient diversity scaffold domain. In some embodiments, one or more residues at the N and/or C terminals of the donor diversity scaffold domain or the recipient diversity scaffold domain may be removed and/or randomised. The recipient diversity scaffold domain retains its original N and C termini, which are not affected by the insertion of the donor diversity scaffold domain into the internal insertion site.

In some embodiments, the orientation of the incoming donor diversity scaffold domain relative to the recipient diversity scaffold domain may be altered by linking the recipient diversity scaffold domain to different positions within the donor diversity scaffold domain. For example, a rotated donor diversity scaffold domain may be designed by cyclising the donor diversity scaffold domain through linkage of the native N and C terminals and linearizing at a different position in the amino acid sequence to generate artificial N and C terminals. These artificial terminals may be linked to the recipient diversity scaffold domain within the fusion protein. In other words, the native N and C termini of a donor diversity scaffold domain, such as a cysteine-rich peptide, may be joined together directly or via a peptide sequence and artificial N and C termini generated at a different position in the sequence of the donor diversity scaffold domain. In a fusion protein generated using these artificial N and C termini, the donor diversity scaffold domain is rotated relative to the recipient diversity scaffold domain compared to a fusion protein comprising the donor diversity scaffold domain with native N and C terminals. For example, the order of the loops within the donor diversity scaffold domain may be altered. Examples of EETI-II donor diversity scaffold domains with altered orientation are shown in Table 28 (SEQ ID NOS: 302-307).

Preferably, the donor diversity scaffold domain completely replaces some or all of a loop sequence of the recipient diversity scaffold domain, such that the donor diversity scaffold domain is directly linked to scaffold residues of the recipient diversity scaffold domain. For example, loop sequences joining secondary structural elements in the recipient domain (e.g. a CDR joining 2 β strands of a β sheet framework elements in an antibody variable domain) may be removed in their entirety. In some embodiments, one or more scaffold residues may be removed or replaced from the donor diversity scaffold domain or the recipient diversity scaffold domain to reduce the distance between them while enabling folding of the component parts of the fusion protein.

Preferably, the donor diversity scaffold domain is positioned in the fusion protein close to the interaction sequence of the recipient diversity scaffold domain. For example, donor diversity scaffold may be located less than 20 Angstroms from the recipient donor scaffold, for example 8-13 Angstroms in the case of the knottin insertion exemplified herein; calculated from the end of the preceding framework to the first cysteine of the donor/knot motif. This proximity allows both interaction sequences to interact with the same or closely apposed sites on the target molecule or complex, such that both donor and recipient domains may contribute simultaneously to binding. For example, the fusion protein may lack rigid stalks and flexible linkers to connect the donor diversity scaffold domain to the recipient diversity scaffold domain.

In some preferred embodiments, the recipient diversity scaffold is an antibody variable domain, for example an antibody VH or VL domain.

The scaffold of a VH, VL kappa or VL lambda recipient domain may comprise residues 1-26, 39-55 and 66-104 (IMGT numbering) of the domain. The scaffold may also comprise residues of framework 4 which are encoded by the last 11 residues encoded by the J segments of the heavy chain and by the last 10 residues encoded by the J segments of the kappa and lambda light chains. The interaction sequence of a VH, VL kappa or VL lambda domain may comprise residues 27 to 38 (CDR1), 56 to 65 (CDR2) and 105 to 117 (CDR3) (IMGT numbering).

Examples of preferred recipient diversity scaffold domains are shown in Table 1 with inserted donor diversity scaffold domains.

Other preferred recipient scaffolds include antibody constant domains, for example a heavy or light chain CH1, CH2 or CH3 domain.

The donor diversity scaffold domain may replace part or more preferably all of a CDR (i.e. CDR1, CDR2 or CDR3) in the recipient antibody variable domain.

Preferably, the donor diversity scaffold domain replaces all or part of the CDR1 or CDR2 of the antibody variable domain. This allows the more diverse and central CDR3 to contribute to the binding activity, as well as the partner antibody variable domain. Insertion of the donor diversity scaffold domain into CDR1 and CDR2 is exemplified below.

The interaction sequence of the donor diversity scaffold domain and one or more CDRs of the recipient antibody variable domain or partner domain may interact with the same epitope on the target molecule. For example, the interaction sequence of the donor diversity scaffold domain and the CDR3 of the antibody variable domain and/or partner domain may interact with the same epitope on the target molecule.

In some preferred embodiments, the recipient diversity scaffold domain is an antibody variable domain, for example a VH or VL domain, and the donor diversity scaffold domain is a knottin or adhiron. Examples of binding members comprising a knottin donor diversity scaffold domain and a VL domain recipient diversity scaffold are shown in Table 1. A binding member comprising an antibody variable domain recipient and a cysteine rich donor domain is termed a "Knotbody" herein.

In one set of preferred embodiments, the recipient diversity scaffold domain is an antibody VL domain, and the donor diversity scaffold domain is a knottin which replaces the CDR2 of the VL domain. Suitable knottins may bind to an ion channel, such as Kv1.3, and may include ShK and Kaliotoxin. The recipient antibody VL domain may show no target binding or may bind to the same target molecule as the knottin, an associated protein in complex with the knottin target molecule or a different target molecule to the knottin.

A suitable binding member may for example comprise a fusion protein having the amino acid sequence of any one of SEQ ID NOS: 31 to 35 (as shown in Table 8B) or may be a fragment or variant of such a sequence. The binding member may further comprise a partner domain which associates with the fusion protein. Suitable partner domains include any VH domain, for example the D12 A12 VH domain shown in Table 8B (SEQ ID NO: 30).

Suitable VH domains may be non-binders, may bind to a different target molecule to the fusion protein or may bind to the same target molecule as the fusion protein, for example to increase binding affinity of the fusion protein.

A fusion protein which is a variant of a reference sequence, such as sequence shown in Table 1 (SEQ ID NOS: 84-139) Table 8B (SEQ ID NOS: 31 to 35), Table 29 (SEQ ID NOS: 308-317) or FIG. 29 (SEQ ID NOS 349 and 351) may comprise an amino acid sequence having at least 20%, at least 30%, at least 40%, at least 50%, at least 60%, at least 70%, at least 80%, at least 90%, at least 95%, or at least 98% sequence identity to the reference sequence. Particular amino acid sequence variants may differ from a fusion protein sequence of Table 1 (SEQ ID NOS: 84-139) Table 8B (SEQ ID NOS: 31 to 35), Table 29 (SEQ ID NOS: 308-317) or FIG. 29 (SEQ ID NOS 349 and 351) by insertion, addition, substitution or deletion of 1 amino acid, 2, 3, 4, 5, 6, 7, 8, 9, or 10 or more than 10 amino acids.

In other preferred embodiments, the recipient diversity scaffold domain may be an immunoglobulin constant domain, for example an immunoglobulin constant domain from an antibody heavy or light chain, and the donor diversity scaffold domain may be a knottin or adhiron.

Preferably, the distance between the framework residues of the recipient diversity scaffold domain and the donor diversity scaffold domain is minimised to reduce proteolytic lability and/or relative flexibility between the domains. This may be useful in promoting binding affinity. For example, the N and C terminals of the donor diversity scaffold domain may each be linked directly to the recipient diversity scaffold domain without a linker or through linkers of 1, 2, 3 or 4 amino acids. The same or different linker sequences may be used to link the N and C terminals of the donor diversity scaffold domain to the recipient diversity scaffold domain.

Examples of suitable linker sequences are shown in Tables 2, 26 and 27.

In some embodiments, it may be preferred that the donor and recipient diversity scaffold domains are joined by a linker other than GGSG (SEQ ID NO: 2), a linker other than GGGS (SEQ ID NO: 32) or a linker that does not comprise GG, such as SGG or GG.

Linker length refers to the number of amino acid residues that are gained or lost from the scaffold elements of the donor and recipient domains when fused together. For example, the removal of scaffold residues and the use of an equal number of randomized residues to join the donor and recipient diversity scaffold domains is considered herein to be randomization of the removed framework residues rather than the introduction of additional linker residues.

In some embodiments, 1, 2, 3 or 4 amino acids at the N and/or C terminal of the donor diversity scaffold domain and/or 1, 2, 3 or 4 amino acids on each side of the insertion site in the recipient scaffold may be replaced through mutagenesis and/or randomisation.

The fusion protein may be associated with the partner domain through a covalent or non-covalent bond.

The partner domain may be associated with the recipient diversity scaffold domain and/or the donor diversity scaffold domain of the fusion protein. Preferably, the partner domain is associated with the recipient diversity scaffold domain.

In some preferred embodiments, the recipient diversity scaffold domain is an antibody light chain variable (VL) domain and the partner domain is an antibody heavy chain variable (VH) domain. In other preferred embodiments, the recipient diversity scaffold domain is an antibody heavy chain variable (VH) domain and the partner domain is an antibody light variable (VL) domain.

In some embodiments, antibody heavy and light chain variable domains of a binding member as described herein may be connected by a flexible linker, for example in a scFv format.

A binding member described herein comprises the fusion protein. The binding member may further comprise a partner domain that is associated with the fusion protein. For example, the binding member may be a heterodimer.

In some embodiments, the binding member may comprise two or more fusion proteins or partner domains. For example, the binding member may be multimeric. In some embodiments, the recipient or donor diversity scaffold domain of the binding member may form a homomultimer, such as a homodimer. The recipient or donor diversity scaffold domain of the binding member may partner with a different form of the same domain, such as a wild-type or mutagenized form of the domain.

In addition to the fusion protein and optional partner domain, the binding member may further comprise a therapeutic moiety, half-life extension moiety or detectable label. The moiety or label may be covalently or non-covalently linked to the fusion protein or the partner domain.

In some embodiments, a binding member may be displayed on a particle or molecular complex, such as a cell, ribosome or phage, for example for screening and selection. The binding member may further comprise a display moiety, such as phage coat protein, to facilitate display on a particle or molecular complex. The phage coat protein may be fused or covalently linked to the fusion protein or the partner domain.

In some embodiments, a binding member as described herein may display advantageous properties, such as increased affinity, stability, solubility, expression, specificity or in vivo half-life relative to the isolated donor and/or recipient diversity scaffold domain.

Other aspects of the invention relate to the generation of libraries of binding members as described herein.

A method of producing a library of binding members may comprise;

- providing a population of nucleic acids encoding a diverse population or repertoire of fusion proteins comprising a donor diversity scaffold domain inserted into a recipient diversity scaffold domain, optionally wherein the N and C terminals of the donor diversity scaffold domain are linked to the recipient diversity scaffold domain with linkers of up to 4 amino acids,
- wherein the donor diversity scaffold domain comprises a donor scaffold and a donor interaction sequence and the recipient diversity scaffold domain comprises a recipient scaffold and a recipient interaction sequence, and
- one, two or all three of the donor interaction sequence, the recipient interaction sequence and the linkers are diverse in said population, and
- expressing said population of nucleic acids to produce the diverse population or repertoire, and
- optionally associating the fusion proteins with a partner domain or population of partner domains, thereby producing a library of binding members.

The population of nucleic acids may be provided by a method comprising inserting a first population of nucleic acids encoding a donor diversity scaffold domain into a second population of nucleic acids encoding a recipient diversity scaffold domain, optionally wherein the first and second nucleic acids are linked with a third population of nucleic acids encoding linkers of up to 4 amino acids, wherein the one, two or all three of the first, second and third populations of nucleic acids are diverse.

The nucleic acids may be contained in vectors, for example expression vectors. Suitable vectors include phage-based[76] or phagemid-based[77] phage display vectors.

The nucleic acids may be recombinantly expressed in a cell or in solution using a cell-free in vitro translation system such as a ribosome, to generate the library. In some preferred embodiments, the library is expressed in a system in which the function of the binding member enables isolation of its encoding nucleic acid. For example, the binding member may be displayed on a particle or molecular complex to enable selection and/or screening. In some embodiments, the library of binding members may be displayed on beads, cell-free ribosomes, bacteriophage, prokaryotic cells or eukaryotic cells. Alternatively, the encoded binding member may be presented within an emulsion where activity of the binding member causes an identifiable change. Alternatively, the encoded binding member may be expressed within or in proximity of a cell where activity of the binding member causes a phenotypic change or changes in the expression of a reporter gene[16, 78, 79].

Eukaryotic cells benefit from chaperone systems to assist the folding of secreted protein domains[80] and these are absent within bacterial expression systems. The data set out below shows that mammalian chaperone systems are not required for the correct folding of the binding members described herein. In addition, binding members identified using prokaryotic phage display systems are by definition amenable to further engineering within the phage display system to create improved binders. Prokaryotic systems, such as phage display, also facilitate construction of larger libraries and facilitate selection, screening and identification of binding members from such libraries. In contrast binding members identified in eukaryotic systems may not be amenable for further engineering within prokaryotic systems.

Preferably, the nucleic acids are expressed in a prokaryotic cell, such as *E coli*. For example, the nucleic acids may be expressed in a prokaryotic cell to generate a library of binding members that is displayed on the surface of bacteriophage. Suitable prokaryotic phage display systems are well known in the art, and are described for example in Kontermann, R & Dubel, S, *Antibody Engineering*, Springer-Verlag New York, LLC; 2001, ISBN: 3540413545, WO92/01047, U.S. Pat. Nos. 5,969,108, 5,565,332, 5,733,743, 5,858,657, 5,871,907, 5,872,215, 5,885,793, 5,962,255, 6,140,471, 6,172,197, 6,225,447, 6,291,650, 6,492,160 and 6,521,404. Phage display systems allow the production of large libraries, for example libraries with $10^8$ or more, $10^9$ or more, or $10^{10}$ or more members.

In other embodiments, the cell may be a eukaryotic cell, such as a yeast, insect, plant or mammalian cell.

A library of binding members, for example a library generated by a method described above, may comprise;

a diverse population of fusion proteins comprising a donor diversity scaffold domain inserted into a recipient diversity scaffold domain, optionally wherein the N and C terminals of the donor diversity scaffold domain are each linked to the recipient diversity scaffold domain with linkers of up to 4 amino acids, wherein the donor diversity scaffold domain comprises a donor scaffold and a donor interaction sequence and the recipient diversity scaffold domain comprises a recipient scaffold and a recipient interaction sequence, and one, two or all three of the donor interaction sequence, the recipient interaction sequence and the linkers are diverse in said population, and optionally wherein each fusion protein in the population is associated with a partner domain.

The sequences of one, two or all three of the donor interaction sequence, the recipient interaction sequence and the linkers may be diverse. For example, the binding members in the library may have diverse donor interaction sequences and the same recipient interaction sequence; diverse recipient interaction sequences and the same donor interaction sequence; diverse linker sequences and the same recipient and donor interaction sequences or; diverse recipient and donor interaction sequences.

A diverse sequence as described herein is a sequence which varies between the members of a population i.e. the sequence is different in different members of the population. A diverse sequence may be random i.e. the identity of the amino acid or nucleotide at each position in the diverse sequence may be randomly selected from the complete set of naturally occurring amino acids or nucleotides or a sub-set thereof.

Diversity may be targeted to donor interaction sequence, recipient interaction sequence, linkers or sequences within the partner domain using approaches known to those skilled in the art, such as oligonucleotide-directed mutagenesis[22, 23], *Molecular Cloning: a Laboratory Manual:* 3rd edition, Russell et al., 2001, Cold Spring Harbor Laboratory Press, and references therein). For example, where the recipient diversity scaffold domain is an antibody variable domain and the donor diversity scaffold domain has replaced one CDR region, amino acid changes, such as diverse sequences, may be introduced into the other CDRs of the recipient domain or partner chain. Where the donor domain is a knottin, diverse sequences may be introduced into regions linking core scaffold elements such as the cysteine knot. The knottin structure has been shown to be able to accommodate over 50% non-native structure[24]. The introduction of diversity into the knottin scaffolds, such as EETI-II[24], kaliotoxin[25], ProTx-1[26], and TRPA1[26] to generate libraries is known in the art.

Diverse sequences may be contiguous or may be distributed within the domain. Suitable methods for introducing diverse sequences into domains are well-described in the art. For example, diversification may be generated using oligonucleotide mixes created using partial or complete randomisation of nucleotides or created using codons mixtures, for example using trinucleotides. Alternatively, a population of diverse oligonucleotides may be synthesised using high throughput gene synthesis methods and combined to create a precisely defined and controlled population of variant domains. Alternatively "doping" techniques in which the original nucleotide predominates with alternative nucleotide(s) present at lower frequency may be used. As an alternative, Example 2 below describes methods for introducing diversity into a domain using diversity from a natural source (an antibody repertoire in this example).

Either donor or recipient domains could be part of a multimeric protein with potential additional diversity being introduced by the partner chain. The entire partner chain can be replaced e.g. by chain shuffling[27]. Alternatively, diversity could be introduced into regions of an existing partner chain of the recipient or donor e.g. the VH partner of a VL recipient of the donor. In general the heterodimeric nature of antibodies and the ability to select variants of the partner chain independently of the recipient chain supporting the donor adds to the power of this approach.

Preferably, the library is a display library. The binding members in the library may be displayed on the surface of particles, or molecular complexes such as beads, ribosomes, cells or viruses, including replicable genetic packages, such as yeast, bacteria or bacteriophage (e.g. Fd, M13 or T7) particles, viruses, cells, including mammalian cells, or covalent, ribosomal or other in vitro display systems. Each particle or molecular complex may comprise nucleic acid that encodes the binding member that is displayed by the particle and optionally also a displayed partner domain if present.

In some preferred embodiments, the binding members in the library are displayed on the surface of a bacteriophage. Suitable methods for the generation and screening of phage display libraries are well known in the art. Phage display is described for example in WO92/01047 and U.S. Pat. Nos. 5,969,108, 5,565,332, 5,733,743, 5,858,657, 5,871,907, 5,872,215, 5,885,793, 5,962,255, 6,140,471, 6,172,197, 6,225,447, 6,291,650, 6,492,160 and 6,521,404.

Libraries as described herein may be screened for binding members which display binding activity, for example binding to a target molecule.

Binding may be measured directly or may be measured indirectly through agonistic or antagonistic effects resulting from binding.

Binding to the target molecule may be mediated by one or more of the donor diversity scaffold domain, the recipient diversity scaffold domain and the partner domain of the binding member.

The interaction sequences of the donor and recipient diversity scaffold domains of the fusion protein may bind to the target molecule, and more preferably the same epitope of the target molecule. The fusion protein and the partner domain of a binding member may bind to the same target molecule or different target molecules. For example, the fusion protein may bind to a first target molecule and the partner domain may bind to a second target molecule.

A binding member may bind the target molecule with the same affinity of a parent donor or recipient diversity scaffold domain, or with a lower or higher affinity. In some embodiments, a binding member may neutralise a biological activity of the target molecule. In other embodiments, a binding member may activate a biological activity of the target molecule.

Suitable target molecules include biological macromolecules, such as proteins. The target molecule may be a receptor, enzyme, antigen or oligosaccharide. In some preferred embodiments, the target may be an integral membrane protein. In some embodiments, the target may be G protein coupled receptor (GPCR) or Type I receptor. Target molecules which are difficult to target with antibodies, such as ion transporters, may be particularly suitable.

In some preferred embodiments, the target molecule may be an ion transporter, such as an ion pump or ion channel.

Suitable ion channels are well known in the art and include Kir1.1, Kir2.1, Kir6.2, SUR2, Kv1.1, KCNQ1, KCNQ, KCNQ4, TRPP2, TRPA1, TRPC6, CNGA1, BK, Nav1.1, Nav1.5, Nav1.6, Nav2.1, Cav1.2, Cav2.1, glycine receptors, GABA-A, CHRNA4[82] Other suitable ion channels include voltage-gated potassium channels such as Kv1.3, L-Type voltage-gated calcium channels, Cav2.2, hERG, ASICs and Eag1.

A binding member described herein may bind to two or more different target epitopes (i.e. the binding member may be multi-specific). The target epitopes bound by the binding member may be on the same or different target molecules. For example, one or more of the donor diversity scaffold domain, recipient diversity scaffold domain and/or partner domain of a multi-specific binding member may bind to a different target epitope to the other domains.

In some embodiments, the binding member may be bi-specific i.e. it may bind to two different epitopes.

A bi-specific binding member may bind to two different target epitopes concurrently. This may be useful in bringing a first and a second epitope into close proximity for example to cross-link molecules or cells. When the target epitopes are located on different target molecules, the target molecules may be brought into close proximity by concurrent binding to the binding member. When the target molecules are located on different cells, concurrent binding of the target molecules to the binding member may bring the cells into close proximity, for example to promote or enhance the interaction of the cells. For example, a binding member which binds to a tumour specific antigen and a T cell antigen, such as CD3, may be useful in bringing T cells into proximity to tumour cells.

Concurrent binding of different target epitopes by a binding member described herein may also be useful in stabilizing a particular conformation of a target molecule or complex of target molecules.

A binding member may bind to the two different target epitopes sequentially i.e. the binding member may bind to one target epitope and then the other. This may be useful, for example in crossing the blood: brain barrier (BBB[120]) or blood: nerve barrier (BNB[121]). For example, a binding member may bind to an epitope on a BBB or BNB receptor. Suitable receptors are well-known in the art and include transferrin (TFR), insulin (IR), leptin (LEP-R), glucose (GLUT1), CD98 (LAT1) and lipoprotein (LRP-1) receptors. Once bound to the BBB or BNB receptor, the binding member may be transcytosed across the BBB or BNB, after which it may then bind independently to an epitope on a second target molecule in the brain or peripheral nervous system, for example an ion channel or protease.

In some preferred embodiment, a binding member may bind to TFR. For example, the binding member may comprise a partner domain that binds to TFR and a fusion protein that binds to a second target molecule in the brain or peripheral nervous system. The recipient scaffold in the fusion protein may be a VL domain and the partner domain may be a VH domain. Suitable VH partner domains for targeting TFR may comprise a sequence shown in Table 20 (SEQ ID NOs: 237-245) or a variant thereof.

Suitable in vitro systems for screening libraries for bi-specific binding members able to cross the BBB or BNB are well known in the art (Nakagawa, S. et al. *Neurochem. Int.* 54, 253-263 (2009); Yosef, N. et al *J. Neuropathol. Exp. Neurol.* 69, 82-97 (2010)) and described in more detail below.

In some preferred embodiments, a first domain on the binding member (e.g. one of the donor diversity scaffold domain, recipient diversity scaffold domain and partner domain) may be directed to a first cell surface target molecule. Binding to this first target molecule may sequester the binding member on the cell surface, thereby facilitating interaction of a second binding domain (e.g. another of the donor diversity scaffold domain, recipient diversity scaffold domain and partner domain) to a second target molecule by increasing the local concentration of the binding member on the cell surface. For example, A bi-specific binding member may consist of a VH partner domain which binds with high affinity to an abundant first target molecule on T cells coupled with a VL-knottin fusion which binds and blocks a second target molecule, such as an ion channel e.g. Kv1.3. A cell-specific binding domain (VH in this example) may be generated, for example, by selecting on recombinant protein representing a candidate target molecule (as described in example 6) or by selecting a library on the cell surface of a target cell to look for a partner domain (VH in this example) which enhances the binding of the second domain. Binding of the first domain to the first target molecule sequesters the binding member on the cell surface and may overcome low affinity, low density or relative inaccessibility of the second binding domain for the second target molecule. This may increase the potency of the second binding domain on cells which express the target recognised by the first binding domain. This approach may also increase the specificity of the binding member, since optimal binding/blocking require both target molecules to be on the same cell. The presence of a first binding molecule has been shown to effect a binding enhancement of a second binding molecule over several orders of magnitude based on affinity and antigen density (Rhoden et al (2016) J Biol. Chem. 291 p 11337-11347).

Target molecules for use in selection and screening may be produced using any convenient technique. For example, integral membrane proteins may be produced using bacterial, baculoviral or mammalian expression systems[86,87], proteoliposomes[88], “nanodiscs”[89] or cell lysates[90].

In some embodiments described herein, an initial “founder” library of binding members may be used to identify one or more founder binding members which allow simultaneous folding of both donor and recipient diversity scaffold domains. These founder binding members may be selected for retained donor and recipient domains which display the desired binding activity, such as binding to a target molecule. In subsequent steps, the founder binding members may be subjected to further modification and screening to optimise binding activity and other properties. Alternatively, an initial “founder” library of binding members may include any library that combines a recipient diversity scaffold domain, a donor diversity scaffold domain and, optionally a linker, as described herein, in which diversity is introduced into any of said recipient diversity scaffold domain, a donor diversity scaffold domain or linker sequence.

A method of screening as described herein may comprise;

(i) providing a founder library of binding members as described herein;

wherein one, two or all three the donor interaction sequence, the recipient interaction sequence and the linkers are diverse in said founder library, (ii) screening the library for binding members which display a binding activity, and (iii) identifying one or more binding members in the founder library which display the binding activity.

The one or more identified binding members may be recovered from the founder library.

In some preferred embodiments, the linker sequences may be diverse in the library. This may be useful in identifying functional fusions of donor and recipient diversity scaffold domains. Examples of diverse linker sequences are presented herein. In some embodiments, diverse linkers of 1, 2, 3, or 4 amino acids may be introduced at the junctions between the donor diversity scaffold domain and the recipient diversity scaffold domain to allow selection of optimal junctional sequences from the resultant libraries.

Optionally, sequences within the recipient diversity scaffold domain may also be diversified to facilitate the identification of a recipient diversity scaffold domain that supports functional fusion to a donor diversity scaffold domain. In some embodiments, one or more amino acid residues of the donor diversity scaffold domain and/or recipient diversity scaffold domain at one or both junctions between the two domains may be diversified (i.e. one or more residues of a domain directly adjacent one or both junctions with the other domain may be diversified). Examples in which framework residues of donor and recipient scaffolds are diversified are provided below. For example, 1, 2, 3, or 4 residues at the N and C terminal junctions of the donor diversity scaffold domain and/or 1, 2, 3, or 4 residues within the recipient diversity scaffold domain at the junctions with the donor domain may be diversified.

The binding activity may be binding to a target molecule. A method of screening a library may comprise;

providing a founder library of binding members as described herein, contacting the founder library with a target molecule, and selecting one or more founder library members which bind to the target molecule.

The one or more identified or selected binding members may be recovered and subjected to further selection and/or screening.

Multiple rounds of panning may be performed in order to identify binding members which display the binding activity. For example, a population of binding members enriched for the binding activity may be recovered or isolated from the founder library and subjected to one or more further rounds of screening for the binding activity to produce one or more further enriched populations. Founder binding members which display binding activity may be identified from the one or more further enriched populations and recovered, isolated and/or further investigated.

Founder binding members which display the binding activity may be further engineering to improve activity or properties or introduce new activity or properties, for example binding properties such as affinity and/or specificity, increased neutralization of the target molecule and/or modulation of a specific activity of the target molecule. Binding members may also be engineered to improve stability, solubility or expression level.

For example, the identified linker sequence of an identified founder binding member may be retained in a modified library with diverse sequences introduced into one or more of the recipient, donor or partner domains depending on the application and desired outcome. In some cases further diversification of the linker may be useful in optimising function of the binding member.

A method of screening as described herein may further comprise;

(iv) introducing diverse amino acid residues at one or more positions in the amino acid sequence of one or more binding members as described herein, for example one or more binding members identified in from a founder library, to produce a modified library of binding members, (v) screening the modified library for modified binding members which display a binding activity and (vi) identifying one or more modified binding members in the modified library which display the binding activity.

The binding activity may be binding to a target molecule. A method of screening a library may comprise;

providing a modified library of binding members as described above, contacting the modified library with a target molecule and selecting one or more modified library members which bind to the target molecule.

The one or more identified or selected binding members may be recovered and subjected to further rounds of screening.

The diverse amino acids may be introduced by any suitable technique as described elsewhere herein, including random mutagenesis or site directed mutagenesis.

One or more modified binding members may be identified which display increased or improved binding activity, for example increased binding affinity and/or specificity, relative to the one or more founder binding members identified in step (iii).

Multiple rounds of panning may be performed in order to identify modified binding members which display the improved binding activity. For example, a population of binding members enriched for the improved binding activity may be recovered or isolated from the library and subjected to one or more further rounds of screening for the binding activity to produce one or more further enriched populations. Modified binding members which display improved binding activity may be identified from the one or more further enriched populations and isolated and/or further investigated.

Founder or modified binding members may be further subjected to further mutagenesis, for example to generate further modified libraries and select binding members with improved or new activity or properties. Amino acid residues may be mutated at one or more positions in the amino acid sequence of one or more identified binding members from the library and/or modified library. For example, amino acid residues within the donor scaffold, donor interaction sequence, recipient scaffold, recipient interaction sequence, linker or partner domain of the one or more identified binding members may be mutated.

The mutation may introduce diverse amino acid residues at the one or more positions to produce a library of further modified binding members. Examples of the deletion or replacement of interaction and scaffold residues of recipient and donor and their replacement with randomised residues are shown below.

To generate binding members in which a partner domain, such as a partner VH or VL domain, contributes additional interaction contacts with a target molecule, a library may be generated in which the original partner domain is replaced by a whole repertoire of alternative partner domain to create a "chain-shuffled" library. Binding members with improved activity due to the beneficial contribution of the newly selected partner domain may be identified, recovered and isolated.

A method of screening as described herein may further comprise;

(vii) associating the fusion protein from the one or more identified binding members or modified binding members as described above, with a diverse population of partner domains to produce a shuffled library of binding members, (viii) screening the shuffled library for shuffled binding members which display a binding activity, (ix) identifying one or more shuffled binding members which display the binding activity.

One or more shuffled binding members may be identified which display increased binding activity relative to the one or more founder binding members identified in step (iii) and/or modified binding members identified in step (vi).

Multiple rounds of panning or functional screening may be performed in order to identify shuffled binding members which display the increased or improved binding activity. For example, a population of shuffled binding members enriched for the improved binding activity may be isolated from the shuffled library and subjected to one or more further rounds of screening for the binding activity to produce one or more further enriched shuffled populations. Shuffled binding members which display improved binding activity may be identified from the one or more further enriched populations and isolated and/or further investigated.

The founder library, modified library or shuffled library may be screened by determining the binding of the binding members in the library to a target molecule Binding may be determined by any suitable technique. For example, the founder library, modified library or shuffled library may be contacted with the target molecule under binding conditions for a time period sufficient for the target molecule to interact with the library and form a binding reaction complex with a least one member thereof.

Binding conditions are those conditions compatible with the known natural binding function of the target molecule. Those compatible conditions are buffer, pH and temperature conditions that maintain the biological activity of the target molecule, thereby maintaining the ability of the molecule to participate in its preselected binding interaction. Typically, those conditions include an aqueous, physiologic solution of pH and ionic strength normally associated with the target molecule of interest.

The founder library, modified library or shuffled library may be contacted with the target molecule in the form of a heterogeneous or homogeneous admixture. Thus, the members of the library can be in the solid phase with the target molecule present in the liquid phase. Alternatively, the target molecule can be in the solid phase with the members of the library present in the liquid phase. Still further, both the library members and the target molecule can be in the liquid phase.

Suitable methods for determining binding of a binding member to a target molecule are well known in the art and include ELISA, bead-based binding assays (e.g. using streptavidin-coated beads in conjunction with biotinylated target molecules, surface plasmon resonance, flow cytometry, Western blotting, immunocytochemistry, immunoprecipitation, and affinity chromatography. Alternatively, biochemical or cell-based assays, such as an HT-1080 cell migration assay or fluorescence-based or luminescence-based reporter assays may be employed.

In some embodiments, binding may be determined by detecting agonism or antagonism (including blocking activity in the case of ion channels and enzymes) resulting from the binding of a binding member to a target molecule, such as a ligand, receptor or ion channel. For example, the founder library, modified library or shuffled library may be screened by expressing the library in reporter cells and identifying one or more reporter cells with altered gene expression or phenotype. Suitable functional screening techniques for screening recombinant populations of binding members are well-known in the art[16, 78, 79, 91].

Systems suitable for the construction of libraries by cloning repertoires of genes into reporter cells have been reported[16, 78]. These systems combine expression and reporting within one cell, and typically introduce a population of antibodies selected against a pre-defined target (e.g. using phage or mammalian display).

A population of nucleic acids encoding binding members as described herein may be introduced into reporter cells to produce a library using standard techniques. Clones within the population with a binding member-directed alteration in phenotype (e.g., altered gene expression or survival) may be identified. For this phenotypic-directed selection to work there is a requirement to retain a linkage between the binding member gene present within the expressing cell (genotype) and the consequence of binding member expression (phenotype). This may be achieved for example by tethering a binding member to the cell surface, as described for antibody display or through the use of semi-solid medium to retain secreted antibodies in the vicinity of producing cells[105]. Alternatively, binding members may be retained inside the cell. Binding members retained on the cell surface or in the surrounding medium may interact with an endogenous or exogenous receptor on the cell surface causing activation of the receptor. This in turn may cause a change in expression of a reporter gene or a change in the phenotype of the cell. As an alternative the binding member may block the receptor or ligand to reduce receptor activation. The nucleic acid encoding the binding member which causes the modified cellular behaviour may then be recovered for production or further engineering.

As an alternative to this "target-directed" approach, it is possible to introduce into a cell a "naïve" binding member population which has not been pre-selected to a particular target molecule. The cellular reporting system is used to identify members of the population with altered behaviour. Since there is no prior knowledge of the target molecule, this non-targeted approach has a particular requirement for a large repertoire, since pre-enrichment of the binding member population to the target molecule is not possible.

The "functional selection" approach may be used in other applications involving libraries in eukaryotic cells, particularly higher eukaryotes such as mammalian cells. For example, a binding member may be fused to a signalling domain such that binding to target molecule causes activation of the receptor. Suitable signalling domains include cytokine receptor domains, such as thrombopoeitin (TPO) receptor, erythropoietin (EPO) receptor, gp130, IL-2 receptor and the EGF receptor. Binding member-receptor chimaeras may be used to drive target molecule dependent gene expression or phenotypic changes in primary or stable reporter cells. This capacity may be used to identify fused binding members in the library which drive a signalling response or binders which inhibit the response[123-125].

Combinations of recipients and linker sequences identified using the methods described herein may be used to present different donor diversity scaffold domains of the same class, for example a cysteine-rich protein with the same number of cysteine residues, or a different class.

The donor diversity scaffold domain may be replaced in the one or more identified binding members from the library, the modified library and/or the shuffled library with a substitute donor diversity scaffold domain.

The donor diversity scaffold domain and the substitute donor diversity scaffold domain may be from the same scaffold class. For example, the donor diversity scaffold domain and the substitute donor diversity scaffold domain may comprise the same scaffold and different interaction sequences. In some embodiments, the donor diversity scaffold domain may be a knottin which binds to a first target molecule and the substitute donor diversity scaffold domain may be a knottin which binds to a second target molecule. A recipient diversity scaffold domain which has been optimised for one knottin donor diversity scaffold domain as described herein may be useful for all knottin donor diversity scaffold domains. For example, a donor knottin domain within the recipient antibody variable domain of a founder binding member may be replaced with a different knottin donor domain, as exemplified below.

The donor diversity scaffold domain and the substitute donor diversity scaffold domain may be from the different scaffold classes. For example, the donor diversity scaffold and the substitute donor diversity scaffold may comprise a different donor scaffold and a different donor interaction sequence. For example, a donor knottin domain within the recipient antibody variable domain of a founder binding member may be replaced with an adhiron donor diversity scaffold domain, as exemplified below.

An additional amino acid sequence may be introduced into the fusion proteins or partner domains of the one or more identified binding members from the library and/or modified library. For example, the donor diversity scaffold domain, for example a knottin donor domain, may be engineered to introduce new binding specificities, for example by rational design, loop grafting and combinatorial library based approaches using in vitro display technologies.

The additional amino acid sequence may be a target binding sequence, such as a VEGF-A binding sequence[92] or a Thrombopoietin (TPO) binding sequence[54].

In some embodiments, a diverse sequence may be introduced into a binding member as described herein to generate a further library for selection of improved variants. For example, diversity may be introduced into the donor or recipient diversity scaffold domain or the partner domain. Suitable diverse sequences may be introduced by oligonucleotide-directed mutagenesis or random mutagenesis[22].

In some embodiments, binding mediated by a first domain selected from the donor diversity scaffold domain, recipient diversity scaffold domain and partner domain within a binding member may be used as a guide domain to direct selection from a library using the method described herein to identify modified or shuffled binding members in which a second domain also contributes to binding.

The second domain may interact with the same target molecule as the first guide domain or may interact with a second target molecule that is closely associated with it. For example, binding to the alpha sub-unit of an ion channel, such as a voltage gated sodium or potassium channel (e.g. a Nav or Kv channel) by a knottin donor diversity scaffold domain may be increased or extended by additional contacts from a partner VH domain or recipient VL domain binding either to the same alpha sub-unit or to an associated sub-unit, such as the beta subunit of an ion channel.

In a second round, the original guide domain may also be modified or replaced. For example, one of the donor diversity scaffold domain, recipient diversity scaffold domain or partner domain of a binding member may act as a first guide domain which binds to the target molecule. Having identified a second domain which contributes to binding the target molecule, a method may comprise modifying or replacing said first guide domain to produce a library of binding members comprising the second domain and a diverse first domain. This results in a final fusion protein which benefited from the availability of the original guide domain during its development as described herein but does not contain the original guide domain. This may be useful, for example if a final binding member is desired which does not contain the fusion of a donor diversity scaffold domain within a recipient diversity scaffold domain.

For example, if a knottin donor diversity scaffold domain within a binding member was used to isolate a partner antibody variable domain (e.g. a VH domain) in a first round of selection, then this partner antibody variable domain can in turn act as a guide in a second round to select for an alternative complementary variable domain (e.g. a VL domain). This complementary domain may be a recipient diversity scaffold domain with a fused donor diversity scaffold domain or may be a normal (i.e. unfused) antibody variable domain. In some embodiments, the antibody variable domain (e.g. VH domain) identified from the first cycle through use of an ion channel binding donor diversity scaffold domain may bind to an associated sub-unit of the ion channel, such as a beta chain which interacts with different alpha chains. This antibody variable domain could then guide the selection of complementary antibody variable domains or VL-donor diversity scaffold domain fusion proteins towards different alpha chains which associate with the same 3 chain.

In some embodiments, the first domain may bind to the target molecule with low to moderate affinity. For example, affinity may be less than a $K_D$ 100 nM. This allows the improvements in binding due to the contribution of the second domain which may bind to the same protein or a closely associated sub-unit. Alternatively the second domain may bind to a non-interacting or weakly interacting molecule on the same cell which sequesters the second domain on the target cell facilitating its interaction with target.

In some embodiments, the target molecule may be presented on the surface of a cell in a tagged or untagged form to determine binding[93]. For example, an integral membrane protein, such as an ion transporter or GPCR, may be expressed with a tag. A library of binding members comprising a partner domain which binds the tag (e.g. an antibody VH or VL domain) and a diverse population of donor diversity scaffold domains presented on a VL or VH recipient domain may be subjected to selection for improved binding to the tagged, cell surface expressed target protein. This may allow the identification of fusion proteins and donor diversity scaffold domains that bind the target protein outside the tag. These fusion proteins and donor diversity scaffold domains may be used in further rounds of screening, for example with diverse partner domains, to identify binding members that bind the untagged target protein.

Various suitable tags are known in the art, including, for example, MRGS$(H)_6$ (SEQ ID NO: 36), DYKDDDDK (SEQ ID NO: 37) (FLAG™), T7-, S-(KETAAAKFERQHMDS; SEQ ID NO: 38), poly-Arg ($R_{5-6}$), poly-His ($H_{2-10}$), poly-Cys ($C_4$) poly-Phe($F_{11}$) poly-Asp($D_{5-16}$), Strept-tag II (WSHPQFEK; SEQ ID NO: 39), c-myc (EQKLISEEDL; SEQ ID NO: 40), Influenza-HA tag (Murray, P. J. et al (1995) *Anal Biochem* 229, 170-9), Glu-Glu-Phe tag (Stammers, D. K. et al (1991) *FEBS Lett* 283, 298-302), Tag.100 (Qiagen; 12 aa tag derived from mammalian MAP kinase 2), Cruz tag 09™ (MKAEFRRQESDR; (SEQ ID NO: 41), Santa Cruz Biotechnology Inc.) and Cruz tag 22™ (MRDALDRLDRLA; (SEQ ID NO: 42), Santa Cruz Biotechnology Inc.). Known tag sequences are reviewed in Terpe (2003) Appl. Microbiol. Biotechnol. 60 523-533.

In some embodiments, a library, modified library and/or shuffled library as described herein may be subjected to selection for binding members in which the donor diversity scaffold domain and/or the recipient diversity scaffold domain adopt their native structure i.e. they are correctly folded into an active conformation.

For example, when the donor diversity scaffold domain binds to a known target molecule, the founder library, modified library and/or shuffled library as described herein may be subjected to selection for binding members bind to the target molecule. Binding members that bind to the target molecule comprise a donor diversity scaffold domain that is active and correctly folded into its native structure. This may be useful, for example, when the actual structure of the donor diversity scaffold domain is not known.

As well as affinity based selection for the correct folding of the donor diversity scaffold, selection systems such as phage display may provide additional selectivity for correct folding of the recipient since it has been shown that phage display enriches for fusions with superior structural integrity[94]. When the recipient diversity scaffold domain is an immunoglobulin or a fragment or domain thereof, the library, modified library and/or shuffled library as described herein may be subjected to selection for binding members that bind to an immunoglobulin binding molecule[95]. Binding members that bind to the immunoglobulin binding molecule comprise a recipient diversity scaffold domain that is active and correctly folded into its native structure despite the fusion of a donor domain. The stringency of the system could be improved further by subjecting the population of displayed elements (e.g. a phage display population) to more disruptive conditions e.g. increased temperature, as has been done previously[94,96].

Suitable immunoglobulin binding molecules are well known in the art and include wild type and engineered forms of protein L, protein G and protein A, as well as anti-Ig antibodies and antibody fragments. In some embodiments, the immunoglobulin binding molecule may be contained in an affinity chromatography medium. Suitable affinity chromatography media are well-known in the art and include KappaSelect™, Lambda Select™, IgSelect™, and GammaBind™ (GE Healthcare).

One or more binding members identified as described above may be further tested, for example to determine the functional effect of binding to the target molecule. A method may comprise determining the effect of the one or more binding members identified from the library, the modified library and/or the shuffled library on the activity of a target molecule.

In some embodiments, the target molecule may be an ion channel and the effect of the one or more identified binding members on ion flow through the channel may be determined Ion flux through a channel may be determined using routine electrophysiological techniques such as patch-clamping. For example, ion flux may be measured using a two electrode voltage clamp following endogenous or heterologous expression of the ion channel. In some embodiments, ion channel function may be determined using fluorescence based screens. For example, cells expressing an endogenous or heterologous ion channel, for example a voltage-gated calcium channel (Cav), may be loaded with a fluorophore, such as Fura3 or Calcium Green. Activation of the ion channel by $K^+$ induced depolarisation causes a transient increase in intracellular ion concentration which can be readily measured. Suitable systems for depolarising cell membranes and recording responses are available in the art (e.g. FlexStation™; Molecular Devices Inc USA).

Ion flux through a channel may also be determined using a fluorescent protein ion sensor. Suitable fluorescent protein ion sensors are available in the art[97].

In some embodiments, the effect of the one or more identified binding members on a panel of target molecules may be determined. For example, the effect of the one or more identified binding members on ion flow through a panel of ion channels may be determined. This may be useful for example, in determining or characterising the specificity of the binding member. Alternatively the effect of the one or more identified binding members on protease activity may be determined where the target is a protease. Alternatively the effect of the one or more identified binding members on cellular signalling may be determined where the target is a receptor.

Following identification as described above, one or more identified binding members may be recovered, isolated and/or purified from a library, modified library and/or shuffled library.

In preferred embodiments, each binding member in the library may be displayed on the surface of a particle, such as a bead, ribosome, cell or virus which comprises the nucleic acid encoding the binding member.

Following selection of binding members which display the binding activity (e.g. bind the target molecule) and are displayed on bacteriophage or other library particles or molecular complexes, nucleic acid may be taken from a bacteriophage or other particle or molecular complex displaying a selected binding member.

Particles displaying the one or more identified binding members may be isolated and/or purified from the library, the modified library and/or the shuffled library. Nucleic acid encoding the one or more identified binding members may be isolated and/or purified from the particles.

The isolated nucleic acid encoding the one or more identified binding members may be amplified, cloned and/or sequenced.

Suitable methods of nucleic acid amplification, cloning and/or sequencing are well known in the art (see for example *Protocols in Molecular Biology*, Second Edition, Ausubel et al. eds. John Wiley & Sons).

The sequence of the isolated nucleic acid may be used in subsequent production of the binding member or fusion protein.

The one or more identified binding members or encoding nucleic acid may be synthesised. For example, the one or more binding members may be generated wholly or partly by chemical synthesis. For example, binding members, or individual donor or recipient diversity scaffold domains or fusion proteins and partner domains thereof may be synthesised using liquid or solid-phase synthesis methods; in solution; or by any combination of solid-phase, liquid phase and solution chemistry, e.g. by first completing the respective peptide portion and then, if desired and appropriate, after removal of any protecting groups being present, by introduction of the residue X by reaction of the respective carbonic or sulfonic acid or a reactive derivative thereof.

Chemical synthesis of polypeptides is well-known in the art (J. M. Stewart and J. D. Young, Solid Phase Peptide Synthesis, 2nd edition, Pierce Chemical Company, Rockford, Illinois (1984); M. Bodanzsky and A. Bodanzsky, The Practice of Peptide Synthesis, Springer Verlag, New York (1984); J. H. Jones, The Chemical Synthesis of Peptides. Oxford University Press, Oxford 1991; in Applied Biosystems 430A User's Manual, ABI Inc., Foster City, California; G. A. Grant, (Ed.) Synthetic Peptides, A User's Guide. W. H. Freeman & Co., New York 1992, E. Atherton and R. C. Sheppard, Solid Phase Peptide Synthesis, A Practical Approach. IRL Press 1989 and in G. B. Fields, (Ed.)

Solid-Phase Peptide Synthesis (Methods in Enzymology Vol. 289). Academic Press, New York and London 1997).

The one or more identified binding members may be recombinantly expressed from encoding nucleic acid. For example, a nucleic acid encoding a binding member may be expressed in a host cell and the expressed polypeptide isolated and/or purified from the cell culture.

Nucleic acid sequences and constructs as described above may be comprised within an expression vector. Suitable vectors can be chosen or constructed, containing appropriate regulatory sequences, including promoter sequences, terminator fragments, polyadenylation sequences, enhancer sequences, marker genes and other sequences as appropriate. Preferably, the vector contains appropriate regulatory sequences to drive the expression of the nucleic acid in a host cell. Suitable regulatory sequences to drive the expression of heterologous nucleic acid coding sequences in expression systems are well-known in the art and include constitutive promoters, for example viral promoters such as CMV or SV40, and inducible promoters, such as Tet-on controlled promoters. A vector may also comprise sequences, such as origins of replication and selectable markers, which allow for its selection and replication and expression in bacterial hosts such as *E. coli* and/or in eukaryotic cells.

Many known techniques and protocols for expression of recombinant polypeptides in cell culture and their subsequent isolation and purification are known in the art (see for example *Protocols in Molecular Biology*, Second Edition, Ausubel et al. eds. John Wiley & Sons, 1992*; Recombinant Gene Expression Protocols* Ed R S Tuan (March 1997) Humana Press Inc).

Suitable host cells include bacteria, mammalian cells, plant cells, filamentous fungi, yeast and baculovirus systems and transgenic plants and animals. The expression of antibodies and antibody fragments in prokaryotic cells is well established in the art. A common bacterial host is *E. coli.*

Expression in eukaryotic cells in culture is also available to those skilled in the art as an option for production of a binding member. Mammalian cell lines available in the art for expression of a heterologous polypeptide include Chinese hamster ovary (CHO) cells, HeLa cells, baby hamster kidney cells, NS0 mouse melanoma cells, YB2/0 rat myeloma cells, human embryonic kidney cells (e.g. HEK293 cells), human embryonic retina cells (e.g. PerC6 cells) and many others.

One or more of the identified binding members may be re-formatted. For example, a binding member comprising an immunoglobulin recipient binding domain or immunoglobulin partner domain may be re-formatted as an scFv, Fab, scFv-Fc, Fc, IgA, IgD, IgM, IgG, or half-antibody. A method may comprise isolating nucleic acid encoding the immunoglobulin domain (e.g. a VH or VL domain) from cells of a clone, amplifying the nucleic acid encoding said domain, and inserting the amplified nucleic acid into a vector to provide a vector encoding the antibody molecule. Re-formatting from an scFv format to a Fab and an IgG format is exemplified below.

In some embodiments, the donor diversity scaffold domain from the one or more identified binding members may be isolated. A method described herein may further comprise synthesising or recombinantly expressing an isolated donor diversity scaffold domain from one or more of the identified binding members from the founder library, the modified library and/or the shuffled library.

The isolated donor diversity scaffold domain may be re-formatted. For example, the donor diversity scaffold domain may be inserted into a different recipient diversity scaffold domain in a binding member described herein or may be inserted into different binding member format, such as a N or C terminal fusion In some embodiments, the isolated donor diversity scaffold domain may be used as an independent binding molecule, free of any recipient domain or fusion partner.

A detectable or functional label or half-life extension moiety may attached to the one or more identified binding members.

A label can be any molecule that produces or can be induced to produce a signal, including but not limited to fluorescers, radiolabels, enzymes, chemiluminescers or photosensitizers. Thus, binding may be detected and/or measured by detecting fluorescence or luminescence, radioactivity, enzyme activity or light absorbance.

Suitable labels include enzymes, such as alkaline phosphatase, glucose-6-phosphate dehydrogenase ("G6PDH"), alpha-D-galactosidase, glucose oxidase, glucose amylase, carbonic anhydrase, acetylcholinesterase, lysozyme, malate dehydrogenase and peroxidase e.g. horseradish peroxidase; dyes; fluorescent labels or fluorescers, such as fluorescein and its derivatives, fluorochrome, rhodamine compounds and derivatives, GFP (GFP for "Green Fluorescent Protein"), dansyl, umbelliferone, phycoerythrin, phycocyanin, allophycocyanin, o-phthaldehyde, and fluorescamine; fluorophores such as lanthanide cryptates and chelates e.g. Europium etc (Perkin Elmer and Cis Biointernational); chemoluminescent labels or chemiluminescers, such as isoluminol, luminol and the dioxetanes; bio-luminescent labels, such as luciferase and luciferin; sensitizers; coenzymes; enzyme substrates; radiolabels including bromine77, carbon14, cobalt57, fluorine8, gallium67, gallium 68, hydrogen3 (tritium), indium111, indium 113m, iodine123m, iodine125, iodine126, iodine131, iodine133, mercury107, mercury203, phosphorous32, rhenium99m, rhenium101, rhenium105, ruthenium95, ruthenium97, ruthenium103, ruthenium105, scandium47, selenium75, sulphur35, technetium99, technetium99m, tellurium121m, tellurium122m, tellurium125m, thulium165, thulium167, thulium168 and yttrium199; particles, such as latex or carbon particles; metal sol; crystallite; liposomes; cells, etc., which may be further labelled with a dye, catalyst or other detectable group; and molecules such as biotin, digoxygenin or 5-bromodeoxyuridine; toxin moieties, such as for example a toxin moiety selected from a group of *Pseudomonas* exotoxin (PE or a cytotoxic fragment or mutant thereof), Diptheria toxin or a cytotoxic fragment or mutant thereof, a botulinum toxin A, B, C, D, E or F, ricin or a cytotoxic fragment thereof e.g. ricin A, abrin or a cytotoxic fragment thereof, saporin or a cytotoxic fragment thereof, pokeweed antiviral toxin or a cytotoxic fragment thereof and bryodin 1 or a cytotoxic fragment thereof.

Suitable enzymes and coenzymes are disclosed in Litman, et al., U.S. Pat. No. 4,275,149, and Boguslaski, et al., U.S. Pat. No. 4,318,980, Suitable fluorescers and chemiluminescers are disclosed in Litman, et al., U.S. Pat. No. 4,275,149. Labels further include chemical moieties, such as biotin that may be detected via binding to a specific cognate detectable moiety, e.g. labelled avidin or streptavidin. Detectable labels may be attached to antibodies of the invention using conventional chemistry known in the art.

Suitable half-life extension moieties include fusions to Fc domains or serum albumin, unstructured peptides such as XTEN[98] or PAS[99] polyethylene glycol (PEG), A method described herein may further comprise formulating the one or more identified binding members from the library, the modified library and/or the shuffled library or the isolated donor diversity scaffold domain with a pharmaceutically acceptable excipient.

The term "pharmaceutically acceptable" as used herein pertains to compounds, materials, compositions, and/or dosage forms which are, within the scope of sound medical judgement, suitable for use in contact with the tissues of a subject (e.g., human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation. Suitable carriers, excipients, etc. can be found in standard pharmaceutical texts, for example, Remington's Pharmaceutical Sciences, 18th edition, Mack Publishing Company, Easton, Pa., 1990.

Another aspect of the invention provides a nucleic acid encoding a fusion protein or a binding member described herein.

Nucleic acid may comprise DNA or RNA and may be wholly or partially synthetic. Reference to a nucleotide sequence as set out herein encompasses a DNA molecule with the specified sequence, and encompasses a RNA molecule with the specified sequence in which U is substituted for T, unless context requires otherwise.

Another aspect of the invention provides a vector comprising a nucleic acid described herein, as well as transcription or expression cassettes comprising the nucleic acid. Vectors may be plasmids, viral e.g. 'phage, or phagemid, as appropriate. For further details see, for example, *Molecular Cloning: a Laboratory Manual:* 3rd edition, Russell et al., 2001, Cold Spring Harbor Laboratory Press.

Another aspect of the invention provides a population of nucleic acids encoding a library of binding members described herein.

The nucleic acids encoding the library may be contained in expression vectors, such as phage or phagemid vectors.

Another aspect of the invention provides a population of particles comprising a library described herein and/or a population of nucleic acids encoding a library described herein.

The library may be displayed on the surface of the viral particles. Each binding member in the library may further comprise a phage coat protein to facilitate display. Each viral particle may comprise nucleic acid encoding the binding member displayed on the particle. Suitable viral particles include bacteriophage, for example filamentous bacteriophage such as M13 and Fd. Techniques for the production of phage display libraries are well known in the art.

Other aspects of the invention provide a host cell comprising a binding member, nucleic acid or vector as described herein, and a population of host cells comprising a library, population of nucleic acids and/or population of viral particles described herein.

Another aspect of the invention provides a pharmaceutical composition comprising a fusion protein or a binding member described herein and a pharmaceutically acceptable excipient.

The pharmaceutical composition may conveniently be presented in unit dosage form and may be prepared by any methods well-known in the art of pharmacy. Such methods include the step of bringing the binding member into association with a carrier which may constitute one or more accessory ingredients. In general, pharmaceutical compositions are prepared by uniformly and intimately bringing into association the active compound with liquid carriers or finely divided solid carriers or both, and then if necessary shaping the product.

Pharmaceutical compositions may be in the form of liquids, solutions, suspensions, emulsions, elixirs, syrups, tablets, lozenges, granules, powders, capsules, cachets, pills, ampoules, suppositories, pessaries, ointments, gels, pastes, creams, sprays, mists, foams, lotions, oils, boluses, electuaries, or aerosols.

A binding member or pharmaceutical composition comprising the binding member may be administered to a subject by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot, for example, subcutaneously or intramuscularly.

Pharmaceutical compositions suitable for oral administration (e.g., by ingestion) may be presented as discrete units such as capsules, cachets or tablets, each containing a predetermined amount of the active compound; as a powder or granules; as a solution or suspension in an aqueous or non-aqueous liquid; or as an oil-in-water liquid emulsion or a water-in-oil liquid emulsion; as a bolus; as an electuary; or as a paste.

Pharmaceutical compositions suitable for parenteral administration (e.g. by injection, including cutaneous, subcutaneous, intramuscular, intravenous and intradermal), include aqueous and non-aqueous isotonic, pyrogen-free, sterile injection solutions which may contain anti-oxidants, buffers, preservatives, stabilisers, bacteriostats, and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such formulations include Sodium Chloride Injection, Ringer's Solution, or Lactated Ringer's Injection. Typically, the concentration of the active compound in the solution is from about 1 ng/ml to about 10 μg/ml, for example, from about 10 ng/ml to about 1 μg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use.

It will be appreciated that appropriate dosages of the binding member, can vary from patient to patient. Determining the optimal dosage will generally involve the balancing of the level of diagnostic benefit against any risk or deleterious side effects of the administration. The selected dosage level will depend on a variety of factors including, but not limited to, the route of administration, the time of administration, the rate of excretion of the imaging agent, the amount of contrast required, other drugs, compounds, and/or materials used in combination, and the age, sex, weight, condition, general health, and prior medical history of the patient. The amount of imaging agent and route of administration will ultimately be at the discretion of the physician, although generally the dosage will be to achieve concentrations of the imaging agent at a site, such as a tumour, a tissue of interest or the whole body, which allow for imaging without causing substantial harmful or deleterious side-effects.

Administration in vivo can be effected in one dose, continuously or intermittently (e.g., in divided doses at appropriate intervals). Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the physician.

Binding members described herein may be used in methods of diagnosis or treatment in human or animal subjects, e.g. human. Binding members for a target molecule, such as an ion channel may be used to treat disorders associated with the target molecule.

Other aspects of the invention provide a fusion protein, binding member or composition described herein for use as a medicament; a fusion protein, binding member or composition described herein for use in the treatment of pain or autoimmune disease; and the use of a fusion protein, binding member or composition described herein in the manufacture of a medicament for the treatment of a condition associated with ion channel activity or dysfunction.

Another aspect of the invention provides a method of treatment comprising administration of a binding member or composition described herein to an individual in need thereof, optionally for the treatment of a condition associated with ion channel activity or dysfunction.

An effective amount of a binding member or composition described herein alone or in a combined therapeutic regimen with another appropriate medicament known in the art or described herein may be used to treat or reduce the severity of at least one symptom of any of a disease or disorder associated with the target molecule in a patient in need thereof, such that the severity of at least one symptom of any of the above disorders is reduced.

Other aspects and embodiments of the invention provide the aspects and embodiments described above with the term "comprising" replaced by the term "consisting of" and the aspects and embodiments described above with the term "comprising" replaced by the term "consisting essentially of".

It is to be understood that the application discloses all combinations of any of the above aspects and embodiments described above with each other, unless the context demands otherwise. Similarly, the application discloses all combinations of the preferred and/or optional features either singly or together with any of the other aspects, unless the context demands otherwise.

Modifications of the above embodiments, further embodiments and modifications thereof will be apparent to the skilled person on reading this disclosure, and as such, these are within the scope of the present invention.

The contents of all documents, websites, databases and sequence database entries mentioned in this specification, including the amino acid and nucleotide sequences disclosed therein, are incorporated herein by reference in their entirety for all purposes.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Certain aspects and embodiments of the invention will now be illustrated by way of example and with reference to the Figures described above.

EXPERIMENTS

1. Summary

The fusion of a donor diversity scaffold (e.g. a knottin) into a recipient diversity scaffold domain (e.g. an antibody VL domain) was first exemplified herein using the trypsin inhibitor; Ecballium elaterium trypsin inhibitor-II (EETI-II). In this knottin scaffold, high affinity binding to trypsin is dependent on correct folding of the knottin. The knottin gene was cloned into either CDR1 or CDR2 of an antibody light chain recipient (demonstrated for both kappa and lambda light chains). A library of variants of the recipient was created to allow selection of those recipient variants which could accommodate the incoming donor. The donor and recipient domains were in close apposition. In the example below, the incoming donor replaced a CDR loop and the ends of the incoming donor domain were fused to the flanking antibody framework residues i.e. β strand sequences of the core structure. In some examples below, framework residues were replaced by random sequences. The binding member was thus constructed in a way that limited the length of sequence joining the donor and recipient scaffold such that few or no additional residues were added. In some cases, there were fewer residues within the junction between framework residues and the donor domain compared to what would be have been generated by a direct fusion of the secondary structural elements of donor and recipient. A library of variants was created wherein the sequence of amino acid residues at the N and C terminal boundary of the incoming domain was varied while maintaining a short linker length to limit conformational flexibility. This library was designed to identify correct fusion combinations having a fixed kappa or lambda sequence preceding the knottin with diversity introduced from a natural light chain repertoire in the region that followed the knottin insertion. Thus, for knottin insertion into CDR1, the sequence from framework 2 (FW2) to the end of the VL domain was from a natural repertoire. Likewise insertion into CDR2 was followed from framework 3 to the end of the VL domain by sequences from a natural repertoire.

The population of genes encoding the fusion of the donor and recipient diversity scaffolds was cloned into a phage display vector, phage particles displaying the fusion were recovered and the population selected on immobilized trypsin using phage display technology[28,100]. In this way, selections were carried out for retained trypsin binding and therefore correct folding of the knottin donor. As well as affinity based selection for the correct folding of the donor, phage display provides additional selectivity for correct folding of the recipient since it has been shown that phage display enriches for fusions with superior structural integrity[94]. Thus, if the donor was correctly folded (and therefore capable of binding trypsin) but folding of the recipient was compromised, then display of the donor would still be compromised (possibly through degradation of the misfolded fusion). Selectivity for folding of an antibody recipient may thus be further enhanced by preselecting on protein L or protein A which have both been shown to bind to certain VL and VH domains respectively[95] with a requirement for correct folding. The stringency of the system may be improved further by subjecting the phage population to more disruptive conditions[94,96].

A panel of light chain variants which support folding and trypsin binding of EETI-II was selected. Once a scaffold has been selected for one member of a donor diversity scaffold family (knottins, in this case) it may be used for additional members of the same donor diversity scaffold family given the shared structural constraints within the donor family. Using two of the selected recipient antibody light chain scaffolds a range of other knottins which block sodium channels[71 72 70], potassium channels[25,73,74] and acid sensitive ion channels[118, 122] were used as donors within the previously selected recipient antibody domain. Some of these were shown to retain blocking activity on the target ion channel, in the case of the voltage gated potassium channel Kv1.3 and the acid sensitive ion channel 1a. Thus the selected recipient domain was shown to provide a generic scaffold which can be used for multiple, distinct donors of the same class of diversity scaffold.

The two binding scaffolds were joined by short, non-flexible linkers to limit flexibility and relative movement between the domains. Given the close proximity of the fused binding scaffolds there is an opportunity for amino acids on the surface of both donor and recipient diversity scaffolds to contribute to the paratope involved in interaction with the same epitope on a single protein. Likewise the surface of partner domains of either donor or recipient diversity scaffolds may contribute to binding of target. Alternatively, both scaffolds may contact closely apposed sites on a target protein complex. Conformational flexibility carries a thermodynamic "entropic penalty" for binding interactions. For the same reason, fixing the conformational relationship between the two fused domains is advantageous, and so it is preferable to avoid flexible linker sequences to join the two domains.

A binding member comprising a donor knottin inserted into an recipient antibody variable domain were crystallised and the protein structure determined. This confirmed the correct folding of the knottin and showed that the knottin presented within the recipient antibody variable domain had the same structure as shown previously for the free knottin. The structure also confirmed correct folding of the antibody and the close apposition of the two domains. Both domains showed the expected structure and the expectation of a relative rigid conformation between the domains is supported by the crystal structure. The fusion of a cysteine-rich donor domain to an antibody recipient domain is hereafter referred to as a KnotBody™

Example 1: Construction of Knottin-VL CDR Fusion Phage Display Libraries

The phage display vector pSANG4[28] is a phagemid-based phage display vector which allows the facile cloning of single chain Fv (scFv) formatted antibodies. In the scFv format the VH gene and the VL gene are joined by DNA encoding a flexible linker peptide. With pSANG4 scFv genes are cloned into the Nco1 and Not 1 sites to create an in-frame fusion with the M13 leader sequence which precedes the Nco1 site and the minor coat protein encoded by gene 3 which follows the Not1 site (FIG. 1A).

A pair of synthetic scFv gene encompassing a fixed VH gene (D12) which does not interact with trypsin (FIG. 2) were synthesised (from Genscript). This D12 VH gene[101] binds to the "TNF alpha converting enzyme" (TACE) and originates from the IGHV3-23 germ line gene (also known as DP47) which is frequently used in antibody responses[102].

The VH gene is coupled to a synthetic gene encoding the N terminal part of either the IGKV1 D-39 germline gene (a member of the V kappa 1 family) or the IGLV1-36 germline gene (a member of the V lambda 1 family) up to the end of FR2 segment followed by a Not 1 restriction site.

This synthetic gene encompassing a partial VL gene will allow the insertion of a knottin gene at either the CDR1 position or the CDR2 position (FIG. 1B, C). The gene introduces a Pml1 restriction site at the end of FR1 which is used to clone a repertoire of knottins flanked at their 5' and 3' ends by a Pml1 and Mfe1 site respectively (FIG. 1B). The Pml site was introduced near the end of FW1 as a result of a silent mutation in the kappa gene. A Ser to Thr mutation was introduced into the FW1 region of the lambda gene to accommodate this same restriction enzyme site. The synthetic genes also introduced a Pst1 site at the end of FW2 which is used to introduce a knottin gene into the CDR2 position using restriction sites Pst1 and BspE1 at the 5' and 3' ends of the knottin gene (FIG. 1C). In assembling a functional VL gene, the remainder of the VL domain (from FR2 in the case of a CDR1 knottin insertion and from FW3 in the case of a CDR2 insertion) was generated by PCR from a light chain repertoire[28] to complete the fusions (see example 2).

These 2 synthetic gene encoding either a kappa or lambda light chain germline gene segment were amplified using primers 2561 (GGTACCTCGCGAATGCATCTAG; SEQ ID NO: 43) and 2562 (CATGCAGGCCTCTGCAGTCG; SEQ ID NO: 44). Purified PCR products were digested with Nco1 and Not1 before ligating into pSANG4 vector[28] cut with the same restriction enzymes. Ligations were transformed into *E. coli* DH5-alpha cells (Life technologies) according to manufacturer's instructions. Plasmid DNA was prepared from the sequence confirmed transformants using Macherey Nagel Midi prep kit (according to the manufacturer's instructions). These vector were named as "pIONTAS1_KB_Kappa" and "pIONTAS1_KB_lambda" and the sequences from the the Nco1 site to the Not1 site are shown in FIGS. 2A and 2B respectively.

To demonstrate the potential of fusing a folded knottin donor with an antibody recipient, Ecballium elaterium trypsin inhibitor-II (EETI-II), a plant derived knottin with trypsin inhibitory activity was used. EETI-II has free N and C termini and trypsin binding is driven by the constrained sequence "PRIL" present in loop 1 (FIG. 3A)[103]. The high affinity for trypsin in the correctly folded state[104] offers the potential to identify donor knottins which retain trypsin binding despite being cloned into a recipient VL domain. The construction of a phage display library where variable fusion sequence have been introduced between the donor and recipient will allow selection of functional knottin-CDR-VL combinations from the libraries based on trypsin binding.

This knottin donor diversity scaffold was fused into either the CDR1 or CDR2 position of either kappa or lambda VL domains. This was done by replacing residues within the incoming knottin donor and the VL recipient with random amino acids in a way that limited the number of added amino acids between the 2 domains or even reduced them (FIG. 3B). We also introduced a repertoire of light chain fragments encompassing the segment of the VL gene following the point of insertion (example 2).

Insertion of Knottins into CDR1

A synthetic EETI-II Knottin donor gene was made and was used to replace the CDR1 positions in the light chain recipient by creating a PCR fragment with Pml1 and Mfe sites (which were introduced by PCR) and cloning into pIONTAS1_KB_Kappa and pIONTAS1_KB_lambda. Framework and CDR designations are as described by the International Immunogenetics Information System (IMGT)[29]. The PCR primers also introduced variable amino acid sequences between the restriction sties and the knottin gene. The PCR primers Pml1-5EETa and Pml1-5EETb each introduced 3 variable codons encoded by the sequence VNS (V=AC or G, N=ACG or T, S=C or G) immediately after the Pml restriction site. The "VNS" degenerate codons encode 16 amino acids (excluding cysteine, tyrosine, tryptophan, phenylalanine and stop codons) at each randomised position from 24 codon combinations.

```
Pml1-5EETa
                                              (SEQ ID NO: 45)
GTGT VNS VNS VNS TGC CCG CGT ATC CTG ATG CGT TGC

Pml1-5EETb
                                              (SEQ ID NO: 46)
GTGT gga VNS VNS VNS TGC CCG CGT ATC CTG ATG CGT

TGC
```

The 5' end of these sequences represents the site created by Pml1, a restriction enzyme recognising the sequence "CACGTG" (SEQ NO: 47) to create a blunt end. To facilitate blunt end cloning of the PCR product primers with 5' phosphorylated termini were synthesised.

The introduction of the PCR products at this point has the effect of replacing the last 3 residues of FW1 and the first residue of EETI-II (which forms part of a β sheet within the knottin) with 3 randomised residues. The net effect is the loss of an amino acid in the join between the framework and donor. Primer Pml1-5EETb encodes an additional Gly residue which restores the number of residues between them (FIG. 3B).

At the 3' end of the knottin gene the antisense primers 1-5EETMfe (encoding an Mfe1 site) was used to amplify EETI-II. The Mfe1 site used for cloning encodes the 2 and 3rd amino acids of FW2 (Asn-Trp). This primer also retained the terminal glycine found in EETI-II and introduced 2 random amino acids encoded by VNS or VNC codons followed by an Mfe1 site.

The consequence of this strategy for introducing a knottin donor gene is to remove the first amino acid of FW2 and join the 2 domains using 2 randomised amino acids (FIG. 3B) with a net addition of 1 amino acid between the donor and framework.

```
1-5EETMfe
                                              (SEQ ID NO: 48)
GTCAGTCCAATTGNBSNBCCCGCA GAAGCCGTTCGGACCGCA
```

Sequences encoding the Mfe1 site are underlined. As an example, the constructs resulting from amplification with Pml1-5EETa and 1-5EETMfe followed by cloning into either pIONTAS1_KB_lambda and pIONTAS1_KB_Kappa are shown in FIGS. 3C and 3D respectively.

Insertion of Knottins into CDR2

The knottin donor was introduced into the CDR2 positions of pIONTAS1_KB_lambda and pIONTAS1_KB_Kappa by creating a PCR fragment with Pst1 and BspE1 sites which was introduced by PCR. It was possible to introduce a Pst1 site into the first two residues of the CDR2 region of the IGKV1 D-39 V kappa gene (within the Ala-Ala sequence). For convenience in cloning the same restriction site and encoded residues were introduced at the end of framework 2 of the V lambda germline gene IGLV1-36. In the lambda germline it was also possible to introduce a BspE1 site into the 4th and 5th residues of the FW3 region encoding Ser-Gly) (FIG. 3E). Again this restriction site and encoded amino acids were also introduced into the V kappa gene (FIG. 3F).

The PCR primers PST1-5EETa was used to amplify EETI-II and introduces 2 Ala codons encompassing a Pst1 site for cloning (underlined) followed by 2 variable codons encoded by the sequence GNS (encoding Val, Ala, Asp or Gly) and VNS (encoding 16 amino acids within 24 codons) immediately after the Pst1 restriction site and preceding the knottin sequence. The VNS codon replaces the first amino acid of EETI-II with the net effect of adding 3 amino acids (2 Ala residues and one of Val, Asp, Ala or Gly) between the donor and recipient framework (FIG. 3B).

```
PST1-5EETa
                                              (SEQ ID NO: 49)
ATC TAT GCT GCA GNS VNS TGC CCG CGT ATC CTG ATG

CGT TGC
```

At the 3' end of the incoming knottin donor, The PCR primers −5EETBse was used to amplify EETI-II. This introduces a BspE1 site for cloning. The PCR product introduces the knottin donor followed by the glycine which naturally follows the last cysteine of EETI-II (FIG. 3A). This is followed by 2 randomised amino acids which adjoin to the 4th and 5th amino acids of FW3 after cloning. This has the effect of replacing the first three residues of FW3 with two randomised amino acids and retains the terminal glycine of the knottin (FIG. 3B). The net effect is the loss of an amino acid between donor and framework 3.

```
1-5EETBse
                                              (SEQ ID NO: 50)
GTCAGAGACTCCGGASNBSNBCCCGCA GAAGCCGTTCGGACCGCA
```

As an example, the constructs resulting from amplification with PST1-5EETa and 1-5EETBse followed by cloning into either pIONTAS1_KB_Kappa or pIONTAS1_KB_lambda are shown in FIGS. 3E and 3F respectively.

Example 2. Introduction of Additional Diversity into the Recipient VL Domain

In humans there are 2 different classes of antibody light chain, (kappa or lambda) which are encoded by approximately 50 and 40 germline genes respectively. These can each be arranged into families on the basis of sequence homology with 7 different kappa families (V kappa 1-Vkappa 7) and 11 different lambda families (V lambda 1-Vlambda 11). Examination of the germline sequences[29] permits the design of sense strand primers ("forward primers") specific for different germline VL gene families.

In the course of antibody maturation individual VL germline genes are recombined with approximately 5 different kappa or lambda-specific J segments at their 3' end. It is possible therefore to design a small number of forward and reverse primers to enable the amplification of re-arranged VL genes from human donors for construction of antibody phage display libraries as described for example in Schofield et al (2007)[28]. In this example we demonstrate how a similar approach can be used to amplify fragments of VL genes beginning at either FW2 or FW3 to the end of the VL gene. This allows introduction of diversity into recipient VL domains which have donor insertions in either CDR1 or CDR2. This approach therefore allows the introduction of additional diversity into a recipient domain downstream of the inserted donor.

Amplification of VL Repertoires Beginning at Framework 2.

Sequences of the families of V kappa and V lambda germline genes were aligned (data from IMGT[29]) and PCR primers were designed to allow amplification of VL repertoires from the beginning at Framework 2. Lambda-specific primers ("Mfelam") capable of amplifying from the FW2 region of V lambda 1, 2 and 3 were designed. These primers were also designed to introduce an Mfe1 site (underlined) which is compatible and in frame with the Mfe1 site introduced at the end of the knottin gene described above. In a similar way, kappa-specific primers ("Mfekap") capable of amplifying from the FW2 region of V kappa 1, 2 and 3, were designed.

```
Mfelam 1
                                    (SEQ ID NO: 51)
GTGTGGAGGTGGC AAT TGG TAC CAG CAG CTC CCA GG

Mfelam 2
                                    (SEQ ID NO: 52)
GTGTGGAGGTGGC AAT TGG TAC CAA CAG CAC CCA GG

Mfelam 3
                                    (SEQ ID NO: 53)
GTGTGGAGGTGGC AAT TGG TAC CAG CAG AAG CCA GG

Mfekap 1
                                    (SEQ ID NO: 54)
GTGTGGAGGTGGC AAT TGG TAT CAG CAG AAA CCA GG

Mfekap 2
                                    (SEQ ID NO: 55)
GTGTGGAGGTGGC AAT TGG TAC CTG CAG AAG CCA GG

Mfekap 3
                                    (SEQ ID NO: 56)
GTGTGGAGGTGGC AAT TGG TAC CAG CAG AAA CCT GG
```

These sense strand forward primers were used to amplify a repertoire of VL genes from a library which had previously been pre-cloned into the Nhe1/Not1 site of a phage display vector (as shown in FIG. 1). The introduced Mfe1 site is underlined and the sequence of Mfelam1 and Mfekap1 are represented at the beginning of FW2 in FIGS. 3E and 3F respectively. For kappa light chains a single reverse primer (JKFOR_Thr2) was designed which straddled the original cloning junction encompassing Not1 including homology to the phagemid vector as well as the beginning of the cloned J kappa segment. For lambda light chains, a single primer (JLFORQP2) was designed which hybridised within the phagemid plasmid sequence, across the Not1 cloning site and into the beginning of J lambda segment.

```
JLFORQP2
                                    (SEQ ID NO: 57)
TGAGATGAGTTTTTGTTCTGCGGCCGCGGGCTGACCTAG

JKFOR_Thr2
                                    (SEQ ID NO: 58)
TGAGATGAGTTTTTGTTCTGCGGCCGCGGTACGTTTGAT
```

Amplification with the paired kappa or lambda forward and reverse primers generated a PCR product encoding:

```
                                    (SEQ ID NO: 59)
Mfe1-FW2-CDR2-FW3-CDR3-FW4-Not1.
```

The primers introduce an Mfe1 site at the 5 end and a Not 1 site at the 3' end, compatible and in frame with the knottin PCR products described above and the phagemid display vector shown in FIG. 1. This will allow the amplification of libraries of VL genes which can be fused to constructs encoding a knottin insertions at CDR1 by using restriction enzymes Mfe1 and Not 1. This introduces additional CDR2 and CDR3 diversity into the recipient VL domain. JLFORQP2 and JKFOR_Thr2 are anti-sense reverse primers and the reverse complementary encoding sense strand is represented in FIGS. 3C, 3D, 3E and 3F respectively as the FW4-Not1 region in the final construct.

Amplification of VL Repertoires Beginning at Framework 3

By a similar approach, sense strand forward primers were designed which hybridised with the beginning of FW3 of lambda VL genes ("Bsplam" primers) or kappa ("BspKap" primers) while introducing a BspE1 restriction site compatible with the BspE1 site introduced into the knottin constructs described above. The introduced BspE1 site is underlined and the sequence of Bsplam1a and BspKap1a are represented at the beginning of FW3 in FIGS. 3E and 3F respectively.

```
Bsplam1a
                                    (SEQ ID NO: 60)
ATCTATGCTGCAGGAGGTGGC TCC GGA GTC TCT GAC CGA TTC
TCT GG

Bsplam1e
                                    (SEQ ID NO: 61)
ATCTATGCTGCAGGAGGTGGC TCC GGA GTC cCT GAC CGA TTC
TCT GG

Bsplam2
                                    (SEQ ID NO: 62)
ATCTATGCTGCAGGAGGTGGC TCC GGA TCC AAG TCT GGC AAC
ACG GG

Bsplam3
                                    (SEQ ID NO: 63)
ATCTATGCTGCAGGAGGTGGC TCC GGA ATC CCT GAG CGA TTC
TCT GG

BspKap1a
                                    (SEQ ID NO: 64)
ATCTATGCTGCAGGAGGTGGC TCC GGA GTC CCA TCA AGG TTC
AGT GG

BspKap1b
                                    (SEQ ID NO: 65)
ATCTATGCTGCAGGAGGTGGC TCC GGA GTC CCA TCA AGG TTC
AGC GG

BspKap2
                                    (SEQ ID NO: 66)
ATCTATGCTGCAGGAGGTGGC TCC GGA GTC CCA GAC AGG TTC
AGT GG

BspKap3
                                    (SEQ ID NO: 67)
ATCTATGCTGCAGGAGGTGGC TCC GGA ATC CCA GcC AGG TTC
AGT GG
```

When lambda-specific forward primers were used with the lambda-specific reverse primer (JLFORQP2) or when kappa-specific forward primers were used with the kappa-specific reverse primers ((JKFOR_Thr2) then a PCR product encoding the sequence below was produced.

BspE1-FW3-CDR3-FW4-Not1

This allowed the amplification of libraries of VL genes which can be fused to constructs with a knottin gene insertions at CDR2 by using restriction enzymes BspE1 and Not 1. This introduced additional CDR3 diversity into the recipient VL domain.

Using standard molecular biology techniques, constructs (as depicted in FIG. 3) were created using gene fragments created as described above. These were cloned into pIONTAS1_KB_Kappa" and "pIONTAS1_KB_lambda and were electroporated into *E. coli* TG1 cells and KnotBody library sizes of 3.5-6.6×$10^8$ were constructed using standard molecular biology techniques e.g. Schofield et al 2007[28].

Example 3: Isolation and Characterisation of Functional Knottin-Antibody Fusion Clones from the KnotBody Libraries Using Phage Display Technology Phage display technology facilitates isolation of binders to any given target from large combinatorial repertoires based on proteins and peptides that can be presented on the surface of filamentous phage[105]. In order to isolate functional knottin-antibody fusions from the KnotBody libraries multiple rounds of phage display selections on trypsin (cognate antigen for the EETI-II donor) were carried out. Phage particles were prepared by rescuing KnotBody libraries using trypsin cleavable helper phage[102,106] Two rounds of phage display selections were performed on 10 μg/ml biotinylated trypsin immobilised on Streptavidin (for Round-1) or Neutravidin (for round-2) coated Maxisorp™ immunotubes (Thermo Scientific, Cat No. 444202). In both rounds of selection, phage libraries were pre-incubated with streptavidin coated paramagnetic beads (Thermo Fisher Scientific, Cat. No. 11205D). These beads were removed prior to the addition the phage to the antigen tubes to limit the streptavidin binders entering the selection. Polyclonal phage preparations from round-2 selection outputs were analysed for trypsin binding using a time resolved fluorescence (TRF) binding assay. In this assay, polyclonal phage binding to biotinylated trypsin immobilised on neutravidin (Thermo Fisher Scientific, Cat. No 31000) coated Maxisorp™ plates (Thermo Scientific, Cat. No. 437111) was detected using a mouse anti-M13 antibody (GE Healthcare, Cat. No. 27-9420-01) followed by europium conjugated anti-mouse antibody (Perkin Elmer, Cat. No. AD0124).

Figure 4:
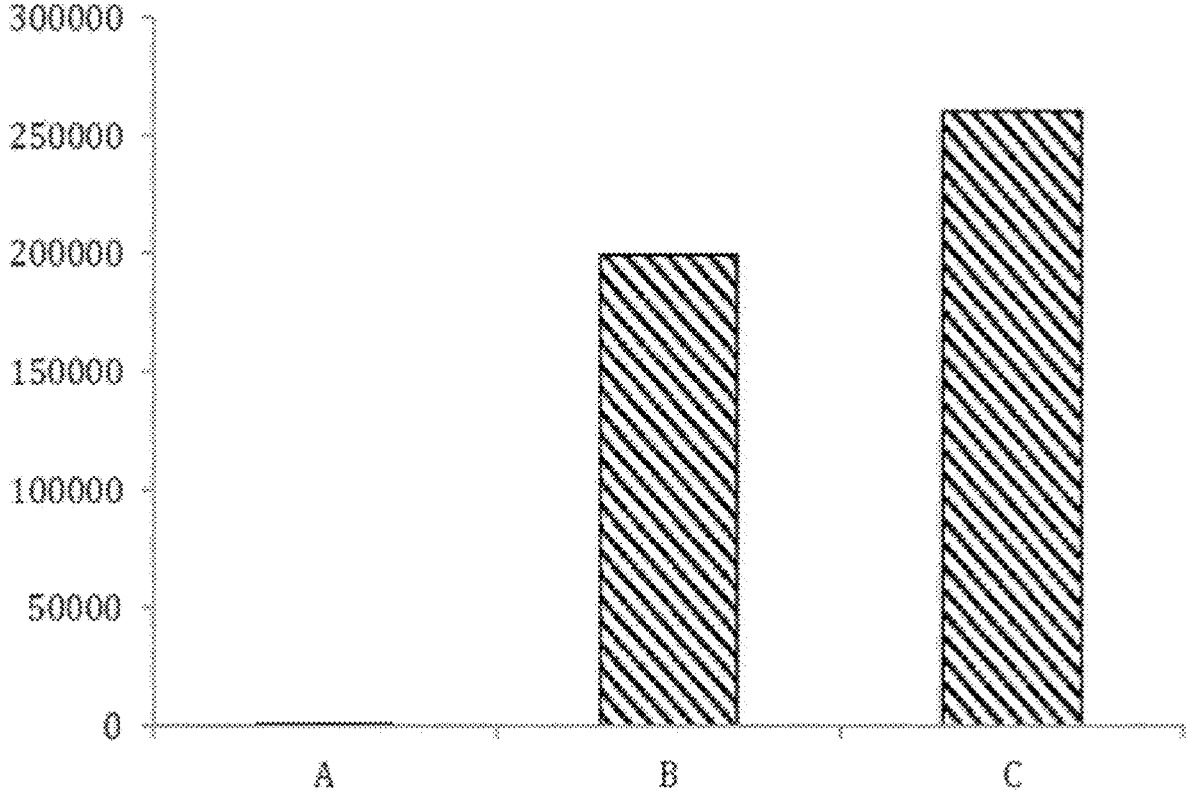
FIG. 4 shows an analysis of polyclonal phage from round-2 selection output. The polyclonal phage (X-axis) from round 2 panning of EETI-II CDR1 library (B) and EETI-II CDR2 library (C) were tested for binding to trypsin. Trypsin binding was not achieved when EETI-II directly fused to the N-terminus of gene-III (A). The Y-axis shows trypsin binding in fluorescent units (FU).

Polyclonal phage from both EETI-II libraries showed good binding to trypsin in this assay, demonstrating the success of phage display selection in enriching KnotBodies that bind to trypsin (FIG. 4). To investigate whether presentation of EETI-II by standard phage display approach would work the EETI-II gene was cloned into a phagemid display vector[28] where it was directly fused to the N-terminus of gene III. Surprisingly EETI-II presented on phage, as a direct N-terminus gene-III fusion showed no detectable binding to trypsin while selected polyclonal phage from both EETI-II CDR fusion libraries showed trypsin binding. Importantly this result demonstrates that indirect presentation of knottins on phage via antibody CDR loops (which is fused to gene-III) could be a superior alternative to direct knottin-gene III fusion.

Figure 5A:
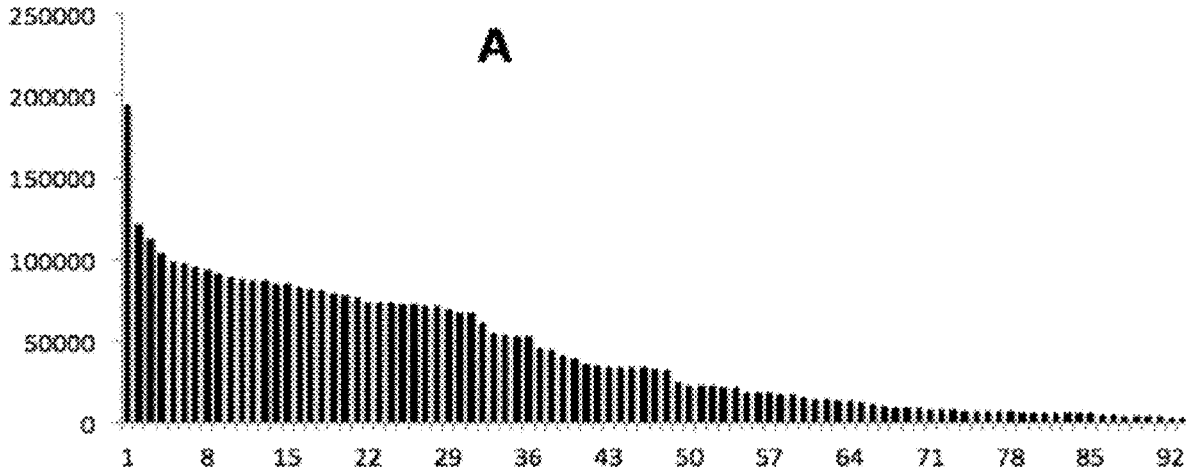
FIG. 5 shows a monoclonal binding assay of KnotBody clones from round-2 selection output. 94 individual clones from EETI-II CDR1 (A) and EETI-II CDR2 (B) library selection output (round-2) were picked into 96 well culture plates and phage were prepared from each clone. The phage supernatant from each clone was tested for binding to biotinylated trypsin immobilised on neutravidin coated Maxisorp™ plates. Phage binding to trypsin was detected using a mouse anti-M13 antibody followed by europium conjugated anti-mouse antibody. The X-axis shows the clone number and the Y-axis shows trypsin binding in fluorescent units (FU).
Figure 5B:
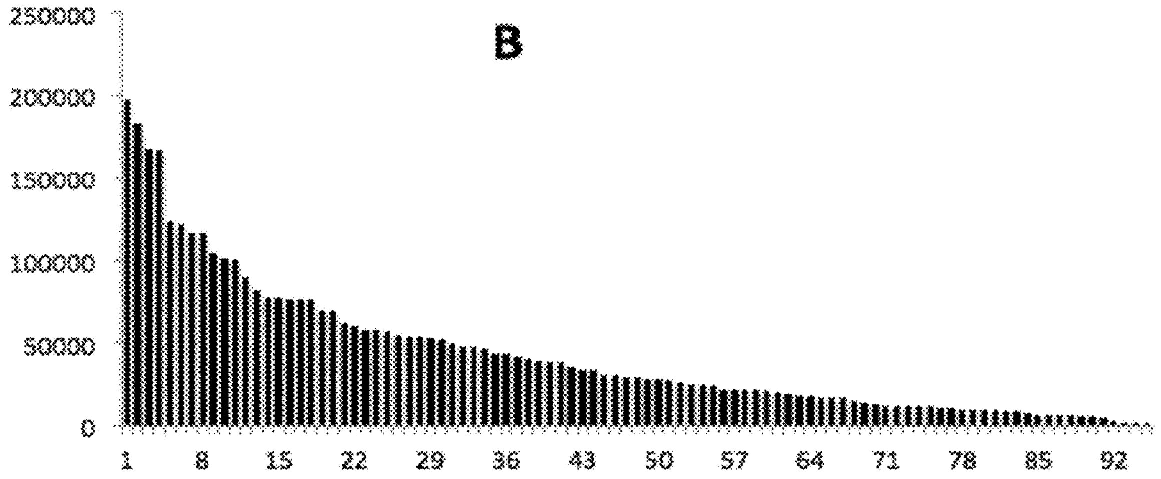

In order to identify monoclonal KnotBodies with desired binding characteristics, 94 individual clones derived from 2 rounds of selection using EETI-II CDR1 or CDR2 libraries were picked into 96 well culture plates and phage were prepared from each clone. Methods for screening by monoclonal phage ELISA are known in the art[107]. The phage supernatant from each clone was tested for binding to biotinylated trypsin immobilised on neutravidin coated Maxisorp™ plates using a TRF assay (as described above). A representative example of the monoclonal binding assay is shown in FIG. 5. Clones with >3× binding signal above background were picked as positive clones and sequenced to identify unique clones. 14 and 42 unique binders were identified from EETI-II CDR1 and EETI-II CDR2 libraries respectively (Table 1). 18 binders from the EETI-II CDR2 library and 3 binders from the EETI-II-CDR1 library were chosen for further characterisation based on their VL and linker sequence diversity. These binders were assigned new clone identification numbers (Table 2).

Figure 6:
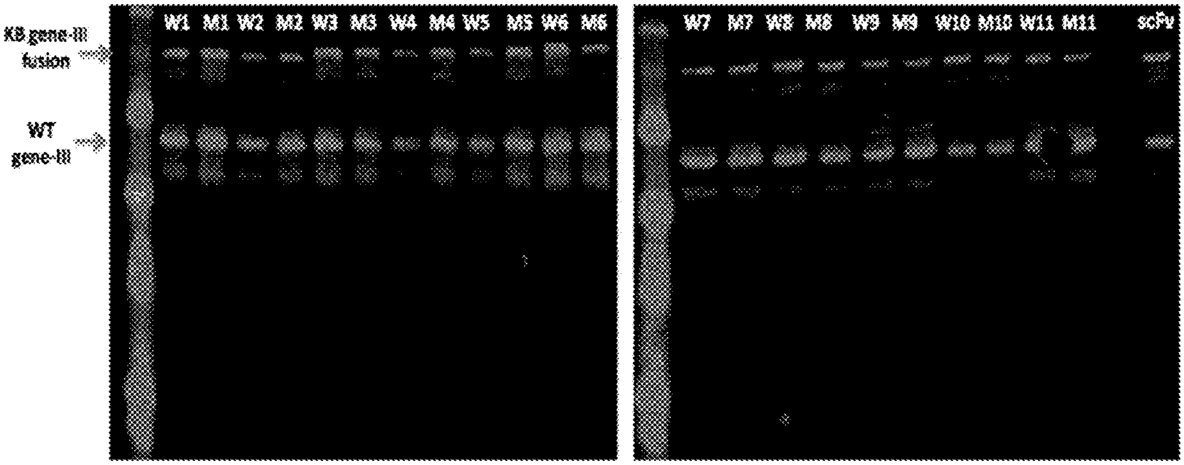
FIG. 6 shows western blot analysis of KnotBody clones and their GlyAla mutants. Phage prepared from 11 (randomly chosen) KnotBodies (referred to as W1-W11) and their GlyAla mutants (referred to as M1-M11) were analysed on a western blot using mouse anti-pIII antibody. Wild type (WT) gene III and KnotBody (KB)-gene III fusion were visualised by an anti-mouse IRDye® 680 (LI-COR, Cat. No. 926-32220) secondary antibody.

The trypsin binding capability of EETI-II is attributed to proline (Pro3) and arginine (Arg4) residues present in its loop1 (GCPRILMRC; SEQ ID NO: 68). In order to show that the selected KnotBodies bind to trypsin via a fully folded EETI-II displayed as a VL CDR fusion (ie not via other CDR loops or C or N-terminal fusion sequences), trypsin-binding residues (Pro3 and Arg4) of EETI-II were substituted for glycine (Gly) and alanine (Ala) respectively. Monoclonal phage was prepared from the 21 selected clones and their mutant equivalents. The phage supernatant from each clone was tested for binding to biotinylated trypsin (immobilised on streptavidin coated Maxisorp™ plates) using a TRF binding assay (as described above). Replacement of the trypsin-binding residues of EETI-II abolished the ability of all KnotBody clones to bind to trypsin (Table 3). In order to confirm that the loss of trypsin binding was not due to reduced expression or display of pIII fusion phage was prepared from 11 (randomly chosen) KnotBodies and their GlyAla variants were analysed on a western blot using an antibody which recognises the product of gene 3 (pIII) using an anti-pIII antibody (MoBiTec GmbH) (FIG. 6). No significant difference in the amount of pIII fusion displayed was observed between any KnotBody clone and its GlyAla substituted variant. These data confirm that the trypsin binding functionality of these Knotody clones is resultant of correct display of the knottin donor (EETI-II) as VL CDR fusion and confirms that trypsin binding is directed by the EETI-II knottin donor.

Example 4. Crystal Structure of KnotBodies Selected from EETI-II CDR2 Library

Figure 7:
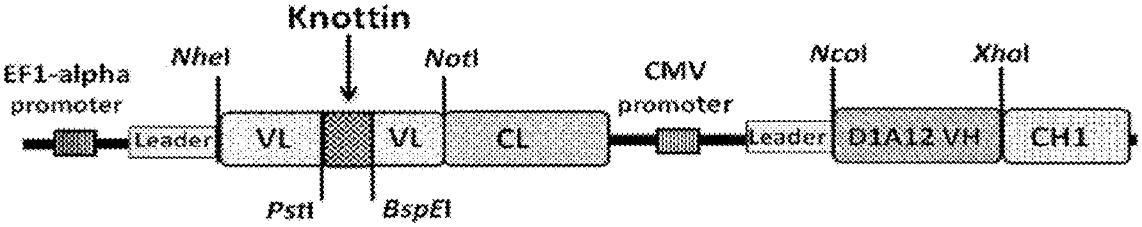
FIG. 7 shows KnotBody Fab expression cassette in pINT12 vector system. In this plasmid, transcription of light chain cassette encoding the EETI-II VL fusion and CL domain is under the control of EF1-alpha promoter. Transcription of the heavy chain cassette encoding D1A12 VH fused to IgG1 constant domain 1(CH1) is controlled by the CMV promoter.

In order to generate crystal structures of KnotBodies, 18 clones isolated from the EETI-II CDR2 library (Table 3) were reformatted as Fabs. In this format the VH (from D1A12) gene is fused to a human IgG1 heavy chain constant domain 1(CH1) and the recipient VL chains containing the EETI-II are fused to a light chain constant domain (CL). Methods for expressing antibodies by transient expression in mammalian cells are well known to those skilled in the art[108]. In order to enable the expression of these KnotBody Fabs in mammalian cells, VL chains encoding the knottin were PCR amplified using primers LLINK2 (CTCTGGCGGTGGCGCTAGC; SEQ ID NO: 69) and NotMycSeq (GGCCCCATTCAGATCCTCTTCTGAGATGAG; SEQ ID NO: 70). Amplified VL genes were digested with restriction enzymes NheI and NotI and ligated into the pINT12 vector (encoding D1A12 heavy chain) pre-digested with the same enzymes. The pINT12 vector (FIG. 7) has a dual promoter expression cassette in which the heavy chain expression is controlled by the cytomegalovirus (CMV) promoter and the light chain expression is driven by elongation factor-1 alpha (EF1-alpha) promoter.

Figure 8A:
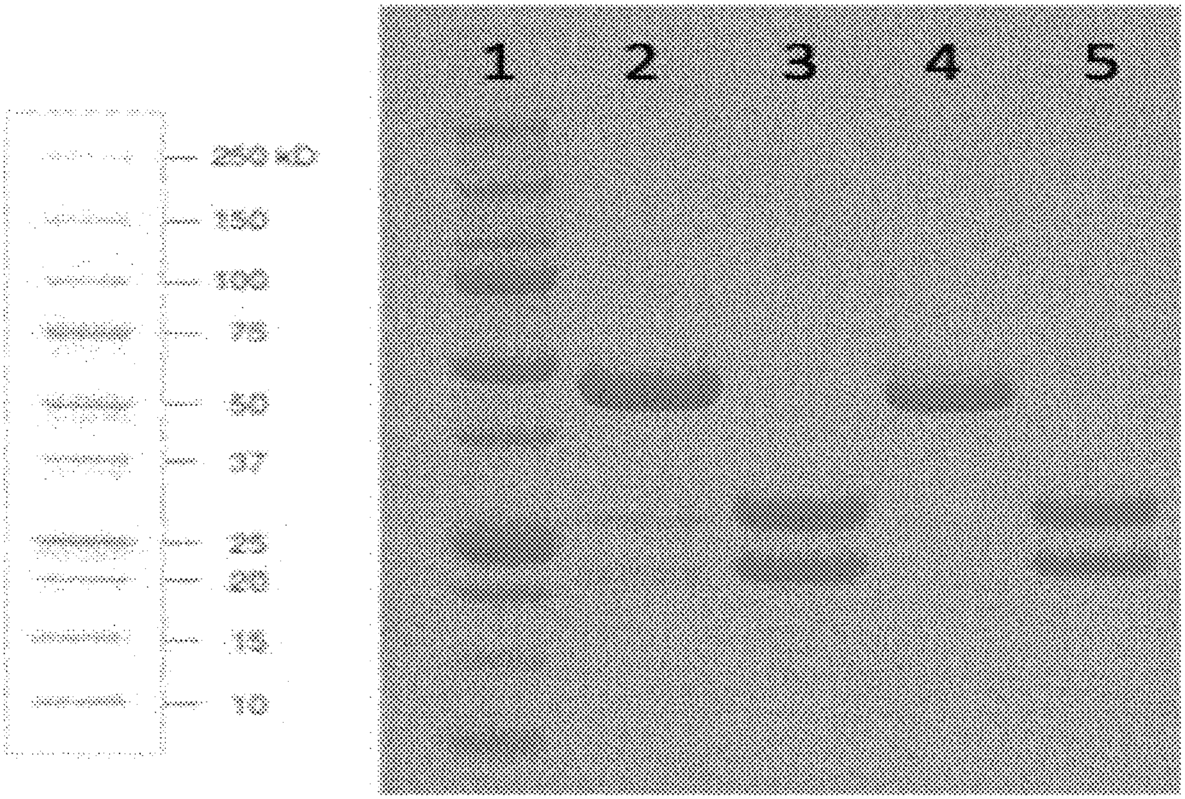
FIG. 8A shows SDS-PAGE analysis of IgG1 KnotBodies expressed in HEK-293F cells (representative example). KnotBody Fabs purified using CaptureSelect affinity matrix were visualised on a SDS-PAGE gel using Coomassie staining. A major band of approximately 50 kD observed for samples prepared under non-reducing conditions correspond to the complete KnotBody Fab molecule (Lane 2 and 4). The upper band (approximately 27 kD) and the lower band (approximately 23 kD) observed for samples prepared under reducing conditions (Lane 3 and 5) correspond to VH-CH1 fusion and Knottin-VL-CL fusion respectively. Lane 1 is a loaded with Biorad protein ladder (Biorad, 161-0373).
Figure 8B:
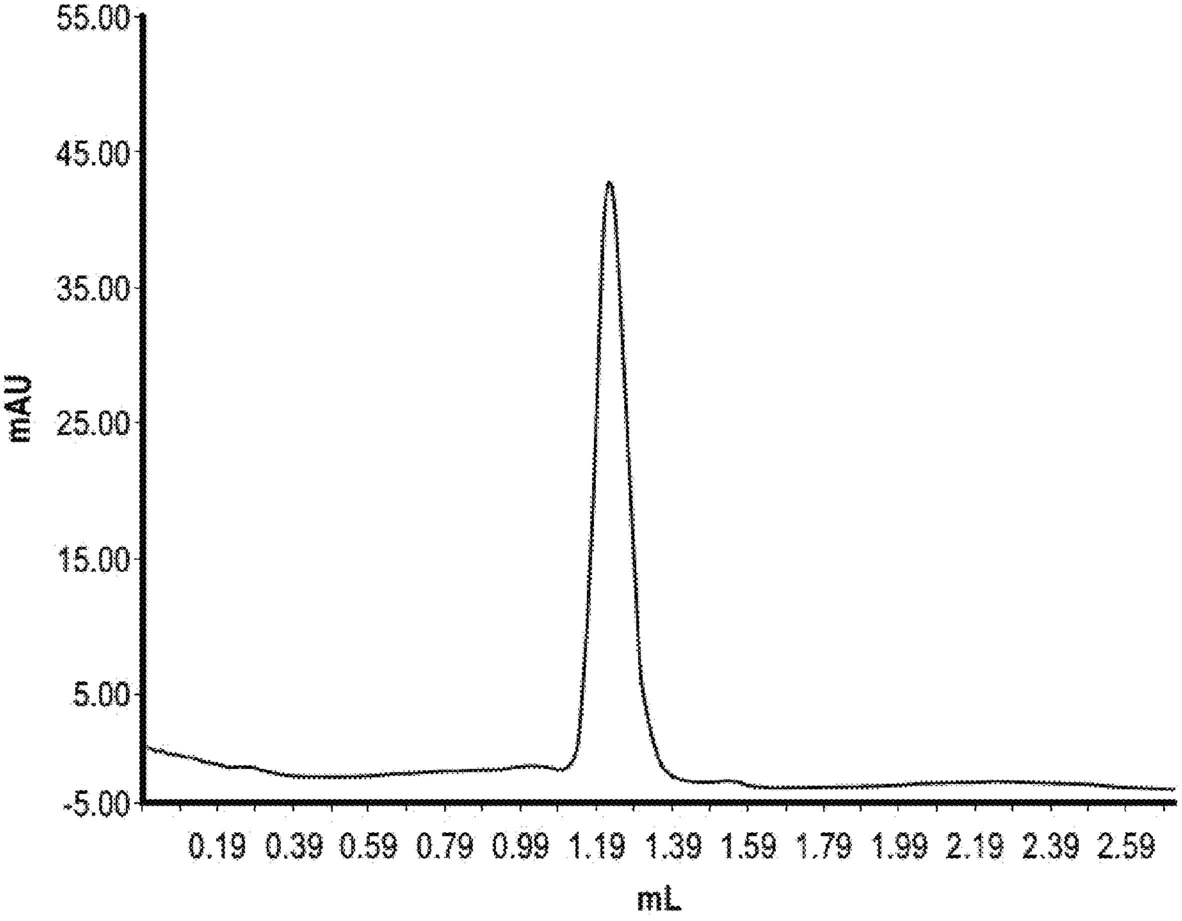
FIG. 8B shows the chromatographic profile of a KnotBody analysed by size exclusion chromatography using over a Superdex200 PC3.2/30 column (GE Healthcare).

In order to express the KnotBody Fabs in HEK-293F cells, transfection quality DNA was prepared using Plasmid Plus Kit (Qiagen, Cat. No 12945). 24 μg of plasmid DNA was incubated with 48 μg of polyethylenimine (PEI) in 2 mls of Freestyle 293 expression medium (Thermo Fisher Scientific, Cat. No. 12338-018) for 15 minutes. After the incubation, DNA:PEI mix was added to 20 mls of HEK-293F cells (Thermo Fisher Scientific, Cat. No. R790-07) seeded at a density of $1\times10^6$ cells/ml in 125 ml tissue culture flasks. Culture flasks were incubated at 37° C. for 5 days (with 5% $CO_2$, 75% humidity and shaking at 800 rpm). All transfection except KB_A03 successfully expressed KnotBody Fabs. Expressed proteins were purified from the cell culture supernatants using CaptureSelect IgG-CH1 affinity matrix (Life Technologies, Cat. No. 194320005) according to manufacturer's instructions. Purified proteins were dialysed against 2×PBS overnight and dialysed samples were visualised on a SDS-PAGE gel using Quick Coomassie staining (Generon, product reference, GEN-QC-STAIN). A representative example is shown in FIG. 8A. The monomeric state of the purified KnotBody Fabs was confirmed by analytical size exclusion chromatography using a Superdex200 2.4 mL column (GE HealthCare, 17-1089-01) and Akta Purifier system (GE Healthcare). All KnotBody Fabs showed chromatographic profiles corresponding to monomeric Fab species (FIG. 8B).

In order to confirm the trypsin binding ability of KnotBodies in Fab format, purified proteins were tested for binding to trypsin using a TRF binding assay. In this assay binding of KnotBody Fabs (at 10 μg/ml, 2.4 μg/ml and 0.5 μg/ml) to biotinylated trypsin (immobilised on streptavidin coated Maxisorp™ plates) was detected using a mouse anti-CH1 antibody followed by a europium conjugated anti-mouse antibody (Table 4). 7 KnotBodies (KB_A04, KB_A01, KB_A05, KB_A07, KB_A08, KB_A10, KB_A12) were chosen for crystallisation. DNA prepared for these clones were transfected into 500 ml HEK-293F cells as described before. Expressed proteins were purified using CaptureSelect IgG-CH1 affinity matrix. Purified proteins were initially subjected to crystallisation trials using commercially available crystallisation screens (Supplier). Well-defined crystals were readily obtained for KB_A12 and KB_A05. Crystallisation conditions for these two clones were further optimised and the following condition was used to generate diffraction quality crystals: 0.1 M MES pH=6.5, 25% w/v PEG MME 2000 and 0.1M Tris.Cl, 50% PEG MME, 10 mM NiCl2. Complete diffraction data was collected on these crystals at 100K under liquid nitrogen stream. Collected data was processed using PROTEUM2 software (Bruker). The crystal structure of the knottin-fused Fab antibodies was resolved using molecular replacement technique[109] using Phenix software v 1.8.1-1168[110]. Resulting structure was further refined using Phenix.Refine[111]. The templates for molecular replacement were downloaded from PDB website (www.rcsb.org/pdb, PDB codes: 3G04 for light chain and 3QOS for heavy chain). KnotBody KB_A12 and KB_A05 sequences are given below. An additional AlaSer sequence is introduced at the N terminus of the light chain from the Nhe1 site used in cloning.

```
KB_A12_Heavy chain
                                        (SEQ ID NO: 71)
EVQLVESGGGLVRPGGSLRLSCAASGFTFSSYAMSWVRQAPGKGLEWVSA

ISGSGGSTYYADSVKGRFTISRDNTKNSLYLQMTSLRADDTAFYYCVDFG
```

-continued

```
PGYGTGWFDYWGPGTLVTVSSASTKGPSVFPLAPSSKSTSGGTAALGCLV

KDYFPEPVTVSWNSGALTSGVHTFPAVLQSSGLYSLSSVVTVPSSSLGTQ

TYICNVNHKPSNTKVDKKVEPKSC

KB_A12_Light chain
                                        (SEQ ID NO: 72)
QSVLTQPPSVSEAPRQRVTITCSGSSSNIGNNAVNWYQQLPGKAPKLLIY

AAGRCPRILMRCKQDSDCLAGCVCGPNGFCGANSGVSDRFSAAKSGTSAS

LAINGLRSEDEADYYCAAWDDSLNGYVFGTGTKLTVLGQPAAAPSVTLFP

PSSEELQANKATLVCLISDFYPGAVTVAWKADSSPVKAGVETTTPSKQSN

NKYAASSYLSLTPEQWKSHKSYSCQVTHEGSTVEKTVAPTECS

KB_A05 Heavy chain
                                        (SEQ ID NO: 73)
Evqlvesggglvrpggslrlscaasgftfssyamswvrqapgkglewvsa

isgsggstyyadsvkgrftisrdntknslylqmtslraddtafyycvdfg

pgygtgwfdywgpgtlvtvssastkgpsvfplapsskstsggtaalgclv

kdyfpepvtvswnsgaltsgvhtfpavlqssglyslssvvtvpssslgtq

tyicnvnhkpsntkvdkkvepksc

KB_A05 Light chain
                                        (SEQ ID NO: 74)
QSVLTQPPSVSEAPRQRVTITCSGSSSNIGNNAVNWYQQLPGKAPKLLIY

AADKCPRILMRCKQDSDCLAGCVCGPNGFCGGGSGIPERFSGSKSGTSAS

LAISGLRSEDEADYYCATWDDNLNGVVFGGGTKLTVLGQPAAAPSVTLFP

PSSEELQANKATLVCLISDFYPGAVTVAWKADSSPVKAGVETTTPSKQSN

NKYAASSYLSLTPEQWKSHKSYSCQVTHEGSTVEKTVAPTECS
```

Figure 9A:
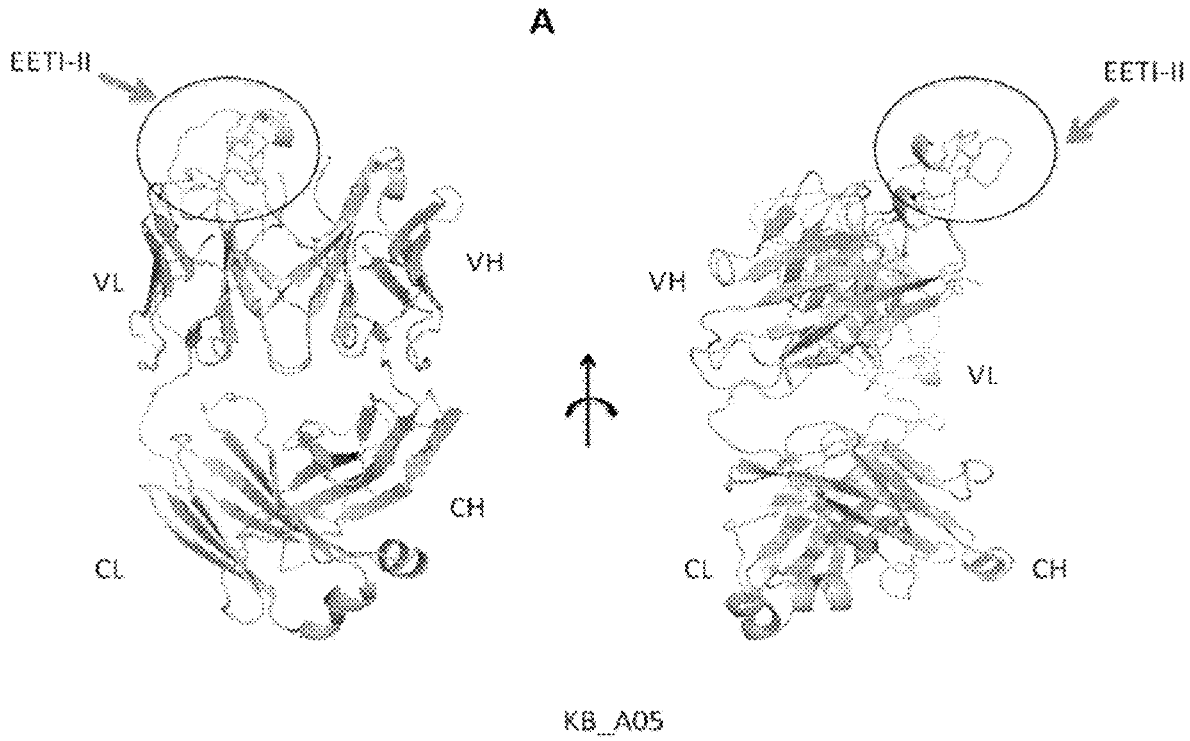
FIG. 9 shows the structure of EETI-Antibody VL CDR2 fusion. Crystal structure of KB_A05 (A) at 1.9 Å and crystal structure of KB_A12 (B) at 2.5 Å.
Figure 9B:
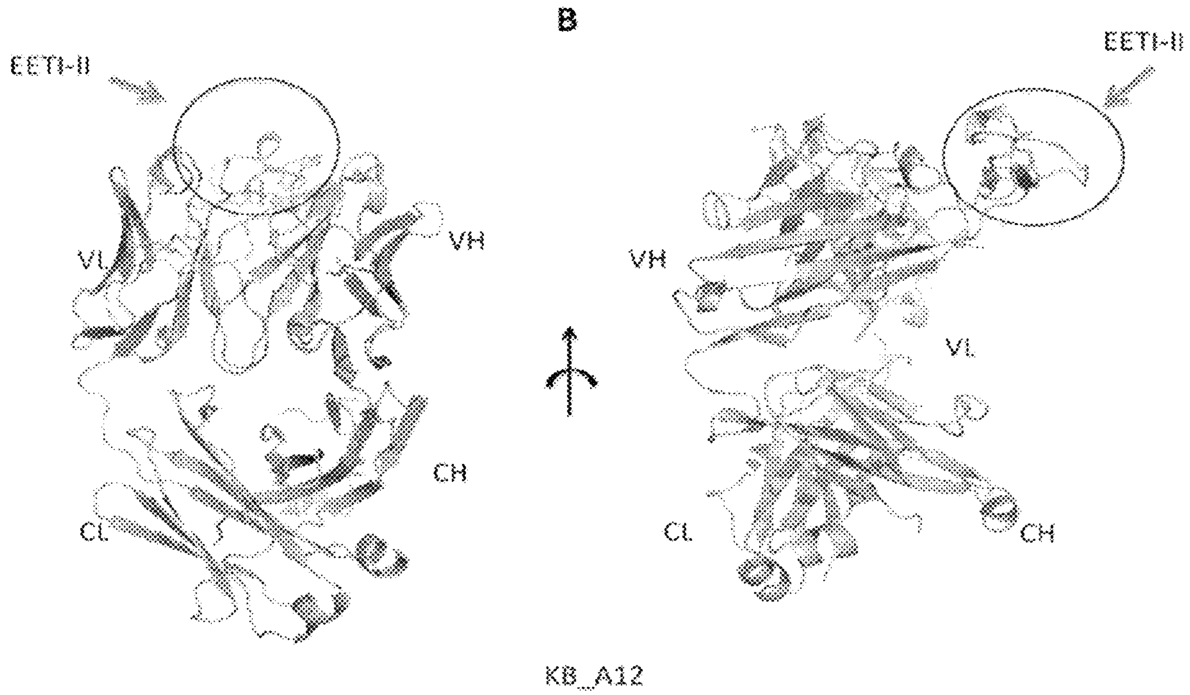
Figure 10A:
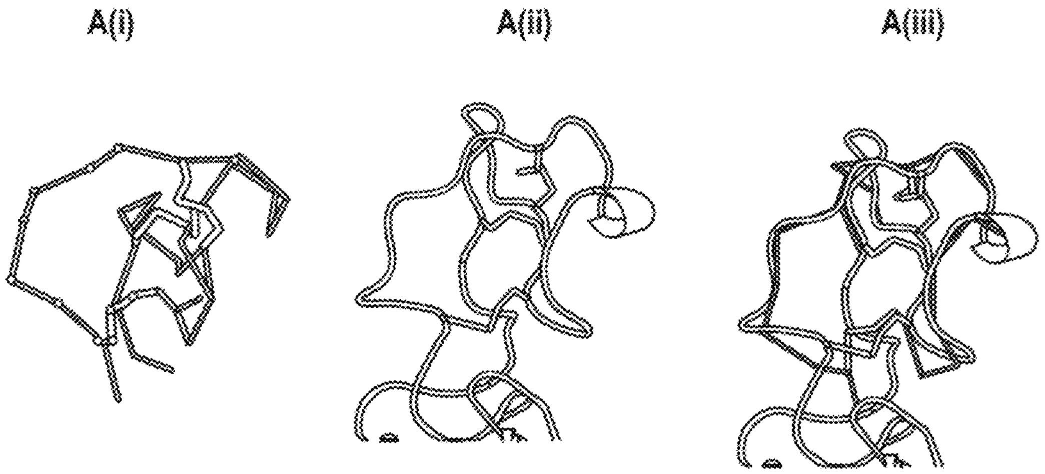
FIG. 10A (i) shows previously published structure of EETI-II shown in ribbon mode (PDB code 1H9I).
Figure 10B:
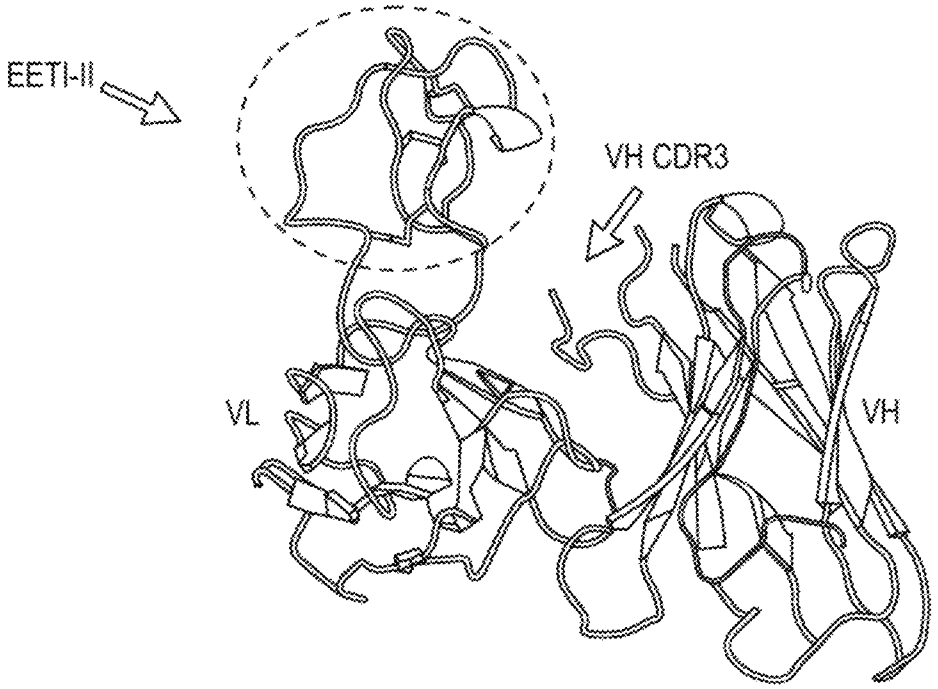
FIG. 10B shows VH and VL (fused to EETI-II) of Fab KB_A05. VH CDR residues are highlighted in black and VH CDR3 is annotated.

For both the data sets, molecular replacement solutions were successful indicating that the overall fold of the knottin-fused Fab did not change. Upon fine refinement (FIG. 9), it was evident that the knottin-fused Fab antibody was correctly folded and the disulphide pattern of the knottin part within the antibody was exactly same as that of EETI-11 (FIG. 10A), which has been reported earlier (PDB ID: 1H9I). In addition the relative arrangement of the EETI-11 part from the Fab indicates that the CDR regions of the heavy chain are accessible for potential binding to other antigen. Lack of electron density for VH CDR3 residues (FIG. 10B) further strengthens this possibility.

Example 5: Demonstration of Bi-Specific Binding Capability of the KnotBody Format The concept of bi-specific antibodies that can bind to two different target antigens is increasingly popular in drug development[112]. Conventional bi-specific antibodies are typically composed of two VH-VL pairs with different specificities (i.e. two distinct VH-VL domain pairs that each recognise a different antigen). In this example, we describe the development of a bi-specific KnotBody format. In this format, the binding determinants required for recognition of two distinct antigens are incorporated within a single VH-VL pair. This was achieved by using the VH to mediate one binding specificity and the knottin-VL fusion to mediate the other binding specificity.

Two well-characterised KnotBody trypsin binders (KB_A07 and KB_A12, see example 3) were used here as model scaffolds for engineering the bi-specific functionality. These KnotBodies contains a common heavy chain gene from D1A12 antibody (anti-TACE antibody)[101] and two distinct light chain genes displaying EETI-II as a CDR2 fusion. The trypsin binding capability of these KnotBodies is completely attributed to the VL domain displaying EETI-II. Therefore, these fusions of recipient VL:donor knottin were recombined with a large repertoire of naïve VH genes[28] to generate a library from which novel molecules with additional VH mediated binding specificities can be isolated.

In a previous work Schofield and colleagues described the cloning of VH and VL gene repertoires into an intermediate antibody library[28]. This intermediate antibody library was used to create a functional antibody phage display library ("McCafferty library" and the "Iontas antibody library"[28]). The same repertoire of VH genes was used in this example for the construction of the KnotBody heavy chain shuffled library. This was achieved by PCR amplifying VH genes from the Iontas antibody library bacterial stocks using primers M13 leaderseq (AAATTATTATTCGCAATTCCTTTGGTTGTTCCT; SEQ ID NO: 75) and HLINK3 (CTGAACCGCCTCCACCACTCGA; SEQ ID NO: 76). Amplified VH genes were digested with restriction enzymes Nco1 and Xho1 and ligated into the pIONTAS1_KB vector (encoding KB_A017 and KB_A12 light chain) pre-digested with the same enzymes. The ligation product was purified using MiniElute PCR purification kit (Qiagen, Cat. No. 28004) and electroporated into *E. coli* TG1 cells (Lucigen, Cat. No. 60502-2). Phage was rescued from this library as described in example 3[107]

Figures 11A, 11B, 11C, 11D, 11E:
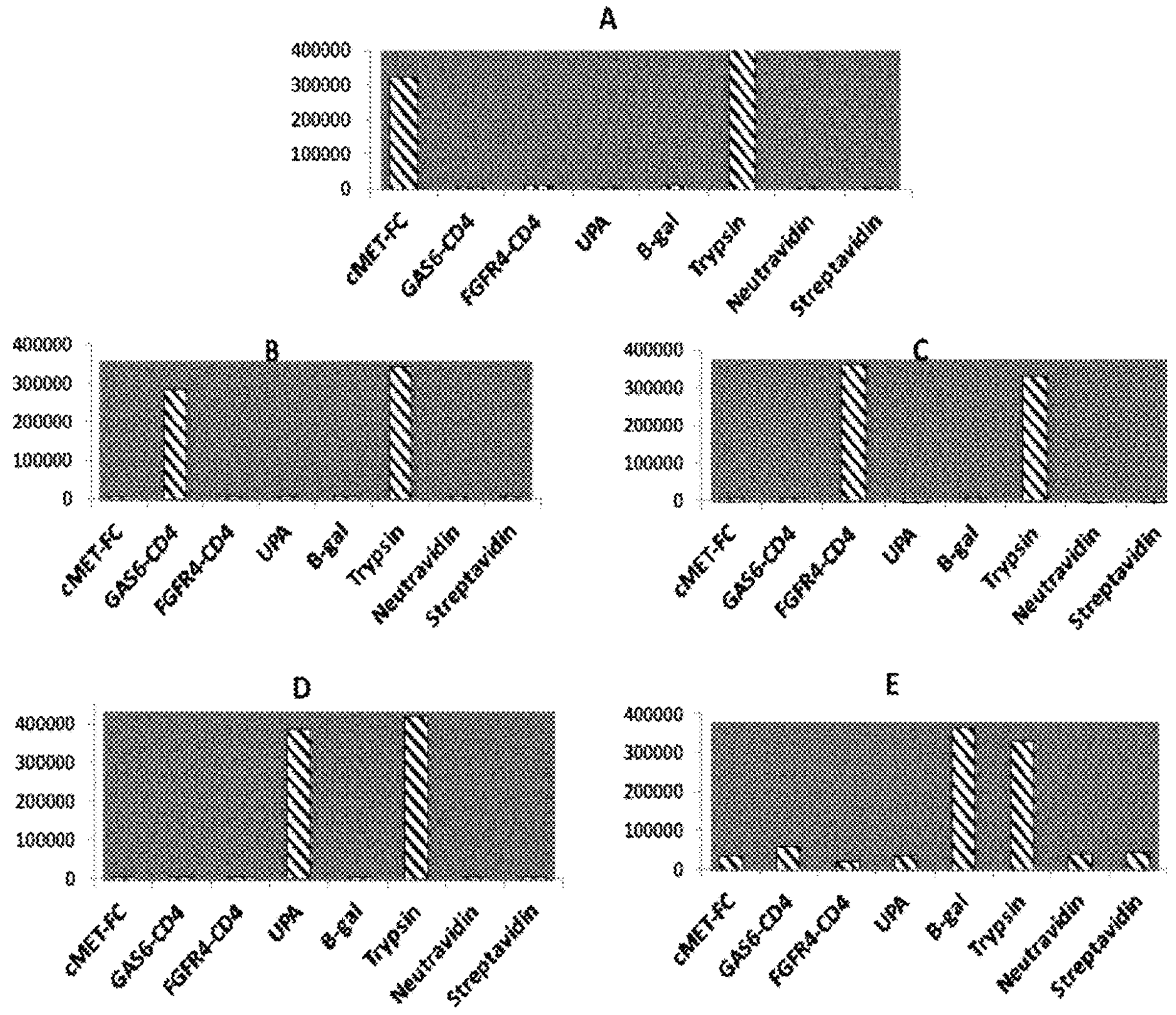
FIG. 11 shows an analysis of polyclonal phage outputs from the phage display selection of KnotBody VH shuffled libraries. Heavy chain shuffled KB_A07 and KB_A12 (combined) libraries were selected on 5 different antigens: cMET-Fc (A), GAS6-CD4 (B), FGFR4-CD4 (C), uPA (D) and B-gal (E). The polyclonal phage from the 5 selections were each tested for binding to trypsin, all the antigens used in selection, neutravidin and streptavidin to determine background binding. X-axis shows antigens immobilised on Maxisorp™ plates and the Y-axis shows polyclonal phage binding to the antigen in fluorescent units (FU).

In order to identify bi-specific KnotBodies with novel binding specificities mediated by the VH domain, two rounds of phage display selections were carried out against 5 different antigens (human-cMET-Fc fusion, mouse-FGFR4-CD4 fusion, human-GAS6-CD4 fusion, human-urokinase type plasminogen activator and β-galactosidase). cMET-Fc, FGFR4-CD4, GAS6-CD4 and urokinase type plasminogen activator (UPA) were immobilised directly on Maxisorp™ immunotubes. biotinylated β-galactosidase (bio-B-gal) was indirectly immobilised on Maxisorp™ immunotubes coated with streptavidin (round-1) or neutravidin (round-2). Phage selections were performed as described in example 3. Polyclonal phage prepared from the round-2 selection outputs were tested in a TRF binding assay (as described in example 3) against all 5 antigens, trypsin and the immobilisation partners (streptavidin and neutravidin). All polyclonal phage populations showed specific binding to trypsin and the antigen they were selected against but not other antigens (FIG. 11). For example, the binding signals obtained for polyclonal phage prepared from cMET-Fc selection were specific to trypsin and cMET. This result demonstrates the success of phage display selection in enriching bi-specific binders. In order to identify monoclonal binders, 48 individual clones were picked from each selection output and monoclonal phage was prepared from each clone (as described in example 3). Monoclonal phage supernatant from each clone was tested for binding to trypsin and the antigen used for selection (representative example of the screen is shown in FIG. 12). Any clone that showed a binding signal above 15000 fluorescent units on both trypsin and the selection antigen was considered to be a bi-specific binder. Large panels of bi-specific binders were identified from each selection output (Table 5).

Figure 13:
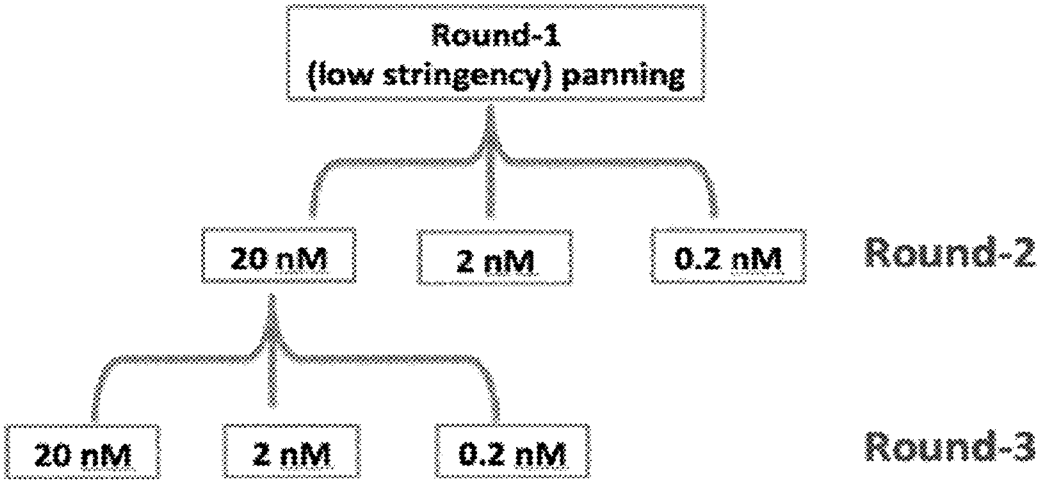
FIG. 13 shows phage selection cascade from the 'heavy chain shuffled' KnotBody library selected on biotinylated trypsin. The optimum antigen concentrations for round-2 and round-3 were determined empirically by selecting the phage KnotBodies against range of trypsin concentrations and comparing the output numbers with a "no antigen control".

Example 6: Demonstration of Bi-Epitopic Binding Capability of the KnotBody Format In the previous example we demonstrated the capability of a knottin scaffold to bind to two different antigens via distinct paratopes, one located on the recipient-donor fusion (ie VL-knottin) and the other on the VH. The same principle can be applied to target two different epitopes within a single target antigen where VH directed binding could be used for increasing the affinity and/or specificity of the original interaction (mediated by the knottin). By this approach, the additional binding properties of the VH domain can be utilised to improve the potency or specificity of knottin based drugs. Alternatively, such additional contribution to binding can also be directed by VL CDR3 using the approach described in example 2. In this example, we demonstrate bi-epitopic binding capability of the knottin scaffolds by improving the affinity of anti-trypsin KnotBodies (KB_A07 and KB_A12, see example 3) by introducing novel heavy chain partners that bind independently to trypsin. KB_A07 and KB_A12 contain a common VH domain (D12) that binds to the dis-cys domain of tumour necrosis factor-α converting enzyme[101] and a VL domain that binds to trypsin via EETI-II (displayed at the CDR2 position). In order to identify novel heavy chain partners that bind to a distinct epitope on trypsin (and improve the overall affinity), a phage display library was generated by replacing the D1A12 VH of these two KnotBodies with a large repertoire of naïve heavy chains (see example 5). Affinity improved clones were isolated from this "chain-shuffled" library by performing three rounds of phage display selections on trypsin under stringent conditions that favour preferential enrichment of high affinity clones. The stringency of selection was controlled by using decreasing amounts of trypsin in each round of selection (FIG. 13). The optimum antigen concentration for each round was determined empirically by selecting the KnotBodies against a range of antigen concentrations and comparing the phage output numbers with a no-antigen control. Round 1 selection was carried out by panning on antigen immobilised on Maxisorb immunotubes as described in example 5. The population from round 2 selections, carried out at 20 nM antigen concentration, was chose for a further round $3^{rd}$ round.

KnotBody genes from round 2 (20 nM selection) and round 3 (2 nM and 0.2 nM selections) outputs were PCR amplified using primers M13 leaderseq (See example 4) and NotMycSeq (GGCCCCATTCAGATCCTCTTCTGAGATGAG; SEQ ID NO: 70). PCR products were digested with NcoI and NotI restriction enzymes and cloned into the pBIOCAM5-3F vector via NcoI and NotI. The pBIOCAM5-3F allows the expression of antibodies as soluble scFv-Fc fusion proteins in mammalian cells[113], hence facilitating the screening for affinity improved KnotBody binders. 352 clones (resulting from the pBIOCAM5-3F cloning) were picked into 4×96 well cultural plates. Transfection quality plasmid DNA was prepared for each clone using the Plasmid Plus 96 kit (Qiagen. Cat. No. 16181). 600 ng of each plasmid DNA was incubated with 1.44 μg of polyethylenimine (PEI) in Freestyle HEK-293F expression medium (Thermo Fisher Scientific, Cat. No. R790-07) for 15 minutes before adding to 96-well deep well plates containing 500 μl/well of exponentially growing HEK-293F cells at a density of $1\times10^6$ cells/ml. Plates were sealed with gas permeable seals and incubated at 37° C. for 5 days (with 5% $CO_2$, 75% humidity and shaking at 800 rpm). Cell culture supernatant containing KnotBody-Fc fusion proteins was used for screening to identify affinity-improved clones.

Figure 14:
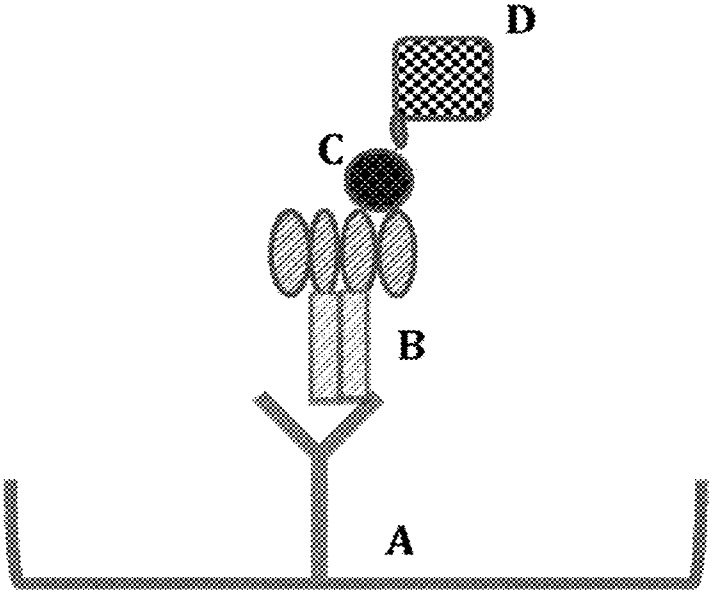
FIG. 14 shows the format of the KnotBody capture assay. KnotBody-scFv-Fcs (B) were captured on Maxisorp™ plates coated with an anti-Fc antibody (A) and the binding biotinylated trypsin (C) to KnotBodies are detected using streptavidin conjugated europium (D).
Figure 15:
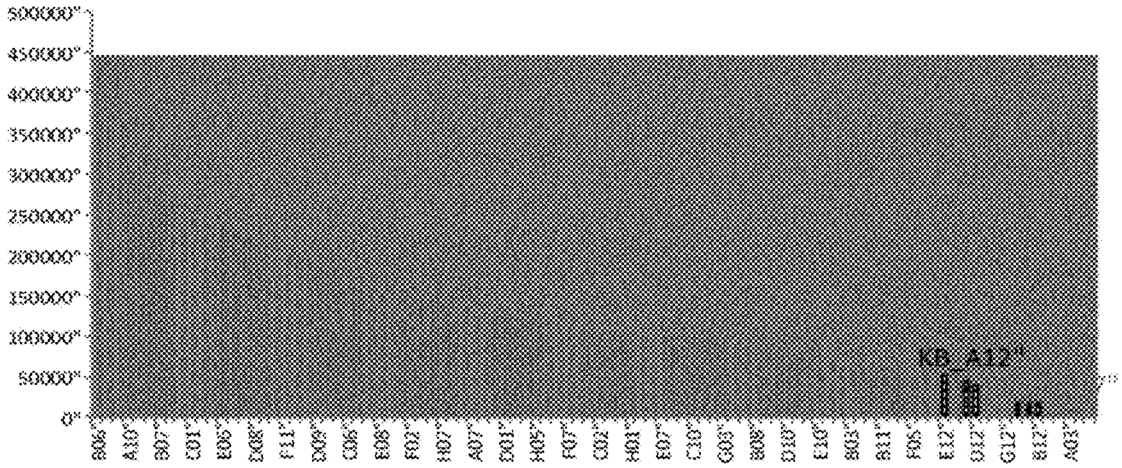
FIG. 15 shows a representative example of the performance of affinity improved clones in KnotBody Fc capture assay. KnotBody-scFv-Fcs were captured on Maxisorp™ plates coated with an anti-Fc antibody and the binding biotinylated trypsin to KnotBodies are detected using streptavidin conjugated europium. The binding signals observed for clones isolated from affinity maturation selections were compared to the parent clones KB_A12 and KB_A07. The X-axis shows clone ID of KnotBodies and the Y-axis shows KnotBody binding to trypsin in fluorescent units.
Figure 16:
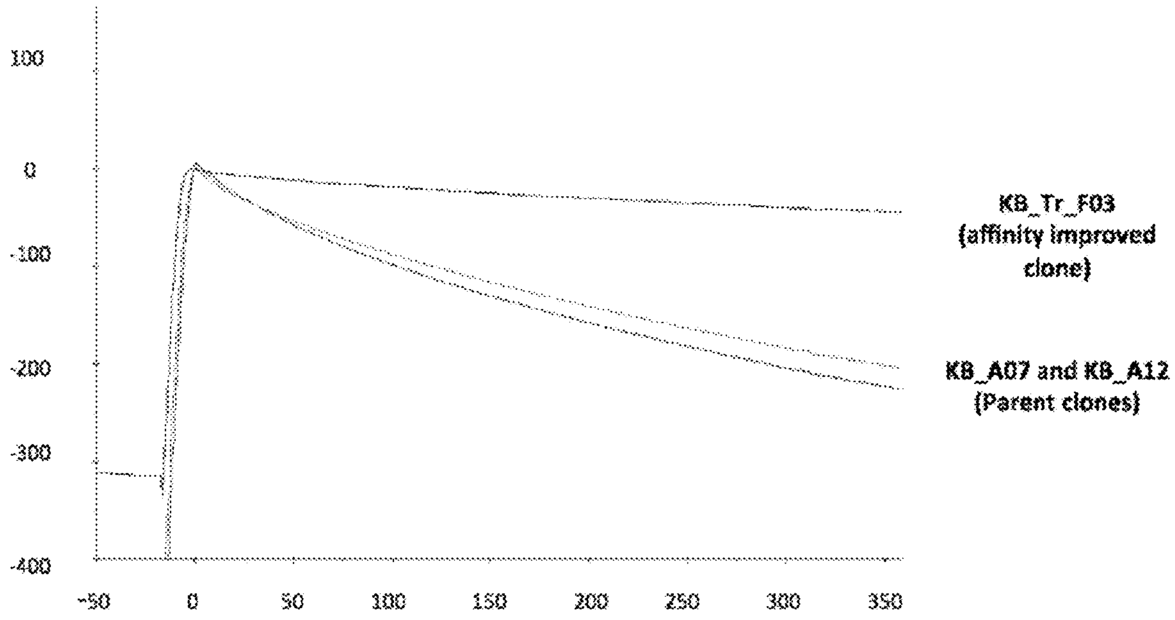
FIG. 16 shows an improvement in trypsin binding after heavy chain shuffling. Off-rate of the clone KB_Tr_F03 selected from the heavy chain shuffled library is compared to the two parent KnotBodies KB_A07 and KB_A12. The X-axis shows off rate analysis in seconds and the Y-axis shows resonance units (RU).

The binding signal observed for a particular clone in the primary binding screen (e.g. TRF binding assay using monoclonal phage supernatant) is a combined function of affinity and expression. Since protein expression can vary significantly from clone to clone, ranking KnotBodies by their binding signal in the primary screen might not necessarily correlate with their affinities. Therefore two expression-independent screening assays were used to rank the KnotBody clones by affinity and compare to them with parent clones. There were (i) TRF capture assay and (ii) Biacore off-rate screen. In the "TRF capture assay" (FIG. 14), KnotBody-scFv-Fcs were captured on Maxisorp™ plates coated with an anti-Fc antibody (Abcam, Cat. No. ab113636) and the binding of biotinylated trypsin to KnotBodies was detected using streptavidin conjugated europium (Perkin Elmer, Cat. No 1244-360). To normalise for differences in KnotBody (scFv-Fc) expression, limiting amounts of anti-Fc antibody was coated on each well. For example, a well coated with 50 μl of anti-Fc antibody at a concentration of 2.5 μg/ml (32 nM) has a maximum (theoretical) capture capacity of 1.6 fmoles of scFv-Fc. However, the average scFv-Fc expression in HEK-293F cells using pBIOCAM5-3F vector system is 10-20 mg/l (83-166 nM) and 50 μl of the raw supernatant used for the assay will have 4.1-8.2 fmoles of scFv-Fc on average, hence saturating the immobilised anti-Fc antibody coated on each well. The majority of the KnotBodies selected from VH shuffled libraries showed higher binding signal against trypsin than the parent clones (representative example is shown in FIG. 15). 90 KnotBodies that gave the highest binding signal in the capture assay were cherry-picked and tested in the "Biacore off-rate screen". In the "Biacore off-rate screen" the dissociation constants (off-rates) of the KnotBody clones were analysed by surface plasmon resonance (using Biacore T100 from GE healthcare). The dissociation constant of an antibody-antigen interaction is concentration independent and therefore normalisation for differential expression was not required. In this assay, a CM5 sensor chip (GE healthcare, Cat. No. BR-1005-30) was coupled to approximately 3000 resonance units (RU) of anti-Fc antibody (human antibody capture kit, GE healthcare, Cat. No. BR-1008-39). Approximately 1200-1600 RU of KnotBody-scfv-Fc was captured on the anti-FC antibody. The trypsin solution (400 nM) was injected for 60 seconds. The dissociation phase of each KnotBody trypsin interaction was monitored for 300 seconds. After each cycle, the chip surface was regenerated by injecting 3M $MgCl_2$. The dissociation constant (kd) for each KnotBody was determined using 1:1 Langmuir binding model (using Biacore T100 evaluation software). Clones that showed 1.5 fold slower dissociation constants than their parent clones were considered to have improved affinity (Table 6). Overall, 22 affinity improved clones were identified using capture assay and the off-rate screen. A representative example of a clone that showed improved off-rate compared to the parent clones is shown in FIG. 16. This improvement in the affinity of the KB_A07 and KB_A12 clones by heavy chain shuffling demonstrates the bi-epitopic binding capability of the KnotBody format.

Example 7: Cloning, Expression and Purification of Various Cysteine-Rich Toxin Donors within CDR3 of an Antibody VL Recipient Scaffold Aberrations in normal ion channel functioning are involved in the pathogenesis of number of disease conditions including pain disorders and auto-immunity. For example defects in the function of the voltage gated sodium channel 1.7 (Nav1.7) play a major role in both hypersensitivity and insensitivity to pain. The voltage gated potassium channel 1.3 (Kv1.3) is implicated in T-cell mediated autoimmunity. The acid sensitive ion channel 1a (ASIC1a) is involved in the sensing and processing of pain signals. Thus, specific modulators of ion channels offer a great therapeutic potential in the treatment of pain and various autoimmune disorders. Number of naturally occurring knottins function as ion channel blocking toxins. As discussed earlier, the only knottin based drug (Ziconotide) approved for therapy is an N-type voltage gated calcium channel blocker derived from the venom of the conus snail.

Figure 17:
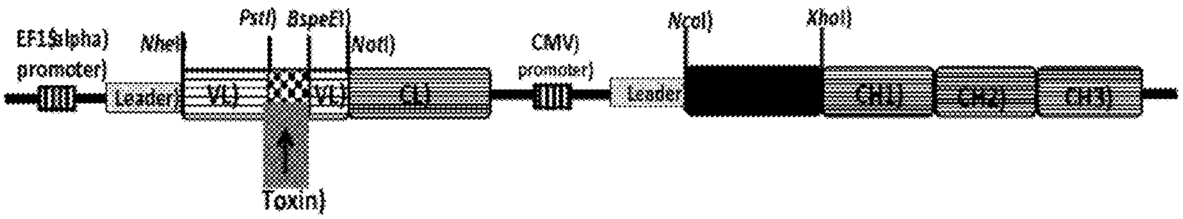
FIG. 17 shows a KnotBody expression cassette in pINT3-hg1 vector system. In this plasmid, transcription of light chain cassette encoding the knottin/toxin VL fusion and CL domain is under the control of EF1-alpha promoter. Transcription of the heavy chain cassette encoding D1A12 VH and IgG1 constant domains (CH1-CH2-CH3) is controlled by the CMV promoter. Pst1 and BspE1 sites in the light chain gene (recipient) allow the insertion of knottins (donor) into the CDR2 position.

This example describes the fusion of alternative cysteine-rich toxin donors into the previously selected recipient VL scaffolds to create KnotBodies directed towards ion channels (Table 7). This was achieved by cloning three Nav1.7 blockers, three Kv1.3 blockers and three acid sensing ion channel 1a (ASIC 1a) blocker into the CDR2 position of two KnotBodies KB_A07 and KB_A12 (i.e. replacing the EETI-II gene at that position, as described in example 3). Genes encoding all toxins (Table 8) were synthesised as gene fragments (from Integrated DNA Technologies). Each toxin gene was PCR amplified using primer sets that encodes junctional sequences specific to KB_A07 and KB_A12 (Table 9). An additional variant of Ssm6a (Ssm6s_GGS) incorporating linker sequences (GGS at the N-terminus and SGG at the C-terminus) was also PCR amplified. In this example, the KnotBody constructs were formatted as IgG molecules where the VH gene is fused to IgG1 heavy chain constant domains (CH1-CH2-CH3) and the recipient VL chains containing the new donor toxins are fused to a light chain constant domain (CL). In order to express these KnotBody constructs in mammalian cells, PCR fragments were cloned into the PstI and BspEI sites of KB_A12 and KB_A07 VL chain (encoded by the pINT3-hg1 vector, FIG. 17). The pINT3-hg1 vector has a dual promoter expression cassette in which the heavy chain expression is controlled by the cytomegalovirus (CMV) promoter and the light chain expression is driven by elongation factor-1 alpha (EF1-alpha) promoter.

Figure 18:
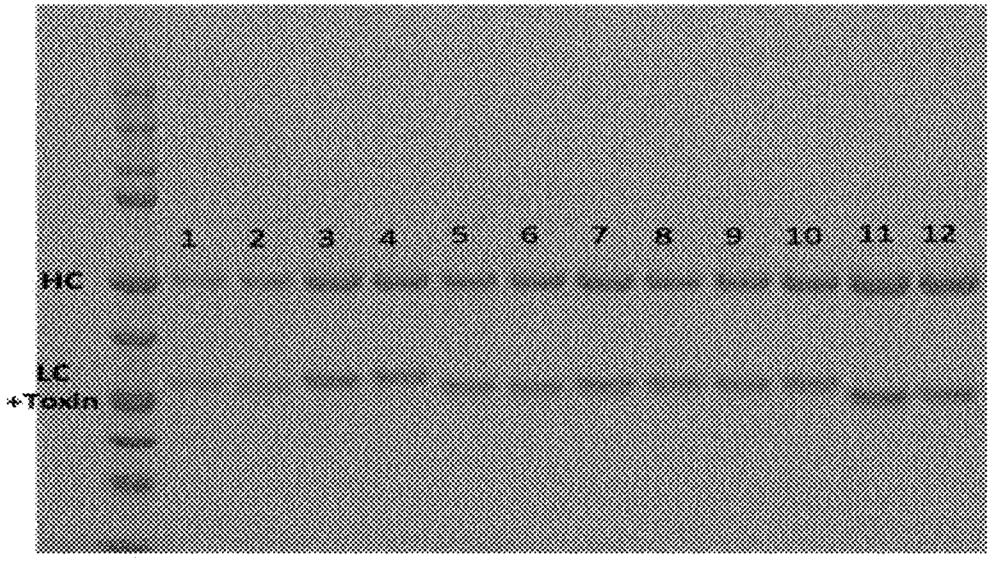
FIG. 18 shows SDS-PAGE analysis of IgG1 KnotBodies expressed in HEK-293F cells. KnotBodies purified using Protein-A affinity chromatography were visualised on a reducing SDS-PAGE gel using Coomassie staining. The top bands correspond to the antibody heavy chains (HC) and the bottom bands corresponds the antibody light chain displaying knottins/toxins as CDR2 fusions. Samples 1-4 are KB_A12 antibody recipient fused NaV1.7 blockers (Huwentoxin-IV, ProTx-II, Ssm6a, and Ssm6a_GGS). Samples 5-10 are Kv1.3 blockers (Kaliotoxin, Moka-1 and Shk) fused to KB_A07 antibody (5, 6 and 7) or KB_A12 antibody (8, 9 and 10). Samples 11 and 12 are parental KnotBody clones (EETI-II fusions) KB_A07 and KB_A12 respectively.

In order to express the KnotBodies in mammalian cells, transfection quality DNA was prepared using Plasmid Plus Kit (Qiagen, Cat. No 12945). 60 μg of plasmid DNA was incubated with 120 μg of polyethylenimine (PEI) in 5 mls Freestyle 293 expression medium (Thermo Fisher Scientific, Cat. No. 12338-018) for 15 minutes before adding to 50 mls of HEK-293F cells (Thermo Fisher Scientific, Cat. No. R790-07) seeded at a density of $1\times10^6$ cells/ml in a 250 ml tissue culture flask. Culture flasks were incubated at 37° C. for 5 days (with 5% $CO_2$, 75% humidity and shaking at 800 rpm). Expressed proteins were purified from the cell culture supernatants using Protein-A affinity chromatography (Protein-A sepharose from Generon, Cat. No. PC-A5). Purified proteins were dialysed against 2×PBS and dialysed samples were visualised on a SDS-PAGE gel using Quick Coomassie staining (Generon, product reference, GEN-QC-STAIN). A representative example is shown in FIG. 18. The average expression levels (7.7 mg/l) obtained for these fusion molecules in HEK293F cells were comparable to that of conventional antibodies produced using the same vector system (4 mg/l). Protein yield after purification is given in Table 10. In the case of mambalgin fusions, DNA was transfected into CHO-Expi cells as described in example 11 and these yields are given.

In summary, results described in this example illustrate that (i) ion channel blocking toxins can be expressed as donors within a fusion with VL domain recipients (e.g. KnotBodies); (ii) knottin scaffolds other than EETI-II can be formatted as KnotBodies or in other words, the KnotBody format is capable of functional presentation of multiple knottins (ii) These fusion molecules can be expressed and purified efficiently as IgGs.

Example 8: Functional Validation of Kv1.3 and ASIC1a Blockers Expressed as KnotBodies Knottin Kv 1.3 and ASIC1a blockers expressed in the KnotBody format (see examples 6 and 7) were tested for their ability to inhibit the function of the ion channel targets. The effect of these KnotBodies on cells expressing the human Kv 1.3 (huKv1.3) or human ASIC1a channels was assessed using QPatch automated whole-cell patch-clamp electrophysiology (Sophion).

For the testing of Kv1.3, CHO cells stably expressing huKv1.3 (Charles River Lab) were analysed using the QPatch electrophysiology assay in the presence or absence of the KnotBody fusions or the antibody isotypes (negative) controls. Internal and external physiological solutions were freshly prepared prior to the assay. The extracellular solution contained 145 mM NaCl, 4 mM KCl, 2 mM CaCl2), 1 mM MgCl2, 10 mM HEPES and 10 mM glucose; the pH was adjusted to 7.4 with NaOH; the osmolarity was ~305 mOsm/L. The intracellular solution contained: KF (120 mM), KCl (20 mM), HEPES (10 mM) and EGTA (10 mM); the pH was adjusted to 7.2 with KOH; osmolarity was ~320 mOsm/L.

Figure 21:
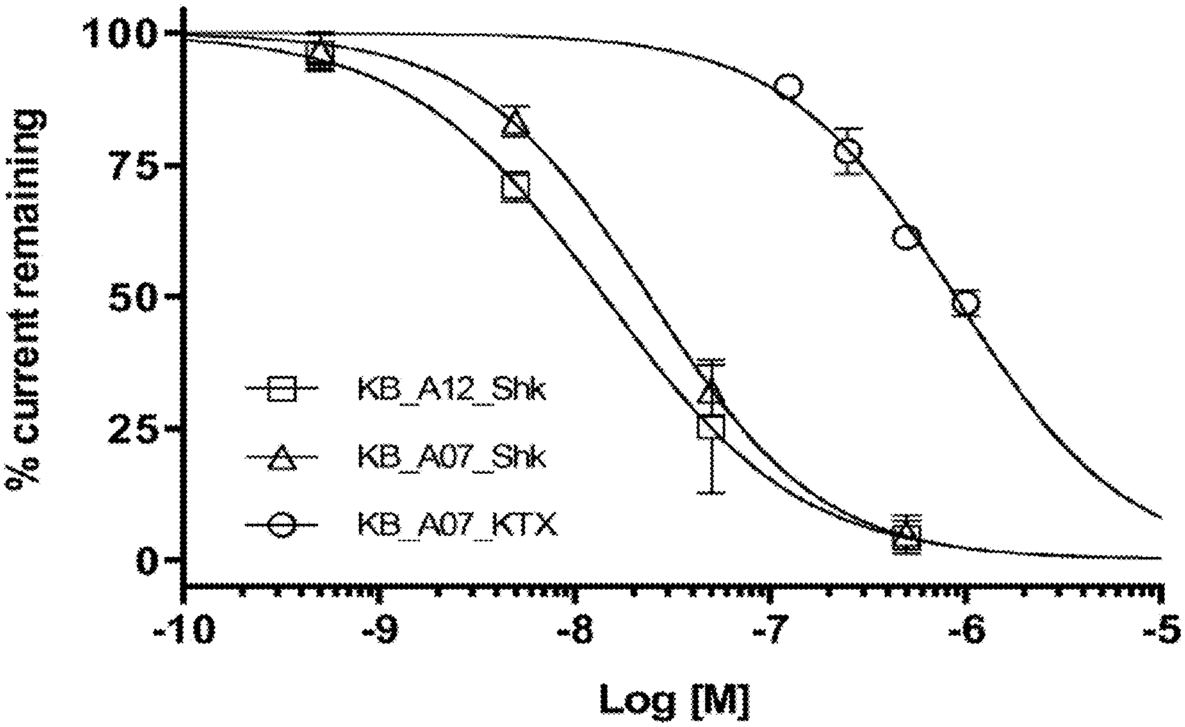
FIG. 21 represents a concentration-response curves showing the concentration dependent inhibition of huKv1.3 channel currents by KnotBodies. Log [M] concentration (x-axis) of toxin fusion KnotBodies KB_A12_Shk (Shk toxin, squares), KB_A07_Shk (Shk toxin, triangles) and KB_A07_KTX (kaliotoxin, circles) plotted versus % current remaining (y-axis). From these concentration-response curves the concentration at which 50% current inhibition ($IC_{50}$; see Table 11 for summary) was determined.

A series of depolarising voltage (channel activating) pulses were used to monitor the channel currents upon adding control (extracellular solution) to define a control baseline of current activity. To these measured control currents ascending concentrations of KnotBodies or parental antibody isotypes (control molecules) were applied to the external bathing solution (2.2 μM-0.5 nM, diluted in the extracellular solution). KnotBodies KB_A12 and KB_A07 (EETI-II fusions) were used as isotype controls for the testing. From a holding voltage of −80 mV a depolarising, activating voltage pulses of +30 or +80 mV were applied for 300 ms, every 5 or 10 seconds. The elicited, maximum outward current values measured during the activating step for each solution exchange period were averaged (n=3-8 for each concentration applied) and plotted as concentration-response curves. From these concentration-response curves (see example plots in FIG. 21) $IC_{50}$ values were calculated (summarised in Table 11A). KB_A07_Shk, KB_A12_Shk and KB_A07_Kaliotoxin (KTX) fusion proteins all inhibited the huKv1.3 currents in a concentration dependent manner with $IC_{50}$s of approximately 20 nM, 40 nM and 900 nM respectively. In comparison, the parental KnotBodies, KB_A12, KB_A07, Moka-1 on both recipient scaffolds and Kaliotoxin on KB_12 showed no significant reduction in measured current (~$IC_{50}$ extrapolated to >10 μM), which were similar in magnitude to the reduction in current recordings made in control external solution additions over the same time period (four applications each of four minutes duration, 16 minutes in total).

To functionally assess the ASIC1a KnotBodies, HEK293 cells stably expressing huASIC1a (Sophion) were analysed using a QPatch electrophysiology assay in the presence or absence of the KnotBody fusions (using KB_A12 as a recipient and replacing the original EETI-II donor as shown in Table 8). The "parental" KB_A12 with the EETI-II donor was used as a negative control. Internal and external physiological solutions were freshly prepared prior to the assay. The extracellular solution contained 145 mM NaCl, 4 mM KCl, 2 mM CaCl2), 1 mM MgCl2, 10 mM HEPES and 10 mM glucose; the pH was adjusted to 7.4 with NaOH (for control, resting-state pH) or 6.0 with MES (for acidic, activating-state pH); the osmolarity was ~305 mOsm/L. The intracellular solution contained: CsF (140 mM), HEPES (10 mM), NaCl (10 mM) and EGTA/CsOH (1 mM/5 mM); the pH was adjusted to 7.3 with CsOH; osmolarity was ~320 mOsm/L.

Throughout ASIC1a recordings the recording cell membrane voltage was clamped at −60 mV. ASIC1a baseline control currents were elicited by applying external solution at activating pH 6.0 for 3000 ms. This activating pH application was repeated three further times, giving four baseline control ASIC1a currents. The recording cells were then pre-incubated with KnotBody diluted in external solution at pH 7.4 for 15-20 minutes. Following this KnotBody pre-incubation the same concentration of KnotBody in external solution at activating pH 6.0 was applied to the cell recording.

At the end of each KnotBody incubation and subsequent ASIC1a current activation, a full blocking concentration (300 nM) of the ASIC1a knottin inhibitor PcTx1 (positive control) was perfused onto the cell recording and a final activating pH 6.0 external solution was applied. The percentage remaining signal between activating pH 6.0 baseline (i.e. pre-KnotBody) and post-KnotBody incubation was determined. From these figures (see Table 11B), it can be seen that KnotBodies KB_A12_PcTx1 and KB_A07_PcTx1 were active, reducing the ASIC1a current to 4.8% which is the same level as seen with positive control application of PcTx1 (1.9-3.8%). KB_A12_Mba-1 and KB_A12_Mba-2 showed the same level of current as the KB_A12 negative control or the "buffer only" control.

The data above illustrates the potential to fuse knottins which have therapeutic potential (i.e. ion channel blockers) into a recipient antibody scaffold which was originally selected for fusing to a different knottin (i.e. EETI-II).

Example 9: Functional Fusion of Non-Knottin Donors to Recipient VL Domains of Antibodies This example describes the fusion of a non-knottin donor diversity scaffold domain to a recipient VL domain. Non-knottin donor diversity scaffold domains that lack disulphide bonds could be valuable alternative to knottins. As discussed before a diverse number of protein scaffolds have been engineered for novel binding specificities[38,114]. Here we use a small protein scaffold (approx. 100 amino acids) called an Adhiron, which is based on consensus sequence of plant-derived phystostatins (protein inhibitors of cysteine proteases). Adhirons shows high thermal stability and express well in *E. coli*[46] They are structurally distinct from knottins and do not contain any cysteine residues.

As donors we chose two engineered adhirons, which bind the lectin-like oxidized low-density lipoprotein receptor-1 (LOX-1) to replace EETI-II at the VL CDR2 position of VL chains (recipients) from KB_A07 and KB_A12 (example 3). Sequences for these adhirons (referred to as Ad-LOX1-A and Ad-LOX1-B, Table 12) were obtained from patent WO2014125290 A1 and were as synthesised as gene fragments to enable cloning (Table 13). Each adhiron gene was amplified using primer sets specific for KB_A07 and KB_A12 (Table 14) using PCR. PCR products were cloned into the Pst1 and BspE1 sites of the pIONTAS1_KB phage display vector (FIG. 1) encoding KB_A12 and KB_A07 genes.

In order to test the functionality of these adhiron-antibody fusions, monoclonal phage prepared from each clone was assessed for binding to LOX-1 in a TRF binding assay. In this assay, LOX-1 (immobilised directly on Maxisorp™ plates) binding of phage displaying adhiron-antibody fusion was detected using a mouse anti-M13 antibody (GE Healthcare) followed by europium conjugated anti-mouse antibody (Perkin Elmer). Parent KnotBodies KB_A07 and KB_A12 (EETI-II fusions) were included as controls. Proteins cMET-FC, GAS6-CD4, FGFR4-CD4, UPA and B-gal were used to examine non-specific binding. The result from this assay (FIG. 19) shows that all adhiron antibody fusions specifically bind to the LOX-1. The parent clones, KB_A07 and KB_A12, showed no detectable binding to the LOX-1 confirming that LOX-1 binding shown by the adhiron-antibody fusion molecules is mediated by the adhirons (displayed in the VL CDR2 loops of these antibodies).

In this example, we have demonstrated that non-knottin donor diversity scaffolds can be inserted into a recipient VL scaffolds to create alternative KnotBody formats.

Example 10. Identification of Loop Regions for Insertion of Donor Sequence or Introduction of Diversity in Donor, Recipient or Partner Sequences The method described in example 1 to insert a donor knottin sequence into a recipient Ig domain can be applied to the identification of sequences which join secondary structural elements of other scaffolds as potential sites for donor insertion.

For Ig domains, the framework and CDR designations are as described by the International Immunogenetics Information System (IMGT) database. According to the IMGT v3.1.10, numbering CDR1, CDR2 and CDR3 sequences occupy amino acid positions 27-38, 56-65 and 105-117 respectively (for all VH and VL sequences). FW1, FW2 and FW3 residues occupy 1-26, 39-55 and 66-104. At the end of the re-arranged V gene FW4 is encode by 6 J segments for VH, 5 J segments for V kappa and 7 J segments for V lambda (in each case encoding 11, 10 and 10 amino acids respectively for each FW4).

In one approach, an individual CDR may be removed in its entirety and replaced by an incoming donor sequence which is flanked by linkers of no more than 4 amino acid residues at each of the N and C termini. In another approach, some CDR residues may be retained but the total number of residues, including CDR residues, which link the incoming donor diversity scaffold to the scaffold of the recipient Ig diversity scaffold may not exceed 4 amino acids at each terminus (to retain close proximity between donor and recipient). In yet another approach, variation framework residues at the boundary of the junction may be removed from the donor or recipient scaffolds and replaced by randomized codons encompassing some or all amino acids. The overall linkage at N and C termini (excluding the replacement framework residues) shall not exceed 4 amino acids.

The gene or population of genes encoding the fusion designed in this way can be created using methods known to those skilled in the art (also exemplified in examples herein). The gene may be made entirely as a synthetic gene or created from gene fragments arising from restriction digestion or PCR and incorporated into the final fusion gene by PCR assembly or ligation. Gene fragments and/or PCR products can be joined ligation independent cloning, Gibson cloning, NEB Builder (NEB) or other methods known to those skilled in the art. The resultant genes can then be cloned into an appropriate expression vector as discussed above.

The approach above takes advantage of the IMGT database as a curated source of sequence information on Ig domains. The same approach described above may be used to cover all domains with a known structure. References to the pdb files which describe individual protein structures can be found in original citations (e.g. in references cited herein or references therein). The RCSB protein data bank ("pdb server") represents a portal to structural information on biological macromolecules such as protein domains. Other sources for accessing structural data, including PDBSUM have been summarised[115]. The data associated with such files also allows identification of secondary structure elements by viewing 3D structures or by using software such as DSSB or websites running such software[116]. Using this approach, secondary structural representations upon a primary amino acid sequence may be derived. Alternatively, structural model or direct sequence alignment between a desired recipient domain and orthologues or paralogues with known structure could be used to identify secondary structure elements. Alternatively, algorithms for prediction of secondary structure elements could be used The structure of the $10^{th}$ type III cell adhesion domain of fibronectin[117] may be used to exemplify an approach to identify potential sites within a candidate recipient domain for insertion donor sequences. The same approach can be used to identify regions which could be amenable to diversification in both donor, recipient and partner chains.

As an example, the pdb file describing the $10^{th}$ type III cell adhesion domain of fibronectin (FnIII-10) is "1FNA". Using the pdb file (e.g. by viewing on the pdb server) a representation of the linear amino acid sequence of FnIII-10 annotated with secondary structural elements can be generated (FIG. 20A). The regions which form beta strands are underlined and the residues which join them on the upper face of the domain are shown in lower case. In a further example the gp2[51] has a structure represented by pdb file 2WMN. A linear representation of the secondary structure elements is represented in FIG. 20B. Residues joining beta strands or a beta strand-alpha helix junction are underlined.

These "joining sequence" represented in lower case represent regions which could be replaced partially or in their entirety while maintaining a short linker between donor and recipient. As discussed above, framework residues may be removed at the boundary of the junction of the recipient scaffolds and replaced by randomized codons encompassing some or all amino acids. These same residues represented in FIG. 20 also represent possible sites amenable to introduction of diversity as described above.

Gp2 is a small protein domain of 64 amino acids with N and C termini which are in proximity and so this molecule also represents an ideal candidate for a donor domain. In addition it has been shown that the N and C termini of Gp2 can be truncated without affecting folding of the domain allowing fusion in close proximity to a recipient domain.

Example 11. Selected Linkers are Required for Functional Expression of Knottin Donor Domains within an Antibody Recipient Domain In contrast to peptide fusion approaches employed by others which utilise long flexible linkers for joining domains, the KnotBody format uses short non-flexible linker sequences to limit the relative movement between the donor and recipient domains. This is an important aspect of the invention. In order to identify suitable linkers permitting correct folding of 2 fused structural domains we have adopted the approach of making a library with variation in the linker. In example 3 and example 12 we have described the isolation of several functional KnotBody molecules with selected, short, non-flexible linker sequences joining the EETI-II (donor domain) with framework residues of VL or VH domains (recipient).

To demonstrate the importance of linker selection the selected short linkers of two well characterised KnotBodies, KB_A07 and KB_A12, were replaced with the long flexible N- and C terminal linkers typically used by others[11, 13, 15] (See table 15). The performance of these linker variants were then compared to that of the original KnotBodies with short non-flexible linkers selected from the library using a trypsin binding assay.

In this example, the KnotBody variants were formatted as Fabs where the VH gene is fused to the heavy chain constant domain-1 (CH1) and the VL chains containing KnotBody linker variants are fused to the light chain constant domain (CL). The VL genes encoding the knottin and linker sequences were synthesised as gene fragments (Integrated DNA Technologies, See table 16). In order to express the KnotBody linker variants in mammalian cells, these gene fragments were cloned into the pINT12 expression vector (encoding D1A12 heavy chain) using Nhe1 and Not1 restriction sites.

The pINT12 vector (FIG. 7) has a dual promoter expression cassette in which the heavy chain expression is controlled by the cytomegalovirus (CMV) promoter and the light chain expression is driven by elongation factor-1 alpha (EF1-alpha) promoter.

In order to express the KnotBodies in mammalian cells transfection quality DNA was prepared using NucleoBond Xtra Midi plus kit (Macherey Nagel, Cat. No. 740412.50). 25 μg of plasmid DNA was incubated with 80 μl of ExpiFectamine CHO transfection reagent (Thermo Fisher scientific, Cat. No. A29129) in 2 mls of OptiPRO Serum Free Medium (Thermo Fisher Scientific, Cat. No. 12309050) for 5 minutes before adding to 25 mls of Expi-CHO cells (Thermo Fisher Scientific, Cat. No. A29133) seeded at a density of $6\times10^6$ cells/ml in a 125 ml tissue culture flask. Culture flasks were incubated at 37° C. for 7 days (with 5% CO2, 75% humidity and shaking at 800 rpm) with a single feed 18-22 hour post transfection. The feed included 6 mls of ExpiCHO feed containing 150 μl of enhancer solution. Expressed proteins were purified from cell culture supernatants using CaptureSelect IgG-CH1 affinity matrix (Thermo Fisher Scientific, Cat. No. 194320005) according to manufacturer's instructions. Purified proteins were dialysed against 2×PBS overnight. Protein concentrations were determined using absorbance at 280 nm and theoretical extinction co-efficient.

Figure 22:
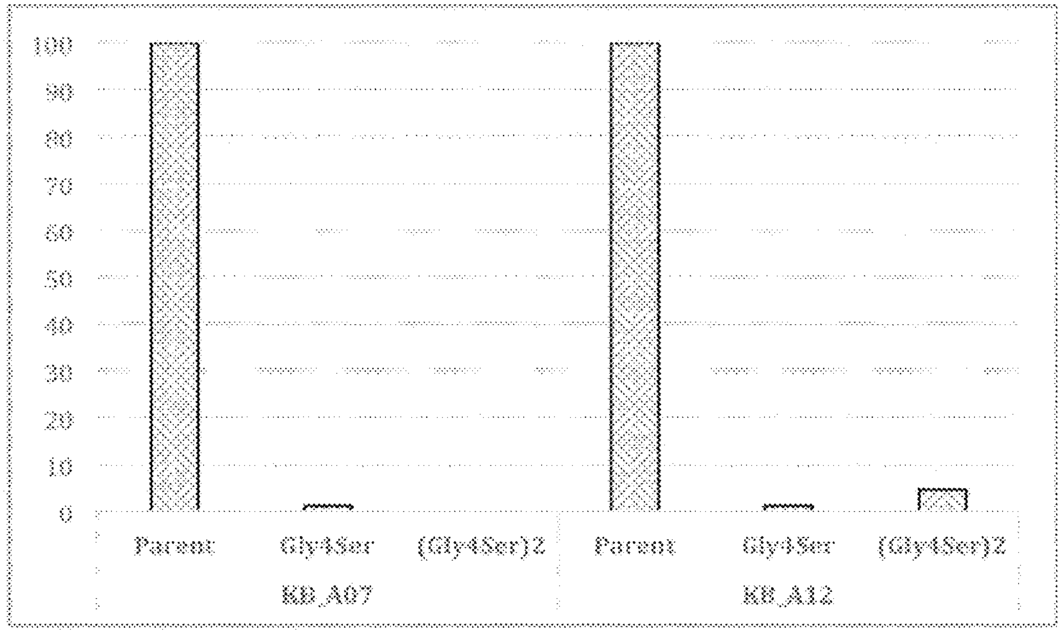
FIG. 22 shows the binding comparison of KnotBody linker variants to trypsin. Binding of KnotBody Fabs (X-axis) to biotinylated trypsin immobilised on streptavidin coated Maxisorp™ plates using a mouse anti-CH1 antibody followed by a europium conjugated anti-mouse antibody. Y-axis shows normalised binding signal (%) where the binding of Gly4Ser controls are normalised against that of their respective parent clone (i.e. 100% binding).

In order to compare the performance of the KnotBodies with short and long linkers, purified Fabs were tested for binding to trypsin by ELISA. In this assay binding of KnotBody Fabs (at 0.5 μg/ml) to biotinylated trypsin (5 μg/ml immobilised on streptavidin coated Maxisorp™ plates) was detected using a mouse anti-CH1 antibody (Hybridoma Reagent Laboratories) followed by a europium conjugated anti-mouse antibody (Perkin Elmer, Cat. No. AD0124). The trypsin binding capability of KB_A07 and KB_A12 KnotBodies were greatly diminished when the short selected linkers were replaced with long and flexible linkers (FIG. 22). This example clearly demonstrates the importance of short non-flexible linkers for generating optimal donor-recipient fusions.

Example 12. Introduction of Diversity into Donor Domain by Randomising Donor Interaction Domains Examples 5 and 6 showed the use of VH shuffling to generate sequence diversity within the binding partner domain of a KnotBody to select for variants with additional specificity or improved binding kinetics. In both examples, diversification was performed on the partner domain (VH domain) and the original binding specificity of the donor domain (knottin) was unchanged. In examples 2 and 3 we illustrated the introduction of diversity into the VL recipient domain. In this example, we demonstrate a different approach to introduce sequence diversity in the donor domain of a KnotBody: replacing the existing loops in the donor knottin with random amino acid sequences. The trypsin binding capability of the KnotBodies described in this patent was conferred by the loop 1 sequences (PRILMR) of the knottin-EETI-II. Here we replaced the loop 1 sequences of KB_A12 KnotBody with randomised sequences of varying lengths (6, 8, 9 and 10 residues) to increase diversity as well as potential binding surface. The resulting loop libraries were then used to generate cMET and β-galactosidase binding specificities using phage display technology. In order to create large phage display libraries with high proportion of loop substituted variants an oligonucleotide-directed mutagenesis approach using Kunkel mutagenesis (Kunkel, T. A., et al. *Meth. Enzymol.* 154, 367-382 (1987), and selective rolling circle amplification Huovinen, T. et al. *PLoS ONE* 7, e31817 (2012) was used. Oligonucleotides used encoded VNS codons (V=A/C/G, N=A/GIC/T and S=G/C) that encode 16 amino acids (excludes cystiene, tyrosine, tryptophan, phenylalanine and stop codons) at a given position. The mutagenic oligonucleotides used, representing the antisense strand (where B=TGC), are given in Table 18.

The template DNA encoding KB_A12 (in the phage display vector, pSANG4[28]) was purified as uracil containing single stranded DNA (dU-ss DNA) from phage rescued from *E. coli* CJ236 (a dut⁻/ung⁻ strain). The antisense oligonucleotides described above were annealed to the dU-ssDNA template and extended using T7 polymerase to produce the complimentary strand. Newly synthesised heteroduplex DNA was subjected to rolling circle amplification using random hexamers (Thermo Fisher Scientific, Cat. No. S0142) and Phi29 polymerase (Thermo Fisher Scientific, Cat. No. EP0091) to selectively amplify the mutant strand. The product of rolling circle amplification was cut to plasmid size units using NotI restriction endonuclease (New England Bio labs, Cat. No. R3189S) and re-circularised by self-ligation.

The ligation product was purified using MiniElute PCR purification kit (Qiagen, Cat. No. 28004) and electroporated into *E. coli* TG1 cells (Lucigen, Cat. No. 60502-2). Methods for kunkel mutagenesis and selective rolling circle amplification are known to those skilled in the art. Phage was rescued from this library as described in example 3.

In order to isolate KnotBody loop binders with novel specificities, two rounds of phage display selections were carried out against human cMET and β-galactosidase immobilised directly on directly on Maxisorp™ immunotubes. Phage selections were performed as described in example 3. KnotBody VL genes from round 2 outputs were PCR amplified using primers LLINK2 (SEQ ID NO: 69) and NotMycSeq (SEQ ID NO: 70). Amplified KnotBody VL genes were digested with NheI and NotI and ligated into the pSANG4 vector (encoding D1A12 heavy chain) pre-digested with the same enzymes. The ligation products were transformed into *E. coli* TG1 cells. In order to identify monoclonal binders, 47 individual clones were picked from each transformation and monoclonal phage was prepared from each clone (as described in example 3). Monoclonal phage supernatant from each clone was tested for binding to the antigen used for selection using a TRF binding assay.

Figures 23A, 23B:
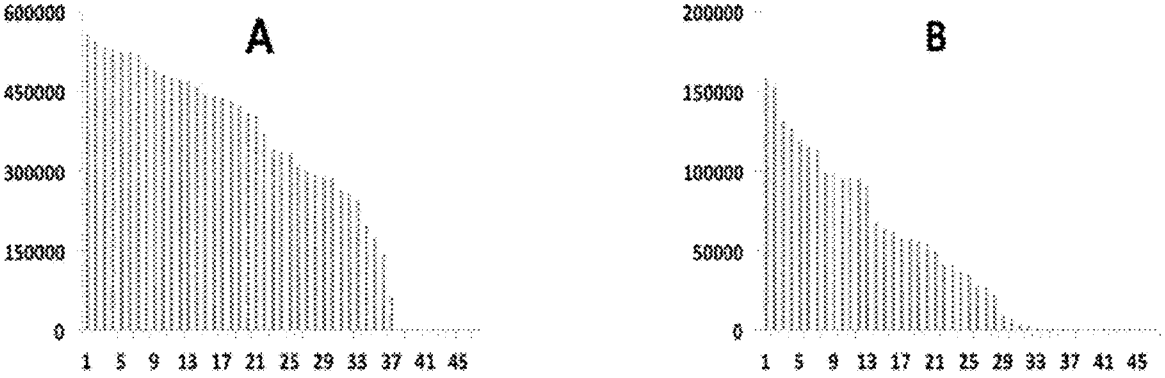
FIG. 23 shows the monoclonal phage binding of clones selected from the KnotBody loop library to β-galactosidase (A) and cMET (B). Monoclonal phage binding to the antigen immobilised directly on Maxisorp™ plates were detected using a mouse anti-M13 antibody followed by europium conjugated anti-mouse antibody. X-axis shows the clone number and the Y-axis shows antigen binding in fluorescent units (FU).

30/47 clones tested bound c-Met and 37/47 clones bound β-galactosidase (FIG. 23). Binders from this assay were sequenced using the primer LMB3 (CAGGAAACAGC-TATGACC: SEQ ID NO: 77). 23 unique sequences were identified for cMET (Table 17A) and 11 unique sequences identified for β-galactosidase (Table 17B). Although the natural length of loop 1 of EETI-II is 6 residues, all novel binders isolated from the loop library possessed a loop size of either 8 or 9 amino acids.

This example clearly demonstrates that additional diversity can be introduced on to a KnotBody by substituting the existing knottin loops with random sequences of varying lengths. This loop substitution/randomisation approach can be used to acquire a new specificity (as described in examples 5) or fine tune the existing specificity or affinity mediated by the donor or recipient domain.

Example 13: Generation of Bi-Specific KnotBodies that can Cross the Blood Brain Barrier (BBB) Via Receptor Mediated Transcytosis (RMT)

Crossing the blood-brain barrier (BBB) constitutes a major challenge for the delivery of peptides and antibodies into the brain for the treatment of neurological disorders (e.g. chronic pain, Alzheimers disease, multiple sclerosis, epilepsy). For example, approximately 0.1% of circulating antibodies cross into the brain (Zuchero, Y. J. Y. et al. Neuron 89 p 70-82 (2015). Alternatively, therapeutics such as Ziconotide (a knottin from Conus snail venom) are administrated using intrusive and expensive intrathecal injection procedures. Hence, the development of effective strategies to deliver molecules across the BBB has been a long-standing goal for the pharmaceutical industry (Niewoehner, J. et al. Neuron 81, 49-60 (2014). In recent years, the main focus of this research has been the generation of molecules capable of shuttling drug moieties across the BBB by taking advantage of endogenous nutrient transport systems for example receptor mediated transcytosis (RMT). This is generally achieved using a bi-specific format that includes a "molecular shuttle" and an active the drug moiety. For example, Yu and co-workers have reported a conventional bi-specific antibody which transports an anti-Beta secretase-1 (BACE) inhibitor across the BBB using a "molecular shuttle" that binds transferrin receptor (TFR) (Yu, Y. J. et al. Sci Transl Med 3, 84ra44-84ra44 (2011)). This bi-specific antibody format consists of 2 distinct VH:VL pairs (ie 2 different Fab arms) which individually recognise either TFR or BACE. In example 5, we have demonstrated the generation of bi-specific KnotBodies where the binding determinants required for recognition of two distinct antigens are incorporated within a single VH-VL pair. In this example, we describe the generation of bi-specific KnotBodies in the same format where VH domains selected against TFR shuttle their partner Knottin-VL fusion domains across the BBB via RMT.

Figure 24:
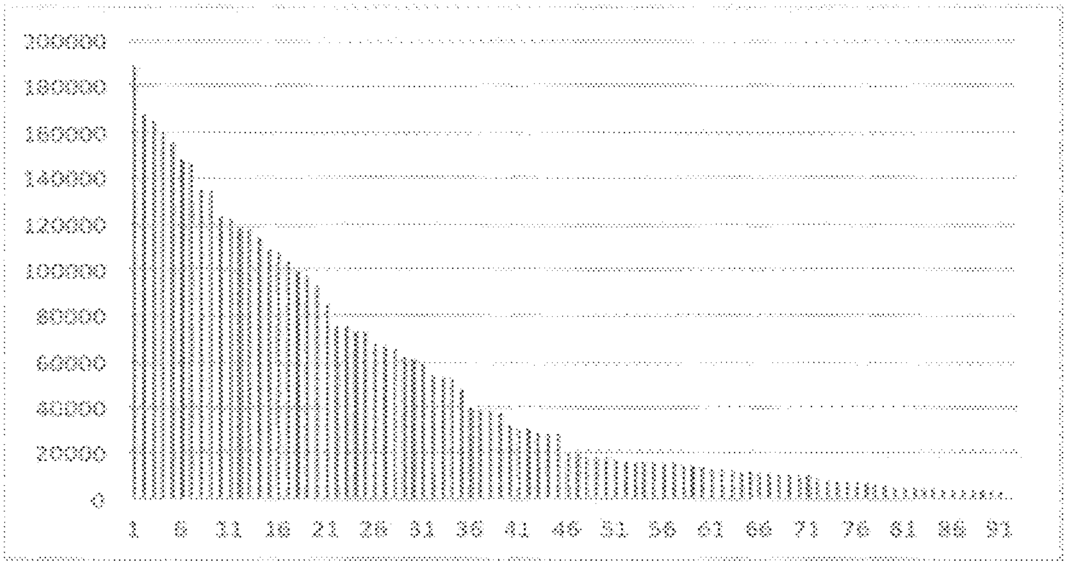
FIG. 24 shows a representative example of the screen for KnotBody binders to rat TFR. Monoclonal phage binding to rat TFR immobilised on Maxisorp™ plates were detected using a mouse anti-M13 antibody followed by europium conjugated anti-mouse antibody. X-axis shows the clone number and the Y-axis shows signal from phage binding to TFR in fluorescent units (FU).

Example 5 describes VH shuffled libraries composed of trypsin binding KnotBody light chains (KB_A07 and KB_A12) partnered with a repertoire of VH genes isolated from non-immunised donors. Anti-TFR bi-specific KnotBodies were selected from these libraries using 2-3 rounds of phage display selections on TFR antigen directly immobilised on Maxisorp™ immunotubes. Round 1 selection was carried out on mouse TFR followed by round 2 selection on rat TFR. In another case, 3 rounds of selections were carried on mouse TFR-mouse TFR-rat TFR (representing antigens used in rounds 1, 2 and 3 respectively). Alternatively, selections were carried out on mouse TFR-human TFR-mouse TFR. 736 individual clones were then picked from the final round of selections and monoclonal phage was prepared from each clone (as described in example 3). Monoclonal phage supernatant from each clone was tested for binding to rat TFR by ELISA (a representative example of the screen is shown in FIG. 24). 376 clones that showed a binding signal above 10,000 fluorescent units were picked and sequenced to identify unique clones. Based on the analysis of VH CDR sequences, 65 unique binders were identified.

In order to enable the expression of these TFR binding KnotBodies as Fabs, VH genes were PCR amplified using primers M13 leaderseq (see example 4) and HLINK3 (CT-GAACCGCCTCCACCACTCGA: SEQ ID 76). Amplified VH genes were digested with restriction enzymes Nco1 and Xho1 and ligated into the pINT12 vector (encoding KB_A07 or KB_A12 light chain) pre-digested with the same enzymes. The pINT12 vector (FIG. 7) has a dual promoter expression cassette in which the heavy chain expression is controlled by the cytomegalovirus (CMV) promoter and the light chain expression is driven by elongation factor-1 alpha (EF1-alpha) promoter. In order to express these KnotBody Fabs in mammalian cells transfection quality DNA was prepared using Plasmid Plus Kit (Qiagen, Cat. No 12945). 15 μg of plasmid DNA was incubated with 48 μl of Expi-Fectamine CHO transfection reagent (Thermo Fisher scientific, Cat. No. A29129) in 1 ml of OptiPRO Serum Free Medium (Thermo Fisher Scientific, Cat. No. 12309050) for 5 minutes before adding to 15 mls of Expi-CHO cells (Thermo Fisher Scientific, Cat. No. A29133) seeded at a density of 6×106 cells/ml in a 125 ml tissue culture flask. Culture flasks were incubated at 37° C. for 7 days (with 5% CO2, 75% humidity and shaking at 800 rpm) with a single feed 18-22 hour post transfection. The feed included 3.6 mls of ExpiCHO feed supplemented with 90 μl of enhancer solution. Expressed proteins were purified from cell culture supernatants using CaptureSelect IgG-CH1 affinity resin (Thermo Fisher Scientific, Cat. No. 194320005) according to manufacturer's instructions. Purified proteins were dialysed against 2×PBS overnight. Protein concentrations were determined using absorbance at 280 nm and theoretical extinction co-efficient.

In order to assess the ability of these KnotBodies to cross the BBB, a ready to use in vitro rat BBB model system (Pharmacocell, Cat. No. RBT-24H) was used. In this model system rat brain endothelial cells were co-cultured with pericytes and astrocytes to mimic the in vivo BBB anatomy (Nakagawa, S. et al. (2009) *Neurochem. Int.* 54, 253-263). The in vitro rat BBB kit was cultured according to manufacturer's instructions and transendothelial electrical resistance (TEER) was measured prior to testing of KnotBodies to verify the integrity of the barrier. All wells had a TEER measurement of >200 Ω/cm2. 21 KnotBody Fabs were tested for their ability to cross the in vitro BBB model system. OX-26, a well characterised anti-rat TFR antibody that has been shown to cross BBB in vivo models (albeit at low levels) was used a positive control (Jefferies, W. A., Brandon, M. R., Williams, A. F. & Hunt, S. V. Immunology 54, 333-341 (1985), Moos, T. & Morgan, E. H. Journal of Neurochemistry 79, 119-129 (2001)). The parent KnotBody KB_A12 was used as a negative control. Both positive and negative controls were expressed and purified in the Fab format as described above. For the assay, test KnotBodies were prepared as 7 oligoclonal mixes each containing 3 different Fab antibodies at a final concentration of 2 μM in the assay buffer (DMEM-F12 with 15 mM HEPES, 0.5% BSA, 500 nM hydrocortisone and 10 μg/ml Na—F). The positive and negative controls were prepared at 1 μM in the same assay buffer. These Fab oligoclonal mixes and controls were added to the upper chamber (referred as blood side) of the co-culture kit and incubated at 37° C. for 6 hours (with 5% CO2 and 75% humidity). The concentration of transcytosed Fabs in the lower chamber (referred as brain side) was determined using a sandwich ELISA. In this ELISA, Fabs were captured using an anti-CH1 antibody (provided by Hybridoma Reagent Laboratories) and detected using rabbit anti-human IgG Kappa light chain antibody (Abcam, Cat. No. ab195576) or anti-human IgG Lambda light chain antibody (Abcam, Cat. No. ab124719) followed by europium conjugated anti-rabbit antibody (Perkin Elmer, Cat. No. AD0105). Oligoclonal KnotBody Fab mixes in wells C2, C3, and C4 showed significant levels of transcytosis compared to the negative controls (see table 19). VH sequences of KnotBodies present in these wells are shown in Table 20. This example demonstrates the use of a VH domain specific to a receptor (i.e. TFR) involved in macromolecule transport into the brain to deliver a Knottin-VL fusion with a different specificity (trypsin binding in this example). The same approach could be used to generate functional Knottin-VL fusions that can modulate the activity of targets that are expressed in the brain (e.g. ion channels inside central nervous system, proteases such as BACE). The level of transcytosis observed can be further improved by optimising the VH domain specificity and/or affinity using methods known to those skilled in the art.

Example 14: Comparison of a KnotBody and a Bovine Antibody with a Natural "Ultra Long VH CDR3 (Cow ULVC-Ab) Presenting a Knottin Insertion (EETI-II Cow ULVC-Ab)

Figure 25:
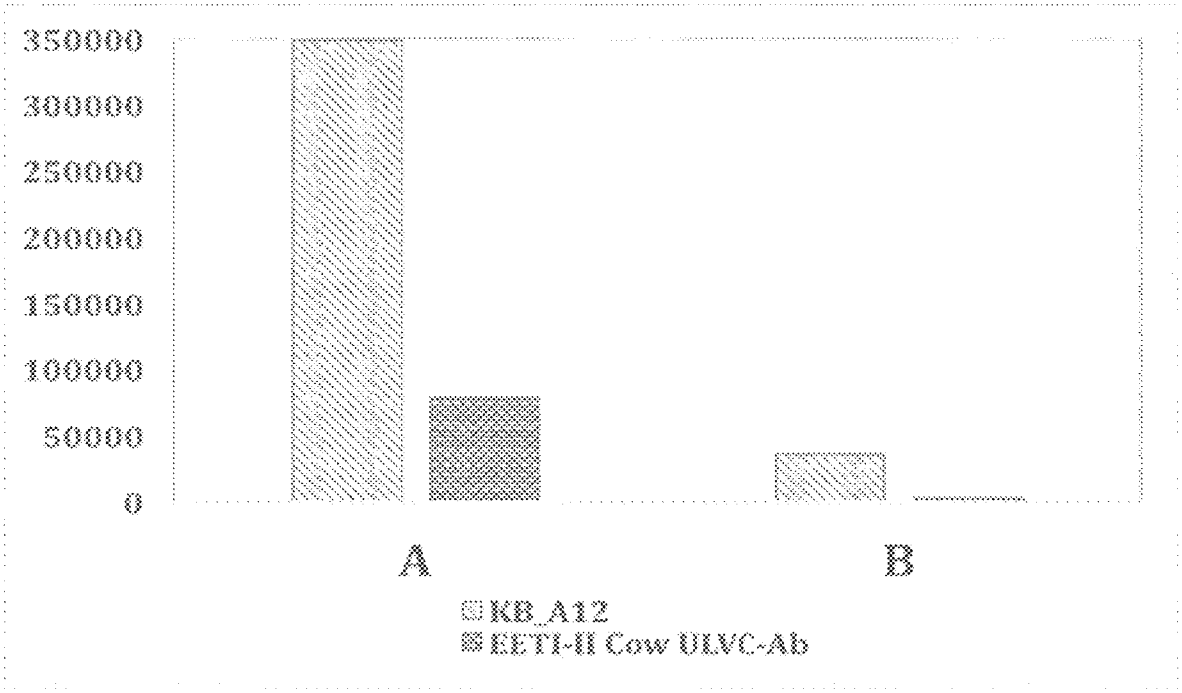
FIG. 25 shows the binding comparison of KnotBody KB_A12 and a format consisting of a bovine antibody with a natural "ultra long VH CDR3 ("cow ULVC-Ab"). The cysteine rich knob of the cow ULVC-Ab was replaced by the EETI-II knottin ("EETI-II cow ULVC-Ab"). Genes encoding these constructs were cloned into pSANG4 and phage rescued from either KB_A12 or the EETI-II cow ULVC-Ab fusion constructs (X-axis) and was PEG precipitated. 12.5× (A) and 0.5× (B) phage (relative to the initial culture volume) were tested for binding against biotinylated trypsin immobilised on streptavidin coated Maxisorp™ plates. Phage binding to trypsin was detected using an anti-M13 antibody followed by europium conjugated anti-mouse antibody. Y axis shows the phage binding signal in fluorescent units (FU).

Bovine antibodies have been described with natural ultra-long VH CDR3s containing a solvent exposed double stranded antiparallel sheet approximately 20 A° in length (referred to as the stalk) presenting a folded domain stabilised by 3 disulphide bonds (referred to as the Knob)[10]. Zhang and colleagues have shown that the Knob domains of these cow ultra-long VH CDR3 antibodies (ULVC-Ab) can be replaced with other folded proteins such as erythropoietin[13]. In this example, we assess the ability of a cow ULVC-Ab to present functional knottin fusions on phage in comparison with a KnotBody. In order to create a Knottin-cow UCLA fusion, the sequence between the first and the last cysteines of the knob region of the Cow ULVC-Ab BLV1 H12 was replaced with the sequence of the trypsin binding knottin; EETI-11 (EETI-11 cow ULVC-Ab). A gene fragment encoding this construct was synthesised (Integrated DNA technologies, Table 21). This synthetic gene was cloned into the phage display vector pSANG4 using restriction sites NcoI and NotI and transformed into *E. coli* TG1 cells. The performance of the Knottin-Cow ULVC-Ab fusion was then compared to the KnotBody KB_A12 (which presents the knottin EETI-II as VL CDR2 fusion) using a trypsin binding assay. In this assay, the binding of phage rescued from EETI-II cow ULVC-Ab and KB_A12 to trypsin was detected using an anti-M13 antibody followed by europium conjugated anti-mouse antibody (as described in example 3). The KnotBody KB_A12 exhibited superior binding to trypsin compared to the EET-11-Cow ULVC-Ab fusion (FIG. 25).

Example 15. Functional Display of KnotBodies on the Surface of Mammalian Cells In examples 1, 2, 3, 5, 6, 9, 12 and 13 phage display technology was employed to enable the display of KnotBodies or derivative libraries and their selection. As an alternative to phage display, display of binders has been carried out on bacterial, yeast and mammalian cells. In these methods, it is possible to use flow sorting to measure binding and expression of the binding molecule as well as binding to target. Thus, the display of libraries of KnotBodies on the surface of cells e.g. mammalian cells will enable the screening and selection of tens of millions of clones by fluorescent activated cell sorting (FACS) for increased affinity to the target and expression level in their final scFv-Fc, Fab or IgG format. Methods for constructing and using display libraries in other systems are known to those skilled in the art.

Figure 26:
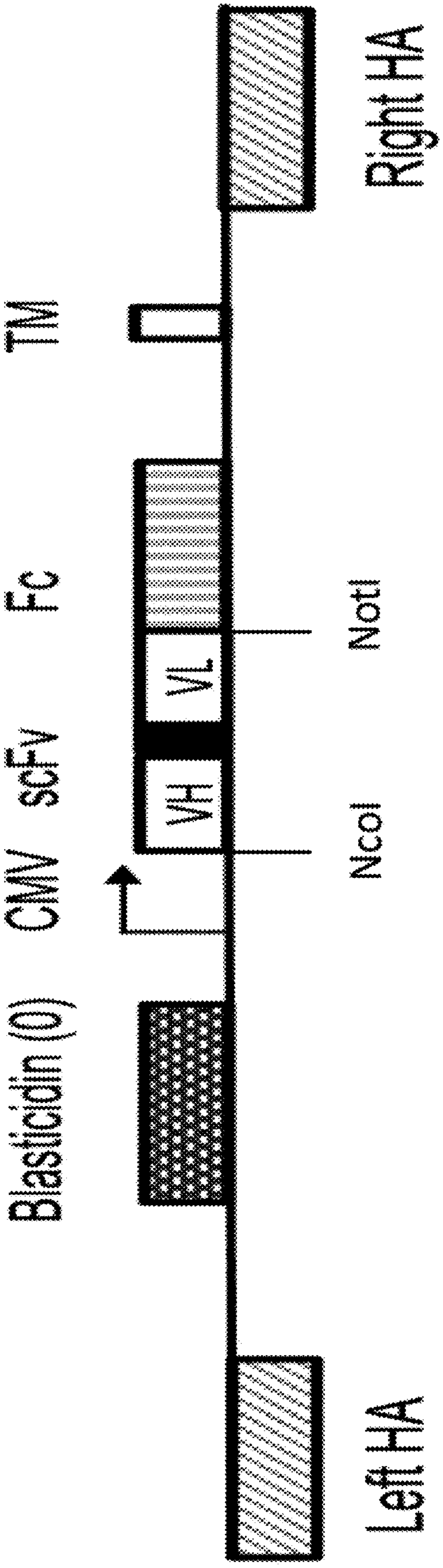
FIG. 26 shows a schematic representation of the mammalian display vector pD6. Antibody genes are targeted to the human AAVS locus which is located within a 4428 bp intron between the first and second exons of the gene encoding protein phosphatase 1, regulatory subunit 12C, PPP1R12C. A pair of Tale nucleases directed to this region are used to cleave the genome at this site. 700-800 bp of the sequences on the 5' and 3' site of the cleavage site are incorporated into donor vectors as left and right homology arms (HA) respectively. The pD6 donor vector is used to insert antibody genes formatted as single chain Fv (scFv) fused with the Fc region of human IgG1. The vector also has a CMV promoter driving expression of the scFv-Fc gene and an exon encoding the transmembrane domain from the "Platelet derived growth factor receptor (PDGFR-TM). The transgene region encoding the scFv-Fc antibody fusion is flanked by left and right homology arms (left HA, right HA) representing the sequences which flank the cleavage site in the AAVS locus. The vector also encodes a promoter-less blasticidin gene which becomes activated by in-frame splicing to exon 1 within the AAVS locus.

Libraries of KnotBodies, (e.g. within recipient, donor, linkers or partner domains) may also be used for direct functional screening for altered cellular phenotypes in mammalian cells as described above. Thus, libraries of displayed or secreted KnotBodies in mammalian cells may provide an efficient route to discovery of the drug candidates or lead molecules. Methods for the construction of libraries in mammalian cells by nuclease directed integration are provided, for example, in WO2015166272 and the references cited therein, all of which are incorporated herein by reference. In this example, we demonstrate that it is possible to display a membrane anchored KnotBody scFv-Fc on the surface of mammalian cells. This was achieved by cloning the KnotBodies KB_A07 and KB_A12 scFv into the targeting vector pD6 (FIG. 26), performing nuclease mediated gene integration into HEK293 cells followed by flow cytometry analysis. The flow cytometry results showed that expression was achieved when staining with labelled anti-Fc and that the displayed knottin was correctly folded because staining was also achieved with fluorophore-labelled trypsin.

The KnotBody genes KB_A07 and KB_A12 were prepared for insertion into a mammalian display vector in a way that can be modified to create linker libraries. 3 fragments were produced and assembled by PCR using overlap at the boundaries to drive the association. In an N terminal to C terminal direction fragment 1 consists of a PCR product encoding the N terminal part of the scFv gene up to the donor insertion point (encoding in this case Nco1 site, entire VH, scFv linker, FW1, CDR1, FW2, overlap). Fragment 2 consists of overlap, incoming knottin donor, overlap. Fragment 3 consists of overlap, FW3, CDR3, FW4 Not 1 site). Description of potential linker sizes and sites are given below. The position of the overlap can be chosen but will typically be homologous to the antibody framework or the donor coding region (allowing diversity to be introduced in one or other fragment internally to the overlap. In examples below the fragments include between 18 to 27 nucleotide homology overlaps to enable their assembly and amplification by PCR. The final scFv product, encompassing the donor is generated by a 3-fragment assembly. This 3-fragment assembly approach is described in detail using the parental KnotBody (without diversification).

Primers described are listed in Table 22. KB_A07 scFv fragment 1 (569 bp) was created by PCR with forward primer 2985 and reverse primer 2999 and DNA template pIONTAS1 harbouring the KB_A07 gene. KB_A07 scFv fragment 2 was created by PCR with primers 2979 and 2980 in the absence of template. Here the primers simply annealed and extended to yield the 137 bp KB_A07 fragment 2. KB_A07 scFv fragment 3 (170 bp) was created by PCR with forward primer 3000 and reverse primer 2995 and DNA template pIONTAS1 harbouring the KB_A07. KB_A12 scFv fragment 1 (572 bp) was created by PCR with forward primer 2985 and reverse primer 3003 and DNA template pIONTAS1 harbouring the KnotBody A12. KB_A12 scFv fragment 2 was created by PCR with primers 2983 and 2984 in the absence of template. Here, the primers simply annealed and extended to yield the 137 bp A12 fragment 2. KB_A12 scFv fragment 3 (179 bp) was created by PCR with forward primer 3004 and reverse primer 3002) and DNA template pIONTAS1 harbouring the KB_A12. Fragments 2 and 3 were gel purified and fragment 1 was purified by spin column. The three fragments were then combined (100 nM each in 10 mM Tris-HCl (pH8)) in a total volume of 10 μl, To this was added 10 μl of KOD Hot Start Master Mix (Merck Millipore, catalogue number 71842). The fragments were then assembled by incubation at 95° C. for 2 minutes followed by 20 cycles of 95° C. (20 s), 60° C. (1 min, 40 s) and 70° C. (30 s). 1 μl of this assembly reaction product was then used as a template in a PCR reaction mix with the outer primers 2985 and 2995 (A07) or 2985 and 3002 (A12). The assembled PCR products encoding the KB_A07 and KB_A12 scFv genes were then digested with NcoI and NotI, gel purified and cloned into the mammalian display targeting vector pD6 (FIG. 26) pre-digested with the same enzymes. Transfection quality plasmid DNA was prepared using the NucleoBond Xtra Midi plus kit (Macherey Nagel, Cat. No. 740412.50).

Electroporation is an efficient way of introducing DNA into cells and the protocols developed by Maxcyte combine high efficiency transfection of mammalian cells combined with high cell viability. HEK293 cells were centrifuged and re-suspended in a final volume of $10^8$ cells/ml in the manufacturer's electroporation buffer (Maxcyte Electroporation buffer, Thermo Fisher Scientific Cat. No. NC0856428)). An aliquot of $4\times10^7$ cells (0.4 ml) was added to an OC-400 electroporation cuvette (Maxcyte, Cat. No. OC400R10) with 88 μg DNA (i.e., 2.2 μg/$10^6$ cells). The DNA mix consisted of 80 μg of plasmid DNA encoding AAVS-SBI TALENs (pZT-AAVS1 L1 and pZT-AAVS R1 Systems Bioscience Cat. No. GE601A-1) as an equimolar mix and 8 μg of the "donor" plasmid pD6 DNA encoding the KB_A07 or KB_A12. Control electroporations were also performed where the TALEN or donor DNA was replaced by pcDNA3.0. Electroporations were performed according to the manufacturer's instructions (Maxcyte). 2 days after transfection (2dpt) blasticidin selection was initiated (5 μg/ml). After 13 days (15 dpt) cells were analysed by flow cytometry for scFv-Fc expression using an anti-Fc phycoerythrin (PE) labelled antibody. The presence of correctly folded knottin was detected by staining the cells with biotinylated trypsin pre-conjugated with allophycocyanin (APC) labeled streptavidin. Analysis was focused on viable cells using forward scatter and 7AAD staining in the FL3 channel. Cells positive for staining in the FL3 channel (representing non-viable cells which took up 7-AAD) were excluded.

Purified trypsin was biotinylated using EZ-Link Sulfo-NHS-LC-Biotin kit (Pierce Cat. No. 21327) according to manufacturer's instructions. Biotinylated trypsin (1.25 μl, 0.1 mg/ml, 4.3 μM) and streptravidin-APC (Molecular Probes, Cat. No. SA1005, 1 μl, 0.2 mg/ml, 3.8 μM) were pre-incubated in PBS/1% BSA (100 μl) for 30 min at room temperature. Cells ($10^6$) per sample, pre-washed with PBS, were re-suspended in the biotinylated trypsin/streptavdin-APC mix prepared above and to this was added anti-human Fc-PE (BioLegend, Cat #409304, 200 μg/ml, 0.5 μl) and incubated for 30 minutes at 4° C. The cells were washed twice in PBS/0.1% BSA, re-suspended in PBS/0.1% BSA containing 7-AAD Viability Staining Solution (eBioscience, Cat #00-6993-50 and analysed using a flow cytometer (Intellicyt iQUE screener).

Figures 27A, 27B, 27C:
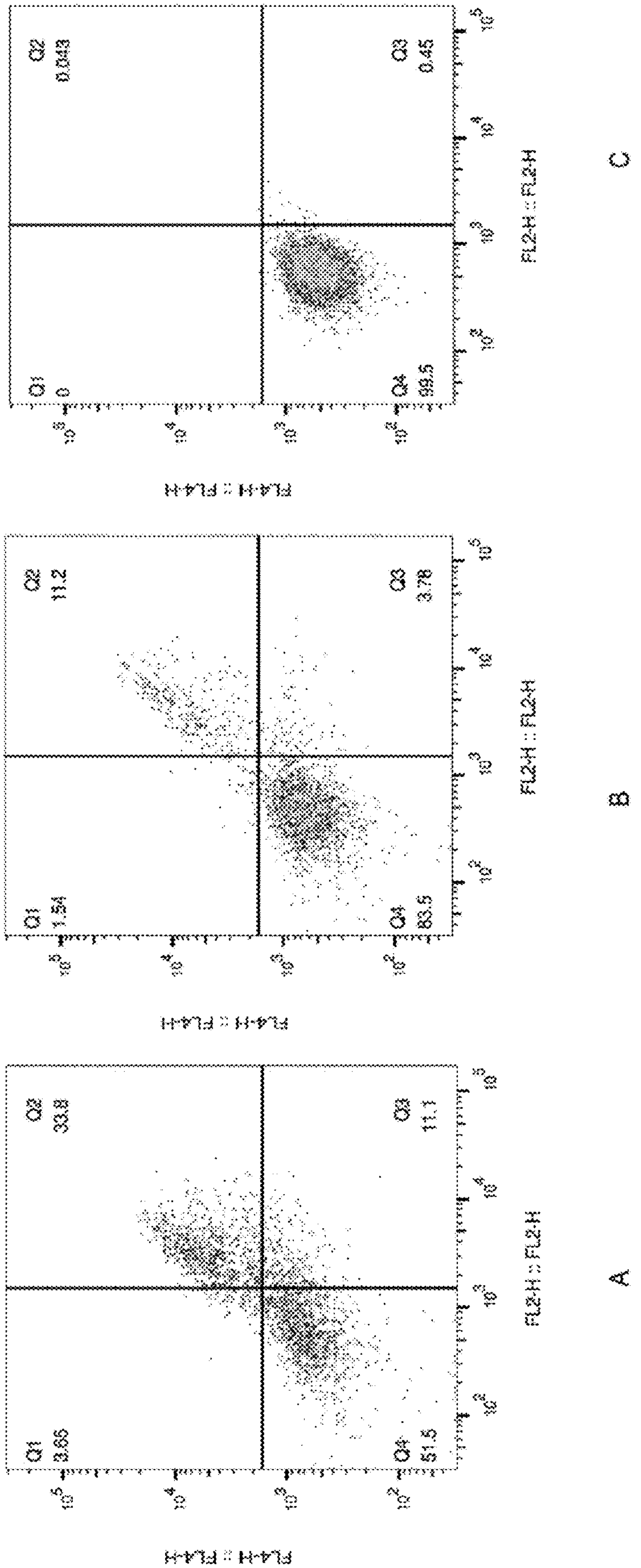
FIG. 27 shows the functional expression of KnotBodies on the cell surface. All cells were stained with PE labelled anti-Fc (FL2 channel) and APC labelled streptavidin/biotinylated trypsin complex (FL4 channel). Following transfection cells were selected in blasticidin and analysed by flow cytometry at 15 days post transfection. Panels show the results for (A) KB_A07 (B) KB_A12 or (C) untransfected HEK293 cells.
Figure 30A:
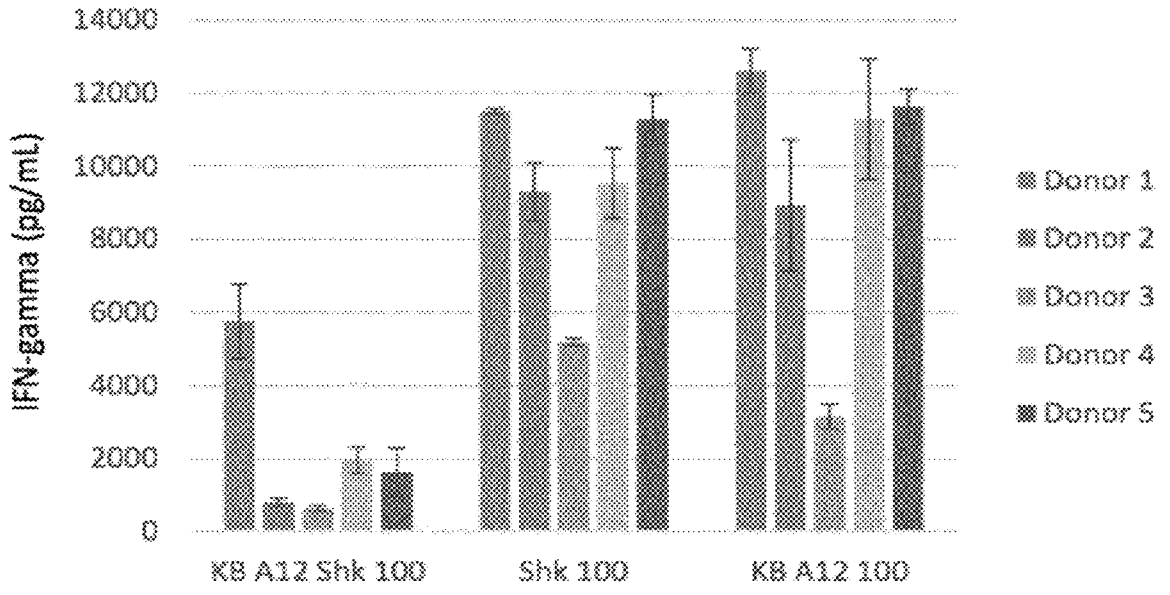
FIG. 30 shows that a KnotBody comprising a Kv1.3 blocking donor domain (Shk) reduces cytokine secretion in T cells. PBMCs were activated with an anti-CD3 antibody and were co-incubated with a KnotBody in which the donor diversity domain is either Shk (KB_A12_Shk) or EET (KB_A12). Free Shk is also used as a positive control. Graphs show the levels of Interferon gamma (IFNγ) (FIG. 30A); Granzyme (FIG. 30B), Interleukin 7A (IL17A) (FIG. 30C), and TNF-alpha (FIG. 30D) following T cell activation in PBMCs.
Figure 30B:
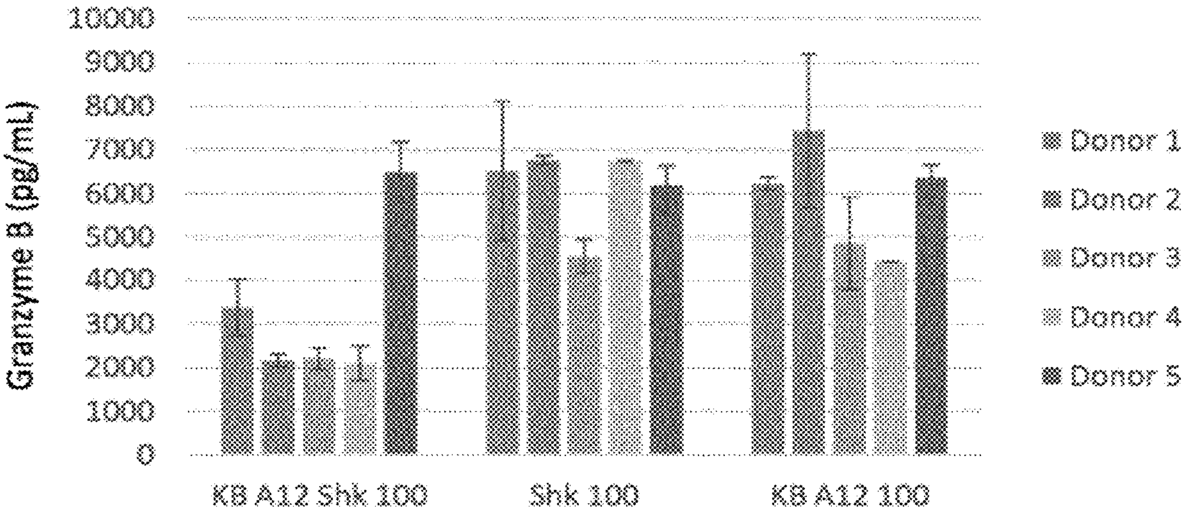
Figure 30C:
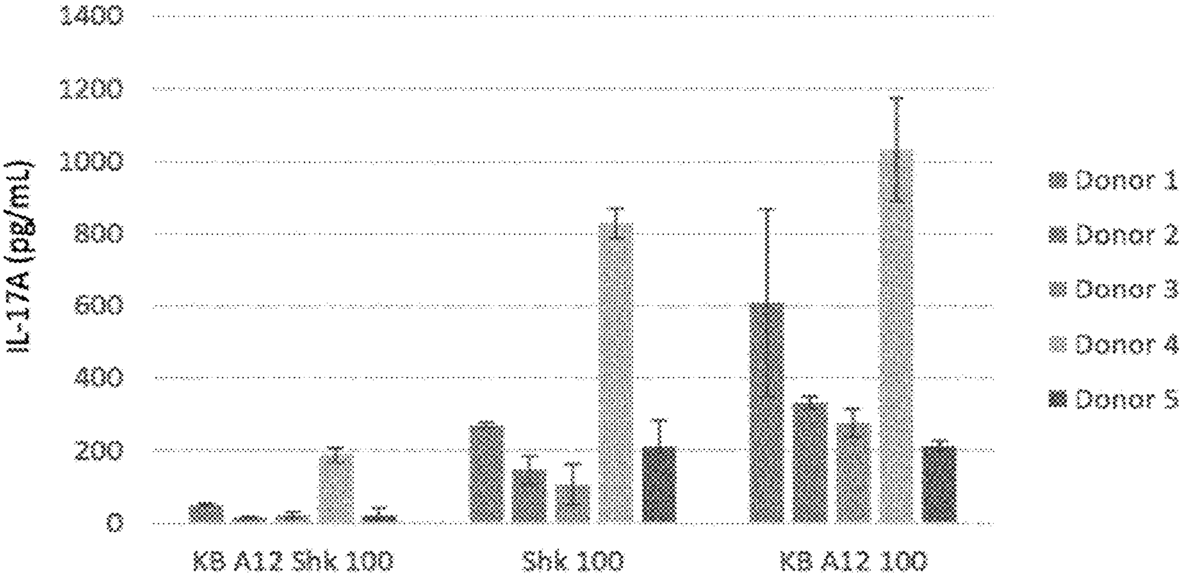
Figure 30D:
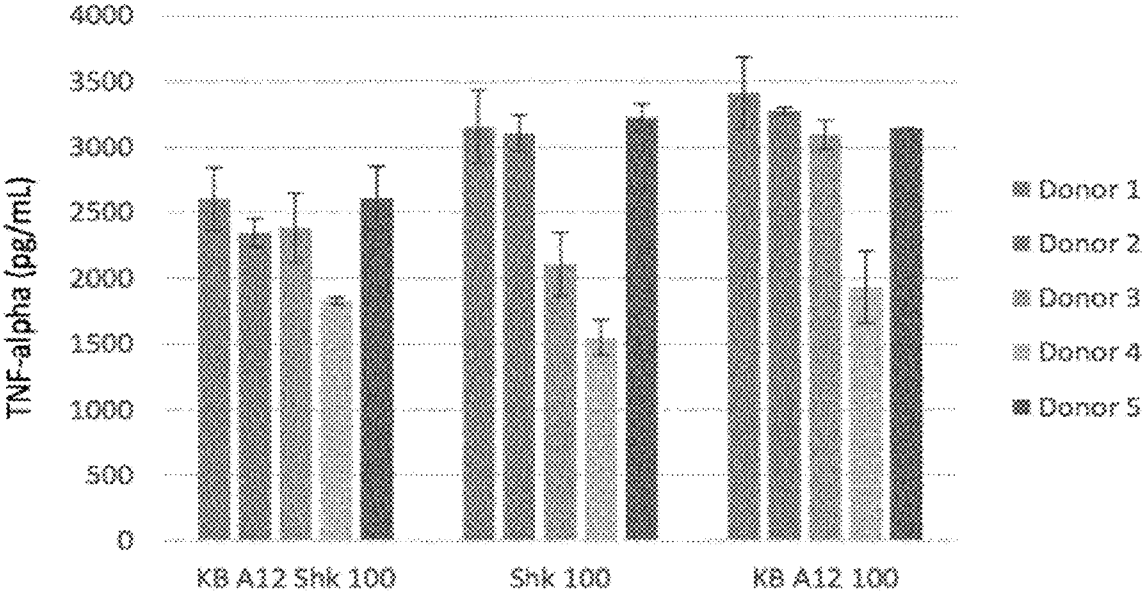

FIG. 27 shows that after 13 days of blasticidin selection (15 dpt), 34% and 11% of the KB_A07 and KB_A12 transfected HEK293 cells were dual stained for Fc and trypsin. No staining of untransfected HEK293 cells was observed. This demonstrates that it is possible to display membrane tethered KnotBodies on the surface of mammalian cells where the knottin donor is correctly folded.

Example 16. Insertion of Knottins into Antibody VH CDR1, VH CDR2, VH CDR3, VL CDR1, VL CDR2 and VL CDR3, with Variable Linker Sequences, their Display on Phage and Selection of Functional KnotBodies Examples 1, 2 and 3 demonstrated knottin insertion into antibody VL CDR1 and VL CDR2, display of the resultant KnotBody on the surface of phage and the selection of functional knotbodies. In Examples 1, 2 and 3 libraries were created where variable fusion sequences were introduced between the donor and recipient which were then selected by phage display and screened to identify the optimal fusion sequences for the display of functional knottins. This identified short linker sequences, which were superior to long flexible linkers for the display of functional knottins, as described in Example 11. Insertion of a knottin into VL CDR1 or VL CDR2 enables additional binding contributions from VL and VH CDRs. For some applications there may be an advantage in alternative configurations where the knottin is inserted into alternative CDRs on either VH or VL. It is likely, as described in Example 3, that only a fraction of variable fusion sequences, linking the donor knottin, to each CDR enable the functional display of knottins. To demonstrate that it is possible to display functional knottin in all the antibody CDRs, variants of D1A12 formatted as a scFv (Tape, C. J. et al. (2011) PNAS USA 108, p 5578-5583), were designed with knottin insertions in VH CDR1, VH CDR2, VH CDR3, VL CDR1, VL CDR2 and VL CDR3 where the two codons flanking the knottin were randomised to enable the creation of "linker library" knottin constructs as shown in FIG. 28. The sequence of the parental anti-TACE scFv[101] is shown in Table 23. In addition, a linker library was created for KB_A07 where the EETI-II donor knottin was inserted into VL CDR2 as shown in FIG. 28. The inserts encoding the knottins, with randomised linker sequences, inserted into each of the six CDRs of D1A12, and a linker library of KB_A07 where the knottin with randomised flanking amino acids was inserted into VL CDR2, was created by a three fragment assembly as described in Example 15, using standard molecular biology techniques known to those skilled in the art e.g. Schofield et al 2007[28]. Phage display libraries were created by cloning into the phage display vector pSANG4 (Schofield et al, 2007), phage rescued, as described in Example 3, selected for binding to trypsin and monoclonal phage ELISA was performed with individual clones. Positive clones were obtained demonstrating that functional display of knottin is possible within all the CDR loops in both the antibody variable heavy and light chains.

The strategy and methodology for the preparation of the scFv knottin linker library inserts by a three fragment PCR assembly is detailed in Example 15 and the primers to create the inserts are listed in Tables 22 and 24. The primer pairs required to create the three fragments for each of the libraries, the DNA template (if required) and product sizes are listed in Table 25 and the method to prepare and purify the individual inserts is described in Example 15. The three fragments for each of the libraries A to G, listed in Table 25, were then combined in an equimolar ratio (e.g. fragments A1, A2 and A3 were combined to create library A) and assembled as described in example 15. It was possible to create fragment E (where diversification was near the end of the scFv gene) using a 2 fragment assembly. The products were amplified by PCR with the forward primer 2985 and either reverse primers D1A12 NotI Rev (libraries A to F) or 2995 (library G). The assembled PCR products encoding libraries A to G were then digested with NcoI and NotI, gel purified and ligated into the phage display vector pSANG4 (pre-digested with the same enzymes) and the ligated product electroporated into *E. coli* TG1 cells (Lucigen, Cat. No. 60502-2) as described in Example 2. Library sizes of between 0.7 to $1.6\times10^{8}$ were achieved. Phage was rescued from the libraries as described in Example 3 to create seven libraries: library A (knottin linker library inserted into D1A12 VH CDR1); library B (knottin linker library inserted into D1A12 VH CDR2); library C (knottin linker library inserted into D1A12 VH CDR3); library D (knottin linker library inserted into D1A12 VL CDR1); library E (knottin linker library inserted into D1A12 VL CDR2); library F (knottin linker library inserted into D1A12 VL CDR3); and library G (knottin linker library inserted into KB_A07 VL CDR2).

To isolate functional knottin-antibody fusions, each of the knottin-antibody linker phage display libraries A to G, described above, were subject to two rounds of phage display selection with biotinylated trypsin as described in Example 3. Individual clones (46 per selection) were picked into 96 well culture plates, phage produced and the phage supernatant from each clone was tested for binding to biotinylated trypsin immobilised on Streptavidin coated Maxisorp™ plates with binding detected using a TRF assay as described in Example 3 (using a coating concentration of biotinylated trypsin of 2.5 μg/ml). The ELISA signals on each 96-well plate were background subtracted with the signal obtained from the average of two negative control readings on the same plate where no phage was added to the well. Specificity for trypsin was confirmed by lack of binding to Streptavidin coated Maxisorp™ in the absence of added trypsin. Screening of clones picked from the unselected knottin linker antibody libraries C, E and G gave 0%, 1% and 32% positive clones respectively indicating that a limited proportion of library members are capable of displaying a functional knottin donor. The hit-rates of clones obtained after phage display selection and monoclonal phage ELISA for libraries A, B, C, D, E, F and G was 11%, 17%, 28%, 4%, 74%, 24% and 93% respectively, demonstrated an enrichment for KnotBodies that display a functional knottin.

Positive clones were sequenced to determine the flanking linker sequences that enabled the display of functional knottins with VH CDR1, VH CDR2, VH CDR3, VL CDR1, VL CDR2 and VL CDR3. The sequences of the linkers sequences identified are listed in Tables 26 and 27. Examples of functional KnotBodies with unique linker sequences were isolated (Table 26) thus demonstrating the insertion of functional knottins into antibody VH CDR1, VH CDR2, VH CDR3, VL CDR1, VL CDR2 and VL CDR3.

Example 17. Alternative Framing of Knottins Inserted into Antibody VL CDR1 and VL CDR2 Domains In the examples above the native N terminus and C terminus of cys-rich peptides (hereafter referred to as knottins irrespective of structure and disulphide bond pattern) are inserted into an antibody CDR residues in a way that retains the natural linear sequence of the knottin with native N and C termini fused to the antibody frameworks. Alternative "framing" strategies between the recipient antibody and donor knottin are possible however and this is exemplified here. In the following description, the sequences between sequential cysteines in the donor are referred to as "loops" and are numbered 1-5 based on their natural order. For example loop 1 extends between the first cysteine and the second cysteine. Loop 5 extends between the $5^{th}$ and $6^{th}$ cysteine. Some cysteine-rich peptides, such as cyclotides are found in a cyclic form where the N and C termini are joined by a peptide sequence. For example MoCoT can be found in a "linear" form (i.e. with free N and C termini) or a cyclic form. The additional peptide sequence joining the first (N terminal) and $6^{th}$ (C terminal) cysteine in the cyclic form is referred to as "loop 6" (Jagadish et al, (2010) Peptide Science 94 p 611-616) and is used in the examples below to join the original N and C termini.

From one perspective the N and C termini of the donor knottin in a KnotBody are joined by an antibody which might be considered the equivalent of "loop 6" "joining" the N and C terminal cysteines in a cyclic knottin. From that same perspective one could consider alternative "framings" where the antibody replaces alternative loops. In this arrangement the native N and C termini of the donor could be linked by an additional "loop 6" peptide as found in cyclic MoCoTI-II. These alternative framing strategies would allow variation in the juxtaposition of different loops relative to the antibody recipient with potential benefits in creation of optimal bi-specific orientations and in engineering strategies e.g. improving affinity or specificity through contact of both donor and recipient with target proteins or complexes. The effective "rotation" of the donor relative to the recipient could increase availability of certain critical loops eg the trypsin binding loop in EET 5-3 is moved to a more central location within the donor relative to EET 1-5 (see below). The addition of an alternative "loop 6" further increases the possibilities for additional contact with target proteins. Finally such framing alternatives could provide superior expression or folding compared to the native KnotBody construct in some cases.

When a knottin is inserted in its native configuration as described in earlier examples the N terminal segment of the antibody recipient is followed by the first cysteine and loop 1 of the donor knottin. The donor ends at loop 5 followed by the terminal cysteine. In the nomenclature adopted here this is referred to as a "1-5" configuration, representing the order of knottin loops 1, 2, 3, 4, 5. In this case the antibody may be considered as the equivalent of loop 6 of a cyclic knottin. Table 28 illustrates different potential strategies for altering the framing between a knottin and antibody. In Table 28, the natural loop 1 is underlined in each case. The original N and C termini of EETI-II are joined to create "loop 6" and the peptide sequence of loop 6 of MoCOTI-II is used (represented in italics). A more detailed representation of the arrangement of loops in the EET_5-3 configuration is given in FIG. 29A. This shows that in alternative configuration EET_5-3 the order of loops is loop 5, 6, 1, 2 and 3 (with the antibody "replacing" loop 4).

To exemplify selection of knottins inserted in an alternative frame, a knottin donor with framing in a EET_5-3 configuration was fused into either the CDR1 or CDR2 position of either kappa or lambda VL domains. This was done by replacing residues within the VL recipient with random amino acids in a way that limited the number of added amino acids between the 2 domains (FIG. 29B).

Insertion of Knottins with Modified Framing into CDR1

A synthetic EETI-II Knottin donor gene with 5-3 framing was made and was used to replace the CDR1 positions in the light chain recipient by creating a PCR fragment with Pml1 and Mfe sites (which were introduced by PCR) and cloning into pIONTAS1_KB_Kappa and pIONTAS1_KB_lambda. Framework and CDR designations are as described by the International Immunogenetics Information System (IMGT)[29]. The PCR primers also introduced variable amino acid sequences between the restriction sites and the knottin gene. The PCR primers Pml5-3EETa and Pml5-3EETb each introduced 3 variable codons encoded by the sequence VNS (V=A, C or G, N=A, C, G or T, S=C or G) immediately after the Pml restriction site. The "VNS" degenerate codons encode 16 amino acids (excluding cysteine, tyrosine, tryptophan, phenylalanine and stop codons) at each randomised position from 24 codon combinations. Pml5-3EETb also introduces an additional glycine residue between donor and recipient compared to Pml5-3EETa.

Pml5-3EETa
(SEQ ID NO: 79)
GTGT VNS VNS VNS TGC GGT CCG AAC GGC TTC TGC

Pml5-3EETb
(SEQ ID NO: 80)
GTGT gga VNS VNS VNS TGC GGT CCG AAC GGC TTC TGC

The 5' end of these sequences represents the site created by Pml1, a restriction enzyme recognising the sequence "CACGTG" to create a blunt end. To facilitate blunt end cloning of the PCR product primers with 5' phosphorylated termini were synthesised.

At the 3' end of the knottin gene the antisense primers 5-3EETMfe (encoding an Mfe1 site) was used to amplify the 5-3 frame of EETI-II. The Mfe1 site used for cloning encodes the 2 and 3rd amino acids of FW2 (Asn-Trp). This primer introduces 2 random amino acids encoded by VNS or VNC codons followed by an Mfe1 site (underlined).

5-3EETMfe
(SEQ ID NO: 81)
GTCAGTCCAATTGNBSNBGCAGCCGGCCAGGCAGTCTGA

FIG. 29C depicts the sequence following insertion of a 5-3 formatted EETI-II into CDR1 of the lambda light chain IGKV1D-39 using primer Pml5-3EETa. A repertoire of light chain fragments encompassing Framework 2-framework 4 was also cloned after the knottin donor as previously described in example 2 using restriction sites Mfe1 and Not1 (underlined).

Insertion of Knottins into CDR2

The knottin donor was introduced into the CDR2 positions of pIONTAS1_KB_lambda and pIONTAS1_KB_Kappa by creating a PCR fragment with Pst1 and BspE1 sites which were introduced by PCR. It was possible to introduce a Pst1 site into the first two residues of the CDR2 region of the IGKV1 D-39 V kappa gene (within the Ala-Ala sequence). For convenience in cloning the same restriction site and encoded residues were introduced at the end of framework 2 of the V lambda germline gene IGLV1-36. In the lambda germline it was also possible to introduce a BspE1 site into the 4th and 5th residues of the FW3 region encoding Ser-Gly) (FIG. 3E). Again this restriction site and encoded amino acids were also introduced into the V kappa gene (FIG. 3F).

The PCR primers PST5-3EETa was used to amplify EETI-II and introduces 2 Ala codons encompassing a Pst1 site for cloning (underlined) followed by 2 variable codons encoded by the sequence GNS (encoding Val, Ala, Asp or Gly) and VNS (encoding 16 amino acids within 24 codons) immediately after the Pst1 restriction site and preceding the knottin sequence. The VNS codon replaces the first amino acid of EETI-II with the net effect of adding 3 amino acids (2 Ala residues and one of Val, Asp, Ala or Gly) between the donor and recipient framework (FIG. 29 B, D).

PST5-3EETa
(SEQ ID NO: 82)
ATC TAT GCT GCA GNS VNS TGC GGT CCG AAC GGC TTC TGC

At the 3' end of the incoming knottin donor, The PCR primers 5-3EETBse was used to amplify the 5-3 framed EETI-II. This introduces a BspE1 site for cloning. The PCR product introduces the knottin donor followed by the glycine which naturally follows the last cysteine of EETI-II (FIG. 3*a*). This is followed by 2 randomised amino acids which adjoin to the 4th and 5th amino acids of FW3 after cloning. This has the effect of replacing the first three residues of FW3 with two randomised amino acids and retains the terminal glycine of the knottin (FIG. 3B).

5-3EETBse
(SEQ ID NO: 83)
GTCAGAGACTCCGGASNBSNBCCCGCAGCCGGCCAGGCAGTCTGA

A repertoire of light chain fragments encompassing Framework 3-framework 4 was also cloned after the knottin donor as previously described in example 2.

FIG. 29D depicts the sequence following insertion of a 5-3 formatted EETI-II into CDR2 of the lambda light chain IGKV1D-39 using primer 5-3EETBse. A repertoire of light chain fragments encompassing Framework 3-framework 4 was also cloned after the knottin donor as previously described in example 2 using restriction sites BspE1 and Not1.

Using standard molecular biology techniques known to those skilled in the art e.g. Schofield et al 2007[28], constructs (as depicted in FIGS. 29B, C and D)) were created using gene fragments created as described above. These were cloned into pIONTAS1_KB_Kappa" and "pIONTAS1_KB_lambda and were electroporated into *E. coli* TG1 cells and KnotBody library sizes of 3.5-6.6×$10^8$ members were constructed Following selection on trypsin, as described in example 3, positive clones were identified by monoclonal phage ELISA and their sequences determined. Examples of positive clones in CDR1 or CDR 2 of kappa and lambda light chains are shown in Table 29 with the linker sequences shown in lower case and the knottin donor in a 5-3 frame shown in italics. Also shown is the value of ELISA signal attained from monoclonal phage ELISA. The specificity of interaction was further confirmed by mutating the pair of Proline-Arginine residues involved in interaction with trypsin to alanine-alanine which diminished binding (as described in example 3).

Example 18: Evaluating the Immunomodulatory Function of Anti-Kv1.3 KnotBodies Kv1.3 plays a key role in maintenance of calcium signalling following activation of T cell receptors thereby modulating T cell activation, proliferation and cytokine release in effector memory T ($T_{EM}$) cells. $T_{EM}$ cells play an important role in the pathogenesis of T lymphocyte mediated autoimmune diseases and so blockade of Kv1.3 activity represents a potential point of therapeutic intervention.

Example 7 describes the generation of Kv1.3 blockers by replacing the trypsin binding knottin EETI-II at the CDR2 position of KnotBodies KB_A07 and KB_A12 with the cysteine rich miniproteins Shk or Kaliotoxin (naturally occurring Kv1.3 blockers from sea anemone venom and scorpion venom respectively). Example 8 demonstrates the blocking activity of these KnotBodies on Kv1.3 determined by electrophysiology. In this example, we assess the ability of KB_A12 Shk to modulate the cytokine secretion by activated T cells.

Methods for measuring cytokine release from T cells are well known to those skilled in the art (eg Tarcha et al, (2012) J Pharmacology and Experimental Therapeutics, 342 p 642-653). Peripheral blood mononuclear cells (PBMCs) were isolated from 5 healthy donors and were simulated by culturing in 96-well plates pre-coated with 500 ng/ml of the anti-CD3 antibody OKT3 (ebioscience, Cat. No. 16-0037-85). PBMCs were suspended at $2\times10^6$ cells/ml and 100 ul of cells suspension mixed with 100 ul of test sample (KB_A12_ShK) or positive control (free Shk toxin, Alomone labs, STS-400) or negative control (parental KnotBody KB_A12) at a final concentration of 100 nM. (Samples were in triplicate for KB_A12_Shk or duplicate for KB_A12 and free Shk). Cells were incubated at 37° C. for 72 hours, centrifuged at 1500 rpm for 5 mins at room temperature before removing 150 ul of supernatant. After 72 hours incubation, the concentration of cytokines and Granzyme-B was determined using a Luminex bead based assay according to manufacturers instructions (Thermo Fisher).

Secretion of Interferon gamma, Granzyme B, interleukin-17A and TNF-alpha was reduced in PBMCs from all 5 different donors when incubated with KB_A12_Shk compared to controls incubated with a control KnotBody (KB_A12) (FIGS. 30A to D). This demonstrates that KB_A12_ShK not only blocks Kv1.3 function as measured by electrophysiology (example 8) but also directly interferes with T cell activation as determined in a T cell functional assay.

TABLE 1

Sequence of unique EETI-II CDR1 and CDR2 KnotBody binders derived from EETI-II CDR1 and CDR2 libraries

| Clone ID | Sequence |
|---|---|
| CDR1_F_10 | QSVLTQPPSVSEAPRQRVTITCGERPCPRILMRCKQDSDCLAGCVCGPNGFCGANNWYQQLPGSSPTTVIYEDNQRPSGVPDRFSGSIDSSSNSASLTISGLKTEDEADYYCQSYDSSNQVFGGGTKVTVLGQP (SEQ ID NO: 84) |
| CDR1_B_01 | QSVLTQPPSVSEAPRQRVTITCGGGRCPRILMRCKQDSDCLAGCVCGPNGFCGTPNWYQQLPGSSPTTLIYEDNQRPSGVPDRFSGSIDSSSNSASLTISGLKTGDEADYYCQSYDSSNQVFGGGTQLTVLGQP (SEQ ID NO: 85) |
| CDR1_F_02 | QSVLTQPPSVSEAPRQRVTITCGSRPCPRILMRCKQDSDCLAGCVCGPNGFCGSHNWYQQLPGSSPTTVIYEDNQRPSGVPDRFSGSIDRSSNSASLTISGLKTEDEADYYCQSYDSSNHRVVFGGGTKLTVLGQP (SEQ ID NO: 86) |
| CDR1_F_05 | QSVLTQPPSVSEAPRQRVTITCGGGRCPRILMRCKQDSDCLAGCVCGPNGFCGTGNWYQQLPGRSPTNVVYEDNQRPPGVSDRFSGSIDSSSNSASLTISGLKTEDEADYYCQSYDSSNQVFGGGTKLTVLGQP (SEQ ID NO: 87) |
| CDR1_C_12 | QSVLTQLPSVSEAPRQRVTITCGRAMCPRILMRCKQDSDCLAGCVCGPNGFCGTGNWYQQHPGKAPKLIIFDVSKRPSGVPDRFSASKSGNTASLTISGLQAEDEADYYCNSYTSSNTWVFGGGTQLTVLGQP (SEQ ID NO: 88) |
| CDR1_G_05 | QSVLTQPPSVSEAPRQRVTITCDRKCPRILMRCKQDSDCLAGCVCGPNGFCGTTNWYQQLPGSSPTTVIYENFQRPSGVPDRFSGSIDSSSNSASLTISGLKTEDEADYYCQSYDSYNQVFGSGTKLTVLGQP (SEQ ID NO: 89) |
| CDR1_C_06 | QSVLTQPPSVSEAPRQRVTITCGRRGCPRILMRCKQDSDCLAGCVCGPNGFCGGDNWYQQHPGSSPTPVIYEDNQRPSGVPDRFSGSIDSSSNSASLTISGLKPEDEADYYCQSHDGSNPWVFGGGTKLTVLGQP (SEQ ID NO: 90) |
| CDR1_A_03 | QSVLTQPPSVSEAPRQRVTITCGGRCPRILMRCKQDSDCLAGCVCGPNGFCGSANWYQQLPDSAPATVIYEDNQRPSGVPDRFSGSIDTSSNSASLTISGLKTEDEADYYCQSYDSSNHWVFGGGTKLTVLGQP (SEQ ID NO: 91) |
| CDR1_D_06 | QSVLTQPPSVSEAPRQRVTITCRGGCPRILMRCKQDSDCLAGCVCGPNGFCGSPNWYQQKPGQAPVLVIYGKNNRPSGIPDRFSGSRSGTPASLTITGAQAEDEADYYCNSRDNDNNHVVFGGGTKLTVLGQP (SEQ ID NO: 92) |
| CDR1_E_08 | QSVLTQPPSVSEAPRQRVTITCGGTGCPRILMRCKQDSDCLAGCVCGPNGFCGSANWYQQLPGSSPTNVIYEDNQRPSGVPDRFSGSIDSSSNSASLTISGLKTEDEADYYCQSNDGTNGVFGGGTKVTVLGQP (SEQ ID NO: 93) |
| CDR1_A_12 | QSVLTQPPSVPEAPRQRVTITCGARPCPRILMRCKQDSDCLAGCVCGPNGFCGASNWYQQLPGSSPTTVIYEDNQRPSGVPDRFSGSIDSSSNSASLTISGLKTEDEADYYCQSYDSINRGVFGGTQLTVLGQP (SEQ ID NO: 94) |
| CDR1_H_03 | QSVLTQPPSVSEAPRQRVTITCGRTGCPRILMRCKQDSDCLAGCVCGPNGFCGTVNWYQQLPGSAPTTVIYEDNQRPSGVPDRFSGPIDSSSNSAPLTISGLKTEDEADYYCQSYDRNNVIFGGGTKLTVLGQP (SEQ ID NO: 95) |

TABLE 1-continued

Sequence of unique EETI-II CDR1 and CDR2 KnotBody binders derived from EETI-II CDR1 and CDR2 libraries

| Clone ID | Sequence |
|---|---|
| CDR1_E_10 | QSVLTQPPSVSEAPRQRVTITCGTRGCPRILMRCKQDSDCLAGCVCGPNGFCGSNNWYQQLPGSSPTTVIYEDNQRPSGVPDRFYGSIDSSSDSASLTISGLETEDEADYFCHSYDSDKWVFGGGTQLTVLGQP (SEQ ID NO: 96) |
| CDR1_E_03 | QSVLTQPPSVSEAPRQRVTITCGGMPCPRILMRCKQDSDCLAGCVCGPNGFCGATNWYQQLPGSSPTTVIYEDNQRPSGVPDRFSGSIDSSSNSASLTISGLKTEDEADYYCQSYDSSNPKVVFGGGTKLTVLGQP (SEQ ID NO: 97) |
| CDR2_D_02 | QSVLTQPPSVSEAPGQRVTITCSGSSSNIGNNAVNWYQQLPGKAPKLLIYAAAKCPRILMRCKQDSDCLAGCVCGPNGFCGTRSGVSDRFSGSKSGTSASLAISGLQSEDEADYYCAAWDDSLSGYVFGTGTKLTVLGQP (SEQ ID NO: 98) |
| CDR2_D_09 | QSVLTQPPSVSEAPRQRVTITCSGSSSNIGNNAVNWYQQLPGKAPKLLIYAADKCPRILMRCKQDSDCLAGCVCGPNGFCGGGSGIPERFSGSKSGTSASLAISGLRSEDEADYYCATWDDNLNGVVFGGGTKLTVLGQP (SEQ ID NO: 99) |
| CDR2_H_09 | QSVLTQPPSVSEAPRQRVTITCSGSSSNIGNNAVNWYQQLPGKAPKLLIYAAVGCPRILMRCKQDSDCLAGCVCGPNGFCGTGSGIPERFSGSKSGNTASLTISGLQAEDEGDYYCAAWDDSLSGPVFGGGTKLTVLGQP (SEQ ID NO: 100) |
| CDR2_F_02 | QSVLTQPPSVSEAPRQRVTITCSGSSSNIGNNAVNWYQQLPGKAPKLLIYAAGRCPRILMRCKQDSDCLAGCVCGPNGFCGARSGIPERFSASKSGTSASLVISGLQSEDEADYYCAAWDDSLNGWVFGGGTKLTVLGQP (SEQ ID NO: 101) |
| CDR2_C_07 | QSVLTQPPSVSEAPRQRVTITCSGSSSNIGNNAVNWYQQLPGKAPKLLIYAAAVCPRILMRCKQDSDCLAGCVCGPNGFCGTRSGIPERFSGSKSGTSAFLAISGLRSEDEADYYCAAWDDSLSGVVFGGGTKLTVLGQP (SEQ ID NO: 102) |
| CDR2_B_07 | QSVLTQPPSVSEAPRQRVTITCSGSSSNIGNNAVNWYQQLPGKAPKLLIYAAARCPRILMRCKQDSDCLAGCVCGPNGFCGHTSGIPERFSGSKSGTSASLAISGLQSEDEADYYCAAWDDSLNGVVFGGGTKLTVLGQP (SEQ ID NO: 103) |
| CDR2_G_05 | QSVLTQPPSVSEAPRQRVTITCSGSSSNIGNNAVNWYQQLPGKAPKLLIYAAGRCPRILMRCKQDSDCLAGCVCGPNGFCGGRSGVSDRFSGSKSGTSASLAISGLQSEDEADYYCAAWDDSLNGYVFGTGTKLTVLGQP (SEQ ID NO: 104) |
| CDR2_H_04 | QSVLTQPPSVSEAPRQRVTITCSGSSSNIGNNAVNWYQQLPGKAPKLLIYAAGRCPRILMRCKQDSDCLAGCVCGPNGFCGANSGVSDRFSAAKSGTSASLAINGLRSEDEADYYCAAWDDSLNGYVFGTGTKLTVLGQP (SEQ ID NO: 105) |
| CDR2_A_01 | QSVLTQPPSVSEAPRQRVTITCSGSSSNIGNNAVNWYQQLPGKAPKLLIYAAEPCPRILMRCKQDSDCLAGCVCGPNGFCGAPSGVPDRFSGSKSGTSASLAITGLQSEDEAHYYCAAWDDSLSAWVFGGGTKLTVLGQP (SEQ ID NO: 106) |
| CDR2_H_07 | QSVLTQPPSVSEAPRQRVTITCSGSSSNIGNNAVNWYQQLPGKAPKLLIYAAAGCPRILMRCKQDSDCLAGCVCGPNGFCGTRSGVSDRFSGSKSGTSASLAISGLRSEDEADYYCAAWDDSLRAYVFGTGTKLTVLGQP (SEQ ID NO: 107) |
| CDR2_B_06 | QSVLTQPPSVSEAPRQRVTITCSGSSSNIGNNAVNWYQQLPGKAPKLLIYAADRCPRILMRCKQDSDCLAGCVCGPNGFCGTDSGIPERFSGSKSGNTASLTISGLQAEDEADYYCAAWDDSLSGPVFGGGTKVTVLGQP (SEQ ID NO: 108) |
| CDR2_F_09 | QSVLTQPPSVSEAPRQRVTITCSGSSSNIGNNAVNWYQQLPGKAPKLLIYAAVICPRILMRCKQDSDCLAGCVCGPNGFCGTGSGVSDRFSGSKSGTSASLAISGLQSEDEADYYCAAWDDSLNGVVFGGGTKLTVLGQP (SEQ ID NO: 109) |
| CDR2_F_11 | QSVLTQPPSVSEAPRQRVTITCSGSSSNIGNNAVNWYQQLPGKAPKLLIYAAERCPRILMRCKQDSDCLAGCVCGPNGFCGGSSGVSDRFSGSKSGTSASLAISGLRSEDEADYYCATWDDNLNGPVFGGGTKLTVLGQP (SEQ ID NO: 110) |
| CDR2_C_02 | QSVLTQPPSVSEAPRQRVTITCSGSSSNIGNNAVNWYQQLPGKAPKLLIYAAVGCPRILMRCKQDSDCLAGCVCGPNGFCGSASGVSDRFSGSKSGTSASLAISGLRSEDEADYYCASWDDSLRGYVFGTGTKVTVLGQP (SEQ ID NO: 111) |
| CDR2_D_08 | QSVLTQPPSVSEAPRQRVTITCSGSSSNIGNNAVNWYQQLPGKAPKLLIYAAGPCPRILMRCKQDSDCLAGCVCGPNGFCGTASGVPDRFSGSKSGTSASLAISGLRSEDEADYYCAAWDDSLSGVVFGGGTKVTVLGQP (SEQ ID NO: 112) |
| CDR2_E_10 | QSVLTQPPSVSEAPRQRVTITCSGSSSNIGNNAVNWYQQLPGKAPKLLIYAAARCPRILMRCKQDSDCLAGCVCGPNGFCGTPSGVPDRFSGSKSGTSASLAISGLQSEDEADYYCAAWDDSLSGYVFGTGTKLTVLGQP (SEQ ID NO: 113) |

TABLE 1-continued

Sequence of unique EETI-II CDR1 and CDR2 KnotBody binders derived from EETI-II CDR1 and CDR2 libraries

| Clone ID | Sequence |
|---|---|
| CDR2_F_05 | QSVLTQPPSVSEAPRQRVTITCSGSSSNIGSNAVNWYQQLPGKAPKLLIYAAGGCPRILMRCKQDSDCLAGCVCGPNGFCGSNSGVPDRFSGSKSGNTASLTISGLQSEDEADYYCAAWDDSLSGVVFGGGTQLTVLGQP (SEQ ID NO: 114) |
| CDR2_G_04 | QSVLTQPPSVSEAPRQRVTITCSGSSSNIGNNAVNWYQQLPGKAPKLLIYAAGMCPRILMRCKQDSDCLAGCVCGPNGFCGGHSGVSDRFSGSKSGTSASLAISGLQSEDEADYYCAAWDDSLNGYVFGTGTQLTVLGQP (SEQ ID NO: 115) |
| CDR2_A_08 | QSVLTQPPSVSEAPRQRVTITCSGSSSNIGNNAVNWYQQLPGKAPKLLIYAAARCPRILMRCKQDSDCLAGCVCGPNGFCGTRSGVSDRFSGSKSGTSASLAISGLQSGDEADYYCAAWDDSLNGWVFGGGTKLTVLGQP (SEQ ID NO: 116) |
| CDR2_E_06 | QSVLTQPPSVSEAPRQRVTITCSGSSSNIGNNAVNWYQQLPGKAPKLLIYAADKCPRILMRCKQDSDCLAGCVCGPNGFCGLTSGVSDRFSGSKSGTSASLAISGLRSEDEADYYCATWDDSLNGVVFGGGTKLTVLGQP (SEQ ID NO: 117) |
| CDR2_B_11 | QSVLTQPPSVSEAPRQRVTITCSGSSSNIGNNAVNWYQQLPGKAPKLLIYAAAKCPRILMRCKQDSDCLAGCVCGPNGFCGGASGVSDRFSGSIDSSSNSASLTISGLKPEDEGDYYCQSYDSSNRWVFGGGTKVTVLGQP (SEQ ID NO: 118) |
| CDR2_G_09 | QSVLTQPPSVSEAPRQRVTITCSGSSSNIGNNAVNWYQQLPGKAPKLLIYAAARCPRILMRCKQDSDCLAGCVCGPNGFCGTTSGVPDRFSGSIDSSSNSASLTISELKTEDEADYYCQSYDSSNQGWVFGGGTKLTVLGQP (SEQ ID NO: 119) |
| CDR2_C_08 | QSVLTQPPSVSEAPRQRVTITCSGSSSNIGNNAVNWYQQLPGKAPKLLIYAAGRCPRILMRCKQDSDCLAGCVCGPNGFCGGGSGVPDRFSGSIDSSSNSASLTISGLRAEDEADYYCQSYDSSNHWVFGGGTKLTVLGQP (SEQ ID NO: 120) |
| CDR2_E_09 | QSVLTQPPSVSEAPRQRVTITCSGSSSNIGNNAVNWYQQLPGKAPKLLIYAAGPCPRILMRCKQDSDCLAGCVCGPNGFCGPRSGVPDRFSGSIDSSSNSASLTISGLKTEDEADYYCQSYDSNNHWVFGGGTKLTVLGQP (SEQ ID NO: 121) |
| CDR2_F_04 | QSVLTQPPSVSEAPRQRVTITCSGSSSNIGNNAVNWYQQLPGKAPKLLIYAAERCPRILMRCKQDSDCLAGCVCGPNGFCGTPSGVPDRFSGSIDTFSNSASLTISGLKTEDEADYYCQSYDSSHHWVFGGGTKLTVLGQP (SEQ ID NO: 122) |
| CDR2_E_05 | QSVLTQPPSVSEAPRQRVTITCSGSSSNIGNNAVNWYQQLPGKAPKLLIYAAGPCPRILMRCKQDSDCLAGCVCGPNGFCGADSGVSDRFSGSKSGTSASLAITGLQAEDEGDYYCAAWDDSLNGLVFGGGTKVTVLGQP (SEQ ID NO: 123) |
| CDR2_D_07 | QSVLTQPPSVSEAPRQRVTITCSGSSSNIGNNAVNWYQQLPGKAPKLLIYAAGRCPRILMRCRQDSDCLAGCVCGPNGFCGTASGVPDRFSGSIDTFSNSASLTISGLKTEDEADYYCQSYDSSNHWVFGGGTKLTVLGQP (SEQ ID NO: 124) |
| CDR2_G_03 | QSVLTQPPSVSEAPRQRVTITCSGSSSNIGNNAVNWYQQLPGKAPKLLIYAAGRCPRILMRCKQDSDCLAGCVCGPNGFCGTNSGIPERFSGSKSGNTASLTISGLQAEDEADYYCQSYDSSLSGWVFGGGTQLTVLGQP (SEQ ID NO: 125) |
| CDR2_A_09 | QSVLTQPPSVSEAPRQRVTITCSGSSSNIGNNAVNWYQQLPGKAPKLLIYAAAPCPRILMRCKQDSDCLAGCVCGPNGFCGAHSGVPDRFSGSIDRSSNSASLTISGLKIEDEADYYCQSYDSSNHVVFGGGTKVTVLGQP (SEQ ID NO: 126) |
| CDR2_D_11 | QSVLTQPPSVSEAPRQRVTITCSGSSSNIGNNAVNWYQQLPGKAPKLLIYAAVRCPRILMRCKQDSDCLAGCVCGPNGFCGTPSGIPERFSGSIDRSTNSASLTISGLKTEDEADYYCQSYDSSNLNWVFGGGTKLTVLGQP (SEQ ID NO: 127) |
| CDR2_C_06 | QSVLTQPPSVSEAPRQRVTITCSGSSSNIGNNAVNWYQQLPGKAPKLLINAADRCPRILMRCKQDSDCLAGCVCGPNGFCGTNSGVPDRFSGSSSGNTASLTITGAQAEDEADYYCNSRDSSGNNWVFGGGTKVTVLGQP (SEQ ID NO: 128) |
| CDR2_F_01 | DIQMTQSPSSLSASVGDRVTITCRASQSISSYLNWYQQKPGKAPKLLIYAAGLCPRILMRCKQDSDCLAGCVCGPNGFCGGESGVPSRFSGSGSGTDFTLTISSLQPEDFATYYCQQSYSTPYTFGQGTKVDIKRT (SEQ ID NO: 129) |
| CDR2_F_12 | DIQMTQSPSSLSASVGDRVTITCRASQSISSYLNWYQQKPGKAPKLLIYAAAPCPRILMRCKQDSDCLAGCVCGPNGFCGSTSGVPSRFSGSGSGTDFTLTISSLQPEDFATYYCQQSYSTPYTFGQGTKVDIKRT (SEQ ID NO: 130) |
| CDR2_E_04 | DIQMTQSPSSLSASVGDRVTITCRASQSISSYLNWYQQKPGKAPKLLIYAAARCPRILMRCKQDSDCLAGCVCGPNGFCGTTSGVPSRFSGSGSGTDFTLTISSLQPEDFATYYCQQSYSTPYTFGQGTKVEIKRT (SEQ ID NO: 131) |

TABLE 1-continued

Sequence of unique EETI-II CDR1 and CDR2 KnotBody binders derived from EETI-II CDR1 and CDR2 libraries

| Clone ID | Sequence |
|---|---|
| CDR2_F_03 | DIQMTQSPSSLSASVGDRVTITCRASQSISSYLNWYQQKPGKAPKLLIYAAAKCPRILMRCK QDSDCLAGCVCGPNGFCGAPSGVPSRFSGSGSGTDFTLTISSLQPEDFATYYCQQSYSTP YTFGQGTKVEIKRT (SEQ ID NO: 132) |
| CDR2_D_03 | DIQMTQSPSSLSASVGDRVTITCRASQSISSYLNWYQQKPGKAPKLLIYAAVVCPRILMRCK QDSDCLAGCVCGPNGFCGSGSGVPSRFSGSGSGTDFTLTISSLQPEDFATYYCQQSYSTP YTFGQGTKLEIKRT (SEQ ID NO: 133) |
| CDR2_D_06 | DIQMTQSPSSLSASVGDRVTITCRASQSISSYLNWYQQKPGKAPKLLIYAAGRCPRILMRCK QDSDCLAGCVCGPNGFCGTASGVPSRFSGGGSGTDFTLTISSLQPEDFATYYCQQSYSTP YTFGQGTKVDIKRT (SEQ ID NO: 134) |
| CDR2_C_09 | DIQMTQSPSSLSASVGDRVTITCRASQSISSYLNWYQQKPGKAPKLLIYAAGGCPRILMRCK QDSDCLAGCVCGPNGFCGAPSGVPSRFSGSGSGTDFTLTISGLQPEDFGTYYCQQSYSTP LTFGGGTKLEIKRT (SEQ ID NO: 135) |
| CDR2_E_08 | DIQMTQSPSSLSASVGDRVTITCRASQSISSYLNWYQQKPGKAPKLLIYAAGVCPRILMRCK QDSDCLAGCVCGPNGFCGSRSGVPSRFSGSGSGTDFTLTISSLQPEDFATYYCQQGASPP YTFGQGTKVEIKRT (SEQ ID NO: 136) |
| CDR2_G_11 | DIQMTQSPSSLSASVGDRVTITCRASQSISSYLNWYQQKPGKAPKLLIYAAGRCPRILMRCK QDSDCLAGCVCGPNGFCGGHSGVPSRFSGSGSGTDFTLTISSLQPEDFATYYCQQSYSTP PTFGQGTKLEIKRT (SEQ ID NO: 137) |
| CDR2_B_03 | DIQMTQSPSSLSASVGDRVTITCRASQSISGYLNWYQQKPGKAPKLLIYAAEVCPRILMRCK QDSDCLAGCVCGPNGFCGGTSGVPSRFSGSRSGTEFTLTISSLQPEDFATYYCQKVDDYP LTFGGGTKVEIKRT (SEQ ID NO: 138) |
| CDR2_H_02 | DIQMTQSPSSLSASVGDRVTITCRASQSISSYLNWYQQKPGKAPKLLIYAAEICPRILMRCKQ DSDCLAGCVCGPNGFCGPSSGIPARFSGSGYGTDFTLTINNIESEDAAYYFCLQHDNFPYT FGQGTKVEIKRT (SEQ ID NO: 139) |

TABLE 2

KnotBodies selected for detailed characterisation.

| Clone number | Clone ID | Library | Tryspin binding signal (FU) | N-terminal linker sequence | C-terminal linker sequence |
|---|---|---|---|---|---|
| 1 | KB_A01 | CDR2_B_03 | 20173 | EV | GT |
| 2 | KB_A02 | CDR2_B_11 | 183150 | AK | GA |
| 3 | KB_A03 | CDR2_C_06 | 28711 | DR | TN |
| 4 | KB_A04 | CDR2_D_03 | 47015 | VV | SG |
| 5 | KB_A05 | CDR2_D_09 | 121458 | DK | GG |
| 6 | KB_A06 | CDR2_D_11 | 24427 | VR | TP |
| 7 | KB_A07 | CDR2_E_08 | 21448 | GV | SR |
| 8 | KB_A08 | CDR2_F_01 | 167526 | GL | GE |
| 9 | KB_A09 | CDR2_F_04 | 57732 | ER | TP |
| 10 | KB_A10 | CDR2_F_05 | 38794 | GG | SN |
| 11 | KB_A11 | CDR2_H_02 | 16399 | EI | PS |
| 12 | KB_A12 | CDR2_H_04 | 69349 | GR | AN |
| 13 | KB_B01 | CDR2_H_07 | 57667 | AG | TR |
| 14 | KB_B02 | CDR2_H_09 | 115848 | VG | GTG |
| 15 | KB_C07 | CDR2_C_02 | 43304 | VG | SA |

TABLE 2-continued

KnotBodies selected for detailed characterisation.

| Clone number | Clone ID | Library | Tryspin binding signal (FU) | N-terminal linker sequence | C-terminal linker sequence |
|---|---|---|---|---|---|
| 16 | KB_C08 | CDR2_C_07 | 76810 | AV | TR |
| 17 | KB_C09 | CDR2_C_08 | 89424 | GR | GG |
| 18 | KB_C10 | CDR2_E_05 | 118631 | GP | AD |
| 19 | KB_B10 | CDR1_C_12 | 9268 | GRAM (SEQ ID NO: 140) | TG |
| 20 | KB_B11 | CDR1_F_02 | 10286 | GSRP (SEQ ID NO: 141) | SH |
| 21 | KB_B12 | CDR1_F_10 | 17356 | GERP (SEQ ID NO: 142) | AN |

TABLE 3

Analysis of trypsin binding of KnotBody GlyAla mutants.

| Clone number | Library | Clone ID | % reduction in binding signal |
|---|---|---|---|
| 1 | EETI-II CDR2 | KB_A01 | 93 |
| 2 | | KB_A02 | 96 |
| 3 | | KB_A03 | 90 |
| 4 | | KB_A04 | 100 |
| 5 | | KB_A05 | 100 |
| 6 | | KB_A06 | 100 |
| 7 | | KB_A07 | 98 |
| 8 | | KB_A08 | 99 |
| 9 | | KB_A09 | 100 |
| 10 | | KB_A10 | 100 |
| 11 | | KB_A11 | 100 |
| 12 | | KB_A12 | 99 |
| 13 | | KB_B01 | 95 |
| 14 | | KB_B02 | 98 |
| 15 | | KB_C07 | 100 |
| 16 | | KB_C08 | 100 |
| 17 | | KB_C09 | 100 |
| 18 | | KB_C10 | 100 |
| 19 | EETI-II CDR1 | KB_B10 | 100 |
| 20 | | KB_B11 | 100 |
| 21 | | KB_B12 | 97 |

TABLE 4

Trypsin binding of KnotBody Fabs.

| Sample ID | TRF signal for 10 ug/mL Fab | TRF signal for 2.4 ug/mL Fab | TRF signal for 0.6 ug/mL Fab |
|---|---|---|---|
| Background (No Fab control) | 420 | 406 | 431 |

TABLE 4-continued

Trypsin binding of KnotBody Fabs.

| Sample ID | TRF signal for 10 ug/mL Fab | TRF signal for 2.4 ug/mL Fab | TRF signal for 0.6 ug/mL Fab |
|---|---|---|---|
| KB_A01 | 55581 | 16598 | 2392 |
| KB_A02 | 255452 | 220577 | 93759 |
| KB_A04 | 264243 | 220697 | 111314 |
| KB_A05 | 217918 | 65386 | 46706 |
| KB_A06 | 241777 | 211701 | 108395 |
| KB_A07 | 226082 | 201003 | 107814 |
| KB_A08 | 152699 | 106949 | 36568 |
| KB_A09 | 161164 | 84131 | 20987 |
| KB_A10 | 68660 | 71860 | 14572 |
| KB_A11 | 212086 | 140605 | 48852 |
| KB_A12 | 252832 | 221989 | 102132 |
| KB_B01 | 256957 | 152908 | 54794 |
| KB_B02 | 56567 | 15884 | 2344 |
| KB_C07 | 276261 | 247038 | 153317 |
| KB_C08 | 182923 | 131246 | 51143 |
| KB_C09 | 288988 | 204878 | 46788 |
| KB_C10 | 238066 | 146488 | 41709 |

TABLE 5

Bi-specific KnotBodies identified from phage display selections.

| Selection antigen | Number of bi-specific binders | Percentage of bi-specific binders |
|---|---|---|
| cMET-FC | 33 | 68.8 |
| GAS6-CD4 | 36 | 75.0 |
| FGFR4-CD4 | 42 | 87.5 |
| UPA | 48 | 100.0 |
| B-gal | 19 | 39.6 |

TABLE 6

KnotBody heavy chain shuffled clones with improved binding to trypsin (HCDR3-SEQ NOs: 143-165)

| Clone ID | Parent Clone | VH germline (DP numbering) | Heavy chain CDR3 sequence | Capture assay signal | Fold imrpovemnt in capture assay signal (x) | kd (1/s) | Fold Improvement in kd (x) |
|---|---|---|---|---|---|---|---|
| KB_Tr_F03 | KB_A12 | Vh1_DP-8,75_(1-02) | HAANWEEPGFDP | 359729 | 8.3 | 0.0006 | 4.4 |
| KB_Tr_E05 | KB_A12 | Vh1_DP-8,75_(1-02) | RSSAGDGAYFDY | 437719 | 10.1 | 0.0011 | 2.6 |
| KB_Tr_E02 | KB_A07 | Vh1_DP-10_(1-69) | DRGLGTSTYYYGMDV | 140056 | 9.0 | 0.0013 | 2.3 |

TABLE 6-continued

KnotBody heavy chain shuffled clones with improved binding to trypsin (HCDR3-SEQ NOs: 143-165)

| Clone ID | Parent Clone | VH germline (DP numbering) | Heavy chain CDR3 sequence | Capture assay signal | Fold imrpovemnt in capture assay signal (x) | kd (1/s) | Fold Improvement in kd (x) |
|---|---|---|---|---|---|---|---|
| KB_Tr_D10 | KB_A12 | Vh1_DP-15_(1-08) | SQSGVGGTGFDP | 401740 | 9.3 | 0.0014 | 1.9 |
| KB_Tr_A08 | KB_A12 | Vh6_DP-74_(6-1) | QLGGTFDV | 182731 | 4.2 | 0.0015 | 1.8 |
| KB_Tr_E10 | KB_A12 | Vh1_DP-10_(1-69) | ALDGAWTDYGDSHEAYGMDV | 125996 | 2.9 | 0.0016 | 1.7 |
| KB_Tr_B08 | KB_A12 | Vh2_DP-27,28_(2-70) | SFDYGDPFDY | 209098 | 4.8 | 0.0016 | 1.7 |
| KB_Tr_C12 | KB_A12 | Vh1_DP-10_(1-69) | SGAVGARDAFDI | 116225 | 2.7 | 0.0016 | 1.7 |
| KB_Tr_F01 | KB_A12 | Vh1_DP-8,75_(1-02) | DRIGEGIPMDV | 278828 | 6.5 | 0.0016 | 1.7 |
| KB_Tr_A10 | KB_A12 | Vh1_DP-5_(1-24) | GGIVGATNDAFDI | 74429 | 1.7 | 0.0016 | 1.7 |
| KB_Tr_B02 | KB_A12 | Vh1_DP-15_(1-08) | AGAGEGGMDV | 339089 | 7.9 | 0.0016 | 1.7 |
| KB_Tr_H03 | KB_A07 | Vh1_DP-5_(1-24) | DNPLRGMDV | 217117 | 14.0 | 0.0017 | 1.7 |
| KB_Tr_A07 | KB_A12 | Vh3_DP-47_(3-23) | ESGGTNGWDAFDM | 99305 | 2.3 | 0.0017 | 1.6 |
| KB_Tr_B07 | KB_A12 | Vh1_DP-10_(1-69) | GERPDYYYYYGMDV | 218284 | 5.1 | 0.0017 | 1.6 |
| KB_Tr_C04 | KB_A12 | Vh6_DP-74_(6-1) | EPGGDSYFDY | 203206 | 4.7 | 0.0017 | 1.5 |
| KB_Tr_D05 | KB_A12 | Vh1_DP-5_(1-24) | MRGYNGGFDL | 220428 | 5.1 | 0.0018 | 1.5 |
| KB_Tr_D01 | KB_A12 | Vh1_DP-88_(1-e) | SGGEGVRAYGMDV | 227897 | 5.3 | 0.0018 | 1.5 |
| KB_Tr_B03 | KB_A12 | Vh1_DP-10_(1-69) | DGNVRGMDV | 168630 | 3.9 | 0.0018 | 1.5 |
| KB_Tr_D03 | KB_A12 | Vh1_DP-10_(1-69) | GGSDYYMDV | 237382 | 5.5 | 0.0018 | 1.5 |
| KB_Tr_H07 | KB_A12 | Vh3_DP-47_(3-23) | GDSSGYGSFDI | 209783 | 4.9 | 0.0018 | 1.5 |
| KB_Tr_G09 | KB_A12 | Vh1_DP-10_(1-69) | SGGLGDAFDI | 237406 | 5.5 | 0.0018 | 1.5 |
| KB_Tr_D07 | KB_A07 | Vh4_DP-63_(4-34) | VSTYSGSQPFDY | 205899 | 13.2 | 0.0018 | 1.6 |
| KB_Tr_D09 | KB_A12 | Vh6_DP-74_(6-1) | GAGEGYFDY | 320628 | 7.4 | 0.0018 | 1.5 |

TABLE 7

Ion channel blocking knottins used for antibody VL CDR2 insertion.

| Toxin | Target Ion channel | Reference | Database Accession |
|---|---|---|---|
| Huwentoxin-IV | Nav 1.7 | 71 | AAP33074.1 GI:30575584 |
| ProTx-II | Nav 1.7 | 72 | P83476.1 GI:25091451 |
| Ssm6a | Nav 1.7 | 70 | 2MUN_A GI:848130036 |
| Kaliotoxin (KTX) | Kv 1.3 | 73, 107 | AAB20997.1 GI:242975 |
| MoKa-1 | Kv 1.3 | 25 | 2KIR_A GI:282403522 |
| Shk | Kv 1.3 | 74, 109 | 4LFS_A GI:530537696 |
| Psalmotoxin (PcTX1) | ASIC1a | 118 | P60514.1 GI:44888346 |

TABLE 7-continued

Ion channel blocking knottins used for antibody VL CDR2 insertion.

| Toxin | Target Ion channel | Reference | Database Accession |
|---|---|---|---|
| EETI-II | n/a | 24 | P12071.2 GI:547744 |
| Conotoxin-ω | Cav 2.2 | 58-60 | 1TTK_A GI:253723132 |
| MCoTI-II | n/a | 119 | P82409.1 GI:8928147 |
| Mambalgin-1 (Mba-1) | ASIC1a/2a/2b | 121 | P0DKR6 (AFT65615.1) |
| Mambalgin-2 (Mba-2) | ASIC1a/2a/2b | 121 | P0DKS3 |

TABLE 8A

DNA and amino acid sequences of ion channel blocking knottins.

| Toxin | Sequence |
|---|---|
| Huwentoxin-IV | GAGTGCCTGGAAATCTTCAAGGCCTGCAACCCCAGCAACGACCAGTGCTGC AAGAGCAGCAAGCTCGTGTGCAGCAGAAAGACCCGGTGGTGCAAGTACCAG ATCTCCAGATGACCCAGAGCCCAAGCAGCCTGAGCGCCA ((SEQ ID NO: 7)<br>ECLEIFKA CNPSNDQCCK SSKLVCSRKT RWCKYQIGK (SEQ ID NO: 8) |
| ProTx-II | TACTGCCAGAAATGGATGTGGACCTGCGACAGCGAGCGGAAGTGCTGCGAG GGCATGGTGTGCCGGCTGTGGTGCAAGAAAAAGCTGTGGTCCAGATGACCC AGAGCCCAAGCAGCCTGAGCGCCA (SEQ ID NO: 9)<br>YCQKWMWTCD SERKCCEGMV CRLWCKKKLW (SEQ ID NO: 10) |
| Ssm6a | GCCGACAACAAGTGCGAGAACAGCCTGCGGAGAGAGATCGCCTGCGGCCA GTGCCGGGACAAAGTGAAAACCGACGGCTACTTCTACGAGTGCTGCACCAG CGACAGCACCTTCAAGAAGTGCCAGGACCTGCTGCACTCCAGATGACCCAG AGCCCAAGCAGCCTGAGCGCCA (SEQ ID NO: 11)<br>ADNKCENSLR REIACGQCRD KVKTDGYFYE CCTSDSTFKK CQDLLH (SEQ ID NO: 12) |
| Kaliotoxin (KTX) | ATCTATGCTGCAGGGAGGGGTGTGGAAATTAACGTGAAGTGTAGCGGGAGC CCACAGTGCCTTAAACCATGCAAAGATGCGGGGATGCGCTTTGGAAAGTGCA TGAACCGTAAATGCCACTGCACGCCGAAGGCCAACTCCGGAGTCTC (SEQ ID NO: 13)<br>GVEINVKCSG SPQCLKPCKD AGMRFGKCMN RKCHCTP (SEQ ID NO: 14) |

TABLE 8A-continued

DNA and amino acid sequences of ion channel blocking knottins.

| Toxin | Sequence |
|---|---|
| Mokatoxin-1<br>(MoKa-1) | ATCAACGTGAAGTGCAGCCTGCCCCAGCAGTGCATCAAGCCCTGCAAGGAC<br>GCCGGCATGAGATTCGGCAAGTGCATGAACAAGAAATGCCGGTGCTACAGC<br>TCCAGATGACCCAGAGCCCAAGCAGCCTGAGCGCCA (SEQ ID NO: 15)<br>INVKCSLPQQ CIKPCKDAGM RFGKCMNKKC RCYS (SEQ ID NO: 16) |
| Shk | AGAAGCTGCATCGACACCATCCCCAAGAGCAGATGCACCGCCTTCCAGTGC<br>AAGCACAGCATGAAGTACCGGCTGAGCTTCTGTAGAAAGACCTGCGGCACC<br>TGTTCCAGATGACCCAGAGCCCAAGCAGCCTGAGCGCCA (SEQ ID NO: 17)<br>RSCIDTIPKS RCTAFQCKHS MKYRLSFCRK TCGTC (SEQ ID NO: 18) |
| PcTX1 | GAGGACTGCATCCCCAAGTGGAAGGGCTGCGTGAACAGACACGGCGACTGT<br>TGCGAGGGCCTGGAATGCTGGAAGCGGAGGCGGAGCTTCGAAGTGTGCGT<br>GCCCAAGACCCCTAAGACCTCCAGATGACCCAGAGCCCAAGCAGCCTGAGC<br>GCCA (SEQ ID NO: 19)<br>EDCIPKWKGC VNRHGDCCEG LECWKRRRSF EVCVPKTPKT (SEQ ID NO: 20) |
| EETI-II | GCPRILMRCK QDSDCLAGCV CGPNGFCGSP (SEQ ID NO: 21) |
| Conotoxin-omega | CKGKGAKCSR LMYDCCTGSC RSGKCX (SEQ ID NO: 22) |
| MCoTI-II | SGSDGGVCPK ILKKCRRDSD CPGACICRGN GYCG (SEQ ID NO: 23) |
| Mambalgin-1<br>(Mba-1) | LKCYQHGKVVTCHRDMKFCYHNTGMPFRNLKLILQGCSSSCSETENNKCCSTD<br>RCNK (SEQ ID NO: 24) |
| Mambalgin-2<br>(Mba-1) | LKCFQHGKVVTCHRDMKFCYHNTGMPFRNLKLILQGCSSSCSETENNKCCSTD<br>RCNK (SEQ ID NO: 25) |

TABLE 8B

Sequences of ion channel blocking recipient: donor fusions (knottin sequence underlined)

| KnotBody domain | Sequence |
|---|---|
| D1 A12 (VH) | EVQLVESGGGLVRPGGSLRLSCAASGFTFSSYAMSWVRQAPGKGLEW<br>VSAISGSGGSTYYADSVKGRFTISRDNTKNSLYLQMTSLRADDTAFYYC<br>VKDFGPGYGTGWFDYWGPGTLVTVSS (SEQ ID NO: 30) |
| KB_A07 ShK (VL) | DIQMTQSPSSLSASVGDRVTITCRASQSISSYLNWYQQKPGKAPKLLIYA<br>AGVRSCIDTIPKSRCTAFQCKHSMKYRLSFCRKTCGTCSRSGVPSRFS<br>GSGSGTDFTLTISSLQPEDFATYYCQQGASPPYTFGQGTKVEIKR (SEQ ID NO: 31) |
| KB_A12 ShK (VL) | QSVLTQPPSVSEAPRQRVTITCSGSSSNIGNNAVNWYQQLPGKAPKLLI<br>YAAGRRSCIDTIPKSRCTAFQCKHSMKYRLSFCRKTCGTCANSGVSDR<br>FSAAKSGTSASLAINGLRSEDEADYYCAAWDDSLNGYVFGTGTKLTVLG<br>(SEQ ID NO: 32) |
| KB_A07 Kaliotoxin (VL) | DIQMTQSPSSLSASVGDRVTITCRASQSISSYLNWYQQKPGKAPKLLIYA<br>AGVGVEINVKCSGSPQCLKPCKDAGMRFGKCMNRKCHCTPKSRSGVP<br>SRFSGSGSGTDFTLTISSLQPEDFATYYCQQGASPPYTFGQGTKVEIKR<br>(SEQ ID NO: 33) |
| KB_A12 PcTx1 (VL) | QSVLTQPPSVSEAPRQRVTITCSGSSSNIGNNAVNWYQQLPGKAPKLLI<br>YAAGREDCIPKWKGCVNRHGDCCEGLECWKRRRSFEVCVPKTPKTAN<br>SGVSDRFSAAKSGTSASLAINGLRSEDEADYYCAAWDDSLNGYVFGTG<br>TKLTVLG (SEQ ID NO: 34) |
| KB_A07 PcTx1 (VL) | DIQMTQSPSSLSASVGDRVTITCRASQSISSYLNWYQQKPGKAPKLLIYA<br>AGVEDCIPKWKGCVNRHGDCCEGLECWKRRRSFEVCVPKTPKTSRSG<br>VPSRFSGSGSGTDFTLTISSLQPEDFATYYCQQGASPPYTFGQGTKVEI<br>KR (SEQ ID NO: 35) |

TABLE 9A

Primers used for the cloning of ion channel blockers (toxins) into the VL CDR2 of KB_A07. Primer name identifies the toxin used for the fusion (e.g. Huwen_A07 Rev is a reverse primer used for cloning Huwentoxin-IV into KB_A07)

| Primer | Sequence |
|---|---|
| Huwen_A07 Fwd | TATGCTGCAGGGGTCGAGTGCCTGGAAATCTTCAAGGCCTGC (SEQ ID NO: 166) |
| Huwen_A07 Rev | TGGGACTCCGGAGCGGCTGATCTGGTACTTGCACCACCGGGT(SEQ ID NO: 167) |
| ProTx-II A07 Rev | TGGGACTCCGGAGCGGCTCCACAGCTTTTTCTTGCACCACAG(SEQ ID NO: 168) |
| ProTx_IIA07 fwd | TATGCTGCAGGGGTCTACTGCCAGAAATGGATGTGGACCTG(SEQ ID NO: 169) |
| Ssm6_A07 Fwd | TATGCTGCAGGGGTCGCCGACAACAAGTGCGAGAACAGCCTG(SEQ ID NO: 170) |
| SSm6_A07 Rev | TGGGACTCCGGAGCGGCTGTGCAGCAGGTCCTGGCACTTCTT(SEQ ID NO: 171) |
| Ssm6_GGS_A07 Fwd | TATGCTGCAGGGGTCGGCGGTAGCGCCGACAACAAGTGCGAGAACAGCCTG(SEQ ID NO: 172) |
| Ssm6_GGS_A07 Rev | GACTCCGGAGCGGCTACCGCCGCTGTGCAGCAGGTCCTGGCACTTCTTGAA(SEQ ID NO: 173) |
| Kalio_A07_Fwd_B | ATCTATGCTGCAGGGGTCGGTGTGGAAATTAACGTGAAGTGT(SEQ ID NO: 174) |
| Kalio_A07 Rev | TGGGACTCCGGAGCGGCTCTTCGGCGTGCAGTGGCATTTACG(SEQ ID NO: 175) |
| Moka-1 A07 Fwd | TATGCTGCAGGGGTCATCAACGTGAAGTGCAGCCTGCCCCAG(SEQ ID NO: 176) |
| Moka-1 A07 Rev | TGGGACTCCGGAGCGGCTGCTGTAGCACCGGCATTTCTTGTT(SEQ ID NO: 177) |
| Shk_A07 Fwd | TATGCTGCAGGGGTCAGAAGCTGCATCGACACCATCCCCAAGA(SEQ ID NO: 178) |
| Shk_A07 Rev | TGGGACTCCGGAGCGGCTACAGGTGCCGCAGGTCTTTCTACA(SEQ ID NO: 179) |
| PcTx-I A07 Fwd | TATGCTGCAGGGGTCGAGGACTGCATCCCCAAGTGGAAGGGC(SEQ ID NO: 180) |
| PcTx-I A07 Rev | TGGGACTCCGGAGCGGCTGGTCTTAGGGGTCTTGGGCACGCA(SEQ ID NO: 181) |

TABLE 9B

Primers used for the cloning of ion channel blockers (toxins) into the VL CDR2 of KB_A12. Primer name identifies the toxin used for the fusion (e.g Huwen_A12 Fwd is a forward primer used for cloning Huwentoxin-IV into KB_A07).

| Primer | Sequence |
|---|---|
| Huwen A12 Rev | GACTCCGGAGTTGGCGATCTGGTACTTGCACCACCGGGTCTTTCT(SEQ ID NO: 182) |
| Huwen_A12 Fwd | TATGCTGCAGGGAGGGAGTGCCTGGAAATCTTCAAGGCCTGC(SEQ ID NO: 183) |
| ProTx-II A12 fwd | TATGCTGCAGGGAGGTACTGCCAGAAATGGATGTGGACCTGC(SEQ ID NO: 184) |
| ProTx-II A12 Rev | GACTCCGGAGTTGGCCCACAGCTTTTTCTTGCACCACAGCCG(SEQ ID NO: 185) |

TABLE 9B-continued

Primers used for the cloning of ion channel blockers (toxins) into the VL CDR2 of KB_A12. Primer name identifies the toxin used for the fusion (e.g Huwen_A12 Fwd is a forward primer used for cloning Huwentoxin-IV into KB_A07).

| Primer | Sequence |
|---|---|
| Ssm6a_A12 Fwd | TATGCTGCAGGGAGGGCCGACAACAAGTGCGAGAACAGCCTG(SEQ ID NO: 186) |
| Ssm6a_A12 Rev | GACTCCGGAGTTGGCGTGCAGCAGGTCCTGGCACTTCTTGAAG(SEQ ID NO: 187) |
| Ssm6a_GGS_A12 Fwd | TATGCTGCAGGGAGGGGCGGTAGCGCCGACAACAAGTGCGAGAACAG CCTG(SEQ ID NO: 188) |
| Ssm6a_GGS_A12 Rev | ACTCCGGAGTTGGCACCGCCGCTGTGCAGCAGGTCCTGGCACTTCTTG AAG(SEQ ID NO: 189) |
| Kalio_A12_Fwd_B | ATCTATGCTGCAGGGAGGGGTGTGGAAATTAACGTGAAGTGT(SEQ ID NO: 190) |
| Kalio_A12 Rev | GAGACTCCGGAGTTGGCCTTCGGCGTGCAGTGGCATTTACG(SEQ ID NO: 191) |
| Moka1 A12 Fwd | TATGCTGCAGGGAGGATCAACGTGAAGTGCAGCCTGCCCCAG(SEQ ID NO: 192) |
| Moka1_A12 Rev | GACTCCGGAGTTGGCGCTGTAGCACCGGCATTTCTTGTTCAT(SEQ ID NO: 193) |
| Shk_A12 Fwd | TATGCTGCAGGGAGGAGAAGCTGCATCGACACCATCCCCAAG(SEQ ID NO: 194) |
| Shk_A12 rev | GACTCCGGAGTTGGCACAGGTGCCGCAGGTCTTTCTACAGAAG(SEQ ID NO: 195) |
| PcTx-1 A12 Fwd | TATGCTGCAGGGAGGGAGGACTGCATCCCCAAGTGGAAGGGC(SEQ ID NO: 196) |
| PcTX-1 A12 Rev | GACTCCGGAGTTGGCGGTCTTAGGGGTCTTGGGCACGCACAC(SEQ ID NO: 197) |

TABLE 10

KnotBody yield after the Protein-A purification of Toxin-antibody fusions.

| Toxin/Knottin | Antibody | IgG1 Yield (mg/L) |
|---|---|---|
| Huwentoxin-IV | KB_A07 | 6.0 |
| ProTx-II | | 1.3 |
| Ssm6a | | 11.6 |
| Ssm6a_GGS | | 9.8 |
| PcTx-I | | 11.5 |
| Shk | | 9.4 |
| Moka-1 | | 3.7 |
| Kaliotoxin (KTX) | | 5.0 |
| Huwentoxin-IV | KB_A12 | 10.7 |
| ProTx-II | | 5.1 |
| Ssm6a | | 7.4 |
| Ssm6a_GGS | | 6.2 |
| PcTx-I | | 11.9 |
| Shk | | 11.8 |
| Moka-1 | | 3.9 |
| Kaliotoxin (KTX) | | 5.3 |
| Mambalgin-1 (Mba-1) | | 14.4 |
| Mambalgin-2 (Mba-1) | | 7.8 |

TABLE 10-continued

KnotBody yield after the Protein-A purification of Toxin-antibody fusions.

| Toxin/Knottin | Antibody | IgG1 Yield (mg/L) |
|---|---|---|
| EETI-II (Control) | KB_A07 | 9.4 |
| EETI-II (Control) | KB_A12 | 11.8 |

TABLE 11A

Summary $IC_{50}$ data for eight samples tested against Kv1.3 channels.

| Sample type | Toxin | Antibody | $IC_{50}$ (nM) |
|---|---|---|---|
| Toxin fusion | Shk | KB_A07 | 40 |
| | MoKa-1 | | N/E* |
| | Kaliotoxin (KTX) | | 900 |
| | Shk | KB_A12 | 20 |
| | MoKa-1 | | N/E* |
| | Kaliotoxin (KTX) | | N/E* |
| Isotype control | None | KB_A07 | N/E* |
| | None | KB_A12 | N/E* |

N/E* = no detectable effect.

TABLE 11B

Percentage ASIC1a current remaining in response to KB__A12 and KB__A07 based KnotBody applications followed by a full blocking concentration of PcTx1

| KnotBody/ Antibody | Concentration (μM) | % current remaining | % current remaining PcTx1 (300 nM) | n |
|---|---|---|---|---|
| KB__A07__PcTx1 | 6.6 | 6.2 | 3.6 | 5 |
| KB__A12__PcTx1 | 5 | 4.8 | 3.8 | 7 |
| KB__A12__Mba-1 | 3 | 69.2 | 2 | 5 |
| KB__A12__Mba-2 | 2.3 | 72.4 | 1.9 | 5 |
| KB__A07 (control) | 6 | 70.9 | 1.9 | 3 |
| KB__A12 (control) | 3.3 | 67.4 | 2.7 | 6 |
| Buffer only (control) | 0 | 74.9 | 3.8 | 6 |

TABLE 12

Amino acid sequences of the LOX-1 binding adhirons.

| Adhiron | Protein Sequence |
|---|---|
| Ad-LOX1-A | ATGVRAVPGNENSLEIEELARFAVDEHNKKENALLEFVRVVKAKEQTAHLDPLMDTMYYLTLEAKDGGKKKLYEAKVWVKFWMISDLIFNFKELQEFKPVGDA (SEQ ID NO: 26) |

TABLE 12-continued

Amino acid sequences of the LOX-1 binding adhirons.

| Adhiron | Protein Sequence |
|---|---|
| Ad-LOX1-B | ATGVRAVPGNENSLEIEELARFAVDEHNKKENALLEFVRVVKAKEQEQPIGEHPVNDTMYYLTLEAKDGGKKKLYEAKVWVKRWLRFTEIYNFKELQEFKPVGDA (SEQ ID NO: 27) |

TABLE 13

Nucleotide sequences of the two adhirons used for this work (SEQ ID NOS: 198, 199)

| Adhiron | gene*sequence |
|---|---|
| Ad#LOX1#A | GCTACAGGCGTGCGGGCTGTGCCCGGCAATGAGAACAGCCTGGAAATCGAGGAACTGGCCAGATTCGCCGTGGACGAGCACAACAAGAAAGAGAACGCCCTGCTGGAATTCGTGCGGGTCGTGAAGGCCAAAGAGCAGTGGAGCGAGGCCGACAACGACTGGCACACCATGTACTACCTGACCCTGGAAGCCAAGGACGGCGGCAAGAAGAAGCTGTACGAGGCCAAAGTGTGGGTCAAGCTGGACCTGGAAACCTGGCAGCACTTCAACTTCAAAGAGCTCCAGGAATTCAAGCCCGTGGGCGACGCT |
| Ad#LOX1#B | GCTACAGGCGTGCGGGCTGTGCCCGGCAATGAGAACAGCCTGGAAATCGAGGAACTGGCCAGATTCGCCGTGGACGAGCACAACAAGAAAGAGAACGCCCTGCTGGAATTCGTGCGGGTCGTGAAGGCCAAAGAGCAGGAACAGCCCATCGGCGAGCACCCCGTGAACGACACCATGTACTACCTGACCCTGGAAGCCAAGGACGGCGGCAAGAAGAAGCTGTACGAGGCCAAAGTGTGGGTCAAGCGGTGGCTGCGGTTCACCGAGATCTACAACTTCAAAGAGCTCCAGGAATTCAAGCCCGTGGGCGACGCT |

TABLE 14 sequences of the primers used for cloning adhirons into the CDR2 position of antibodies KB_A07 (SEQ ID NOS: 200 & 201) and KB_A12 (SEQ ID NOS: 202 & 203).

| Antibody | Primer-name | Sequence |
|---|---|---|
| KB_A07 | Ad_SUMO_10*A07*Fwd | ATCTATGCTGCAGGGGTCGCTACAGGCGTGCGGGCTGTGCCCGGC |
| | Ad*SUMO10_A07*Rev | GGGACTCCGGAGCGGCTTGCGTCGCCCACGGGCTTGAATTCCTGG |
| KB_A12 | Ad_SUMO_10*A12*Fwd | ATCTATGCTGCAGGGAGGGCTACAGGCGTGCGGGCTGTGCCCGGC |
| | Ad*SUMO10_*A12*Rev | GAGACTCCGGAGTTGGCGGCGTCGCCCACGGGCTTGAATTCCTGG |

TABLE 15

N and C terminal linker sequences of "selected" KnotBodies and their variants.

| KnotBody construct | N-terminal linker sequence | C-terminal linker sequence |
|---|---|---|
| KB_A07 (Parent) | GV | SR |
| KB_A07 Gly4Ser | GGGGS (SEQ ID NO: 1) | GGGGS (SEQ ID NO: 1) |
| KB_A07 (Gly4Ser)2 | GGGGSGGGGS (SEQ ID NO: 204) | GGGGSGGGGS (SEQ ID NO: 204) |

TABLE 15-continued

N and C terminal linker sequences of "selected" KnotBodies and their variants.

| KnotBody construct | N-terminal linker sequence | C-terminal linker sequence |
|---|---|---|
| KB_A12 (Parent) | GR | AN |
| KB_A12 Gly4Ser | GGGGS (SEQ ID NO: 1) | GGGGS (SEQ ID NO: 1) |
| KB_A12 (Gly4Ser)2 | GGGGSGGGGS (SEQ ID NO: 204) | GGGGSGGGGS (SEQ ID NO: 204) |

TABLE 16

Sequences of KnotBody linker variants.

| KnotBody construct | Sequence |
|---|---|
| KB_A07 | GGTGGCGCTAGCGACATACAAATGACCCAATCACCTAGCTCTCTTAGTGCCTCTGTTGGGGATCGG GTCACCATCACTTGTAGAGCGAGCCAGAGTATCTCATCATACTTGAACTGGTACCAGCAGAAGCCAG GGAAGGCCCCCAAGCTGTTGATTTACGCGGCTGGGGTCTGCCCGCGCATCTTGATGAGGTGCAAA CAAGACTCAGACTGCCTGGCTGGATGTGTTTGCGGACCAAATGGTTTCTGCGGAAGCCGCTCAGGC GTGCCATCAAGATTTAGTGGTTCAGGAAGTGGTACGGACTTCACGCTGACGATTTCATCTCTTCAAC CCGAAGATTTCGCCACGTACTACTGTCAACAGGGTGCTTCTCCACCTTATACTTTCGGTCAGGGTAC CAAGGTTGAGATTAAGCGCACCGCGGCCGCAATC (SEQ ID NO: 205) |
| KB_A07 $Gly_4Ser$ | GGTGGCGCTAGCGACATACAAATGACCCAAAGTCCGAGCTCCTTGAGTGCCTCCGTAGGTGATAGG GTCACTATTACTTGCAGAGCGTCTCAGTCCATCTCCTCCTATTTGAATTGGTACCAACAGAAACCGG GGAAAGCCCCTAAGCTCCTGATCTACGCCGCTGGGGGAGGCGGGAGTGGGGGGGGCGGGTCCTG TCCGCGCATCCTTATGCGGTGTAAACAGGACAGTGATTGCCTTGCTGGTTGTGTCTGCGGCCCCAA TGGTTTTTGCGGGGGTGGGGGGGGCAGCGGTGGGGGCGGTTCCTCCGGGGTGCCATCTCGCTTT AGCGGTTCAGGTAGTGGAACGGACTTTACACTGACAATATCATCTTTGCAACCAGAGGATTTCGCCA CGTACTACTGTCAGCAAGGTGCCTCTCCACCTTACACGTTTGGACAAGGCACCAAAGTAGAGATTAA GCGGACCGCGGCCGCAATC (SEQ ID NO: 206) |
| KB_A07 $(Gly_4Ser)_2$ | GGTGGCGCTAGCGACATACAAATGACCCAATCACCTAGCTCTCTTAGTGCCTCTGTTGGGGATCGG GTCACCATCACTTGTAGAGCGAGCCAGAGTATCTCATCATACTTGAACTGGTACCAGCAGAAGCCA GGGAAGGCCCCCAAGCTGTTGATTTACGCGGCTGGCGGAGGAGGGTCCTGCCCGCGCATCTTGAT GAGGTGCAAACAAGACTCAGACTGCCTGGCTGGATGTGTTTGCGGACCAAATGGTTTCTGCGGAGG AGGCGGAGGTTCCTCAGGCGTGCCATCAAGATTTAGTGGTTCAGGAAGTGGTACGGACTTCACGCT GACGATTTCATCTCTTCAACCCGAAGATTTCGCCACGTACTACTGTCAACAGGGTGCTTCTCCACCT TATACTTTCGGTCAGGGTACCAAGGTTGAGATTAAGCGCACCGCGGCCGCAATC (SEQ ID NO: 207) |
| KB_A12 | GGTGGCGCTAGCCAGAGTGTCTTGACGCAGCCACCTTCTGTCAGCGAGGCCCCACGCCAGAGGGT TACCATAACATGTTCCGGGTCCAGCTCTAACATAGGGAATAACGCGGTAAACTGGTATCAGCAATTG CCCGGCAAAGCACCGAAACTCTTGATCTATGCAGCGGGGAGGTGTCCTCGAATACTGATGCGATGT AAACAGGACTCCGATTGTCTTGCGGGATGTGTGTGTGGTCCGAATGGGTTTTGCGGCGCCAACAGC GGCGTAAGTGATCGATTCTCAGCGGCGAAATCCGGCACATCCGCCTCACTGGCGATCAACGGATTG CGAAGTGAGGACGAAGCTGACTATTATTGCGCGGCCTGGGATGATTCCTTGAACGGGTATGTATTT GGCACAGGAACGAAGCTGACTGTGCTGGGACAACCCGCGGCCGCAATC (SEQ ID NO: 208) |
| KB_A12 $Gly_4Ser$ | GGTGGCGCTAGCCAGAGCGTACTGACGCAGCCGCCTTCTGTTAGCGAGGCTCCCCGACAGCGAGT AACGATAACGTGCAGCGGTTCAAGCAGTAATATCGGGAATAATGCAGTAAATTGGTATCAGCAACTG CCTGGAAAAGCGCCCAAGCTGCTCATATATGCGGCCGGGGGCGGGGGTAGCGGCGGAGGGGGAA GCTGCCCAAGAATCTTGATGCGGTGTAAACAAGATTCAGACTGTTTGGCCGGTTGCGTATGCGGTC CAAATGGGTTCTGCGGAGGTGGTGGTGGGTCCGGTGGAGGAGGTAGTAGCGGGGTTAGTGATCGA TTCTCCGCGGCGAAGTCCGGCACCAGTGCAAGTCTCGCTATAAACGGGCTCAGGTCAGAAGATGA GGCAGATTATTACTGTGCCGCATGGGACGACAGTTTGAACGGCTATGTCTTCGGAACGGGGACTAA ACTTACCGTACTTGGACAGCCCGCGGCCGCAATC (SEQ ID NO: 209) |
| KB_A12 $(Gly_4Ser)_2$ | GGTGGCGCTAGCCAGAGTGTCTTGACGCAGCCACCTTCTGTCAGCGAGGCCCCACGCCAGAGGGT TACCATAACATGTTCCGGGTCCAGCTCTAACATAGGGAATAACGCGGTAAACTGGTATCAGCAATTG CCCGGCAAAGCACCGAAACTCTTGATCTATGCAGCGGGAGGGGGAGGCTCTTGTCCTCGAATACT GATGCGATGTAAACAGGACTCCGATTGTCTTGCGGGATGTGTGTGTGGTCCGAATGGGTTTTGCGG CGGTGGGGGCGGCTCTAGCGGCGTAAGTGATCGATTCTCAGCGGCGAAATCCGGCACATCCGCCT CACTGGCGATCAACGGATTGCGAAGTGAGGACGAAGCTGACTATTATTGCGCGGCCTGGGATGATT CCTTGAACGGGTATGTATTTGGCACAGGAACGAAGCTGACTGTGCTGGGACAACCCGCGGCCGCA ATC (SEQ ID NO: 210) |

TABLE 17A

Loop1 sequences of unique cMET binders isolated from the KnotBody loop library. Cysteines flanking the loop 1 residues are highlighted in bold.

| Clone ID | Loop 1 sequence | TRF signal |
|---|---|---|
| KB_A12_cMET_H01 | **C**HRMSGTGR**C** (SEQ ID NO: 211) | 131578 |
| KB_A12_cMET_F05 | **C**KRLMSGAGR**C** (SEQ ID NO: 212) | 59604 |
| KB_A12_cMET_G01 | **C**QRQSGTGR**C** (SEQ ID NO: 213) | 98924 |
| KB_A12_cMET_G07 | **C**RASSGTGR**C** (SEQ ID NO: 214) | 57958 |
| KB_A12_cMET_E07 | **C**PKRHTGTGR**C** (SEQ ID NO: 215) | 95275 |
| KB_A12_cMET_E04 | **C**GHLSGTGR**C** (SEQ ID NO: 216) | 41255 |
| KB_A12_cMET_F02 | **C**GRASGTGR**C** (SEQ ID NO: 217) | 98503 |
| KB_A12_cMET_H05 | **C**NRASGAGR**C** (SEQ ID NO: 218) | 152852 |
| KB_A12_cMET_H03 | **C**RGMTGVGR**C** (SEQ ID NO: 219) | 54161 |
| KB_A12_cMET_H08 | **C**QTGRSGTGR**C** (SEQ ID NO: 220) | 6730 |
| KB_A12_cMET_E05 | **C**DRKAGTGR**C** (SEQ ID NO: 221) | 115765 |
| KB_A12_cMET_E11 | **C**AKKSGTGR**C** (SEQ ID NO: 222) | 158497 |
| KB_A12_cMET_E12 | **C**AKRSGTGR**C** (SEQ ID NO: 223) | 95895 |
| KB_A12_cMET_H04 | **C**PQMTGTGR**C** (SEQ ID NO: 224) | 112989 |
| KB_A12_cMET_E01 | **C**NLTSGTGR**C** (SEQ ID NO: 225) | 22439 |
| KB_A12_cMET_G10 | **C**EKHSGTGR**C** (SEQ ID NO: 226) | 64760 |
| KB_A12_cMET_H02 | **C**AKRTGTGR**C** (SEQ ID NO: 227) | 35448 |
| KB_A12_cMET_F06 | **C**PHQTGTGR**C** (SEQ ID NO: 228) | 56209 |
| KB_A12_cMET_F10 | **C**RSLMSGTGR**C** (SEQ ID NO: 229) | 51323 |
| KB_A12_cMET_F12 | **C**KAQSGSGR**C** (SEQ ID NO: 230) | 119476 |
| KB_A12_cMET_G06 | **C**NKSGGTGR**C** (SEQ ID NO: 231) | 62077 |
| KB_A12_cMET_E02 | **C**RKKSGANR**C** (SEQ ID NO: 232) | 9482 |
| KB_A12_cMET_G08 | **C**ARLSGSGR**C** (SEQ ID NO: 233) | 27930 |

TABLE 17B

Loop1 sequences of unique β-galactosidase binders isolated from the KnotBody loop library. Cysteines flanking the loop 1 residues are highlighted in bold.

| | | |
|---|---|---|
| KB_A12_B-gal_F02 | **C**RTTSTIRR**C** (SEQ ID NO: 234) | 476399 |
| KB_A12_B-gal_G05 | **C**LDTVNLRR**C** (SEQ ID NO: 235) | 529017 |
| KB_A12_B-gal_H03 | **C**NQTMSIRRP**C** (SEQ ID NO: 236) | 517907 |
| KB_A12_B-gal_E04 | **C**LATTSIRRP**C** (SEQ ID NO: 237) | 523482 |

TABLE 17B-continued

Loop1 sequences of unique β-galactosidase binders isolated from the KnotBody loop library. Cysteines flanking the loop 1 residues are highlighted in bold.

| | | |
|---|---|---|
| KB_A12_B-gal_E05 | **C**RETSSLRRP**C** (SEQ ID NO: 238) | 311927 |
| KB_A12_B-gal_F09 | **C**IATSHIRRH**C** (SEQ ID NO: 239) | 257676 |
| KB_A12_B-gal_F11 | **C**HETAQIRRR**C** (SEQ ID NO: 240) | 531474 |
| KB_A12_B-gal_H07 | **C**TQTALIRRR**C** (SEQ ID NO: 241) | 62049 |
| KB_A12_B-gal_H02 | **C**EQTSVIRRH**C** (SEQ ID NO: 242) | 501461 |
| KB_A12_B-gal_F03 | **C**LATTSIRRH**C** (SEQ ID NO: 243) | 288901 |
| KB_A12_B-gal_F07 | **C**RTTANVRRH**C** (SEQ ID NO: 244) | 246274 |

TABLE 18

Nucleotide sequences of mutagenic oligos used for constructing KnotBody loop library.

| Mutagenic oligo | Nucleotide sequence |
|---|---|
| A12_L1 (6) | ACAGGCAGTCTGAGTCCTGTTTGCASNBSNBSNBSNBSNBSNBSNBGCACCTCCCTGCAGCATAGATCAG (*SEQ ID NO*: 245) |
| A12_L1 (8) | CAGGCAGTCTGAGTCCTGTTTGCASNBSNBSNBSNBSNBSNBSNBSNBSNBGCACCTCCCTGCAGCATAGATCAG (*SEQ ID NO*: 246) |
| A12_L1 (9) | CAGGCAGTCTGAGTCCTGTTTGCASNBSNBSNBSNBSNBSNBSNBSNBSNBSNBGCACCTCCCTGCAGCATAGATCAG (*SEQ ID NO*: 247) |
| A12_L1 (10) | CAGGCAGTCTGAGTCCTGTTTGCASNBSNBSNBSNBSNBSNBSNBSNBSNBSNBSNBGCACCTCCCTGCAGCATAGATCAG (*SEQ ID NO*: 248) |

TABLE 19

Percentage transcytosis of 21 test KnotBodies and controls across the BBB in an in vitro model system.

| Test well | Clones | % transcytosis after 6 h |
|---|---|---|
| C1 | KB_TFR_B01<br>KB_TFR_B02<br>KB_TFR_B03 | 0.0 |
| C2 | KB_TFR_B05<br>KB_TFR_B07<br>KB_TFR_B09 | 1.3 |
| C3 | KB_TFR_B11<br>KB_TFR_C01<br>KB_TFR_C03 | 0.9 |
| C4 | KB_TFR_C05<br>KB_TFR_C06<br>KB_TFR_C07 | 0.7 |
| C5 | KB_TFR_D02<br>KB_TFR_D05<br>KB_TFR_D07 | 0.0 |
| C6 | KB_TFR_D10<br>KB_TFR_E03 | 0.1 |

TABLE 19-continued

Percentage transcytosis of 21 test KnotBodies and controls across the BBB in an in vitro model system.

| Test well | Clones | % transcytosis after 6 h |
|---|---|---|
| B1 | KB_TFR_E06<br>KB_TFR_A05<br>KB_TFR_A06<br>KB_TFR_A07 | 0.0 |
| OX26-Fab | Positive Control | 0.2 |
| KB_A12 | Negative control | 0.1 |

TABLE 20

Amino acid sequences of anti-TFR VHs that could potentially cross BBB.

| Name | Sequence |
|---|---|
| KB_TFR_B05 | QVQLVQSGAEVKKPGSSVKVSCKASGGTFSSYAISWVRQAPGQGLEWMGRNIPILGIANYAQKSRGRVTITADESTSTAYMELSSLRSEDTAVYYCARVAPYSSGWANVDAFDIWGQGTLVTVSS (SEQ ID NO: 249) |
| KB_TFR_B07 | QVQLVQSEPEVKKPGASVKVSCKASGYTFTSYGISWVRQAPGQGLEWMGRIIPIFGIANYAQKFQGRVTITADKSTSTAYMELSSLRSEDTAVYYCAGITGTNGPHDAFDIWGQGTMVTVSS (SEQ ID NO: 250) |
| KB_TFR_B09 | QVQLVQSGAEVKKPGSSVKVSCKASGGTFSSYTISWVRQAPGQGLEWMGRIIPILSIANYAQKFQSRVTITADESTSTAYMELSSLRSEDTAVYYCARVRPYYDSSADLDAFDIWGQGTMVTVSS (SEQ ID NO: 251) |
| KB_TFR_B11 | EVQLVQFGAEVKKPGASVKVSCKASGYTFTGYYMHWVRQAPGQGLEWMGRINPNSGGTNYAQKFQGRVTMTRDTSISTAYMELSRLRSEDTAVYYCARGRGPLSYWGQGTLVTVSS (SEQ ID NO: 252) |
| KB_TFR_C01 | QVQLVQSGAEVKKPGSSVKVSCKASGGTYSSNTFTWVRQAPGQGLEWMGRIIPVLDLTNSAVNFQDRVTITADESTSTVYMELSSLRSEDTAVYYCASTTAMVPTDAFDIWGQGTMVTVSS (SEQ ID NO: 253) |
| KB_TFR_C03 | EVQLVESGAEVKKPGSSVKVSCKASGGTVSSYAISWVRQAPGQGLEWMGGIIPIFGTANYAQKFQGRVTITADESTSTAYMELSSLRSEDTAVYYCARDLFQRSGSYPYYYYYYGMDVWGQGTMVTVSS (SEQ ID NO: 254) |
| KB_TFR_C05 | QVQLVQSGAEVKKPGSSVKVSCKASGGTYSSNTFTWVRQAPGQGLEWMGRIIPILGIANYAQKFQGRVTITADESTSTAYMVLSSLRSEDTAVYYCARVRPYYDSSADLDAFDIWGQGTLVTVSS (SEQ ID NO: 255) |
| KB_TFR_C06 | QVQLVESGAEVKKPGSSVKVSCKASGGTFSSYAISWVRQAPGQGLEWMGGIIPIFGTANYAQKFQGRVTITADESTSTAYMELSSLRSEDTAVYYCAIALRDSSGYYTDALDIWGQGTLVTVSS (SEQ ID NO: 256) |
| KB_TFR_C07 | QMQLVQSGAEVKKPGASVKVSCKASGYTFTSYGISWVRQAPGQGLEWMGGIIPIFGTANYAQKFQGRVTITADESTGTAYMELSSLRSEDTAVYYCAGPGGYYDILTGYPTDAFDIWGQGTMVTVSS (SEQ ID NO: 257) |

TABLE 21

Nucleotide sequences of EETI-II-Cow ULVC-Ab synthetic gene.

| Name | Sequence |
|---|---|
| EETI-II Cow ULVC-Ab | CAGCCGGCCATGGCCCAAGTGCAACTTCGCGAAAGCGGGCCTTCCTTGGTTAAACCATCGCAGACCCTGAGTCTTACGTGCACGGCCAGCGGTTTTTCCCTGTCCGATAAAGCAGTAGGGTGGGTGCGCCAAGCGCCGGGAAAGGCATTAGAGTGGCTTGGTTCCATTGATACGGGGGGGAACACAGGATACAATCCCGGCTTGAAGTCTCGCCTTTCAATCACCAAAGACAACTCAAAGTCTCAAGTCTCCCTGAGCGTCTCATCGGTTACCACCGAGGACTCAGCCACGTACTACTGCACATCCGTTCATCAGGAGACCAAAAAATACCAATCTTGTCCCCGCATCCTGATGCGTTGTAAACAAGACAGCGACTGCCTGGCAGGTTGTGTATGCGGTCCTAATGGGTTTTGTGGATTAACCACTCTGCCAGTCTCATATTCTTACACTTATAATTATGAGTGGCATGTTGATGTCTGGGGGCAGGGGCTTCTTGTCACGGTCTCGAGTGGTGGAGGCGGTTCAGGCGGAGGTGGCTCTGGCGGTGGCGCTAGCCAGGCTGTTTTAAACCAACCCAGCTCGGTTAGTGGATCGTTGGGGCAGCGCGTCTCAATCACTTGTTCCGGCTCCTCCTCGAATGTTGGTAATGGATATGTTTCCTGGTACCAGCTTATCCCCGGTAGCGCTCCTCGCACCTTAATTTATGGTGACACGTCCCGTGCCAGCGGTGT |

TABLE 21-continued

Nucleotide sequences of EETI-II-Cow ULVC-Ab synthetic gene.

| Name | Sequence |
|---|---|
| | CCCTGATCGTTTCTCTGGGAGCCGTTCCGGGAACACCGCCACACTTACAATT AGTAGCCTTCAAGCTGAGGACGAAGCGGACTATTTTTGTGCCTCTGCAGAGG ATTCATCCTCTAACGCTGTGTTTGGCAGTGGCACCACCCTTACTGTGTTAGGG GCGGCCGCAGAT (SEQ ID NO: 258) |

TABLE 22

Primers used to create inserts for the cloning of KnotBodies and linker libraries for mammalian display.

| Primer | Sequence |
|---|---|
| 2979 | CTAAGCTCCTGATCTATGCTGCAGGGGTCTGCCCGCGTATCCTG ATGCGTTGCAAACAGGACTCAGACTGCCTG G (SEQ ID NO: 259) |
| 2980 | GAACCTTGATGGGACTCCGGAGCGGCTCCCGCAGAAGCCGTTCG GACCGCATACGCAGCCGGCCAGGCAGTCTGAGTCCT G (SEQ ID NO: 260) |
| 2983 | CTAAGCTCCTGATCTATGCTGCAGGGAGGTGCCCGCGTATCCTG ATGCGTTGCAAACAGGACTCAGACTGCCTG G (SEQ ID NO: 261) |
| 2984 | GAATCGGTCAGAGACTCCGGAGTTGGCCCCGCAGAAGCCGTTCG GACCGCATACGCAGCCGGCCAGGCAGTCTGAGTCCT G (SEQ ID NO: 262) |
| 2985 | TTTTTTCCATGGCTGAAGTCCAACTG (SEQ ID NO: 263) |
| 2995 | TTTTTTGCGGCCGCGGTACGTTTG (SEQ ID NO: 264) |
| 2999 | TGCAGCATAGATCAGGAGCTTAG (SEQ ID NO: 265) |
| 3000 | TCCGGAGTCCCATCAAGGTTC (SEQ ID NO: 266) |

TABLE 22-continued

Primers used to create inserts for the cloning of KnotBodies and linker libraries for mammalian display.

| Primer | Sequence |
|---|---|
| 3002 | TTTTTTGCGGCCGCAGGCTGACCTAG (SEQ ID NO: 267) |
| 3003 | TGCAGCATAGATCAGGAGCTTAG (SEQ ID NO: 268) |
| 3004 | TCCGGAGTCTCTGACCGATTC (SEQ ID NO: 269) |

TABLE 23

Amino acid sequence of the parental anti-TACE D1A12 scFv[101] used for knottin linker library insertion into VH and VL CDRs 1 to 3.

| |
|---|
| EVQLVESGGGLVRPGGSLRLSCAASGFTFSSYAMSWVRQAPGKGLE WVSAISGSGGSTYYADSVKGRFTISRDNTKNSLYLQMTSLRADDTAFYY CVDFGPGYGTGWFDYWGPGTLVTVSSGGGGSGGGGSGGGASDIQMT QSPSSLSASVGDRVTITCRASQSISSYLNWYQQKPGKAPKLLIHDASSL QSGVPSRFSGSGSGTDFTLTISSLQPEDFATYYCQQSFSIPLTFGGGTK MDIKRT (SEQ ID NO: 270) |

TABLE 24

Primers used to create inserts for the cloning of KnotBodies and linker libraries for phage display selection.

| Primer | Sequence |
|---|---|
| 2965 | GCGTCGGGTTTTACCTTTAGCVNSVNSTGTCCCCGGATACTTATGAGATGTAAGCAA GATAGTGATTGCCTCGC (SEQ ID NO: 271) |
| 2966 | CGGAGCCTGACGAACCCASNBSNBGCCACAAAACCCGTTGGGACCACAGACACAT CCGGCGAGGCAATCACTATCTTGC (SEQ ID NO: 272) |
| 2967 | GTAAAGGCCTGGAATGGGTCTCCVNSVNSTGTCCCCGGATACTTATGAGATGTAAG CAAGATAGTGATTGCCTCGC (SEQ ID NO: 273) |
| 2968 | GTCGCGAGAGATGGTGAAACGSNBSNBGCCACAAAACCCGTTGGGACCACAGACA CATCCGGCGAGGCAATCACTATCTTGC (SEQ ID NO: 274) |
| 2969 | CACGGCTTTTTATTACTGCGTTGATVNSVNSTGTCCCCGGATACTTATGAGATGTAA GCAAGATAGTGATTGCCTCGC (SEQ ID NO: 275) |
| 2970 | CAGGGTGCCCGGACCCCASNBSNBGCCACAAAACCCGTTGGGACCACAGACACAT CCGGCGAGGCAATCACTATCTTGC (SEQ ID NO: 276) |
| 2971 | GAGACAGAGTCACCATCACTTGCVNSVNSTGTCCCCGGATACTTATGAGATGTAAG CAAGATAGTGATTGCCTCGC (SEQ ID NO: 277) |
| 2972 | CCTGGCTTCTGCTGATACCASNBSNBGCCACAAAACCCGTTGGGACCACAGACACA TCCGGCGAGGCAATCACTATCTTGC (SEQ ID NO: 278) |
| 2973 | CCCTAAGCTCCTGATCCATGATVNSVNSTGTCCCCGGATACTTATGAGATGTAAGCA AGATAGTGATTGCCTCGC (SEQ ID NO: 279) |

TABLE 24-continued

| Primers used to create inserts for the cloning of KnotBodies and linker libraries for phage display selection. | |
|---|---|
| Primer | Sequence |
| 2974 | CTGAACCTTGATGGGACCCCSNBSNBGCCACAAAACCCGTTGGGACCACAGACAC ATCCGGCGAGGCAATCACTATCTTGC (SEQ ID NO: 280) |
| 2975 | CCTGAAGATTTTGCAACTTACTACTGTVNSVNSTGTCCCCGGATACTTATGAGATGT AAGCAAGATAGTGATTGCCTCGC (SEQ ID NO: 281) |
| 2976 | CATTTTGGTCCCTCCGCCGAASNBSNBGCCACAAAACCCGTTGGGACCACAGACAC ATCCGGCGAGGCAATCACTATCTTGC (SEQ ID NO: 282) |
| 2977 | CTAAGCTCCTGATCTATGCTGCAVNSVNSTGCCCGCGTATCCTGATGCGTTGCAAA CAGGACTCAGACTGCCTGG (SEQ ID NO: 283) |
| 2978 | GAACCTTGATGGGACTCCGGASNBSNBCCCGCAGAAGCCGTTCGGACCGCATACG CAGCCGGCCAGGCAGTCTGAGTCCTG (SEQ ID NO: 284) |
| 2981 | CTAAGCTCCTGATCTATGCTGCAVNSVNSTGCCCGCGTATCCTGATGCGTTGCAAA CAGGACTCAGACTGCCTGG (SEQ ID NO: 285) |
| 2982 | GAATCGGTCAGAGACTCCGGAGTTGGCCCCGCAGAAGCCGTTCGGACCGCATACG CAGCCGGCCAGGCAGTCTGAGTCCTG (SEQ ID NO: 286) |
| 2986 | GCTAAAGGTAAAACCCGACGC (SEQ ID NO: 287) |
| 2987 | TGGGTTCGTCAGGCTCCG (SEQ ID NO: 288) |
| 2988 | **TTTTTT**CTCGAGACGGTCACCAGG (SEQ ID NO: 289) |
| 2989 | GGAGACCCATTCCAGGCCTTTAC (SEQ ID NO: 290) |
| 2990 | CGTTTCACCATCTCTCGCGAC (SEQ ID NO: 291) |
| 2991 | ATCAACGCAGTAATAAAAAGCCGTG (SEQ ID NO: 292) |
| 2992 | **TTTTTT**GCTAGCGACATCCAGATGACC (SEQ ID NO: 293) |
| 2993 | GCAAGTGATGGTGACTCTGTCTC (SEQ ID NO: 294) |
| 2994 | TGGTATCAGCAGAAGCCAGG (SEQ ID NO: 295) |
| 2996 | ATCATGGATCAGGAGCTTAGGG (SEQ ID NO: 296) |
| 2997 | GGGGTCCCATCAAGGTTCAG (SEQ ID NO: 297) |
| 2998 | ACAGTAGTAAGTTGCAAAATCTTCAGG (SEQ ID NO: 298) |
| 3001 | **TTTTTT**GCTAGCCAGTCTGTGCTGAC (SEQ ID NO: 299) |
| 3005 | AAATTTACTCGAGACGGTCACCAGGGTGCCCGGACCCCA (SEQ ID NO: 300) |
| 3006 | TTTTTTGCGGCCGCGGTACGTTTGATATCCATTTTGGTCCCTCCGCCGAA (SEQ ID NO: 300) |
| 3012 | TGGGGTCCGGGCACCCTG (SEQ ID NO: 301) |
| D1A12 NotI Rev | TTCTGCGGCCGCGGTACGTTTGATATCCATT (SEQ ID NO: 78) |

TABLE 25

Primers pairs required to create the DNA inserts needed for the three fragment assembly to create the knottin linker libraries. The VL CDR3 knottin linker library was created by a 2 fragment assembly with inserts F1 and F2.

| Library | CDR insertion | Insert | Primer pairs | Template scFv | PCR size (bp) |
|---|---|---|---|---|---|
| A | VH CDR1 | A1 | 2985/2986 | D1A12 | 98 |
| | | A2 | 2965/2966 | None | 132 |
| | | A3 | 2987/2995 | D1A12 | 638 |

TABLE 25-continued

Primers pairs required to create the DNA inserts needed for the three fragment assembly to create the knottin linker libraries. The VL CDR3 knottin linker library was created by a 2 fragment assembly with inserts F1 and F2.

| Library | CDR insertion | Insert | Primer pairs | Template scFv | PCR size (bp) |
|---|---|---|---|---|---|
| B | VH CDR2 | B1 | 2985/2989 | D1A12 | 155 |
| | | B2 | 2967/2968 | None | 137 |
| | | B3 | 2990/2995 | D1A12 | 545 |

TABLE 25-continued

Primers pairs required to create the DNA inserts needed for the three fragment assembly to create the knottin linker libraries. The VL CDR3 knottin linker library was created by a 2 fragment assembly with inserts F1 and F2.

| Library | CDR insertion | Insert | Primer pairs | Template scFv | PCR size (bp) |
|---|---|---|---|---|---|
| C | VH CDR3 | C1 | 2985/2991 | D1A12 | 302 |
| | | C2 | 2969/2970 | None | 136 |
| | | C3 | 3012/2995 | D1A12 | 413 |
| D | VL CDR1 | D1 | 2985/2993 | D1A12 | 485 |
| | | D2 | 2971/2972 | None | 136 |
| | | D3 | 2994/2995 | D1A12 | 233 |
| E | VL CDR2 | E1 | 2985/2996 | D1A12 | 566 |
| | | E2 | 2973/2974 | None | 135 |
| | | E3 | 2997/2995 | D1A12 | 167 |
| F | VL CDR3 | F1 | 2985/2998 | D1A12 | 680 |
| | | F2 | 2975/2976 | None N/A | 141 |
| G | KB_A07 | G1 | 2985/2999 | A07-knotbody | 569 |
| | | G2 | 2977/2978 | None | 137 |
| | | G3 | 3000/2995 | A07-knotbody | 170 |

TABLE 26

Sequences of linkers capable of functional knottin display embedded in D1A12 VH CDR1, VH CDR2, VH CDR3, VL CDR1, VL CDR2 and VL CDR3. XX represents the randomised residues indicated in FIG. 28.

| Clone | CDR insertion | N-term XX | C-term XX |
|---|---|---|---|
| A_A01 | VH CDR1 | AV | TK |
| A_A02 | VH CDR1 | KM | SD |
| A_A03 | VH CDR1 | PI | LP |
| A_A04 | VH CDR1 | EK | PR |
| B_A05 | VH CDR2 | GK | TP |
| B_A06 | VH CDR2 | RL | ED |
| B_A07 | VH CDR2 | PK | GN |
| B_A08 | VH CDR2 | RP | TP |
| B_A10 | VH CDR2 | VP | SL |
| B_A11 | VH CDR2 | KG | TN |
| B_A12 | VH CDR2 | GT | SD |
| C_B01 | VH CDR3 | KP | TK |
| C_B02 | VH CDR3 | RP | SQ |
| C_B03 | VH CDR3 | PT | TV |
| C_B04 | VH CDR3 | KG | QG |
| C_B05 | VH CDR3 | RP | GP |
| C_B06 | VH CDR3 | KG | QG |
| C_B07 | VH CDR3 | RP | DN |
| C_B08 | VH CDR3 | KG | QG |
| D_B09 | VL CDR1 | RG | QD |
| D_B10 | VL CDR1 | IS | HM |
| E_B11 | VL CDR2 | RA | AQ |
| E_B12 | VL CDR2 | RK | SR |
| E_C01 | VL CDR2 | QP | TR |
| E_C02 | VL CDR2 | RP | SR |
| E_C03 | VL CDR2 | RK | VN |
| E_C04 | VL CDR2 | KA | HQ |
| E_C05 | VL CDR2 | VP | HT |
| E_C06 | VL CDR2 | EK | TP |
| E_C08 | VL CDR2 | KV | TE |
| E_C09 | VL CDR2 | RR | GE |
| E_C10 | VL CDR2 | KP | AN |
| E_C11 | VL CDR2 | LP | SI |
| E_C12 | VL CDR2 | HP | SS |
| E_D01 | VL CDR2 | KP | AT |
| E_D02 | VL CDR2 | AP | VD |
| E_D03 | VL CDR2 | LK | SP |
| E_D04 | VL CDR2 | HR | DT |
| E_D05 | VL CDR2 | KG | TN |
| E_D06 | VL CDR2 | RP | DH |
| E_D07 | VL CDR2 | KP | HK |
| E_D08 | VL CDR2 | QP | HE |
| E_D09 | VL CDR2 | TK | AR |
| E_D10 | VL CDR2 | VK | NP |

TABLE 26-continued

Sequences of linkers capable of functional knottin display embedded in D1A12 VH CDR1, VH CDR2, VH CDR3, VL CDR1, VL CDR2 and VL CDR3. XX represents the randomised residues indicated in FIG. 28.

| Clone | CDR insertion | N-term XX | C-term XX |
|---|---|---|---|
| E_D11 | VL CDR2 | TK | TT |
| E_D12 | VL CDR2 | KP | AN |
| E_E01 | VL CDR2 | TK | DT |
| E_E02 | VL CDR2 | QP | TT |
| E_E03 | VL CDR2 | RV | DD |
| E_E04 | VL CDR2 | RK | SN |
| E_E05 | VL CDR2 | RG | HS |
| E_E06 | VL CDR2 | QP | SH |
| E_E07 | VL CDR2 | AK | TR |
| E_E08 | VL CDR2 | RP | TS |
| F_E09 | VL CDR3 | RG | QH |
| F_E10 | VL CDR3 | RG | ND |
| F_E11 | VL CDR3 | PK | TR |
| F_E12 | VL CDR3 | KP | GQ |
| F_F01 | VL CDR3 | QI | SR |
| F_F02 | VL CDR3 | EK | SN |
| F_F03 | VL CDR3 | RG | TH |
| F_F04 | VL CDR3 | EK | TH |
| F_F05 | VL CDR3 | PI | SE |
| F_F06 | VL CDR3 | KG | QH |
| F_F07 | VL CDR3 | KG | HE |

TABLE 27

Sequences of linkers capable of functional knottin display embedded in KB_A07 VL CDR2. XX represents the randomised residues indicated in FIG. 28.

| Clone | CDR insertion | N-term linker | C-term linker | DELFIA signal |
|---|---|---|---|---|
| G_F08 | VL CDR2 | EK | AH | 15940 |
| G_F09 | VL CDR2 | PR | AS | 13431 |
| G_F10 | VL CDR2 | PP | TK | 11667 |
| G_F11 | VL CDR2 | HK | SR | 14160 |
| G_F12 | VL CDR2 | GK | SR | 11209 |
| G_G01 | VL CDR2 | QK | TV | 10863 |
| G_G03 | VL CDR2 | TP | ST | 14493 |
| G_G04 | VL CDR2 | LP | AR | 14330 |
| G_G05 | VL CDR2 | GV | GE | 10429 |
| G_G06 | VL CDR2 | NK | AP | 10255 |
| G_G07 | VL CDR2 | KP | TR | 26510 |
| G_G08 | VL CDR2 | KP | HR | 13848 |
| G_G09 | VL CDR2 | KP | TE | 24701 |
| G_G10 | VL CDR2 | RP | NS | 12258 |
| G_G11 | VL CDR2 | PR | SD | 15883 |
| G_G12 | VL CDR2 | PR | TS | 14911 |
| G_H01 | VL CDR2 | TK | AA | 10714 |
| G_H02 | VL CDR2 | RR | TR | 11930 |
| G_H03 | VL CDR2 | RV | SG | 12457 |
| G_H04 | VL CDR2 | RR | TE | 20675 |
| G_H05 | VL CDR2 | TR | TT | 10654 |
| G_H06 | VL CDR2 | PG | TL | 17126 |

TABLE 28

Alternative framings of EETI-II donor

| Name of format | Sequence | SEQ ID |
|---|---|---|
| EET 1-5 | CPRILMRCKQDSDCLAGCVCGPNGFC | 302 |
| EET 2-6 | CKQDSDCLAGCVCGPNGFC*GSGSDGGV*C | 303 |
| EET 3-1 | CLAGCVCGPNGFC*GSGSDGGV*CPRILMRC | 304 |
| EET 4-2 | CVCGPNGFC*GSGSDGGV*CPRILMRCKQDSDC | 305 |

TABLE 28-continued

| Alternative framings of EETI-II donor | | |
|---|---|---|
| Name of format | Sequence | SEQ ID |
| EET 5-3 | CGPNGFC*GSGSDGGV*CPRILMRCKQDSDCLAGC | 306 |
| EET 6-4 | C*GSGSDGGV*CPRILMRCKQDSDCLAGCVC | 307 |

TABLE 29

Sequence of KnotBodies with alternative framing of EETI_II

C09 (9820)
(SEQ ID NO: 308)
QSVLTQPPSVSEAPRQRVTITCggkr*CGPNGFCGSGSDGGVCPRILMRCKQDSDCLAGC*tsNWYQQKPGQAPVLVVQDDSVRPSGIPERFSGSNSGNTATLTISRVEAGDGADYYCQVWDISSDLGVFGGGTKLTVLGQP E01 (127988)
(SEQ ID NO: 309)
QSVLTQPPSVSEAPRQRVTITCSGSSSNIGNNAVNWYQQLPGKAPKLLIYaagg*CGPNGFCGSGSDGGVCPRILMRCKQDSDCLAGC*gihSGVSDRFSDSKSGTSASLAISGLQSEDEADYYCAAWDDSLNGYVFGTGTKLTVLGQP E08 (121047)
(SEQ ID NO: 310)
QSVLTQPPSVSEAPRQRVTITCSGSSSNIGNNAVNWYQQLPGKAPKLLIYaagg*CGPNGFCGSGSDGGVCPRILMRCKQDSDCLAGC*giqSGIPERFSGSKSGTSASLAISGLRSEDEADYYCAAWDDNLSGYVFGTGTKLTVLGQP E05 (118631)
(SEQ ID NO: 311)
QSVLTQPPSVSEAPRQRVTITCSGSSSNIGNNAVNWYQQLPGKAPKLLIYaagg*CGPNGFCGSGSDGGVCPRILMRCKQDSDCLAGC*gaqSGIPERFSGSKSGTSASLAISGLQSEDEAHYYCAAWDDSLNGYVFGTGTKVTVLGQP F01 (101798)
(SEQ ID NO: 312)
DIQMTQSPSSLSASVGDRVTITCRASQSISSYLNWYQQKPGKAPKLLIDaage*CGPNGFCGSGSDGGVCPRINMRCKQDSDCLAGC*grdSGVPSRFSGSGSGTDFTLTISSLQPEDFATYYCQQSYSTPWTFGQGTKVEIKRT E03 (82495)
(SEQ ID NO: 313)
QSVLTQPPSVSEAPRQRVTITCSGSSSNIGNNAVNWYQQLPGKAPKLLIYaagg*CGPNGFCGSGSDGGVCPRILMRCKQDSDCLAGC*grnSGIPERFSGSKSGHTATLTISRVEAGDEADYYCQVWDSSSDHVLFGGGTKLTVLGQP F07 (72824)
(SEQ ID NO: 314)
QSVLTQPPSVSEAPRQRVTITCSGSSSNIGNNAVNWYQQLPGKAPKLLIYaagg*CGPNGFCGSGSDGGVCPRILMRCKQDSDCLAGC*ggqSGVPDRFSGSKSGTSASLAISRLQSEDEADYYCAAWDDSLNAYVFGTGTKVTVLGQP TABLE 29-continued Sequence of KnotBodies with alternative framing of EETI_II E09 (70274)
(SEQ ID NO: 315)
QSVLTQPPSVSEAPRQRVTITCSGSSSNIGNNAVNWYQQLPGKAPKLLIYaagg*CGPNGFCGSGSDGGVCPRILMRCKQDSDCLAGC*gtqSGIPERFSGSKSGTSASLAISGLRSEDEADYYCAAWDDSLRAYVFGTGTQLTVLGQP F03 (67972)
(SEQ ID NO: 316)
QSVLTQPPSVSEAPRQRVTITCSGSSSNIGNNAVNWYQQLPGRAPKLLIYaagg*CGPNGFCGSGGDGGVCPRILMRCKQDSDCLAGC*gahSGIPERFSGSKSGTSASLAISGLRSEDEADYYCAAWDDSLNGWVFGGGTKVTVLGQP G11 (27650)
(SEQ ID NO: 317)
QSVLTQPPSVSEAPRQRVTITCSGSSSNIGNNAVNWYQQLPGKAPKLLIYaagg*CGPNGFCGSGSDGGVCPRILMRCKQDSDCLAGC*gqsSGVSDRFSGSKSGTSATLDITGLQTGDEADYYCGTWDNSLSVGVFGGGTKVTVLGQP

REFERENCES

1. Jones, P. T., et al. *Nature* 321, 522-525 (1986).
2. Barbas, C. F., et al. *PNAS USA* 90, 10003-10007 (1993).
3. Frederickson, S. et al. *PNAS USA,* 14307-14312 (2006).
4. Wrighton, N. C. et al. *Science* (New York, N. Y273, 458-464 (1996).
5. Liu, T. et al. *J. Am. Chem. Soc.* 136, 10557-10560 (2014).
6. Kogelberg, H. et al. *Journal of molecular biology* 382, 385-401 (2008).
7. Man, Y. K. S. et al. *PLoS ONE* 8, e70452 (2013).
8. Saini, S. S. et al *Eur. J. Immunol.* 29, 2420-2426 (1999).
9. Saini, S. S., et al. *Int. Immunol.* 15, 845-853 (2003).
10. Wang, F. et al. *Cell* 153, 1379-1393 (2013).
11. Zhang, Y. et al. *Angew. Chem. Int. Ed. Engl.* 53, 132-135 (2014).
12. Zhang, Y. et al. *Angew. Chem. Int. Ed. Engl.* 52, 8295-8298 (2013).
13. Zhang, Y. et al. *AACS Chem. Biol.* 8, 2117-2121 (2013).
14. Liu, T. et al. *PNAS USA* 112, 1356-1361 (2015).
15. Peng, Y. et al. *Chem. Biol.* 22, 1134-1143 (2015).
16. Melidoni, A. N. et al. *PNAS USA* 110, 17802-17807 (2013).
17. Betton, J. M. et al. *Nature* (1997).
18. Collinet, B. et al. 275, 17428-17433 (2000).
19. Ruth, N. et al. *FEBS Journal* 275, 5150-5160 (2008).
20. Vandevenne, M. et al. *Protein Engineering Design and Selection* 21, 443-451 (2008).
21. Crasson, O. et al. *Protein Eng. Des. Sel.* 28, 451-460 (2015).
22. Neylon, C. *Nucleic Acids Res.* 32, 1448-1459 (2004).
23. Banta, S. et al. *Annu Rev Biomed Eng* 15, 93-113 (2013).
24. Kimura, R. H. et al. *PLoS ONE 6, el* 6112 (2011).
25. Takacs, Z. et al. *PNAS* 106, 22211-22216 (2009).
26. Gui, J. et al. *Curr. Biol.* (2014). doi:10.1016/j.cub.2014.01.013
27. Dyson, M. R. et al. *Anal Biochem* 417, 25-35 (2011).
28. Schofield, D. J. et al. *Genome biology* 8, R254 (2007).
29. Lefranc, M.-P. et al. *Nucleic Acids Res.* 43, D413-22 (2015).

30. Katz, B. A. e. *Biochemistry* 34, 15421-15429 (1995).
31. Katz, B. A. *Annu Rev Biophys Biomol Struct* 26, 27-45 (1997).
32. Lowman, H. B. *Annu Rev Biophys Biomol Struct* 26, 401-424 (1997).
33. Giebel, L. B. et al. *Biochemistry* 34, 15430-15435 (1995).
34. Holler, P. D. et al. *PNAS USA* 97, 5387-5392 (2000).
35. Li, Y. et al. *Nat. Biotechnol.* 23, 349-354 (2005).
36. Wozniak-Knopp, G. et al. *Protein Eng. Des. Sel.* 23, 289-297 (2010).
37. Ying, T. et al. *Biochim. Biophys. Acta* 1844, 1977-1982 (2014).
38. Binz, H. K. et al. *Nature biotechnology* 23, 1257-1268 (2005).
39. Skerra, A. *Curr. Opin. Biotechnol.* 18, 295-304 (2007).
40. Gebauer, M. & Skerra, A. *Curr Opin Chem Biol* 13, 245-255 (2009).
41. Hufton, S. E. et al. *FEBS Lett.* 475, 225-231 (2000).
42. Nord, K. et al. *Nat. Biotechnol.* 15, 772-777 (1997).
43. Nygren, P.-A. & Skerra, A. *J Immunol Methods* 290, 3-28 (2004).
44. Koide, A. et al. *Journal of molecular biology* 415, 393-405 (2012).
45. Steiner, D. et al. *Journal of Molecular Biology* 382, 1211-1227 (2008).
46. Tiede, C. et al. *Protein Eng. Des. Sel.* 27, 145-155 (2014).
47. Gebauer, M. & Skerra, A. *Meth. Enzymol.* 503, 157-188 (2012).
48. Colas, P. et al. *Nature* 380, 548-550 (1996).
49. De Meyer, T et al. *Trends Biotechnol.* 32, 263-270 (2014).
50. Shao, C.-Y. et al. *Mol. Immunol.* 44, 656-665 (2007).
51. Kruziki, M. A., et al. *Chem. Biol.* 22, 946-956 (2015).
52. Nygren, P.-A. *FEBS J.* 275, 2668-2676 (2008).
53. Jost, C. & Plückthun, A. *Curr. Opin. Struct. Biol.* 27, 102-112 (2014).
54. Kolmar, H. *FEBS J.* 275, 2684-2690 (2008).
55. Mouhat, S. et al *Current Pharmaceutical Design* 14, 2503-2518 (2008).
56. Wang, X. et al. *Nat. Struct. Biol.* 7, 505-513 (2000).
57. Gracy, J. et al. *Nucleic Acids Res.* 36, D314-9 (2008).
58. England, S. & de Groot, M. *J. Br. J. Pharmacol.* 158, 1413-1425 (2009).
59. Clare, J. *J. Expert Opin Investig Drugs* 19, 45-62 (2010).
60. Kolmar, H. *Expert Rev Mol Diagn* 10, 361-368 (2010).
61. Gelly, J.-C. et al. *Nucleic Acids Res.* 32, D156-9 (2004).
62. Combelles, et al. *Proteins* 73, 87-103 (2008).
63. Heitz, A., et al. *Eur. J. Biochem.* 233, 837-846 (1995).
64. Cheek, S. et al. *Journal of molecular biology* 359, 215-237 (2006).
65. Yu, F. H. *Pharmacological Reviews* 57, 387-395 (2005).
66. Escoubas, P. *Mol. Divers.* 10, 545-554 (2006).
67. Klint, J. K. et al. *Toxicon* 60, 478-491 (2012).
68. Shu, Q. et al. *Protein Sci.* 11, 245-252 (2002).
69. Ueberheide, B. M. et al *PNAS USA* 106, 6910-6915 (2009).
70. Yang, S. et al. *NAS USA* (2013). doi:10.1073/pnas.1306285110
71. Peng, K. et al. *The Journal of biological chemistry* 277, 47564-47571 (2002).
72. Xiao, Y. et al. *Mol Pharmacol* 78, 1124-1134 (2010).
73. Crest, M. et al. *The Journal of biological chemistry* 267, 1640-1647 (1992).
74. Tudor, J. E. et al. *Nat. Struct. Biol.* 3, 317-320 (1996)
75. Galat, A., et al. *FEBS J.* 275, 3207-3225 (2008).
76. McCafferty, J et al. *Nature* 348, 552-554
77. Hoogenboom, H. R. et al. *Nucleic Acids Res.* 19, 4133-4137 (1991).
78. Zhang, H. et al. *PNAS USA* 109, 15728-15733 (2012).
79. Xie, J. et al. *PNAS USA* 110, 8099-8104 (2013).
80. Nishimiya, D. *Appl. Microbiol. Biotechnol.* 98, 1031-1042 (2014).
81. Vendel, M. C. et al. *Arch. Biochem. Biophys.* 526, 188-193 (2012).
82. Bagal, S. K. et al. *J. Med. Chem.* 56, 593-624 (2013).
83. Hübner, C. A. & Jentsch, T. *J. Hum. Mol. Genet.* 11, 2435-2445 (2002).
84. Jentsch, T. J., et al. *Nat. Cell Biol.* 6, 1039-1047 (2004).
85. Lü, Q. & An, W. F. *Combinatorial chemistry & high throughput screening* 11, 185-194 (2008).
86. Tate, C. G. *FEBS Lett.* 504, 94-98 (2001).
87. Shintre, C. A. et al. *PNAS USA* 110, 9710-9715 (2013).
88. Suharni et al. *Monoclon Antib Immunodiagn Immunother* 33, 378-385 (2014).
89. Pavlidou, M. et al. *PLoS ONE* 8, e72272 (2013).
90. Tillotson, B. J. et al. *Protein Eng. Des. Sel.* 26, 101-112 (2013).
91. Zhang, H. et al. *Chem. Biol.* 20, 734-741 (2013).
92. Gunasekera, S. et al. *J. Med. Chem.* 51, 7697-7704 (2008).
93. Keller, T. et al. *PLoS ONE* 10, e0127169 (2015).
94. Jung, S. & Pluckthun, A. *Protein Eng.* 10, 959-966 (1997).
95. Akerström, B. et al. *J Immunol Methods* 177, 151-163 (1994).
96. Jespers, L et al. *Nat. Biotechnol.* 22, 1161-1165 (2004).
97. Richler, E. et al. *Nature methods* 5, 87-93 (2007).
98. Podust, V. N. et al. *J Control Release* (2015). doi:10.1016/j.jconrel.2015.10.038
99. Schlapschy, M. et al. *Protein Eng. Des. Sel.* 26, 489-501 (2013).
100. Pershad, K. et al. *Protein Engineering Design and Selection* 23, 279-288 (2010).
101. Tape, C. J. et al. *PNAS USA* 108, 5578-5583 (2011).
102. Vaughan, T. J. et al. *Nature biotechnology* 14, 309-314 (1996).
103. Favel, A. et al. *Int. J. Pept. Protein Res.* 33, 202-208 (1989).
104. Chiche, L. et al. *Current Protein & Peptide Science* 5, 341-349
105. Azzazy, H. M. E. & Highsmith, W. E. *Clin. Biochem.* 35, 425-445 (2002).
106. Goletz, S. et al. *Journal of molecular biology* 315, 1087-1097 (2002).
107. Lee, C. M. Y., et al. *Nature Protocols* 2, 3001-3008 (2007).
108. Hacker, D. L. et al. *Protein expression and purification* 92, 67-76 (2013).
109. Phaser crystallographic software. 40, 658-674 (2007).
110. PHENIX: a comprehensive Python-based system for macromolecular structure solution. 66, 213-221 (2010).
111. Afonine, P. V. et al. *Acta Crystallogr. D Biol. Crystallogr.* 68, 352-367 (2012).
112. Spiess, C. *Mol. Immunol.* 67, 95-106 (2015).
113. Falk, R. et al. *Methods* 58, 69-78 (2012).
114. Hosse, R. J. et al. *Protein Sci.* 15, 14-27 (2006).
115. Fernández-Suárez, X. M., et al. *Nucleic Acids Res.* 42, D1-6 (2014).
116. Rocha, L. *Journal of Molecular Structure* (2014).
117. Dickinson, C. D. et al. *Journal of molecular biology* 236, 1079-1092 (1994).
118. Dawson, R. J. P. et al. *Nat Commun* 3, 936 (2012).

119 Hernandez et al *Biochemistry* 39 (19), 5722-5730 (2000)
120. Obermeier, B et al. *Nat Med* 19, 1584-1596 (2013))
121. Ubogu, E. E. *J. Vasc. Res.* 50, 289-303 (2013)).
122. Diochot S et al, *Nature* 490, 552-555 (2012).
123. Kawahara, M. et al *Biochem Biophys Res Commun,* 315, 132-138. (2004)
124. Kawahara, M. et al *Journal of Biotechnology,* 133, 154-161. (2008).
125. Kawahara, M. et al *Cytokine,* 55, 402-408. (2011)

The invention claimed is:

1. A library of binding members comprising:

a diverse population of fusion proteins, each fusion protein comprising a donor diversity scaffold domain inserted into a recipient diversity scaffold domain, wherein the donor diversity scaffold domain comprises a donor scaffold and a donor interaction sequence and the recipient diversity scaffold domain comprises a recipient scaffold and a recipient interaction sequence, wherein the donor diversity scaffold domain is a knottin, and wherein the recipient diversity scaffold domain is an antibody variable domain and the donor diversity scaffold domain is a replacement for all or part of one of VH CDR1, VH CDR2, VH CDR3, VL CDR1, VL CDR2 or VL CDR3 of the antibody variable domain, wherein the donor diversity scaffold domain:

a) is a peptide that consists of 100 or fewer amino acids, and b) comprises two or more disulphide bridges formed by four or more cysteine residues within the donor scaffold, wherein the donor diversity scaffold is located 8 Angstroms to 13 Angstroms from the recipient diversity scaffold domain, calculated from the end of a preceding framework of the antibody variable domain of the recipient diversity scaffold domain to a first cysteine residue of the donor diversity scaffold domain wherein one or both of the donor interaction sequence and the recipient interaction sequence are diverse in said diverse population of fusion proteins.

2. A fusion protein comprising a donor diversity scaffold domain inserted into a recipient diversity scaffold domain, wherein the donor diversity scaffold domain comprises a donor scaffold and a donor interaction sequence and the recipient diversity scaffold domain comprises a recipient scaffold and a recipient interaction sequence, wherein the donor diversity scaffold domain is a knottin, and wherein the N terminal and C terminal of the donor diversity scaffold domain are linked to the recipient diversity scaffold domain without linkers or with linkers of up to 4 amino acids, wherein the recipient diversity scaffold domain is an antibody variable domain and the donor diversity scaffold domain is a replacement for all or part of one of VH CDR1, VH CDR2, VH CDR3, VL CDR1, VL CDR2 or VL CDR3 of the antibody variable domain, wherein the donor diversity scaffold domain:

a) is a peptide that consists of 100 or fewer amino acids and b) comprises two or more disulphide bridges formed by four or more cysteine residues within the donor scaffold, and wherein the donor diversity scaffold is located 8 Angstroms to 13 Angstroms from the recipient diversity scaffold domain, calculated from the end of a preceding framework of the antibody variable domain of the recipient diversity scaffold domain to a first cysteine residue of the donor diversity scaffold domain.

3. A binding member comprising a fusion protein according to claim 2 and a partner domain.

4. The fusion protein of claim 2, wherein the recipient diversity scaffold domain is an antibody light chain variable (VL) domain.

5. The fusion protein of claim 4, which is associated with a partner domain, wherein the partner domain is an antibody heavy chain variable (VH) domain.

6. The fusion protein of claim 5, wherein the VL domain and the VH domain are connected by a linker.

7. The fusion protein of claim 4, wherein the donor diversity scaffold domain is a replacement for the entirety of one the CDR1 or CDR2 of the antibody VL domain.

8. The fusion protein of claim 2, wherein the donor diversity scaffold domain is Ecballium elaterium trypsin inhibitor-II (EETI-II).

9. The fusion protein of claim 2, wherein a native N terminal and a native C terminal of the donor diversity scaffold domain are each linked to the recipient diversity scaffold domain.

10. The fusion protein of claim 2, wherein an artificial N terminal and an artificial C terminal generated by cyclisation and linearization of the donor diversity scaffold domain are each linked to the recipient diversity scaffold domain.

11. The library of claim 1, wherein the binding members in the library comprise;

(i) diverse donor interaction sequences and the same recipient interaction sequence, (ii) diverse recipient interaction sequences and the same donor interaction sequence, or (iii) diverse recipient and diverse donor interaction sequences.

12. The library of claim 11, wherein the binding members in the library have diverse linker sequences.

13. The library of claim 1, wherein the binding members in the library have the same recipient interaction sequences, the same donor interaction sequences, and diverse linker sequences.

14. The library of claim 1, wherein the binding members in the library further comprise partner domains.

15. The library of claim 1, wherein each binding member in the library is displayed on the surface of a ribosome which comprises nucleic acid encoding the binding member, a cell which comprises nucleic acid encoding the binding member, or a virus which comprises nucleic acid encoding the binding member.

16. The library of claim 1, wherein the binding members are displayed on the surface of a bacteriophage or the surface of a eukaryotic cell.

17. The library of claim 1, wherein the fusion protein of the binding member is fused to a coat protein of a filamentous phage.

18. The binding member of claim 3, wherein the recipient diversity scaffold domain of the fusion protein is associated with a partner domain through a covalent or non-covalent bond.

19. The binding member of claim 3, wherein the binding member further comprises multiple partner domains.

20. The binding member of claim 3, wherein the fusion protein and the partner domain bind to the same target molecule, or wherein one of the fusion protein and the partner domain binds to a first target molecule and the other of the fusion protein and the partner domain binds to a second target molecule.

21. The binding member of claim 20, wherein the same target molecule, first target molecule, or second target molecule is an integral membrane protein.

22. The binding member of claim 21, wherein the integral membrane protein is an ion channel, a G protein-coupled receptor (GPCR), or Type I receptor.

23. The fusion protein of claim 2, wherein the recipient diversity scaffold domain is an antibody heavy chain variable (VH) domain.

24. The fusion protein of claim 23, wherein the partner domain is an antibody light chain variable (VL) domain.

25. The fusion protein of claim 2, wherein the interaction sequence of the donor diversity scaffold domain and one or more CDRs of the antibody variable domain interact with the same epitope on a target molecule.

26. The fusion protein of claim 25, wherein the one or more CDRs of the antibody variable domain that interact with the same epitope on the target molecule is a VH CDR3 or a VL CDR3.

27. The fusion protein of claim 2, wherein the donor diversity scaffold domain consists of at least 15 amino acids.

28. The library of binding members of claim 1, wherein the linkers are diverse in said population.

29. The library of binding members of claim 1, wherein the linkers are diverse in said population; and wherein one or both of the donor interaction sequence and the recipient interaction sequence are diverse in said population.

30. The library of binding members of claim 1, wherein the fusion proteins are associated with binding partners to form heterodimers.

31. The library of binding members of claim 1, wherein the donor diversity scaffold domain is a replacement for all or part of one of VH CDR1, VH CDR2, VL CDR1, or VL CDR2 of the antibody variable domain.

32. The fusion protein of claim 2, wherein the donor diversity scaffold domain is a replacement for all or part of one of VH CDR1, VH CDR2, VL CDR1, or VL CDR2 of the antibody variable domain.

33. The library of binding members of claim 1, wherein the N terminal and C terminal of the donor diversity scaffold domain are linked to the recipient diversity scaffold domain without linkers or with linkers of up to 4 amino acids.

* * * * *

SEQUENCE LISTING

```
<160> NUMBER OF SEQ ID NOS: 363

<210> SEQ ID NO 1
<211> LENGTH: 5
<212> TYPE: PRT
<213> ORGANISM: Artificial Sequence
<220> FEATURE:
<223> OTHER INFORMATION: cytokine linker

<400> SEQUENCE: 1

Gly Gly Gly Gly Ser
1               5


<210> SEQ ID NO 2
<211> LENGTH: 4
<212> TYPE: PRT
<213> ORGANISM: Artificial Sequence
<220> FEATURE:
<223> OTHER INFORMATION: cytokine linker

<400> SEQUENCE: 2

Gly Gly Ser Gly
1


<210> SEQ ID NO 3
<211> LENGTH: 4
<212> TYPE: PRT
<213> ORGANISM: Artificial Sequence
<220> FEATURE:
<223> OTHER INFORMATION: amino acid linker

<400> SEQUENCE: 3

Asp Pro Gly Gly
1


<210> SEQ ID NO 4
<211> LENGTH: 5
<212> TYPE: PRT
<213> ORGANISM: Artificial Sequence
<220> FEATURE:
<223> OTHER INFORMATION: amino acid linker

<400> SEQUENCE: 4

Tyr Pro Gly Asp Pro
1               5


<210> SEQ ID NO 5
<211> LENGTH: 5
<212> TYPE: PRT
<213> ORGANISM: Artificial Sequence
<220> FEATURE:
<223> OTHER INFORMATION: amino acid linker

<400> SEQUENCE: 5

Pro Asp Pro Gly Gly
1               5


<210> SEQ ID NO 6
<211> LENGTH: 5
<212> TYPE: PRT
<213> ORGANISM: Artificial Sequence
```

<220> FEATURE:
<223> OTHER INFORMATION: amino acid linker

<400> SEQUENCE: 6

Tyr Pro Gly Gly Pro
1 5

<210> SEQ ID NO 7
<211> LENGTH: 141
<212> TYPE: DNA
<213> ORGANISM: Artificial Sequence
<220> FEATURE:
<223> OTHER INFORMATION: Huwentoxin-IV

<400> SEQUENCE: 7
gagtgcctgg aaatcttcaa ggcctgcaac cccagcaacg accagtgctg caagagcagc 60
aagctcgtgt gcagcagaaa gacccggtgg tgcaagtacc agatctccag atgacccaga 120
gcccaagcag cctgagcgcc a 141

<210> SEQ ID NO 8
<211> LENGTH: 37
<212> TYPE: PRT
<213> ORGANISM: Artificial Sequence
<220> FEATURE:
<223> OTHER INFORMATION: Huwentoxin-IV

<400> SEQUENCE: 8

Glu Cys Leu Glu Ile Phe Lys Ala Cys Asn Pro Ser Asn Asp Gln Cys
1 5 10 15

Cys Lys Ser Ser Lys Leu Val Cys Ser Arg Lys Thr Arg Trp Cys Lys
20 25 30

Tyr Gln Ile Gly Lys
35

<210> SEQ ID NO 9
<211> LENGTH: 126
<212> TYPE: DNA
<213> ORGANISM: Artificial Sequence
<220> FEATURE:
<223> OTHER INFORMATION: ProTx-II

<400> SEQUENCE: 9
tactgccaga aatggatgtg gacctgcgac agcgagcgga agtgctgcga gggcatggtg 60
tgccggctgt ggtgcaagaa aaagctgtgg tccagatgac ccagagccca agcagcctga 120
gcgcca 126

<210> SEQ ID NO 10
<211> LENGTH: 30
<212> TYPE: PRT
<213> ORGANISM: Artificial Sequence
<220> FEATURE:
<223> OTHER INFORMATION: ProTx-II

<400> SEQUENCE: 10

Tyr Cys Gln Lys Trp Met Trp Thr Cys Asp Ser Glu Arg Lys Cys Cys
1 5 10 15

Glu Gly Met Val Cys Arg Leu Trp Cys Lys Lys Lys Leu Trp
20 25 30

<210> SEQ ID NO 11
<211> LENGTH: 174
<212> TYPE: DNA

<213> ORGANISM: Artificial Sequence
<220> FEATURE:
<223> OTHER INFORMATION: Ssm6a

<400> SEQUENCE: 11
gccgacaaca agtgcgagaa cagcctgcgg agagagatcg cctgcggcca gtgccgggac 60
aaagtgaaaa ccgacggcta cttctacgag tgctgcacca gcgacagcac cttcaagaag 120
tgccaggacc tgctgcactc cagatgaccc agagcccaag cagcctgagc gcca 174

<210> SEQ ID NO 12
<211> LENGTH: 46
<212> TYPE: PRT
<213> ORGANISM: Artificial Sequence
<220> FEATURE:
<223> OTHER INFORMATION: Ssm6a

<400> SEQUENCE: 12

Ala Asp Asn Lys Cys Glu Asn Ser Leu Arg Arg Glu Ile Ala Cys Gly
1 5 10 15

Gln Cys Arg Asp Lys Val Lys Thr Asp Gly Tyr Phe Tyr Glu Cys Cys
20 25 30

Thr Ser Asp Ser Thr Phe Lys Lys Cys Gln Asp Leu Leu His
35 40 45

<210> SEQ ID NO 13
<211> LENGTH: 149
<212> TYPE: DNA
<213> ORGANISM: Artificial Sequence
<220> FEATURE:
<223> OTHER INFORMATION: Kaliotoxin (KTX)

<400> SEQUENCE: 13
atctatgctg cagggagggg tgtggaaatt aacgtgaagt gtagcgggag cccacagtgc 60
cttaaaccat gcaaagatgc ggggatgcgc tttggaaagt gcatgaaccg taaatgccac 120
tgcacgccga aggccaactc cggagtctc 149

<210> SEQ ID NO 14
<211> LENGTH: 37
<212> TYPE: PRT
<213> ORGANISM: Artificial Sequence
<220> FEATURE:
<223> OTHER INFORMATION: Kaliotoxin (KTX)

<400> SEQUENCE: 14

Gly Val Glu Ile Asn Val Lys Cys Ser Gly Ser Pro Gln Cys Leu Lys
1 5 10 15

Pro Cys Lys Asp Ala Gly Met Arg Phe Gly Lys Cys Met Asn Arg Lys
20 25 30

Cys His Cys Thr Pro
35

<210> SEQ ID NO 15
<211> LENGTH: 138
<212> TYPE: DNA
<213> ORGANISM: Artificial Sequence
<220> FEATURE:
<223> OTHER INFORMATION: Mokatoxin-1 (MoKa-1)

<400> SEQUENCE: 15
atcaacgtga agtgcagcct gccccagcag tgcatcaagc cctgcaagga cgccggcatg 60
agattcggca agtgcatgaa caagaaatgc cggtgctaca gctccagatg acccagagcc 120
caagcagcct gagcgcca 138

<210> SEQ ID NO 16
<211> LENGTH: 34
<212> TYPE: PRT
<213> ORGANISM: Artificial Sequence
<220> FEATURE:
<223> OTHER INFORMATION: Mokatoxin-1 (MoKa-1)

<400> SEQUENCE: 16

Ile Asn Val Lys Cys Ser Leu Pro Gln Gln Cys Ile Lys Pro Cys Lys
1 5 10 15

Asp Ala Gly Met Arg Phe Gly Lys Cys Met Asn Lys Lys Cys Arg Cys
20 25 30

Tyr Ser

<210> SEQ ID NO 17
<211> LENGTH: 141
<212> TYPE: DNA
<213> ORGANISM: Artificial Sequence
<220> FEATURE:
<223> OTHER INFORMATION: Shk

<400> SEQUENCE: 17
agaagctgca tcgacaccat ccccaagagc agatgcaccg ccttccagtg caagcacagc 60
atgaagtacc ggctgagctt ctgtagaaag acctgcggca cctgttccag atgacccaga 120
gcccaagcag cctgagcgcc a 141

<210> SEQ ID NO 18
<211> LENGTH: 35
<212> TYPE: PRT
<213> ORGANISM: Artificial Sequence
<220> FEATURE:
<223> OTHER INFORMATION: Shk

<400> SEQUENCE: 18

Arg Ser Cys Ile Asp Thr Ile Pro Lys Ser Arg Cys Thr Ala Phe Gln
1 5 10 15

Cys Lys His Ser Met Lys Tyr Arg Leu Ser Phe Cys Arg Lys Thr Cys
20 25 30

Gly Thr Cys
35

<210> SEQ ID NO 19
<211> LENGTH: 156
<212> TYPE: DNA
<213> ORGANISM: Artificial Sequence
<220> FEATURE:
<223> OTHER INFORMATION: PcTX1

<400> SEQUENCE: 19
gaggactgca tccccaagtg gaagggctgc gtgaacagac acggcgactg ttgcgagggc 60
ctggaatgct ggaagcggag gcggagcttc gaagtgtgcg tgcccaagac ccctaagacc 120
tccagatgac ccagagccca agcagcctga gcgcca 156

<210> SEQ ID NO 20
<211> LENGTH: 40
<212> TYPE: PRT
<213> ORGANISM: Artificial Sequence
<220> FEATURE:
<223> OTHER INFORMATION: PcTX1

<400> SEQUENCE: 20

Glu Asp Cys Ile Pro Lys Trp Lys Gly Cys Val Asn Arg His Gly Asp
1               5                   10                  15

Cys Cys Glu Gly Leu Glu Cys Trp Lys Arg Arg Arg Ser Phe Glu Val
            20                  25                  30

Cys Val Pro Lys Thr Pro Lys Thr
        35                  40

<210> SEQ ID NO 21
<211> LENGTH: 30
<212> TYPE: PRT
<213> ORGANISM: Artificial Sequence
<220> FEATURE:
<223> OTHER INFORMATION: EETI-II

<400> SEQUENCE: 21

Gly Cys Pro Arg Ile Leu Met Arg Cys Lys Gln Asp Ser Asp Cys Leu
1               5                   10                  15

Ala Gly Cys Val Cys Gly Pro Asn Gly Phe Cys Gly Ser Pro
            20                  25                  30

<210> SEQ ID NO 22
<211> LENGTH: 26
<212> TYPE: PRT
<213> ORGANISM: Artificial Sequence
<220> FEATURE:
<223> OTHER INFORMATION: Conotoxin-omega
<220> FEATURE:
<221> NAME/KEY: misc_feature
<222> LOCATION: (26)..(26)
<223> OTHER INFORMATION: Xaa can be any naturally occurring amino acid

<400> SEQUENCE: 22

Cys Lys Gly Lys Gly Ala Lys Cys Ser Arg Leu Met Tyr Asp Cys Cys
1               5                   10                  15

Thr Gly Ser Cys Arg Ser Gly Lys Cys Xaa
            20                  25

<210> SEQ ID NO 23
<211> LENGTH: 34
<212> TYPE: PRT
<213> ORGANISM: Artificial Sequence
<220> FEATURE:
<223> OTHER INFORMATION: MCoTI-II

<400> SEQUENCE: 23

Ser Gly Ser Asp Gly Gly Val Cys Pro Lys Ile Leu Lys Lys Cys Arg
1               5                   10                  15

Arg Asp Ser Asp Cys Pro Gly Ala Cys Ile Cys Arg Gly Asn Gly Tyr
            20                  25                  30

Cys Gly

<210> SEQ ID NO 24
<211> LENGTH: 57
<212> TYPE: PRT
<213> ORGANISM: Artificial Sequence
<220> FEATURE:
<223> OTHER INFORMATION: Mambalgin-1 (Mba-1)

<400> SEQUENCE: 24

Leu Lys Cys Tyr Gln His Gly Lys Val Val Thr Cys His Arg Asp Met
1               5                   10                  15

```
Lys Phe Cys Tyr His Asn Thr Gly Met Pro Phe Arg Asn Leu Lys Leu
            20                  25                  30

Ile Leu Gln Gly Cys Ser Ser Ser Cys Ser Glu Thr Glu Asn Asn Lys
        35                  40                  45

Cys Cys Ser Thr Asp Arg Cys Asn Lys
    50                  55


<210> SEQ ID NO 25
<211> LENGTH: 57
<212> TYPE: PRT
<213> ORGANISM: Artificial Sequence
<220> FEATURE:
<223> OTHER INFORMATION: Mambalgin-2 (Mba-2)

<400> SEQUENCE: 25

Leu Lys Cys Phe Gln His Gly Lys Val Val Thr Cys His Arg Asp Met
1               5                   10                  15

Lys Phe Cys Tyr His Asn Thr Gly Met Pro Phe Arg Asn Leu Lys Leu
            20                  25                  30

Ile Leu Gln Gly Cys Ser Ser Ser Cys Ser Glu Thr Glu Asn Asn Lys
        35                  40                  45

Cys Cys Ser Thr Asp Arg Cys Asn Lys
    50                  55


<210> SEQ ID NO 26
<211> LENGTH: 103
<212> TYPE: PRT
<213> ORGANISM: Artificial Sequence
<220> FEATURE:
<223> OTHER INFORMATION: Ad-LOX1-A

<400> SEQUENCE: 26

Ala Thr Gly Val Arg Ala Val Pro Gly Asn Glu Asn Ser Leu Glu Ile
1               5                   10                  15

Glu Glu Leu Ala Arg Phe Ala Val Asp Glu His Asn Lys Lys Glu Asn
            20                  25                  30

Ala Leu Leu Glu Phe Val Arg Val Val Lys Ala Lys Glu Gln Thr Ala
        35                  40                  45

His Leu Asp Pro Leu Met Asp Thr Met Tyr Tyr Leu Thr Leu Glu Ala
    50                  55                  60

Lys Asp Gly Gly Lys Lys Lys Leu Tyr Glu Ala Lys Val Trp Val Lys
65                  70                  75                  80

Phe Trp Met Ile Ser Asp Leu Ile Phe Asn Phe Lys Glu Leu Gln Glu
                85                  90                  95

Phe Lys Pro Val Gly Asp Ala
            100


<210> SEQ ID NO 27
<211> LENGTH: 105
<212> TYPE: PRT
<213> ORGANISM: Artificial Sequence
<220> FEATURE:
<223> OTHER INFORMATION: Ad-LOX1-B

<400> SEQUENCE: 27

Ala Thr Gly Val Arg Ala Val Pro Gly Asn Glu Asn Ser Leu Glu Ile
1               5                   10                  15

Glu Glu Leu Ala Arg Phe Ala Val Asp Glu His Asn Lys Lys Glu Asn
            20                  25                  30

Ala Leu Leu Glu Phe Val Arg Val Val Lys Ala Lys Glu Gln Glu Gln
```

35 40 45

Pro Ile Gly Glu His Pro Val Asn Asp Thr Met Tyr Tyr Leu Thr Leu
50 55 60

Glu Ala Lys Asp Gly Gly Lys Lys Lys Leu Tyr Glu Ala Lys Val Trp
65 70 75 80

Val Lys Arg Trp Leu Arg Phe Thr Glu Ile Tyr Asn Phe Lys Glu Leu
85 90 95

Gln Glu Phe Lys Pro Val Gly Asp Ala
100 105

<210> SEQ ID NO 28
<211> LENGTH: 91
<212> TYPE: PRT
<213> ORGANISM: Artificial Sequence
<220> FEATURE:
<223> OTHER INFORMATION: fibronectin domain

<400> SEQUENCE: 28

Arg Asp Leu Glu Val Val Ala Ala Thr Pro Thr Ser Leu Leu Ile Ser
1 5 10 15

Trp Asp Ala Pro Ala Val Thr Val Arg Tyr Tyr Arg Ile Thr Tyr Gly
20 25 30

Glu Thr Gly Gly Asn Ser Pro Val Gln Glu Phe Thr Val Pro Gly Ser
35 40 45

Lys Ser Thr Ala Thr Ile Ser Gly Leu Lys Pro Gly Val Asp Tyr Thr
50 55 60

Ile Thr Val Tyr Ala Val Thr Gly Arg Gly Asp Ser Pro Ala Ser Ser
65 70 75 80

Lys Pro Ile Ser Ile Asn Tyr Arg Thr Glu Ile
85 90

<210> SEQ ID NO 29
<211> LENGTH: 64
<212> TYPE: PRT
<213> ORGANISM: Artificial Sequence
<220> FEATURE:
<223> OTHER INFORMATION: T7 Gp2 protein

<400> SEQUENCE: 29

Met Ser Asn Val Asn Thr Gly Ser Leu Ser Val Asp Asn Lys Lys Phe
1 5 10 15

Trp Ala Thr Val Glu Ser Ser Glu His Ser Phe Glu Val Pro Ile Tyr
20 25 30

Ala Glu Thr Leu Asp Glu Ala Leu Glu Leu Ala Glu Trp Gln Tyr Val
35 40 45

Pro Ala Gly Phe Glu Val Thr Arg Val Arg Pro Cys Val Ala Pro Lys
50 55 60

<210> SEQ ID NO 30
<211> LENGTH: 122
<212> TYPE: PRT
<213> ORGANISM: Artificial Sequence
<220> FEATURE:
<223> OTHER INFORMATION: D1 A12 (VH)

<400> SEQUENCE: 30

Glu Val Gln Leu Val Glu Ser Gly Gly Gly Leu Val Arg Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Gly Ser Gly Gly Ser Thr Tyr Tyr Ala Asp Ser Val
50 55 60

Lys Gly Arg Phe Thr Ile Ser Arg Asp Asn Thr Lys Asn Ser Leu Tyr
65 70 75 80

Leu Gln Met Thr Ser Leu Arg Ala Asp Asp Thr Ala Phe Tyr Tyr Cys
85 90 95

Val Lys Asp Phe Gly Pro Gly Tyr Gly Thr Gly Trp Phe Asp Tyr Trp
100 105 110

Gly Pro Gly Thr Leu Val Thr Val Ser Ser
115 120

<210> SEQ ID NO 31
<211> LENGTH: 143
<212> TYPE: PRT
<213> ORGANISM: Artificial Sequence
<220> FEATURE:
<223> OTHER INFORMATION: KB_A07 ShK (VL)

<400> SEQUENCE: 31

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Ala Ala Gly Val Arg Ser Cys Ile Asp Thr Ile Pro Lys Ser Arg
50 55 60

Cys Thr Ala Phe Gln Cys Lys His Ser Met Lys Tyr Arg Leu Ser Phe
65 70 75 80

Cys Arg Lys Thr Cys Gly Thr Cys Ser Arg Ser Gly Val Pro Ser Arg
85 90 95

Phe Ser Gly Ser Gly Ser Gly Thr Asp Phe Thr Leu Thr Ile Ser Ser
100 105 110

Leu Gln Pro Glu Asp Phe Ala Thr Tyr Tyr Cys Gln Gln Gly Ala Ser
115 120 125

Pro Pro Tyr Thr Phe Gly Gln Gly Thr Lys Val Glu Ile Lys Arg
130 135 140

<210> SEQ ID NO 32
<211> LENGTH: 146
<212> TYPE: PRT
<213> ORGANISM: Artificial Sequence
<220> FEATURE:
<223> OTHER INFORMATION: KB_A12 ShK (VL)

<400> SEQUENCE: 32

Gln Ser Val Leu Thr Gln Pro Pro Ser Val Ser Glu Ala Pro Arg Gln
1 5 10 15

Arg Val Thr Ile Thr Cys Ser Gly Ser Ser Ser Asn Ile Gly Asn Asn
20 25 30

Ala Val Asn Trp Tyr Gln Gln Leu Pro Gly Lys Ala Pro Lys Leu Leu
35 40 45

Ile Tyr Ala Ala Gly Arg Arg Ser Cys Ile Asp Thr Ile Pro Lys Ser
50 55 60

Arg Cys Thr Ala Phe Gln Cys Lys His Ser Met Lys Tyr Arg Leu Ser

```
65                  70                  75                  80

Phe Cys Arg Lys Thr Cys Gly Thr Cys Ala Asn Ser Gly Val Ser Asp
                85                  90                  95

Arg Phe Ser Ala Ala Lys Ser Gly Thr Ser Ala Ser Leu Ala Ile Asn
            100                 105                 110

Gly Leu Arg Ser Glu Asp Glu Ala Asp Tyr Tyr Cys Ala Ala Trp Asp
        115                 120                 125

Asp Ser Leu Asn Gly Tyr Val Phe Gly Thr Gly Thr Lys Leu Thr Val
    130                 135                 140

Leu Gly
145


<210> SEQ ID NO 33
<211> LENGTH: 146
<212> TYPE: PRT
<213> ORGANISM: Artificial Sequence
<220> FEATURE:
<223> OTHER INFORMATION: KB_A-07 Kaliotoxin (VL)

<400> SEQUENCE: 33

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Gly Val Gly Val Glu Ile Asn Val Lys Cys Ser Gly Ser
    50                  55                  60

Pro Gln Cys Leu Lys Pro Cys Lys Asp Ala Gly Met Arg Phe Gly Lys
65                  70                  75                  80

Cys Met Asn Arg Lys Cys His Cys Thr Pro Lys Ser Arg Ser Gly Val
                85                  90                  95

Pro Ser Arg Phe Ser Gly Ser Gly Ser Gly Thr Asp Phe Thr Leu Thr
            100                 105                 110

Ile Ser Ser Leu Gln Pro Glu Asp Phe Ala Thr Tyr Tyr Cys Gln Gln
        115                 120                 125

Gly Ala Ser Pro Pro Tyr Thr Phe Gly Gln Gly Thr Lys Val Glu Ile
    130                 135                 140

Lys Arg
145


<210> SEQ ID NO 34
<211> LENGTH: 151
<212> TYPE: PRT
<213> ORGANISM: Artificial Sequence
<220> FEATURE:
<223> OTHER INFORMATION: KB_A12 PcTx1 (VL)

<400> SEQUENCE: 34

Gln Ser Val Leu Thr Gln Pro Pro Ser Val Ser Glu Ala Pro Arg Gln
1               5                   10                  15

Arg Val Thr Ile Thr Cys Ser Gly Ser Ser Ser Asn Ile Gly Asn Asn
            20                  25                  30

Ala Val Asn Trp Tyr Gln Gln Leu Pro Gly Lys Ala Pro Lys Leu Leu
        35                  40                  45

Ile Tyr Ala Ala Gly Arg Glu Asp Cys Ile Pro Lys Trp Lys Gly Cys
    50                  55                  60
```

-continued

Val Asn Arg His Gly Asp Cys Cys Glu Gly Leu Glu Cys Trp Lys Arg
65 70 75 80

Arg Arg Ser Phe Glu Val Cys Val Pro Lys Thr Pro Lys Thr Ala Asn
85 90 95

Ser Gly Val Ser Asp Arg Phe Ser Ala Ala Lys Ser Gly Thr Ser Ala
100 105 110

Ser Leu Ala Ile Asn Gly Leu Arg Ser Glu Asp Glu Ala Asp Tyr Tyr
115 120 125

Cys Ala Ala Trp Asp Asp Ser Leu Asn Gly Tyr Val Phe Gly Thr Gly
130 135 140

Thr Lys Leu Thr Val Leu Gly
145 150

<210> SEQ ID NO 35
<211> LENGTH: 148
<212> TYPE: PRT
<213> ORGANISM: Artificial Sequence
<220> FEATURE:
<223> OTHER INFORMATION: KB_A07 PcTx1 (VL)

<400> SEQUENCE: 35

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Ala Ala Gly Val Glu Asp Cys Ile Pro Lys Trp Lys Gly Cys Val
50 55 60

Asn Arg His Gly Asp Cys Cys Glu Gly Leu Glu Cys Trp Lys Arg Arg
65 70 75 80

Arg Ser Phe Glu Val Cys Val Pro Lys Thr Pro Lys Thr Ser Arg Ser
85 90 95

Gly Val Pro Ser Arg Phe Ser Gly Ser Gly Ser Gly Thr Asp Phe Thr
100 105 110

Leu Thr Ile Ser Ser Leu Gln Pro Glu Asp Phe Ala Thr Tyr Tyr Cys
115 120 125

Gln Gln Gly Ala Ser Pro Pro Tyr Thr Phe Gly Gln Gly Thr Lys Val
130 135 140

Glu Ile Lys Arg
145

<210> SEQ ID NO 36
<211> LENGTH: 10
<212> TYPE: PRT
<213> ORGANISM: Artificial Sequence
<220> FEATURE:
<223> OTHER INFORMATION: tag protein

<400> SEQUENCE: 36

Met Arg Gly Ser His His His His His His
1 5 10

<210> SEQ ID NO 37
<211> LENGTH: 8
<212> TYPE: PRT
<213> ORGANISM: Artificial Sequence
<220> FEATURE:
<223> OTHER INFORMATION: tag protein

<400> SEQUENCE: 37

Asp Tyr Lys Asp Asp Asp Asp Lys
1 5

<210> SEQ ID NO 38
<211> LENGTH: 15
<212> TYPE: PRT
<213> ORGANISM: Artificial Sequence
<220> FEATURE:
<223> OTHER INFORMATION: tag protein

<400> SEQUENCE: 38

Lys Glu Thr Ala Ala Ala Lys Phe Glu Arg Gln His Met Asp Ser
1 5 10 15

<210> SEQ ID NO 39
<211> LENGTH: 8
<212> TYPE: PRT
<213> ORGANISM: Artificial Sequence
<220> FEATURE:
<223> OTHER INFORMATION: tag protein

<400> SEQUENCE: 39

Trp Ser His Pro Gln Phe Glu Lys
1 5

<210> SEQ ID NO 40
<211> LENGTH: 10
<212> TYPE: PRT
<213> ORGANISM: Artificial Sequence
<220> FEATURE:
<223> OTHER INFORMATION: tag protein

<400> SEQUENCE: 40

Glu Gln Lys Leu Ile Ser Glu Glu Asp Leu
1 5 10

<210> SEQ ID NO 41
<211> LENGTH: 12
<212> TYPE: PRT
<213> ORGANISM: Artificial Sequence
<220> FEATURE:
<223> OTHER INFORMATION: tag protein

<400> SEQUENCE: 41

Met Lys Ala Glu Phe Arg Arg Gln Glu Ser Asp Arg
1 5 10

<210> SEQ ID NO 42
<211> LENGTH: 12
<212> TYPE: PRT
<213> ORGANISM: Artificial Sequence
<220> FEATURE:
<223> OTHER INFORMATION: tag protein

<400> SEQUENCE: 42

Met Arg Asp Ala Leu Asp Arg Leu Asp Arg Leu Ala
1 5 10

<210> SEQ ID NO 43
<211> LENGTH: 22
<212> TYPE: DNA
<213> ORGANISM: Artificial Sequence
<220> FEATURE:
<223> OTHER INFORMATION: light chain germline gene segment

<400> SEQUENCE: 43
ggtacctcgc gaatgcatct ag 22

<210> SEQ ID NO 44
<211> LENGTH: 20
<212> TYPE: DNA
<213> ORGANISM: Artificial Sequence
<220> FEATURE:
<223> OTHER INFORMATION: light chain germline gene segment

<400> SEQUENCE: 44
catgcaggcc tctgcagtcg 20

<210> SEQ ID NO 45
<211> LENGTH: 37
<212> TYPE: DNA
<213> ORGANISM: Artificial Sequence
<220> FEATURE:
<223> OTHER INFORMATION: Pml1-5EETa
<220> FEATURE:
<221> NAME/KEY: misc_feature
<222> LOCATION: (5)..(5)
<223> OTHER INFORMATION: V=A, C or G
<220> FEATURE:
<221> NAME/KEY: misc_feature
<222> LOCATION: (6)..(6)
<223> OTHER INFORMATION: N=A, C, G or T
<220> FEATURE:
<221> NAME/KEY: misc_feature
<222> LOCATION: (7)..(7)
<223> OTHER INFORMATION: S=C or G
<220> FEATURE:
<221> NAME/KEY: misc_feature
<222> LOCATION: (8)..(8)
<223> OTHER INFORMATION: V=A, C or G
<220> FEATURE:
<221> NAME/KEY: misc_feature
<222> LOCATION: (9)..(9)
<223> OTHER INFORMATION: N=A, C, G or T
<220> FEATURE:
<221> NAME/KEY: misc_feature
<222> LOCATION: (10)..(10)
<223> OTHER INFORMATION: S=C or G
<220> FEATURE:
<221> NAME/KEY: misc_feature
<222> LOCATION: (11)..(11)
<223> OTHER INFORMATION: V=A, C or G
<220> FEATURE:
<221> NAME/KEY: misc_feature
<222> LOCATION: (12)..(12)
<223> OTHER INFORMATION: N=A, C, G or T
<220> FEATURE:
<221> NAME/KEY: misc_feature
<222> LOCATION: (13)..(13)
<223> OTHER INFORMATION: S=C or G

<400> SEQUENCE: 45
gtgtvnsvns vnstgcccgc gtatcctgat gcgttgc 37

<210> SEQ ID NO 46
<211> LENGTH: 40
<212> TYPE: DNA
<213> ORGANISM: Artificial Sequence
<220> FEATURE:
<223> OTHER INFORMATION: Pml1-5EETb
<220> FEATURE:
<221> NAME/KEY: misc_feature
<222> LOCATION: (8)..(8)
<223> OTHER INFORMATION: V=A, C or G
<220> FEATURE:
<221> NAME/KEY: misc_feature
<222> LOCATION: (9)..(9)
<223> OTHER INFORMATION: N=A, C, G or T
<220> FEATURE:

<221> NAME/KEY: misc_feature
<222> LOCATION: (10)..(10)
<223> OTHER INFORMATION: S=C or G
<220> FEATURE:
<221> NAME/KEY: misc_feature
<222> LOCATION: (11)..(11)
<223> OTHER INFORMATION: V=A, C or G
<220> FEATURE:
<221> NAME/KEY: misc_feature
<222> LOCATION: (12)..(12)
<223> OTHER INFORMATION: N=A, C, G or T
<220> FEATURE:
<221> NAME/KEY: misc_feature
<222> LOCATION: (13)..(13)
<223> OTHER INFORMATION: S=C or G
<220> FEATURE:
<221> NAME/KEY: misc_feature
<222> LOCATION: (14)..(14)
<223> OTHER INFORMATION: V=A, C or G
<220> FEATURE:
<221> NAME/KEY: misc_feature
<222> LOCATION: (15)..(15)
<223> OTHER INFORMATION: N=A, C, G or T
<220> FEATURE:
<221> NAME/KEY: misc_feature
<222> LOCATION: (16)..(16)
<223> OTHER INFORMATION: S=C or G

<400> SEQUENCE: 46
gtgtggavns vnsvnstgcc cgcgtatcct gatgcgttgc 40

<210> SEQ ID NO 47
<211> LENGTH: 6
<212> TYPE: DNA
<213> ORGANISM: Artificial Sequence
<220> FEATURE:
<223> OTHER INFORMATION: restriction enzyme sequence

<400> SEQUENCE: 47 cacgtg 6

<210> SEQ ID NO 48
<211> LENGTH: 42
<212> TYPE: DNA
<213> ORGANISM: Artificial Sequence
<220> FEATURE:
<223> OTHER INFORMATION: 1-5EETMfe
<220> FEATURE:
<221> NAME/KEY: misc_feature
<222> LOCATION: (14)..(14)
<223> OTHER INFORMATION: N=A, C, G or T
<220> FEATURE:
<221> NAME/KEY: misc_feature
<222> LOCATION: (15)..(15)
<223> OTHER INFORMATION: B=T, G or C
<220> FEATURE:
<221> NAME/KEY: misc_feature
<222> LOCATION: (16)..(16)
<223> OTHER INFORMATION: S=C or G
<220> FEATURE:
<221> NAME/KEY: misc_feature
<222> LOCATION: (17)..(17)
<223> OTHER INFORMATION: N=A, C, G or T
<220> FEATURE:
<221> NAME/KEY: misc_feature
<222> LOCATION: (18)..(18)
<223> OTHER INFORMATION: B=T, G or C

<400> SEQUENCE: 48
gtcagtccaa ttgnbsnbcc cgcagaagcc gttcggaccg ca 42

<210> SEQ ID NO 49
<211> LENGTH: 42

```
<212> TYPE: DNA
<213> ORGANISM: Artificial Sequence
<220> FEATURE:
<223> OTHER INFORMATION: PST1-5EETa
<220> FEATURE:
<221> NAME/KEY: misc_feature
<222> LOCATION: (14)..(14)
<223> OTHER INFORMATION: N= A, C, G or T
<220> FEATURE:
<221> NAME/KEY: misc_feature
<222> LOCATION: (15)..(15)
<223> OTHER INFORMATION: S=C or G
<220> FEATURE:
<221> NAME/KEY: misc_feature
<222> LOCATION: (16)..(16)
<223> OTHER INFORMATION: V=A, C or G
<220> FEATURE:
<221> NAME/KEY: misc_feature
<222> LOCATION: (17)..(17)
<223> OTHER INFORMATION: N= A, C, G or T
<220> FEATURE:
<221> NAME/KEY: misc_feature
<222> LOCATION: (18)..(18)
<223> OTHER INFORMATION: S=C or G

<400> SEQUENCE: 49

atctatgctg cagnsvnstg cccgcgtatc ctgatgcgtt gc                          42


<210> SEQ ID NO 50
<211> LENGTH: 45
<212> TYPE: DNA
<213> ORGANISM: Artificial Sequence
<220> FEATURE:
<223> OTHER INFORMATION: 1-5EETBse
<220> FEATURE:
<221> NAME/KEY: misc_feature
<222> LOCATION: (16)..(16)
<223> OTHER INFORMATION: S=C or G
<220> FEATURE:
<221> NAME/KEY: misc_feature
<222> LOCATION: (17)..(17)
<223> OTHER INFORMATION: N=A, C, G or T
<220> FEATURE:
<221> NAME/KEY: misc_feature
<222> LOCATION: (18)..(18)
<223> OTHER INFORMATION: B=T, G or C
<220> FEATURE:
<221> NAME/KEY: misc_feature
<222> LOCATION: (19)..(19)
<223> OTHER INFORMATION: S=C or G
<220> FEATURE:
<221> NAME/KEY: misc_feature
<222> LOCATION: (20)..(20)
<223> OTHER INFORMATION: N=A, C, G or T
<220> FEATURE:
<221> NAME/KEY: misc_feature
<222> LOCATION: (21)..(21)
<223> OTHER INFORMATION: B=T, G or C

<400> SEQUENCE: 50

gtcagagact ccggasnbsn bcccgcagaa gccgttcgga ccgca                       45


<210> SEQ ID NO 51
<211> LENGTH: 36
<212> TYPE: DNA
<213> ORGANISM: Artificial Sequence
<220> FEATURE:
<223> OTHER INFORMATION: Mfelam 1

<400> SEQUENCE: 51

gtgtggaggt ggcaattggt accagcagct cccagg                                 36


<210> SEQ ID NO 52
```

<211> LENGTH: 36
<212> TYPE: DNA
<213> ORGANISM: Artificial Sequence
<220> FEATURE:
<223> OTHER INFORMATION: Mfelam 2

<400> SEQUENCE: 52
gtgtggaggt ggcaattggt accaacagca cccagg 36

<210> SEQ ID NO 53
<211> LENGTH: 34
<212> TYPE: DNA
<213> ORGANISM: Artificial Sequence
<220> FEATURE:
<223> OTHER INFORMATION: Mfelam 3

<400> SEQUENCE: 53
gtgtggaggt ggcaattggt accagcagaa gcca 34

<210> SEQ ID NO 54
<211> LENGTH: 36
<212> TYPE: DNA
<213> ORGANISM: Artificial Sequence
<220> FEATURE:
<223> OTHER INFORMATION: Mfekap 1

<400> SEQUENCE: 54
gtgtggaggt ggcaattggt atcagcagaa accagg 36

<210> SEQ ID NO 55
<211> LENGTH: 36
<212> TYPE: DNA
<213> ORGANISM: Artificial Sequence
<220> FEATURE:
<223> OTHER INFORMATION: Mfekap 2

<400> SEQUENCE: 55
gtgtggaggt ggcaattggt acctgcagaa gccagg 36

<210> SEQ ID NO 56
<211> LENGTH: 36
<212> TYPE: DNA
<213> ORGANISM: Artificial Sequence
<220> FEATURE:
<223> OTHER INFORMATION: Mfekap 3

<400> SEQUENCE: 56
gtgtggaggt ggcaattggt accagcagaa acctgg 36

<210> SEQ ID NO 57
<211> LENGTH: 39
<212> TYPE: DNA
<213> ORGANISM: Artificial Sequence
<220> FEATURE:
<223> OTHER INFORMATION: JLFORQP2

<400> SEQUENCE: 57
tgagatgagt ttttgttctg cggccgcggg ctgacctag 39

<210> SEQ ID NO 58
<211> LENGTH: 39
<212> TYPE: DNA
<213> ORGANISM: Artificial Sequence
<220> FEATURE:
<223> OTHER INFORMATION: JKFOR_Thr2

<400> SEQUENCE: 58
tgagatgagt ttttgttctg cggccgcggt acgtttgat 39

<210> SEQ ID NO 59

<400> SEQUENCE: 59

000

<210> SEQ ID NO 60
<211> LENGTH: 47
<212> TYPE: DNA
<213> ORGANISM: Artificial Sequence
<220> FEATURE:
<223> OTHER INFORMATION: Bsplam1a

<400> SEQUENCE: 60
atctatgctg caggaggtgg ctccggagtc tctgaccgat tctctgg 47

<210> SEQ ID NO 61
<211> LENGTH: 47
<212> TYPE: DNA
<213> ORGANISM: Artificial Sequence
<220> FEATURE:
<223> OTHER INFORMATION: Bsplam1e

<400> SEQUENCE: 61
atctatgctg caggaggtgg ctccggagtc cctgaccgat tctctgg 47

<210> SEQ ID NO 62
<211> LENGTH: 47
<212> TYPE: DNA
<213> ORGANISM: Artificial Sequence
<220> FEATURE:
<223> OTHER INFORMATION: Bsplam2

<400> SEQUENCE: 62
atctatgctg caggaggtgg ctccggatcc aagtctggca acacggg 47

<210> SEQ ID NO 63
<211> LENGTH: 47
<212> TYPE: DNA
<213> ORGANISM: Artificial Sequence
<220> FEATURE:
<223> OTHER INFORMATION: Bsplam3

<400> SEQUENCE: 63
atctatgctg caggaggtgg ctccggaatc cctgagcgat tctctgg 47

<210> SEQ ID NO 64
<211> LENGTH: 47
<212> TYPE: DNA
<213> ORGANISM: Artificial Sequence
<220> FEATURE:
<223> OTHER INFORMATION: BspKap1a

<400> SEQUENCE: 64
atctatgctg caggaggtgg ctccggagtc ccatcaaggt tcagtgg 47

<210> SEQ ID NO 65
<211> LENGTH: 47
<212> TYPE: DNA
<213> ORGANISM: Artificial Sequence
<220> FEATURE:
<223> OTHER INFORMATION: BspKap1b

<400> SEQUENCE: 65
atctatgctg caggaggtgg ctccggagtc ccatcaaggt tcagcgg 47

<210> SEQ ID NO 66
<211> LENGTH: 47
<212> TYPE: DNA
<213> ORGANISM: Artificial Sequence
<220> FEATURE:
<223> OTHER INFORMATION: BspKap2

<400> SEQUENCE: 66
atctatgctg caggaggtgg ctccggagtc ccagacaggt tcagtgg 47

<210> SEQ ID NO 67
<211> LENGTH: 47
<212> TYPE: DNA
<213> ORGANISM: Artificial Sequence
<220> FEATURE:
<223> OTHER INFORMATION: BspKap3

<400> SEQUENCE: 67
atctatgctg caggaggtgg ctccggaatc ccagccaggt tcagtgg 47

<210> SEQ ID NO 68
<211> LENGTH: 9
<212> TYPE: PRT
<213> ORGANISM: Artificial Sequence
<220> FEATURE:
<223> OTHER INFORMATION: EETI-II loop1

<400> SEQUENCE: 68

Gly Cys Pro Arg Ile Leu Met Arg Cys
1 5

<210> SEQ ID NO 69
<211> LENGTH: 19
<212> TYPE: DNA
<213> ORGANISM: Artificial Sequence
<220> FEATURE:
<223> OTHER INFORMATION: VL chain

<400> SEQUENCE: 69
ctctggcggt ggcgctagc 19

<210> SEQ ID NO 70
<211> LENGTH: 30
<212> TYPE: DNA
<213> ORGANISM: Artificial Sequence
<220> FEATURE:
<223> OTHER INFORMATION: VL chain

<400> SEQUENCE: 70
ggccccattc agatcctctt ctgagatgag 30

<210> SEQ ID NO 71
<211> LENGTH: 224
<212> TYPE: PRT
<213> ORGANISM: Artificial Sequence
<220> FEATURE:
<223> OTHER INFORMATION: KB_A12_Heavy chain

<400> SEQUENCE: 71

Glu Val Gln Leu Val Glu Ser Gly Gly Gly Leu Val Arg Pro Gly Gly
1 5 10 15

Ser Leu Arg Leu Ser Cys Ala Ala Ser Gly Phe Thr Phe Ser Ser Tyr
20 25 30

```
Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Thr Lys Asn Ser Leu Tyr
65                  70                  75                  80

Leu Gln Met Thr Ser Leu Arg Ala Asp Asp Thr Ala Phe Tyr Tyr Cys
                85                  90                  95

Val Asp Phe Gly Pro Gly Tyr Gly Thr Gly Trp Phe Asp Tyr Trp Gly
            100                 105                 110

Pro Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220
```

<210> SEQ ID NO 72
<211> LENGTH: 243
<212> TYPE: PRT
<213> ORGANISM: Artificial Sequence
<220> FEATURE:
<223> OTHER INFORMATION: KB_A12_Light chain

<400> SEQUENCE: 72

```
Gln Ser Val Leu Thr Gln Pro Pro Ser Val Ser Glu Ala Pro Arg Gln
1               5                   10                  15

Arg Val Thr Ile Thr Cys Ser Gly Ser Ser Ser Asn Ile Gly Asn Asn
            20                  25                  30

Ala Val Asn Trp Tyr Gln Gln Leu Pro Gly Lys Ala Pro Lys Leu Leu
        35                  40                  45

Ile Tyr Ala Ala Gly Arg Cys Pro Arg Ile Leu Met Arg Cys Lys Gln
    50                  55                  60

Asp Ser Asp Cys Leu Ala Gly Cys Val Cys Gly Pro Asn Gly Phe Cys
65                  70                  75                  80

Gly Ala Asn Ser Gly Val Ser Asp Arg Phe Ser Ala Ala Lys Ser Gly
                85                  90                  95

Thr Ser Ala Ser Leu Ala Ile Asn Gly Leu Arg Ser Glu Asp Glu Ala
            100                 105                 110

Asp Tyr Tyr Cys Ala Ala Trp Asp Asp Ser Leu Asn Gly Tyr Val Phe
        115                 120                 125

Gly Thr Gly Thr Lys Leu Thr Val Leu Gly Gln Pro Ala Ala Ala Pro
    130                 135                 140

Ser Val Thr Leu Phe Pro Pro Ser Ser Glu Glu Leu Gln Ala Asn Lys
145                 150                 155                 160

Ala Thr Leu Val Cys Leu Ile Ser Asp Phe Tyr Pro Gly Ala Val Thr
                165                 170                 175
```

Val Ala Trp Lys Ala Asp Ser Ser Pro Val Lys Ala Gly Val Glu Thr
180 185 190

Thr Thr Pro Ser Lys Gln Ser Asn Asn Lys Tyr Ala Ala Ser Ser Tyr
195 200 205

Leu Ser Leu Thr Pro Glu Gln Trp Lys Ser His Lys Ser Tyr Ser Cys
210 215 220

Gln Val Thr His Glu Gly Ser Thr Val Glu Lys Thr Val Ala Pro Thr
225 230 235 240

Glu Cys Ser

<210> SEQ ID NO 73
<211> LENGTH: 224
<212> TYPE: PRT
<213> ORGANISM: Artificial Sequence
<220> FEATURE:
<223> OTHER INFORMATION: KB_A05 Heavy chain

<400> SEQUENCE: 73

Glu Val Gln Leu Val Glu Ser Gly Gly Gly Leu Val Arg Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Gly Ser Gly Gly Ser Thr Tyr Tyr Ala Asp Ser Val
50 55 60

Lys Gly Arg Phe Thr Ile Ser Arg Asp Asn Thr Lys Asn Ser Leu Tyr
65 70 75 80

Leu Gln Met Thr Ser Leu Arg Ala Asp Asp Thr Ala Phe Tyr Tyr Cys
85 90 95

Val Asp Phe Gly Pro Gly Tyr Gly Thr Gly Trp Phe Asp Tyr Trp Gly
100 105 110

Pro Gly Thr Leu Val Thr Val Ser Ser Ala Ser Thr Lys Gly Pro Ser
115 120 125

Val Phe Pro Leu Ala Pro Ser Ser Lys Ser Thr Ser Gly Gly Thr Ala
130 135 140

Ala Leu Gly Cys Leu Val Lys Asp Tyr Phe Pro Glu Pro Val Thr Val
145 150 155 160

Ser Trp Asn Ser Gly Ala Leu Thr Ser Gly Val His Thr Phe Pro Ala
165 170 175

Val Leu Gln Ser Ser Gly Leu Tyr Ser Leu Ser Ser Val Val Thr Val
180 185 190

Pro Ser Ser Ser Leu Gly Thr Gln Thr Tyr Ile Cys Asn Val Asn His
195 200 205

Lys Pro Ser Asn Thr Lys Val Asp Lys Lys Val Glu Pro Lys Ser Cys
210 215 220

<210> SEQ ID NO 74
<211> LENGTH: 243
<212> TYPE: PRT
<213> ORGANISM: Artificial Sequence
<220> FEATURE:
<223> OTHER INFORMATION: KB_A05 Light chain

<400> SEQUENCE: 74

Gln Ser Val Leu Thr Gln Pro Pro Ser Val Ser Glu Ala Pro Arg Gln
1 5 10 15

```
Arg Val Thr Ile Thr Cys Ser Gly Ser Ser Ser Asn Ile Gly Asn Asn
            20                  25                  30

Ala Val Asn Trp Tyr Gln Gln Leu Pro Gly Lys Ala Pro Lys Leu Leu
        35                  40                  45

Ile Tyr Ala Ala Asp Lys Cys Pro Arg Ile Leu Met Arg Cys Lys Gln
    50                  55                  60

Asp Ser Asp Cys Leu Ala Gly Cys Val Cys Gly Pro Asn Gly Phe Cys
65                  70                  75                  80

Gly Gly Gly Ser Gly Ile Pro Glu Arg Phe Ser Gly Ser Lys Ser Gly
                85                  90                  95

Thr Ser Ala Ser Leu Ala Ile Ser Gly Leu Arg Ser Glu Asp Glu Ala
            100                 105                 110

Asp Tyr Tyr Cys Ala Thr Trp Asp Asp Asn Leu Asn Gly Val Val Phe
        115                 120                 125

Gly Gly Gly Thr Lys Leu Thr Val Leu Gly Gln Pro Ala Ala Ala Pro
    130                 135                 140

Ser Val Thr Leu Phe Pro Pro Ser Ser Glu Glu Leu Gln Ala Asn Lys
145                 150                 155                 160

Ala Thr Leu Val Cys Leu Ile Ser Asp Phe Tyr Pro Gly Ala Val Thr
                165                 170                 175

Val Ala Trp Lys Ala Asp Ser Ser Pro Val Lys Ala Gly Val Glu Thr
            180                 185                 190

Thr Thr Pro Ser Lys Gln Ser Asn Asn Lys Tyr Ala Ala Ser Ser Tyr
        195                 200                 205

Leu Ser Leu Thr Pro Glu Gln Trp Lys Ser His Lys Ser Tyr Ser Cys
    210                 215                 220

Gln Val Thr His Glu Gly Ser Thr Val Glu Lys Thr Val Ala Pro Thr
225                 230                 235                 240

Glu Cys Ser


<210> SEQ ID NO 75
<211> LENGTH: 33
<212> TYPE: DNA
<213> ORGANISM: Artificial Sequence
<220> FEATURE:
<223> OTHER INFORMATION: M13 leaderseq

<400> SEQUENCE: 75

aaattattat tcgcaattcc tttggttgtt cct                                33


<210> SEQ ID NO 76
<211> LENGTH: 22
<212> TYPE: DNA
<213> ORGANISM: Artificial Sequence
<220> FEATURE:
<223> OTHER INFORMATION: HLINK3

<400> SEQUENCE: 76

ctgaaccgcc tccaccactc ga                                            22


<210> SEQ ID NO 77
<211> LENGTH: 18
<212> TYPE: DNA
<213> ORGANISM: Artificial Sequence
<220> FEATURE:
<223> OTHER INFORMATION: LMB3 primer

<400> SEQUENCE: 77
```

caggaaacag ctatgacc 18

<210> SEQ ID NO 78
<211> LENGTH: 31
<212> TYPE: DNA
<213> ORGANISM: Artificial Sequence
<220> FEATURE:
<223> OTHER INFORMATION: D1A12-Notl Rev

<400> SEQUENCE: 78
ttctgcggcc gcggtacgtt tgatatccat t 31

<210> SEQ ID NO 79
<211> LENGTH: 34
<212> TYPE: DNA
<213> ORGANISM: Artificial Sequence
<220> FEATURE:
<223> OTHER INFORMATION: PmI5-3EETa
<220> FEATURE:
<221> NAME/KEY: misc_feature
<222> LOCATION: (5)..(5)
<223> OTHER INFORMATION: V=A, C or G
<220> FEATURE:
<221> NAME/KEY: misc_feature
<222> LOCATION: (6)..(6)
<223> OTHER INFORMATION: N=A, C, G, or T
<220> FEATURE:
<221> NAME/KEY: misc_feature
<222> LOCATION: (7)..(7)
<223> OTHER INFORMATION: S=C or G
<220> FEATURE:
<221> NAME/KEY: misc_feature
<222> LOCATION: (8)..(8)
<223> OTHER INFORMATION: V=A, C or G
<220> FEATURE:
<221> NAME/KEY: misc_feature
<222> LOCATION: (9)..(9)
<223> OTHER INFORMATION: N=A, C, G, or T
<220> FEATURE:
<221> NAME/KEY: misc_feature
<222> LOCATION: (10)..(10)
<223> OTHER INFORMATION: S=C or G
<220> FEATURE:
<221> NAME/KEY: misc_feature
<222> LOCATION: (11)..(11)
<223> OTHER INFORMATION: V=A, C or G
<220> FEATURE:
<221> NAME/KEY: misc_feature
<222> LOCATION: (12)..(12)
<223> OTHER INFORMATION: N=A, C, G, or T
<220> FEATURE:
<221> NAME/KEY: misc_feature
<222> LOCATION: (13)..(13)
<223> OTHER INFORMATION: S=C or G

<400> SEQUENCE: 79
gtgtvnsvns vnstgcggtc cgaacggctt ctgc 34

<210> SEQ ID NO 80
<211> LENGTH: 34
<212> TYPE: DNA
<213> ORGANISM: Artificial Sequence
<220> FEATURE:
<223> OTHER INFORMATION: PmI5-3EETb
<220> FEATURE:
<221> NAME/KEY: misc_feature
<222> LOCATION: (8)..(8)
<223> OTHER INFORMATION: V=A, C or G
<220> FEATURE:
<221> NAME/KEY: misc_feature
<222> LOCATION: (9)..(9)
<223> OTHER INFORMATION: N=A, C, G or T
<220> FEATURE:
<221> NAME/KEY: misc_feature
<222> LOCATION: (10)..(10)
<223> OTHER INFORMATION: S=C or G
<220> FEATURE:
<221> NAME/KEY: misc_feature
<222> LOCATION: (11)..(11)
<223> OTHER INFORMATION: V=A, C or G
<220> FEATURE:
<221> NAME/KEY: misc_feature
<222> LOCATION: (12)..(12)
<223> OTHER INFORMATION: N=A, C, G or T
<220> FEATURE:
<221> NAME/KEY: misc_feature
<222> LOCATION: (13)..(13)
<223> OTHER INFORMATION: S=C or G
<220> FEATURE:
<221> NAME/KEY: misc_feature
<222> LOCATION: (14)..(14)
<223> OTHER INFORMATION: V=A, C or G
<220> FEATURE:
<221> NAME/KEY: misc_feature
<222> LOCATION: (15)..(15)
<223> OTHER INFORMATION: N=A, C, G or T
<220> FEATURE:
<221> NAME/KEY: misc_feature
<222> LOCATION: (16)..(16)
<223> OTHER INFORMATION: S=C or G

<400> SEQUENCE: 80
gtgtggavns vnsvnstgcg gtccgaacgg cttc 34

<210> SEQ ID NO 81
<211> LENGTH: 39
<212> TYPE: DNA
<213> ORGANISM: Artificial Sequence
<220> FEATURE:
<223> OTHER INFORMATION: 5-3EETMfe
<220> FEATURE:
<221> NAME/KEY: misc_feature
<222> LOCATION: (14)..(14)
<223> OTHER INFORMATION: N=A, C, G or T
<220> FEATURE:
<221> NAME/KEY: misc_feature
<222> LOCATION: (15)..(15)
<223> OTHER INFORMATION: B=T, G or C
<220> FEATURE:
<221> NAME/KEY: misc_feature
<222> LOCATION: (16)..(16)
<223> OTHER INFORMATION: S=C or G
<220> FEATURE:
<221> NAME/KEY: misc_feature
<222> LOCATION: (17)..(17)
<223> OTHER INFORMATION: N=A, C, G or T
<220> FEATURE:
<221> NAME/KEY: misc_feature
<222> LOCATION: (18)..(18)
<223> OTHER INFORMATION: B=T, G or C

<400> SEQUENCE: 81
gtcagtccaa ttgnbsnbgc agccggccag gcagtctga 39

<210> SEQ ID NO 82
<211> LENGTH: 39
<212> TYPE: DNA
<213> ORGANISM: Artificial Sequence
<220> FEATURE:
<223> OTHER INFORMATION: PST5-3EETa
<220> FEATURE:
<221> NAME/KEY: misc_feature
<222> LOCATION: (14)..(14)
<223> OTHER INFORMATION: N=A, C, T or G
<220> FEATURE:
<221> NAME/KEY: misc_feature
<222> LOCATION: (15)..(15)
<223> OTHER INFORMATION: S=C or G
<220> FEATURE:

<221> NAME/KEY: misc_feature
<222> LOCATION: (16)..(16)
<223> OTHER INFORMATION: V=A, C or G
<220> FEATURE:
<221> NAME/KEY: misc_feature
<222> LOCATION: (17)..(17)
<223> OTHER INFORMATION: N=A, C, T or G
<220> FEATURE:
<221> NAME/KEY: misc_feature
<222> LOCATION: (18)..(18)
<223> OTHER INFORMATION: S=C or G

<400> SEQUENCE: 82
atctatgctg cagnsvnstg cggtccgaac ggcttctgc 39

<210> SEQ ID NO 83
<211> LENGTH: 45
<212> TYPE: DNA
<213> ORGANISM: Artificial Sequence
<220> FEATURE:
<223> OTHER INFORMATION: 5-3EETBse
<220> FEATURE:
<221> NAME/KEY: misc_feature
<222> LOCATION: (16)..(16)
<223> OTHER INFORMATION: S=C or G
<220> FEATURE:
<221> NAME/KEY: misc_feature
<222> LOCATION: (17)..(17)
<223> OTHER INFORMATION: N=A, C, G or T
<220> FEATURE:
<221> NAME/KEY: misc_feature
<222> LOCATION: (18)..(18)
<223> OTHER INFORMATION: B=T, G or C
<220> FEATURE:
<221> NAME/KEY: misc_feature
<222> LOCATION: (19)..(19)
<223> OTHER INFORMATION: S=C or G
<220> FEATURE:
<221> NAME/KEY: misc_feature
<222> LOCATION: (20)..(20)
<223> OTHER INFORMATION: N=A, C, G or T
<220> FEATURE:
<221> NAME/KEY: misc_feature
<222> LOCATION: (21)..(21)
<223> OTHER INFORMATION: B=T, G or C

<400> SEQUENCE: 83
gtcagagact ccggasnbsn bcccgcagcc ggccaggcag tctga 45

<210> SEQ ID NO 84
<211> LENGTH: 134
<212> TYPE: PRT
<213> ORGANISM: Artificial Sequence
<220> FEATURE:
<223> OTHER INFORMATION: CDR1_F_10

<400> SEQUENCE: 84

Gln Ser Val Leu Thr Gln Pro Pro Ser Val Ser Glu Ala Pro Arg Gln
1 5 10 15

Arg Val Thr Ile Thr Cys Gly Glu Arg Pro Cys Pro Arg Ile Leu Met
20 25 30

Arg Cys Lys Gln Asp Ser Asp Cys Leu Ala Gly Cys Val Cys Gly Pro
35 40 45

Asn Gly Phe Cys Gly Ala Asn Asn Trp Tyr Gln Gln Leu Pro Gly Ser
50 55 60

Ser Pro Thr Thr Val Ile Tyr Glu Asp Asn Gln Arg Pro Ser Gly Val
65 70 75 80

Pro Asp Arg Phe Ser Gly Ser Ile Asp Ser Ser Ser Asn Ser Ala Ser
85 90 95

Leu Thr Ile Ser Gly Leu Lys Thr Glu Asp Glu Ala Asp Tyr Tyr Cys
100 105 110

Gln Ser Tyr Asp Ser Ser Asn Gln Val Phe Gly Gly Gly Thr Lys Val
115 120 125

Thr Val Leu Gly Gln Pro
130

<210> SEQ ID NO 85
<211> LENGTH: 134
<212> TYPE: PRT
<213> ORGANISM: Artificial Sequence
<220> FEATURE:
<223> OTHER INFORMATION: CDR1_B_01

<400> SEQUENCE: 85

Gln Ser Val Leu Thr Gln Pro Pro Ser Val Ser Glu Ala Pro Arg Gln
1 5 10 15

Arg Val Thr Ile Thr Cys Gly Gly Gly Arg Cys Pro Arg Ile Leu Met
20 25 30

Arg Cys Lys Gln Asp Ser Asp Cys Leu Ala Gly Cys Val Cys Gly Pro
35 40 45

Asn Gly Phe Cys Gly Thr Pro Asn Trp Tyr Gln Gln Leu Pro Gly Ser
50 55 60

Ser Pro Thr Thr Leu Ile Tyr Glu Asp Asn Gln Arg Pro Ser Gly Val
65 70 75 80

Pro Asp Arg Phe Ser Gly Ser Ile Asp Ser Ser Ser Asn Ser Ala Ser
85 90 95

Leu Thr Ile Ser Gly Leu Lys Thr Gly Asp Glu Ala Asp Tyr Tyr Cys
100 105 110

Gln Ser Tyr Asp Ser Ser Asn Gln Val Phe Gly Gly Gly Thr Gln Leu
115 120 125

Thr Val Leu Gly Gln Pro
130

<210> SEQ ID NO 86
<211> LENGTH: 136
<212> TYPE: PRT
<213> ORGANISM: Artificial Sequence
<220> FEATURE:
<223> OTHER INFORMATION: CDR1_F_02

<400> SEQUENCE: 86

Gln Ser Val Leu Thr Gln Pro Pro Ser Val Ser Glu Ala Pro Arg Gln
1 5 10 15

Arg Val Thr Ile Thr Cys Gly Ser Arg Pro Cys Pro Arg Ile Leu Met
20 25 30

Arg Cys Lys Gln Asp Ser Asp Cys Leu Ala Gly Cys Val Cys Gly Pro
35 40 45

Asn Gly Phe Cys Gly Ser His Asn Trp Tyr Gln Gln Leu Pro Gly Ser
50 55 60

Ser Pro Thr Thr Val Ile Tyr Glu Asp Asn Gln Arg Pro Ser Gly Val
65 70 75 80

Pro Asp Arg Phe Ser Gly Ser Ile Asp Arg Ser Ser Asn Ser Ala Ser
85 90 95

Leu Thr Ile Ser Gly Leu Lys Thr Glu Asp Glu Ala Asp Tyr Tyr Cys
100 105 110

Gln Ser Tyr Asp Ser Ser Asn His Arg Val Val Phe Gly Gly Gly Thr

```
        115                 120                 125

Lys Leu Thr Val Leu Gly Gln Pro
    130                 135


<210> SEQ ID NO 87
<211> LENGTH: 134
<212> TYPE: PRT
<213> ORGANISM: Artificial Sequence
<220> FEATURE:
<223> OTHER INFORMATION: CDR1_F_05

<400> SEQUENCE: 87

Gln Ser Val Leu Thr Gln Pro Pro Ser Val Ser Glu Ala Pro Arg Gln
1               5                   10                  15

Arg Val Thr Ile Thr Cys Gly Gly Gly Arg Cys Pro Arg Ile Leu Met
            20                  25                  30

Arg Cys Lys Gln Asp Ser Asp Cys Leu Ala Gly Cys Val Cys Gly Pro
        35                  40                  45

Asn Gly Phe Cys Gly Thr Gly Asn Trp Tyr Gln Gln Leu Pro Gly Arg
    50                  55                  60

Ser Pro Thr Asn Val Val Tyr Glu Asp Asn Gln Arg Pro Pro Gly Val
65                  70                  75                  80

Ser Asp Arg Phe Ser Gly Ser Ile Asp Ser Ser Ser Asn Ser Ala Ser
                85                  90                  95

Leu Thr Ile Ser Gly Leu Lys Thr Glu Asp Glu Ala Asp Tyr Tyr Cys
            100                 105                 110

Gln Ser Tyr Asp Ser Ser Asn Gln Val Phe Gly Gly Gly Thr Lys Leu
        115                 120                 125

Thr Val Leu Gly Gln Pro
    130


<210> SEQ ID NO 88
<211> LENGTH: 133
<212> TYPE: PRT
<213> ORGANISM: Artificial Sequence
<220> FEATURE:
<223> OTHER INFORMATION: CDR1_C_12

<400> SEQUENCE: 88

Gln Ser Val Leu Thr Gln Leu Pro Ser Val Ser Glu Ala Pro Arg Gln
1               5                   10                  15

Arg Val Thr Ile Thr Cys Gly Arg Ala Met Cys Pro Arg Ile Leu Met
            20                  25                  30

Arg Cys Lys Gln Asp Ser Asp Cys Leu Ala Gly Cys Val Cys Gly Pro
        35                  40                  45

Asn Gly Phe Cys Gly Thr Gly Asn Trp Tyr Gln Gln His Pro Gly Lys
    50                  55                  60

Ala Pro Lys Leu Ile Ile Phe Asp Val Ser Lys Arg Pro Ser Gly Val
65                  70                  75                  80

Pro Asp Arg Phe Ser Ala Ser Lys Ser Gly Asn Thr Ala Ser Leu Thr
                85                  90                  95

Ile Ser Gly Leu Gln Ala Glu Asp Glu Ala Asp Tyr Tyr Cys Asn Ser
            100                 105                 110

Tyr Thr Ser Ser Asn Thr Trp Val Phe Gly Gly Gly Thr Gln Leu Thr
        115                 120                 125

Val Leu Gly Gln Pro
    130
```

<210> SEQ ID NO 89
<211> LENGTH: 133
<212> TYPE: PRT
<213> ORGANISM: Artificial Sequence
<220> FEATURE:
<223> OTHER INFORMATION: CDR1_G_05

<400> SEQUENCE: 89

Gln Ser Val Leu Thr Gln Pro Pro Ser Val Ser Glu Ala Pro Arg Gln
1 5 10 15

Arg Val Thr Ile Thr Cys Asp Arg Lys Cys Pro Arg Ile Leu Met Arg
20 25 30

Cys Lys Gln Asp Ser Asp Cys Leu Ala Gly Cys Val Cys Gly Pro Asn
35 40 45

Gly Phe Cys Gly Thr Thr Asn Trp Tyr Gln Gln Leu Pro Gly Ser Ser
50 55 60

Pro Thr Thr Val Ile Tyr Glu Asn Phe Gln Arg Pro Ser Gly Val Pro
65 70 75 80

Asp Arg Phe Ser Gly Ser Ile Asp Ser Ser Ser Asn Ser Ala Ser Leu
85 90 95

Thr Ile Ser Gly Leu Lys Thr Glu Asp Glu Ala Asp Tyr Tyr Cys Gln
100 105 110

Ser Tyr Asp Ser Tyr Asn Gln Val Phe Gly Ser Gly Thr Lys Leu Thr
115 120 125

Val Leu Gly Gln Pro
130

<210> SEQ ID NO 90
<211> LENGTH: 135
<212> TYPE: PRT
<213> ORGANISM: Artificial Sequence
<220> FEATURE:
<223> OTHER INFORMATION: CDR1_C_06

<400> SEQUENCE: 90

Gln Ser Val Leu Thr Gln Pro Pro Ser Val Ser Glu Ala Pro Arg Gln
1 5 10 15

Arg Val Thr Ile Thr Cys Gly Arg Arg Gly Cys Pro Arg Ile Leu Met
20 25 30

Arg Cys Lys Gln Asp Ser Asp Cys Leu Ala Gly Cys Val Cys Gly Pro
35 40 45

Asn Gly Phe Cys Gly Gly Asp Asn Trp Tyr Gln Gln His Pro Gly Ser
50 55 60

Ser Pro Thr Pro Val Ile Tyr Glu Asp Asn Gln Arg Pro Ser Gly Val
65 70 75 80

Pro Asp Arg Phe Ser Gly Ser Ile Asp Ser Ser Ser Asn Ser Ala Ser
85 90 95

Leu Thr Ile Ser Gly Leu Lys Pro Glu Asp Glu Ala Asp Tyr Tyr Cys
100 105 110

Gln Ser His Asp Gly Ser Asn Pro Trp Val Phe Gly Gly Gly Thr Lys
115 120 125

Leu Thr Val Leu Gly Gln Pro
130 135

<210> SEQ ID NO 91
<211> LENGTH: 134
<212> TYPE: PRT
<213> ORGANISM: Artificial Sequence

<220> FEATURE:
<223> OTHER INFORMATION: CDR1_A_03

<400> SEQUENCE: 91

Gln Ser Val Leu Thr Gln Pro Pro Ser Val Ser Glu Ala Pro Arg Gln
1               5                   10                  15

Arg Val Thr Ile Thr Cys Gly Gly Arg Cys Pro Arg Ile Leu Met Arg
            20                  25                  30

Cys Lys Gln Asp Ser Asp Cys Leu Ala Gly Cys Val Cys Gly Pro Asn
        35                  40                  45

Gly Phe Cys Gly Ser Ala Asn Trp Tyr Gln Gln Leu Pro Asp Ser Ala
    50                  55                  60

Pro Ala Thr Val Ile Tyr Glu Asp Asn Gln Arg Pro Ser Gly Val Pro
65                  70                  75                  80

Asp Arg Phe Ser Gly Ser Ile Asp Thr Ser Ser Asn Ser Ala Ser Leu
                85                  90                  95

Thr Ile Ser Gly Leu Lys Thr Glu Asp Glu Ala Asp Tyr Tyr Cys Gln
            100                 105                 110

Ser Tyr Asp Ser Ser Asn His Trp Val Phe Gly Gly Gly Thr Lys Leu
        115                 120                 125

Thr Val Leu Gly Gln Pro
    130

<210> SEQ ID NO 92
<211> LENGTH: 133
<212> TYPE: PRT
<213> ORGANISM: Artificial Sequence
<220> FEATURE:
<223> OTHER INFORMATION: CDR1_D_06

<400> SEQUENCE: 92

Gln Ser Val Leu Thr Gln Pro Pro Ser Val Ser Glu Ala Pro Arg Gln
1               5                   10                  15

Arg Val Thr Ile Thr Cys Arg Gly Gly Cys Pro Arg Ile Leu Met Arg
            20                  25                  30

Cys Lys Gln Asp Ser Asp Cys Leu Ala Gly Cys Val Cys Gly Pro Asn
        35                  40                  45

Gly Phe Cys Gly Ser Pro Asn Trp Tyr Gln Gln Lys Pro Gly Gln Ala
    50                  55                  60

Pro Val Leu Val Ile Tyr Gly Lys Asn Asn Arg Pro Ser Gly Ile Pro
65                  70                  75                  80

Asp Arg Phe Ser Gly Ser Arg Ser Gly Thr Pro Ala Ser Leu Thr Ile
                85                  90                  95

Thr Gly Ala Gln Ala Glu Asp Glu Ala Asp Tyr Tyr Cys Asn Ser Arg
            100                 105                 110

Asp Asn Asp Asn Asn His Val Val Phe Gly Gly Gly Thr Lys Leu Thr
        115                 120                 125

Val Leu Gly Gln Pro
    130

<210> SEQ ID NO 93
<211> LENGTH: 134
<212> TYPE: PRT
<213> ORGANISM: Artificial Sequence
<220> FEATURE:
<223> OTHER INFORMATION: CDR1_E_08

<400> SEQUENCE: 93

```
Gln Ser Val Leu Thr Gln Pro Pro Ser Val Ser Glu Ala Pro Arg Gln
1               5                   10                  15

Arg Val Thr Ile Thr Cys Gly Gly Thr Gly Cys Pro Arg Ile Leu Met
            20                  25                  30

Arg Cys Lys Gln Asp Ser Asp Cys Leu Ala Gly Cys Val Cys Gly Pro
        35                  40                  45

Asn Gly Phe Cys Gly Ser Ala Asn Trp Tyr Gln Gln Leu Pro Gly Ser
    50                  55                  60

Ser Pro Thr Asn Val Ile Tyr Glu Asp Asn Gln Arg Pro Ser Gly Val
65                  70                  75                  80

Pro Asp Arg Phe Ser Gly Ser Ile Asp Ser Ser Ser Asn Ser Ala Ser
                85                  90                  95

Leu Thr Ile Ser Gly Leu Lys Thr Glu Asp Glu Ala Asp Tyr Tyr Cys
            100                 105                 110

Gln Ser Asn Asp Gly Thr Asn Gly Val Phe Gly Gly Gly Thr Lys Val
        115                 120                 125

Thr Val Leu Gly Gln Pro
    130


<210> SEQ ID NO 94
<211> LENGTH: 134
<212> TYPE: PRT
<213> ORGANISM: Artificial Sequence
<220> FEATURE:
<223> OTHER INFORMATION: CDR1_A_12

<400> SEQUENCE: 94

Gln Ser Val Leu Thr Gln Pro Pro Ser Val Pro Glu Ala Pro Arg Gln
1               5                   10                  15

Arg Val Thr Ile Thr Cys Gly Ala Arg Pro Cys Pro Arg Ile Leu Met
            20                  25                  30

Arg Cys Lys Gln Asp Ser Asp Cys Leu Ala Gly Cys Val Cys Gly Pro
        35                  40                  45

Asn Gly Phe Cys Gly Ala Ser Asn Trp Tyr Gln Gln Leu Pro Gly Ser
    50                  55                  60

Ser Pro Thr Thr Val Ile Tyr Glu Asp Asn Gln Arg Pro Ser Gly Val
65                  70                  75                  80

Pro Asp Arg Phe Ser Gly Ser Ile Asp Ser Ser Ser Asn Ser Ala Ser
                85                  90                  95

Leu Thr Ile Ser Gly Leu Lys Thr Glu Asp Glu Ala Asp Tyr Tyr Cys
            100                 105                 110

Gln Ser Tyr Asp Ser Ile Asn Arg Gly Val Phe Gly Gly Thr Gln Leu
        115                 120                 125

Thr Val Leu Gly Gln Pro
    130


<210> SEQ ID NO 95
<211> LENGTH: 134
<212> TYPE: PRT
<213> ORGANISM: Artificial Sequence
<220> FEATURE:
<223> OTHER INFORMATION: CDR1_H_03

<400> SEQUENCE: 95

Gln Ser Val Leu Thr Gln Pro Pro Ser Val Ser Glu Ala Pro Arg Gln
1               5                   10                  15

Arg Val Thr Ile Thr Cys Gly Arg Thr Gly Cys Pro Arg Ile Leu Met
            20                  25                  30
```

```
Arg Cys Lys Gln Asp Ser Asp Cys Leu Ala Gly Cys Val Cys Gly Pro
        35                  40                  45

Asn Gly Phe Cys Gly Thr Val Asn Trp Tyr Gln Gln Leu Pro Gly Ser
    50                  55                  60

Ala Pro Thr Thr Val Ile Tyr Glu Asp Asn Gln Arg Pro Ser Gly Val
65                  70                  75                  80

Pro Asp Arg Phe Ser Gly Pro Ile Asp Ser Ser Ser Asn Ser Ala Pro
                85                  90                  95

Leu Thr Ile Ser Gly Leu Lys Thr Glu Asp Glu Ala Asp Tyr Tyr Cys
            100                 105                 110

Gln Ser Tyr Asp Arg Asn Asn Val Ile Phe Gly Gly Gly Thr Lys Leu
        115                 120                 125

Thr Val Leu Gly Gln Pro
    130
```

<210> SEQ ID NO 96
<211> LENGTH: 134
<212> TYPE: PRT
<213> ORGANISM: Artificial Sequence
<220> FEATURE:
<223> OTHER INFORMATION: CDR1_E_10

<400> SEQUENCE: 96

```
Gln Ser Val Leu Thr Gln Pro Pro Ser Val Ser Glu Ala Pro Arg Gln
1               5                   10                  15

Arg Val Thr Ile Thr Cys Gly Thr Arg Gly Cys Pro Arg Ile Leu Met
            20                  25                  30

Arg Cys Lys Gln Asp Ser Asp Cys Leu Ala Gly Cys Val Cys Gly Pro
        35                  40                  45

Asn Gly Phe Cys Gly Ser Asn Asn Trp Tyr Gln Gln Leu Pro Gly Ser
    50                  55                  60

Ser Pro Thr Thr Val Ile Tyr Glu Asp Asn Gln Arg Pro Ser Gly Val
65                  70                  75                  80

Pro Asp Arg Phe Tyr Gly Ser Ile Asp Ser Ser Ser Asp Ser Ala Ser
                85                  90                  95

Leu Thr Ile Ser Gly Leu Glu Thr Glu Asp Glu Ala Asp Tyr Phe Cys
            100                 105                 110

His Ser Tyr Asp Ser Asp Lys Trp Val Phe Gly Gly Gly Thr Gln Leu
        115                 120                 125

Thr Val Leu Gly Gln Pro
    130
```

<210> SEQ ID NO 97
<211> LENGTH: 136
<212> TYPE: PRT
<213> ORGANISM: Artificial Sequence
<220> FEATURE:
<223> OTHER INFORMATION: CDR1_E_03

<400> SEQUENCE: 97

```
Gln Ser Val Leu Thr Gln Pro Pro Ser Val Ser Glu Ala Pro Arg Gln
1               5                   10                  15

Arg Val Thr Ile Thr Cys Gly Gly Met Pro Cys Pro Arg Ile Leu Met
            20                  25                  30

Arg Cys Lys Gln Asp Ser Asp Cys Leu Ala Gly Cys Val Cys Gly Pro
        35                  40                  45

Asn Gly Phe Cys Gly Ala Thr Asn Trp Tyr Gln Gln Leu Pro Gly Ser
```

50 55 60

Ser Pro Thr Thr Val Ile Tyr Glu Asp Asn Gln Arg Pro Ser Gly Val
65 70 75 80

Pro Asp Arg Phe Ser Gly Ser Ile Asp Ser Ser Ser Asn Ser Ala Ser
85 90 95

Leu Thr Ile Ser Gly Leu Lys Thr Glu Asp Glu Ala Asp Tyr Tyr Cys
100 105 110

Gln Ser Tyr Asp Ser Ser Asn Pro Lys Val Val Phe Gly Gly Gly Thr
115 120 125

Lys Leu Thr Val Leu Gly Gln Pro
130 135

<210> SEQ ID NO 98
<211> LENGTH: 140
<212> TYPE: PRT
<213> ORGANISM: Artificial Sequence
<220> FEATURE:
<223> OTHER INFORMATION: CDR2_D_02

<400> SEQUENCE: 98

Gln Ser Val Leu Thr Gln Pro Pro Ser Val Ser Glu Ala Pro Gly Gln
1 5 10 15

Arg Val Thr Ile Thr Cys Ser Gly Ser Ser Ser Asn Ile Gly Asn Asn
20 25 30

Ala Val Asn Trp Tyr Gln Gln Leu Pro Gly Lys Ala Pro Lys Leu Leu
35 40 45

Ile Tyr Ala Ala Ala Lys Cys Pro Arg Ile Leu Met Arg Cys Lys Gln
50 55 60

Asp Ser Asp Cys Leu Ala Gly Cys Val Cys Gly Pro Asn Gly Phe Cys
65 70 75 80

Gly Thr Arg Ser Gly Val Ser Asp Arg Phe Ser Gly Ser Lys Ser Gly
85 90 95

Thr Ser Ala Ser Leu Ala Ile Ser Gly Leu Gln Ser Glu Asp Glu Ala
100 105 110

Asp Tyr Tyr Cys Ala Ala Trp Asp Asp Ser Leu Ser Gly Tyr Val Phe
115 120 125

Gly Thr Gly Thr Lys Leu Thr Val Leu Gly Gln Pro
130 135 140

<210> SEQ ID NO 99
<211> LENGTH: 140
<212> TYPE: PRT
<213> ORGANISM: Artificial Sequence
<220> FEATURE:
<223> OTHER INFORMATION: CDR2_D_09

<400> SEQUENCE: 99

Gln Ser Val Leu Thr Gln Pro Pro Ser Val Ser Glu Ala Pro Arg Gln
1 5 10 15

Arg Val Thr Ile Thr Cys Ser Gly Ser Ser Ser Asn Ile Gly Asn Asn
20 25 30

Ala Val Asn Trp Tyr Gln Gln Leu Pro Gly Lys Ala Pro Lys Leu Leu
35 40 45

Ile Tyr Ala Ala Asp Lys Cys Pro Arg Ile Leu Met Arg Cys Lys Gln
50 55 60

Asp Ser Asp Cys Leu Ala Gly Cys Val Cys Gly Pro Asn Gly Phe Cys
65 70 75 80

```
Gly Gly Gly Ser Gly Ile Pro Glu Arg Phe Ser Gly Ser Lys Ser Gly
                85                  90                  95

Thr Ser Ala Ser Leu Ala Ile Ser Gly Leu Arg Ser Glu Asp Glu Ala
            100                 105                 110

Asp Tyr Tyr Cys Ala Thr Trp Asp Asp Asn Leu Asn Gly Val Val Phe
        115                 120                 125

Gly Gly Gly Thr Lys Leu Thr Val Leu Gly Gln Pro
    130                 135                 140


<210> SEQ ID NO 100
<211> LENGTH: 140
<212> TYPE: PRT
<213> ORGANISM: Artificial Sequence
<220> FEATURE:
<223> OTHER INFORMATION: CDR2_H_09

<400> SEQUENCE: 100

Gln Ser Val Leu Thr Gln Pro Pro Ser Val Ser Glu Ala Pro Arg Gln
1               5                   10                  15

Arg Val Thr Ile Thr Cys Ser Gly Ser Ser Ser Asn Ile Gly Asn Asn
            20                  25                  30

Ala Val Asn Trp Tyr Gln Gln Leu Pro Gly Lys Ala Pro Lys Leu Leu
        35                  40                  45

Ile Tyr Ala Ala Val Gly Cys Pro Arg Ile Leu Met Arg Cys Lys Gln
    50                  55                  60

Asp Ser Asp Cys Leu Ala Gly Cys Val Cys Gly Pro Asn Gly Phe Cys
65                  70                  75                  80

Gly Thr Gly Ser Gly Ile Pro Glu Arg Phe Ser Gly Ser Lys Ser Gly
                85                  90                  95

Asn Thr Ala Ser Leu Thr Ile Ser Gly Leu Gln Ala Glu Asp Glu Gly
            100                 105                 110

Asp Tyr Tyr Cys Ala Ala Trp Asp Asp Ser Leu Ser Gly Pro Val Phe
        115                 120                 125

Gly Gly Gly Thr Lys Leu Thr Val Leu Gly Gln Pro
    130                 135                 140


<210> SEQ ID NO 101
<211> LENGTH: 140
<212> TYPE: PRT
<213> ORGANISM: Artificial Sequence
<220> FEATURE:
<223> OTHER INFORMATION: CDR2_F_02

<400> SEQUENCE: 101

Gln Ser Val Leu Thr Gln Pro Pro Ser Val Ser Glu Ala Pro Arg Gln
1               5                   10                  15

Arg Val Thr Ile Thr Cys Ser Gly Ser Ser Ser Asn Ile Gly Asn Asn
            20                  25                  30

Ala Val Asn Trp Tyr Gln Gln Leu Pro Gly Lys Ala Pro Lys Leu Leu
        35                  40                  45

Ile Tyr Ala Ala Gly Arg Cys Pro Arg Ile Leu Met Arg Cys Lys Gln
    50                  55                  60

Asp Ser Asp Cys Leu Ala Gly Cys Val Cys Gly Pro Asn Gly Phe Cys
65                  70                  75                  80

Gly Ala Arg Ser Gly Ile Pro Glu Arg Phe Ser Ala Ser Lys Ser Gly
                85                  90                  95

Thr Ser Ala Ser Leu Val Ile Ser Gly Leu Gln Ser Glu Asp Glu Ala
            100                 105                 110
```

Asp Tyr Tyr Cys Ala Ala Trp Asp Asp Ser Leu Asn Gly Trp Val Phe
115 120 125

Gly Gly Gly Thr Lys Leu Thr Val Leu Gly Gln Pro
130 135 140

<210> SEQ ID NO 102
<211> LENGTH: 140
<212> TYPE: PRT
<213> ORGANISM: Artificial Sequence
<220> FEATURE:
<223> OTHER INFORMATION: CDR2_C_07

<400> SEQUENCE: 102

Gln Ser Val Leu Thr Gln Pro Pro Ser Val Ser Glu Ala Pro Arg Gln
1 5 10 15

Arg Val Thr Ile Thr Cys Ser Gly Ser Ser Ser Asn Ile Gly Asn Asn
20 25 30

Ala Val Asn Trp Tyr Gln Gln Leu Pro Gly Lys Ala Pro Lys Leu Leu
35 40 45

Ile Tyr Ala Ala Ala Val Cys Pro Arg Ile Leu Met Arg Cys Lys Gln
50 55 60

Asp Ser Asp Cys Leu Ala Gly Cys Val Cys Gly Pro Asn Gly Phe Cys
65 70 75 80

Gly Thr Arg Ser Gly Ile Pro Glu Arg Phe Ser Gly Ser Lys Ser Gly
85 90 95

Thr Ser Ala Phe Leu Ala Ile Ser Gly Leu Arg Ser Glu Asp Glu Ala
100 105 110

Asp Tyr Tyr Cys Ala Ala Trp Asp Asp Ser Leu Ser Gly Val Val Phe
115 120 125

Gly Gly Gly Thr Lys Leu Thr Val Leu Gly Gln Pro
130 135 140

<210> SEQ ID NO 103
<211> LENGTH: 140
<212> TYPE: PRT
<213> ORGANISM: Artificial Sequence
<220> FEATURE:
<223> OTHER INFORMATION: CDR2_B_07

<400> SEQUENCE: 103

Gln Ser Val Leu Thr Gln Pro Pro Ser Val Ser Glu Ala Pro Arg Gln
1 5 10 15

Arg Val Thr Ile Thr Cys Ser Gly Ser Ser Ser Asn Ile Gly Asn Asn
20 25 30

Ala Val Asn Trp Tyr Gln Gln Leu Pro Gly Lys Ala Pro Lys Leu Leu
35 40 45

Ile Tyr Ala Ala Ala Arg Cys Pro Arg Ile Leu Met Arg Cys Lys Gln
50 55 60

Asp Ser Asp Cys Leu Ala Gly Cys Val Cys Gly Pro Asn Gly Phe Cys
65 70 75 80

Gly His Thr Ser Gly Ile Pro Glu Arg Phe Ser Gly Ser Lys Ser Gly
85 90 95

Thr Ser Ala Ser Leu Ala Ile Ser Gly Leu Gln Ser Glu Asp Glu Ala
100 105 110

Asp Tyr Tyr Cys Ala Ala Trp Asp Asp Ser Leu Asn Gly Val Val Phe
115 120 125

Gly Gly Gly Thr Lys Leu Thr Val Leu Gly Gln Pro 130 135 140

<210> SEQ ID NO 104
<211> LENGTH: 140
<212> TYPE: PRT
<213> ORGANISM: Artificial Sequence
<220> FEATURE:
<223> OTHER INFORMATION: CDR2_G_05

<400> SEQUENCE: 104

Gln Ser Val Leu Thr Gln Pro Pro Ser Val Ser Glu Ala Pro Arg Gln
1 5 10 15

Arg Val Thr Ile Thr Cys Ser Gly Ser Ser Ser Asn Ile Gly Asn Asn
20 25 30

Ala Val Asn Trp Tyr Gln Gln Leu Pro Gly Lys Ala Pro Lys Leu Leu
35 40 45

Ile Tyr Ala Ala Gly Arg Cys Pro Arg Ile Leu Met Arg Cys Lys Gln
50 55 60

Asp Ser Asp Cys Leu Ala Gly Cys Val Cys Gly Pro Asn Gly Phe Cys
65 70 75 80

Gly Gly Arg Ser Gly Val Ser Asp Arg Phe Ser Gly Ser Lys Ser Gly
85 90 95

Thr Ser Ala Ser Leu Ala Ile Ser Gly Leu Gln Ser Glu Asp Glu Ala
100 105 110

Asp Tyr Tyr Cys Ala Ala Trp Asp Asp Ser Leu Asn Gly Tyr Val Phe
115 120 125

Gly Thr Gly Thr Lys Leu Thr Val Leu Gly Gln Pro
130 135 140

<210> SEQ ID NO 105
<211> LENGTH: 140
<212> TYPE: PRT
<213> ORGANISM: Artificial Sequence
<220> FEATURE:
<223> OTHER INFORMATION: CDR2_H_04

<400> SEQUENCE: 105

Gln Ser Val Leu Thr Gln Pro Pro Ser Val Ser Glu Ala Pro Arg Gln
1 5 10 15

Arg Val Thr Ile Thr Cys Ser Gly Ser Ser Ser Asn Ile Gly Asn Asn
20 25 30

Ala Val Asn Trp Tyr Gln Gln Leu Pro Gly Lys Ala Pro Lys Leu Leu
35 40 45

Ile Tyr Ala Ala Gly Arg Cys Pro Arg Ile Leu Met Arg Cys Lys Gln
50 55 60

Asp Ser Asp Cys Leu Ala Gly Cys Val Cys Gly Pro Asn Gly Phe Cys
65 70 75 80

Gly Ala Asn Ser Gly Val Ser Asp Arg Phe Ser Ala Ala Lys Ser Gly
85 90 95

Thr Ser Ala Ser Leu Ala Ile Asn Gly Leu Arg Ser Glu Asp Glu Ala
100 105 110

Asp Tyr Tyr Cys Ala Ala Trp Asp Asp Ser Leu Asn Gly Tyr Val Phe
115 120 125

Gly Thr Gly Thr Lys Leu Thr Val Leu Gly Gln Pro
130 135 140

<210> SEQ ID NO 106
<211> LENGTH: 140

<212> TYPE: PRT
<213> ORGANISM: Artificial Sequence
<220> FEATURE:
<223> OTHER INFORMATION: CDR2_A_01

<400> SEQUENCE: 106

```
Gln Ser Val Leu Thr Gln Pro Pro Ser Val Ser Glu Ala Pro Arg Gln
1               5                   10                  15

Arg Val Thr Ile Thr Cys Ser Gly Ser Ser Ser Asn Ile Gly Asn Asn
            20                  25                  30

Ala Val Asn Trp Tyr Gln Gln Leu Pro Gly Lys Ala Pro Lys Leu Leu
        35                  40                  45

Ile Tyr Ala Ala Glu Pro Cys Pro Arg Ile Leu Met Arg Cys Lys Gln
    50                  55                  60

Asp Ser Asp Cys Leu Ala Gly Cys Val Cys Gly Pro Asn Gly Phe Cys
65                  70                  75                  80

Gly Ala Pro Ser Gly Val Pro Asp Arg Phe Ser Gly Ser Lys Ser Gly
                85                  90                  95

Thr Ser Ala Ser Leu Ala Ile Thr Gly Leu Gln Ser Glu Asp Glu Ala
            100                 105                 110

His Tyr Tyr Cys Ala Ala Trp Asp Asp Ser Leu Ser Ala Trp Val Phe
        115                 120                 125

Gly Gly Gly Thr Lys Leu Thr Val Leu Gly Gln Pro
    130                 135                 140
```

<210> SEQ ID NO 107
<211> LENGTH: 140
<212> TYPE: PRT
<213> ORGANISM: Artificial Sequence
<220> FEATURE:
<223> OTHER INFORMATION: CDR2_H_07

<400> SEQUENCE: 107

```
Gln Ser Val Leu Thr Gln Pro Pro Ser Val Ser Glu Ala Pro Arg Gln
1               5                   10                  15

Arg Val Thr Ile Thr Cys Ser Gly Ser Ser Ser Asn Ile Gly Asn Asn
            20                  25                  30

Ala Val Asn Trp Tyr Gln Gln Leu Pro Gly Lys Ala Pro Lys Leu Leu
        35                  40                  45

Ile Tyr Ala Ala Ala Gly Cys Pro Arg Ile Leu Met Arg Cys Lys Gln
    50                  55                  60

Asp Ser Asp Cys Leu Ala Gly Cys Val Cys Gly Pro Asn Gly Phe Cys
65                  70                  75                  80

Gly Thr Arg Ser Gly Val Ser Asp Arg Phe Ser Gly Ser Lys Ser Gly
                85                  90                  95

Thr Ser Ala Ser Leu Ala Ile Ser Gly Leu Arg Ser Glu Asp Glu Ala
            100                 105                 110

Asp Tyr Tyr Cys Ala Ala Trp Asp Asp Ser Leu Arg Ala Tyr Val Phe
        115                 120                 125

Gly Thr Gly Thr Lys Leu Thr Val Leu Gly Gln Pro
    130                 135                 140
```

<210> SEQ ID NO 108
<211> LENGTH: 140
<212> TYPE: PRT
<213> ORGANISM: Artificial Sequence
<220> FEATURE:
<223> OTHER INFORMATION: CDR2_B_06

<400> SEQUENCE: 108

Gln Ser Val Leu Thr Gln Pro Pro Ser Val Ser Glu Ala Pro Arg Gln
1 5 10 15

Arg Val Thr Ile Thr Cys Ser Gly Ser Ser Ser Asn Ile Gly Asn Asn
20 25 30

Ala Val Asn Trp Tyr Gln Gln Leu Pro Gly Lys Ala Pro Lys Leu Leu
35 40 45

Ile Tyr Ala Ala Asp Arg Cys Pro Arg Ile Leu Met Arg Cys Lys Gln
50 55 60

Asp Ser Asp Cys Leu Ala Gly Cys Val Cys Gly Pro Asn Gly Phe Cys
65 70 75 80

Gly Thr Asp Ser Gly Ile Pro Glu Arg Phe Ser Gly Ser Lys Ser Gly
85 90 95

Asn Thr Ala Ser Leu Thr Ile Ser Gly Leu Gln Ala Glu Asp Glu Ala
100 105 110

Asp Tyr Tyr Cys Ala Ala Trp Asp Asp Ser Leu Ser Gly Pro Val Phe
115 120 125

Gly Gly Gly Thr Lys Val Thr Val Leu Gly Gln Pro
130 135 140

<210> SEQ ID NO 109
<211> LENGTH: 140
<212> TYPE: PRT
<213> ORGANISM: Artificial Sequence
<220> FEATURE:
<223> OTHER INFORMATION: CDR2_F_09

<400> SEQUENCE: 109

Gln Ser Val Leu Thr Gln Pro Pro Ser Val Ser Glu Ala Pro Arg Gln
1 5 10 15

Arg Val Thr Ile Thr Cys Ser Gly Ser Ser Ser Asn Ile Gly Asn Asn
20 25 30

Ala Val Asn Trp Tyr Gln Gln Leu Pro Gly Lys Ala Pro Lys Leu Leu
35 40 45

Ile Tyr Ala Ala Val Ile Cys Pro Arg Ile Leu Met Arg Cys Lys Gln
50 55 60

Asp Ser Asp Cys Leu Ala Gly Cys Val Cys Gly Pro Asn Gly Phe Cys
65 70 75 80

Gly Thr Gly Ser Gly Val Ser Asp Arg Phe Ser Gly Ser Lys Ser Gly
85 90 95

Thr Ser Ala Ser Leu Ala Ile Ser Gly Leu Gln Ser Glu Asp Glu Ala
100 105 110

Asp Tyr Tyr Cys Ala Ala Trp Asp Asp Ser Leu Asn Gly Val Val Phe
115 120 125

Gly Gly Gly Thr Lys Leu Thr Val Leu Gly Gln Pro
130 135 140

<210> SEQ ID NO 110
<211> LENGTH: 140
<212> TYPE: PRT
<213> ORGANISM: Artificial Sequence
<220> FEATURE:
<223> OTHER INFORMATION: CDR2_F_11

<400> SEQUENCE: 110

Gln Ser Val Leu Thr Gln Pro Pro Ser Val Ser Glu Ala Pro Arg Gln
1 5 10 15

```
Arg Val Thr Ile Thr Cys Ser Gly Ser Ser Ser Asn Ile Gly Asn Asn
            20                  25                  30

Ala Val Asn Trp Tyr Gln Gln Leu Pro Gly Lys Ala Pro Lys Leu Leu
        35                  40                  45

Ile Tyr Ala Ala Glu Arg Cys Pro Arg Ile Leu Met Arg Cys Lys Gln
    50                  55                  60

Asp Ser Asp Cys Leu Ala Gly Cys Val Cys Gly Pro Asn Gly Phe Cys
65                  70                  75                  80

Gly Gly Ser Ser Gly Val Ser Asp Arg Phe Ser Gly Ser Lys Ser Gly
                85                  90                  95

Thr Ser Ala Ser Leu Ala Ile Ser Gly Leu Arg Ser Glu Asp Glu Ala
            100                 105                 110

Asp Tyr Tyr Cys Ala Thr Trp Asp Asp Asn Leu Asn Gly Pro Val Phe
        115                 120                 125

Gly Gly Gly Thr Lys Leu Thr Val Leu Gly Gln Pro
    130                 135                 140


<210> SEQ ID NO 111
<211> LENGTH: 140
<212> TYPE: PRT
<213> ORGANISM: Artificial Sequence
<220> FEATURE:
<223> OTHER INFORMATION: CDR2_C_02

<400> SEQUENCE: 111

Gln Ser Val Leu Thr Gln Pro Pro Ser Val Ser Glu Ala Pro Arg Gln
1               5                   10                  15

Arg Val Thr Ile Thr Cys Ser Gly Ser Ser Ser Asn Ile Gly Asn Asn
            20                  25                  30

Ala Val Asn Trp Tyr Gln Gln Leu Pro Gly Lys Ala Pro Lys Leu Leu
        35                  40                  45

Ile Tyr Ala Ala Val Gly Cys Pro Arg Ile Leu Met Arg Cys Lys Gln
    50                  55                  60

Asp Ser Asp Cys Leu Ala Gly Cys Val Cys Gly Pro Asn Gly Phe Cys
65                  70                  75                  80

Gly Ser Ala Ser Gly Val Ser Asp Arg Phe Ser Gly Ser Lys Ser Gly
                85                  90                  95

Thr Ser Ala Ser Leu Ala Ile Ser Gly Leu Arg Ser Glu Asp Glu Ala
            100                 105                 110

Asp Tyr Tyr Cys Ala Ser Trp Asp Asp Ser Leu Arg Gly Tyr Val Phe
        115                 120                 125

Gly Thr Gly Thr Lys Val Thr Val Leu Gly Gln Pro
    130                 135                 140


<210> SEQ ID NO 112
<211> LENGTH: 140
<212> TYPE: PRT
<213> ORGANISM: Artificial Sequence
<220> FEATURE:
<223> OTHER INFORMATION: CDR2_D_08

<400> SEQUENCE: 112

Gln Ser Val Leu Thr Gln Pro Pro Ser Val Ser Glu Ala Pro Arg Gln
1               5                   10                  15

Arg Val Thr Ile Thr Cys Ser Gly Ser Ser Ser Asn Ile Gly Asn Asn
            20                  25                  30

Ala Val Asn Trp Tyr Gln Gln Leu Pro Gly Lys Ala Pro Lys Leu Leu
        35                  40                  45
```

Ile Tyr Ala Ala Gly Pro Cys Pro Arg Ile Leu Met Arg Cys Lys Gln
50 55 60

Asp Ser Asp Cys Leu Ala Gly Cys Val Cys Gly Pro Asn Gly Phe Cys
65 70 75 80

Gly Thr Ala Ser Gly Val Pro Asp Arg Phe Ser Gly Ser Lys Ser Gly
85 90 95

Thr Ser Ala Ser Leu Ala Ile Ser Gly Leu Arg Ser Glu Asp Glu Ala
100 105 110

Asp Tyr Tyr Cys Ala Ala Trp Asp Asp Ser Leu Ser Gly Val Val Phe
115 120 125

Gly Gly Gly Thr Lys Val Thr Val Leu Gly Gln Pro
130 135 140

<210> SEQ ID NO 113
<211> LENGTH: 140
<212> TYPE: PRT
<213> ORGANISM: Artificial Sequence
<220> FEATURE:
<223> OTHER INFORMATION: CDR2_E_10

<400> SEQUENCE: 113

Gln Ser Val Leu Thr Gln Pro Pro Ser Val Ser Glu Ala Pro Arg Gln
1 5 10 15

Arg Val Thr Ile Thr Cys Ser Gly Ser Ser Ser Asn Ile Gly Asn Asn
20 25 30

Ala Val Asn Trp Tyr Gln Gln Leu Pro Gly Lys Ala Pro Lys Leu Leu
35 40 45

Ile Tyr Ala Ala Ala Arg Cys Pro Arg Ile Leu Met Arg Cys Lys Gln
50 55 60

Asp Ser Asp Cys Leu Ala Gly Cys Val Cys Gly Pro Asn Gly Phe Cys
65 70 75 80

Gly Thr Pro Ser Gly Val Pro Asp Arg Phe Ser Gly Ser Lys Ser Gly
85 90 95

Thr Ser Ala Ser Leu Ala Ile Ser Gly Leu Gln Ser Glu Asp Glu Ala
100 105 110

Asp Tyr Tyr Cys Ala Ala Trp Asp Asp Ser Leu Ser Gly Tyr Val Phe
115 120 125

Gly Thr Gly Thr Lys Leu Thr Val Leu Gly Gln Pro
130 135 140

<210> SEQ ID NO 114
<211> LENGTH: 140
<212> TYPE: PRT
<213> ORGANISM: Artificial Sequence
<220> FEATURE:
<223> OTHER INFORMATION: CDR2_F_05

<400> SEQUENCE: 114

Gln Ser Val Leu Thr Gln Pro Pro Ser Val Ser Glu Ala Pro Arg Gln
1 5 10 15

Arg Val Thr Ile Thr Cys Ser Gly Ser Ser Ser Asn Ile Gly Ser Asn
20 25 30

Ala Val Asn Trp Tyr Gln Gln Leu Pro Gly Lys Ala Pro Lys Leu Leu
35 40 45

Ile Tyr Ala Ala Gly Gly Cys Pro Arg Ile Leu Met Arg Cys Lys Gln
50 55 60

Asp Ser Asp Cys Leu Ala Gly Cys Val Cys Gly Pro Asn Gly Phe Cys 65 70 75 80

Gly Ser Asn Ser Gly Val Pro Asp Arg Phe Ser Gly Ser Lys Ser Gly
85 90 95

Asn Thr Ala Ser Leu Thr Ile Ser Gly Leu Gln Ser Glu Asp Glu Ala
100 105 110

Asp Tyr Tyr Cys Ala Ala Trp Asp Asp Ser Leu Ser Gly Val Val Phe
115 120 125

Gly Gly Gly Thr Gln Leu Thr Val Leu Gly Gln Pro
130 135 140

<210> SEQ ID NO 115
<211> LENGTH: 140
<212> TYPE: PRT
<213> ORGANISM: Artificial Sequence
<220> FEATURE:
<223> OTHER INFORMATION: CDR2_G_04

<400> SEQUENCE: 115

Gln Ser Val Leu Thr Gln Pro Pro Ser Val Ser Glu Ala Pro Arg Gln
1 5 10 15

Arg Val Thr Ile Thr Cys Ser Gly Ser Ser Ser Asn Ile Gly Asn Asn
20 25 30

Ala Val Asn Trp Tyr Gln Gln Leu Pro Gly Lys Ala Pro Lys Leu Leu
35 40 45

Ile Tyr Ala Ala Gly Met Cys Pro Arg Ile Leu Met Arg Cys Lys Gln
50 55 60

Asp Ser Asp Cys Leu Ala Gly Cys Val Cys Gly Pro Asn Gly Phe Cys
65 70 75 80

Gly Gly His Ser Gly Val Ser Asp Arg Phe Ser Gly Ser Lys Ser Gly
85 90 95

Thr Ser Ala Ser Leu Ala Ile Ser Gly Leu Gln Ser Glu Asp Glu Ala
100 105 110

Asp Tyr Tyr Cys Ala Ala Trp Asp Asp Ser Leu Asn Gly Tyr Val Phe
115 120 125

Gly Thr Gly Thr Gln Leu Thr Val Leu Gly Gln Pro
130 135 140

<210> SEQ ID NO 116
<211> LENGTH: 140
<212> TYPE: PRT
<213> ORGANISM: Artificial Sequence
<220> FEATURE:
<223> OTHER INFORMATION: CDR2_A_08

<400> SEQUENCE: 116

Gln Ser Val Leu Thr Gln Pro Pro Ser Val Ser Glu Ala Pro Arg Gln
1 5 10 15

Arg Val Thr Ile Thr Cys Ser Gly Ser Ser Ser Asn Ile Gly Asn Asn
20 25 30

Ala Val Asn Trp Tyr Gln Gln Leu Pro Gly Lys Ala Pro Lys Leu Leu
35 40 45

Ile Tyr Ala Ala Ala Arg Cys Pro Arg Ile Leu Met Arg Cys Lys Gln
50 55 60

Asp Ser Asp Cys Leu Ala Gly Cys Val Cys Gly Pro Asn Gly Phe Cys
65 70 75 80

Gly Thr Arg Ser Gly Val Ser Asp Arg Phe Ser Gly Ser Lys Ser Gly
85 90 95

```
Thr Ser Ala Ser Leu Ala Ile Ser Gly Leu Gln Ser Gly Asp Glu Ala
            100                 105                 110

Asp Tyr Tyr Cys Ala Ala Trp Asp Asp Ser Leu Asn Gly Trp Val Phe
        115                 120                 125

Gly Gly Gly Thr Lys Leu Thr Val Leu Gly Gln Pro
    130                 135                 140


<210> SEQ ID NO 117
<211> LENGTH: 140
<212> TYPE: PRT
<213> ORGANISM: Artificial Sequence
<220> FEATURE:
<223> OTHER INFORMATION: CDR2_E_06

<400> SEQUENCE: 117

Gln Ser Val Leu Thr Gln Pro Pro Ser Val Ser Glu Ala Pro Arg Gln
1               5                   10                  15

Arg Val Thr Ile Thr Cys Ser Gly Ser Ser Ser Asn Ile Gly Asn Asn
            20                  25                  30

Ala Val Asn Trp Tyr Gln Gln Leu Pro Gly Lys Ala Pro Lys Leu Leu
        35                  40                  45

Ile Tyr Ala Ala Asp Lys Cys Pro Arg Ile Leu Met Arg Cys Lys Gln
    50                  55                  60

Asp Ser Asp Cys Leu Ala Gly Cys Val Cys Gly Pro Asn Gly Phe Cys
65                  70                  75                  80

Gly Leu Thr Ser Gly Val Ser Asp Arg Phe Ser Gly Ser Lys Ser Gly
                85                  90                  95

Thr Ser Ala Ser Leu Ala Ile Ser Gly Leu Arg Ser Glu Asp Glu Ala
            100                 105                 110

Asp Tyr Tyr Cys Ala Thr Trp Asp Asp Ser Leu Asn Gly Val Val Phe
        115                 120                 125

Gly Gly Gly Thr Lys Leu Thr Val Leu Gly Gln Pro
    130                 135                 140


<210> SEQ ID NO 118
<211> LENGTH: 141
<212> TYPE: PRT
<213> ORGANISM: Artificial Sequence
<220> FEATURE:
<223> OTHER INFORMATION: CDR2_B_11

<400> SEQUENCE: 118

Gln Ser Val Leu Thr Gln Pro Pro Ser Val Ser Glu Ala Pro Arg Gln
1               5                   10                  15

Arg Val Thr Ile Thr Cys Ser Gly Ser Ser Ser Asn Ile Gly Asn Asn
            20                  25                  30

Ala Val Asn Trp Tyr Gln Gln Leu Pro Gly Lys Ala Pro Lys Leu Leu
        35                  40                  45

Ile Tyr Ala Ala Ala Lys Cys Pro Arg Ile Leu Met Arg Cys Lys Gln
    50                  55                  60

Asp Ser Asp Cys Leu Ala Gly Cys Val Cys Gly Pro Asn Gly Phe Cys
65                  70                  75                  80

Gly Gly Ala Ser Gly Val Ser Asp Arg Phe Ser Gly Ser Ile Asp Ser
                85                  90                  95

Ser Ser Asn Ser Ala Ser Leu Thr Ile Ser Gly Leu Lys Pro Glu Asp
            100                 105                 110

Glu Gly Asp Tyr Tyr Cys Gln Ser Tyr Asp Ser Ser Asn Arg Trp Val
        115                 120                 125
```

Phe Gly Gly Gly Thr Lys Val Thr Val Leu Gly Gln Pro
130 135 140

<210> SEQ ID NO 119
<211> LENGTH: 142
<212> TYPE: PRT
<213> ORGANISM: Artificial Sequence
<220> FEATURE:
<223> OTHER INFORMATION: CDR2_G_09

<400> SEQUENCE: 119

Gln Ser Val Leu Thr Gln Pro Pro Ser Val Ser Glu Ala Pro Arg Gln
1 5 10 15

Arg Val Thr Ile Thr Cys Ser Gly Ser Ser Ser Asn Ile Gly Asn Asn
20 25 30

Ala Val Asn Trp Tyr Gln Gln Leu Pro Gly Lys Ala Pro Lys Leu Leu
35 40 45

Ile Tyr Ala Ala Ala Arg Cys Pro Arg Ile Leu Met Arg Cys Lys Gln
50 55 60

Asp Ser Asp Cys Leu Ala Gly Cys Val Cys Gly Pro Asn Gly Phe Cys
65 70 75 80

Gly Thr Thr Ser Gly Val Pro Asp Arg Phe Ser Gly Ser Ile Asp Ser
85 90 95

Ser Ser Asn Ser Ala Ser Leu Thr Ile Ser Glu Leu Lys Thr Glu Asp
100 105 110

Glu Ala Asp Tyr Tyr Cys Gln Ser Tyr Asp Ser Ser Asn Gln Gly Trp
115 120 125

Val Phe Gly Gly Gly Thr Lys Leu Thr Val Leu Gly Gln Pro
130 135 140

<210> SEQ ID NO 120
<211> LENGTH: 141
<212> TYPE: PRT
<213> ORGANISM: Artificial Sequence
<220> FEATURE:
<223> OTHER INFORMATION: CDR2_C_08

<400> SEQUENCE: 120

Gln Ser Val Leu Thr Gln Pro Pro Ser Val Ser Glu Ala Pro Arg Gln
1 5 10 15

Arg Val Thr Ile Thr Cys Ser Gly Ser Ser Ser Asn Ile Gly Asn Asn
20 25 30

Ala Val Asn Trp Tyr Gln Gln Leu Pro Gly Lys Ala Pro Lys Leu Leu
35 40 45

Ile Tyr Ala Ala Gly Arg Cys Pro Arg Ile Leu Met Arg Cys Lys Gln
50 55 60

Asp Ser Asp Cys Leu Ala Gly Cys Val Cys Gly Pro Asn Gly Phe Cys
65 70 75 80

Gly Gly Gly Ser Gly Val Pro Asp Arg Phe Ser Gly Ser Ile Asp Ser
85 90 95

Ser Ser Asn Ser Ala Ser Leu Thr Ile Ser Gly Leu Arg Ala Glu Asp
100 105 110

Glu Ala Asp Tyr Tyr Cys Gln Ser Tyr Asp Ser Ser Asn His Trp Val
115 120 125

Phe Gly Gly Gly Thr Lys Leu Thr Val Leu Gly Gln Pro
130 135 140

<210> SEQ ID NO 121
<211> LENGTH: 141
<212> TYPE: PRT
<213> ORGANISM: Artificial Sequence
<220> FEATURE:
<223> OTHER INFORMATION: CDR2_E_09

<400> SEQUENCE: 121

Gln Ser Val Leu Thr Gln Pro Pro Ser Val Ser Glu Ala Pro Arg Gln
1 5 10 15

Arg Val Thr Ile Thr Cys Ser Gly Ser Ser Ser Asn Ile Gly Asn Asn
20 25 30

Ala Val Asn Trp Tyr Gln Gln Leu Pro Gly Lys Ala Pro Lys Leu Leu
35 40 45

Ile Tyr Ala Ala Gly Pro Cys Pro Arg Ile Leu Met Arg Cys Lys Gln
50 55 60

Asp Ser Asp Cys Leu Ala Gly Cys Val Cys Gly Pro Asn Gly Phe Cys
65 70 75 80

Gly Pro Arg Ser Gly Val Pro Asp Arg Phe Ser Gly Ser Ile Asp Ser
85 90 95

Ser Ser Asn Ser Ala Ser Leu Thr Ile Ser Gly Leu Lys Thr Glu Asp
100 105 110

Glu Ala Asp Tyr Tyr Cys Gln Ser Tyr Asp Ser Asn Asn His Trp Val
115 120 125

Phe Gly Gly Gly Thr Lys Leu Thr Val Leu Gly Gln Pro
130 135 140

<210> SEQ ID NO 122
<211> LENGTH: 141
<212> TYPE: PRT
<213> ORGANISM: Artificial Sequence
<220> FEATURE:
<223> OTHER INFORMATION: CDR2_F_04

<400> SEQUENCE: 122

Gln Ser Val Leu Thr Gln Pro Pro Ser Val Ser Glu Ala Pro Arg Gln
1 5 10 15

Arg Val Thr Ile Thr Cys Ser Gly Ser Ser Ser Asn Ile Gly Asn Asn
20 25 30

Ala Val Asn Trp Tyr Gln Gln Leu Pro Gly Lys Ala Pro Lys Leu Leu
35 40 45

Ile Tyr Ala Ala Glu Arg Cys Pro Arg Ile Leu Met Arg Cys Lys Gln
50 55 60

Asp Ser Asp Cys Leu Ala Gly Cys Val Cys Gly Pro Asn Gly Phe Cys
65 70 75 80

Gly Thr Pro Ser Gly Val Pro Asp Arg Phe Ser Gly Ser Ile Asp Thr
85 90 95

Phe Ser Asn Ser Ala Ser Leu Thr Ile Ser Gly Leu Lys Thr Glu Asp
100 105 110

Glu Ala Asp Tyr Tyr Cys Gln Ser Tyr Asp Ser Ser His His Trp Val
115 120 125

Phe Gly Gly Gly Thr Lys Leu Thr Val Leu Gly Gln Pro
130 135 140

<210> SEQ ID NO 123
<211> LENGTH: 140
<212> TYPE: PRT
<213> ORGANISM: Artificial Sequence
<220> FEATURE:

```
<223> OTHER INFORMATION: CDR2_E_05

<400> SEQUENCE: 123

Gln Ser Val Leu Thr Gln Pro Pro Ser Val Ser Glu Ala Pro Arg Gln
1               5                   10                  15

Arg Val Thr Ile Thr Cys Ser Gly Ser Ser Ser Asn Ile Gly Asn Asn
            20                  25                  30

Ala Val Asn Trp Tyr Gln Gln Leu Pro Gly Lys Ala Pro Lys Leu Leu
        35                  40                  45

Ile Tyr Ala Ala Gly Pro Cys Pro Arg Ile Leu Met Arg Cys Lys Gln
    50                  55                  60

Asp Ser Asp Cys Leu Ala Gly Cys Val Cys Gly Pro Asn Gly Phe Cys
65                  70                  75                  80

Gly Ala Asp Ser Gly Val Ser Asp Arg Phe Ser Gly Ser Lys Ser Gly
                85                  90                  95

Thr Ser Ala Ser Leu Ala Ile Thr Gly Leu Gln Ala Glu Asp Glu Gly
            100                 105                 110

Asp Tyr Tyr Cys Ala Ala Trp Asp Asp Ser Leu Asn Gly Leu Val Phe
        115                 120                 125

Gly Gly Gly Thr Lys Val Thr Val Leu Gly Gln Pro
    130                 135                 140


<210> SEQ ID NO 124
<211> LENGTH: 141
<212> TYPE: PRT
<213> ORGANISM: Artificial Sequence
<220> FEATURE:
<223> OTHER INFORMATION: CDR2_D_07

<400> SEQUENCE: 124

Gln Ser Val Leu Thr Gln Pro Pro Ser Val Ser Glu Ala Pro Arg Gln
1               5                   10                  15

Arg Val Thr Ile Thr Cys Ser Gly Ser Ser Ser Asn Ile Gly Asn Asn
            20                  25                  30

Ala Val Asn Trp Tyr Gln Gln Leu Pro Gly Lys Ala Pro Lys Leu Leu
        35                  40                  45

Ile Tyr Ala Ala Gly Arg Cys Pro Arg Ile Leu Met Arg Cys Arg Gln
    50                  55                  60

Asp Ser Asp Cys Leu Ala Gly Cys Val Cys Gly Pro Asn Gly Phe Cys
65                  70                  75                  80

Gly Thr Ala Ser Gly Val Pro Asp Arg Phe Ser Gly Ser Ile Asp Thr
                85                  90                  95

Phe Ser Asn Ser Ala Ser Leu Thr Ile Ser Gly Leu Lys Thr Glu Asp
            100                 105                 110

Glu Ala Asp Tyr Tyr Cys Gln Ser Tyr Asp Ser Ser Asn His Trp Val
        115                 120                 125

Phe Gly Gly Gly Thr Lys Leu Thr Val Leu Gly Gln Pro
    130                 135                 140


<210> SEQ ID NO 125
<211> LENGTH: 140
<212> TYPE: PRT
<213> ORGANISM: Artificial Sequence
<220> FEATURE:
<223> OTHER INFORMATION: CDR2_G_03

<400> SEQUENCE: 125

Gln Ser Val Leu Thr Gln Pro Pro Ser Val Ser Glu Ala Pro Arg Gln
```

1 5 10 15

Arg Val Thr Ile Thr Cys Ser Gly Ser Ser Ser Asn Ile Gly Asn Asn
20 25 30

Ala Val Asn Trp Tyr Gln Gln Leu Pro Gly Lys Ala Pro Lys Leu Leu
35 40 45

Ile Tyr Ala Ala Gly Arg Cys Pro Arg Ile Leu Met Arg Cys Lys Gln
50 55 60

Asp Ser Asp Cys Leu Ala Gly Cys Val Cys Gly Pro Asn Gly Phe Cys
65 70 75 80

Gly Thr Asn Ser Gly Ile Pro Glu Arg Phe Ser Gly Ser Lys Ser Gly
85 90 95

Asn Thr Ala Ser Leu Thr Ile Ser Gly Leu Gln Ala Glu Asp Glu Ala
100 105 110

Asp Tyr Tyr Cys Gln Ser Tyr Asp Ser Ser Leu Ser Gly Trp Val Phe
115 120 125

Gly Gly Gly Thr Gln Leu Thr Val Leu Gly Gln Pro
130 135 140

<210> SEQ ID NO 126
<211> LENGTH: 141
<212> TYPE: PRT
<213> ORGANISM: Artificial Sequence
<220> FEATURE:
<223> OTHER INFORMATION: CDR2_A_09

<400> SEQUENCE: 126

Gln Ser Val Leu Thr Gln Pro Pro Ser Val Ser Glu Ala Pro Arg Gln
1 5 10 15

Arg Val Thr Ile Thr Cys Ser Gly Ser Ser Ser Asn Ile Gly Asn Asn
20 25 30

Ala Val Asn Trp Tyr Gln Gln Leu Pro Gly Lys Ala Pro Lys Leu Leu
35 40 45

Ile Tyr Ala Ala Ala Pro Cys Pro Arg Ile Leu Met Arg Cys Lys Gln
50 55 60

Asp Ser Asp Cys Leu Ala Gly Cys Val Cys Gly Pro Asn Gly Phe Cys
65 70 75 80

Gly Ala His Ser Gly Val Pro Asp Arg Phe Ser Gly Ser Ile Asp Arg
85 90 95

Ser Ser Asn Ser Ala Ser Leu Thr Ile Ser Gly Leu Lys Ile Glu Asp
100 105 110

Glu Ala Asp Tyr Tyr Cys Gln Ser Tyr Asp Ser Ser Asn His Val Val
115 120 125

Phe Gly Gly Gly Thr Lys Val Thr Val Leu Gly Gln Pro
130 135 140

<210> SEQ ID NO 127
<211> LENGTH: 142
<212> TYPE: PRT
<213> ORGANISM: Artificial Sequence
<220> FEATURE:
<223> OTHER INFORMATION: CDR2_D_11

<400> SEQUENCE: 127

Gln Ser Val Leu Thr Gln Pro Pro Ser Val Ser Glu Ala Pro Arg Gln
1 5 10 15

Arg Val Thr Ile Thr Cys Ser Gly Ser Ser Ser Asn Ile Gly Asn Asn
20 25 30

```
Ala Val Asn Trp Tyr Gln Gln Leu Pro Gly Lys Ala Pro Lys Leu Leu
        35                  40                  45

Ile Tyr Ala Ala Val Arg Cys Pro Arg Ile Leu Met Arg Cys Lys Gln
    50                  55                  60

Asp Ser Asp Cys Leu Ala Gly Cys Val Cys Gly Pro Asn Gly Phe Cys
65                  70                  75                  80

Gly Thr Pro Ser Gly Ile Pro Glu Arg Phe Ser Gly Ser Ile Asp Arg
                85                  90                  95

Ser Thr Asn Ser Ala Ser Leu Thr Ile Ser Gly Leu Lys Thr Glu Asp
            100                 105                 110

Glu Ala Asp Tyr Tyr Cys Gln Ser Tyr Asp Ser Ser Asn Leu Asn Trp
        115                 120                 125

Val Phe Gly Gly Gly Thr Lys Leu Thr Val Leu Gly Gln Pro
    130                 135                 140


<210> SEQ ID NO 128
<211> LENGTH: 140
<212> TYPE: PRT
<213> ORGANISM: Artificial Sequence
<220> FEATURE:
<223> OTHER INFORMATION: CDR2_C_06

<400> SEQUENCE: 128

Gln Ser Val Leu Thr Gln Pro Pro Ser Val Ser Glu Ala Pro Arg Gln
1               5                   10                  15

Arg Val Thr Ile Thr Cys Ser Gly Ser Ser Ser Asn Ile Gly Asn Asn
            20                  25                  30

Ala Val Asn Trp Tyr Gln Gln Leu Pro Gly Lys Ala Pro Lys Leu Leu
        35                  40                  45

Ile Asn Ala Ala Asp Arg Cys Pro Arg Ile Leu Met Arg Cys Lys Gln
    50                  55                  60

Asp Ser Asp Cys Leu Ala Gly Cys Val Cys Gly Pro Asn Gly Phe Cys
65                  70                  75                  80

Gly Thr Asn Ser Gly Val Pro Asp Arg Phe Ser Gly Ser Ser Ser Gly
                85                  90                  95

Asn Thr Ala Ser Leu Thr Ile Thr Gly Ala Gln Ala Glu Asp Glu Ala
            100                 105                 110

Asp Tyr Tyr Cys Asn Ser Arg Asp Ser Ser Gly Asn Asn Trp Val Phe
        115                 120                 125

Gly Gly Gly Thr Lys Val Thr Val Leu Gly Gln Pro
    130                 135                 140


<210> SEQ ID NO 129
<211> LENGTH: 136
<212> TYPE: PRT
<213> ORGANISM: Artificial Sequence
<220> FEATURE:
<223> OTHER INFORMATION: CDR2_F_01

<400> SEQUENCE: 129

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Gly Leu Cys Pro Arg Ile Leu Met Arg Cys Lys Gln Asp
    50                  55                  60
```

Ser Asp Cys Leu Ala Gly Cys Val Cys Gly Pro Asn Gly Phe Cys Gly
65 70 75 80

Gly Glu Ser Gly Val Pro Ser Arg Phe Ser Gly Ser Gly Ser Gly Thr
85 90 95

Asp Phe Thr Leu Thr Ile Ser Ser Leu Gln Pro Glu Asp Phe Ala Thr
100 105 110

Tyr Tyr Cys Gln Gln Ser Tyr Ser Thr Pro Tyr Thr Phe Gly Gln Gly
115 120 125

Thr Lys Val Asp Ile Lys Arg Thr
130 135

<210> SEQ ID NO 130
<211> LENGTH: 136
<212> TYPE: PRT
<213> ORGANISM: Artificial Sequence
<220> FEATURE:
<223> OTHER INFORMATION: CDR2_F_12

<400> SEQUENCE: 130

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Ala Ala Ala Pro Cys Pro Arg Ile Leu Met Arg Cys Lys Gln Asp
50 55 60

Ser Asp Cys Leu Ala Gly Cys Val Cys Gly Pro Asn Gly Phe Cys Gly
65 70 75 80

Ser Thr Ser Gly Val Pro Ser Arg Phe Ser Gly Ser Gly Ser Gly Thr
85 90 95

Asp Phe Thr Leu Thr Ile Ser Ser Leu Gln Pro Glu Asp Phe Ala Thr
100 105 110

Tyr Tyr Cys Gln Gln Ser Tyr Ser Thr Pro Tyr Thr Phe Gly Gln Gly
115 120 125

Thr Lys Val Asp Ile Lys Arg Thr
130 135

<210> SEQ ID NO 131
<211> LENGTH: 136
<212> TYPE: PRT
<213> ORGANISM: Artificial Sequence
<220> FEATURE:
<223> OTHER INFORMATION: CDR2_E_04

<400> SEQUENCE: 131

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Ala Ala Ala Arg Cys Pro Arg Ile Leu Met Arg Cys Lys Gln Asp
50 55 60

Ser Asp Cys Leu Ala Gly Cys Val Cys Gly Pro Asn Gly Phe Cys Gly
65 70 75 80

Thr Thr Ser Gly Val Pro Ser Arg Phe Ser Gly Ser Gly Ser Gly Thr

```
                85                  90                  95

Asp Phe Thr Leu Thr Ile Ser Ser Leu Gln Pro Glu Asp Phe Ala Thr
            100                 105                 110

Tyr Tyr Cys Gln Gln Ser Tyr Ser Thr Pro Tyr Thr Phe Gly Gln Gly
        115                 120                 125

Thr Lys Val Glu Ile Lys Arg Thr
    130                 135


<210> SEQ ID NO 132
<211> LENGTH: 136
<212> TYPE: PRT
<213> ORGANISM: Artificial Sequence
<220> FEATURE:
<223> OTHER INFORMATION: CDR2_F_03

<400> SEQUENCE: 132

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ala Lys Cys Pro Arg Ile Leu Met Arg Cys Lys Gln Asp
    50                  55                  60

Ser Asp Cys Leu Ala Gly Cys Val Cys Gly Pro Asn Gly Phe Cys Gly
65                  70                  75                  80

Ala Pro Ser Gly Val Pro Ser Arg Phe Ser Gly Ser Gly Ser Gly Thr
                85                  90                  95

Asp Phe Thr Leu Thr Ile Ser Ser Leu Gln Pro Glu Asp Phe Ala Thr
            100                 105                 110

Tyr Tyr Cys Gln Gln Ser Tyr Ser Thr Pro Tyr Thr Phe Gly Gln Gly
        115                 120                 125

Thr Lys Val Glu Ile Lys Arg Thr
    130                 135


<210> SEQ ID NO 133
<211> LENGTH: 136
<212> TYPE: PRT
<213> ORGANISM: Artificial Sequence
<220> FEATURE:
<223> OTHER INFORMATION: CDR2_D_03

<400> SEQUENCE: 133

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Val Val Cys Pro Arg Ile Leu Met Arg Cys Lys Gln Asp
    50                  55                  60

Ser Asp Cys Leu Ala Gly Cys Val Cys Gly Pro Asn Gly Phe Cys Gly
65                  70                  75                  80

Ser Gly Ser Gly Val Pro Ser Arg Phe Ser Gly Ser Gly Ser Gly Thr
                85                  90                  95

Asp Phe Thr Leu Thr Ile Ser Ser Leu Gln Pro Glu Asp Phe Ala Thr
            100                 105                 110
```

```
Tyr Tyr Cys Gln Gln Ser Tyr Ser Thr Pro Tyr Thr Phe Gly Gln Gly
        115                 120                 125

Thr Lys Leu Glu Ile Lys Arg Thr
    130                 135


<210> SEQ ID NO 134
<211> LENGTH: 136
<212> TYPE: PRT
<213> ORGANISM: Artificial Sequence
<220> FEATURE:
<223> OTHER INFORMATION: CDR2_D_06

<400> SEQUENCE: 134

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Gly Arg Cys Pro Arg Ile Leu Met Arg Cys Lys Gln Asp
    50                  55                  60

Ser Asp Cys Leu Ala Gly Cys Val Cys Gly Pro Asn Gly Phe Cys Gly
65                  70                  75                  80

Thr Ala Ser Gly Val Pro Ser Arg Phe Ser Gly Gly Gly Ser Gly Thr
                85                  90                  95

Asp Phe Thr Leu Thr Ile Ser Ser Leu Gln Pro Glu Asp Phe Ala Thr
            100                 105                 110

Tyr Tyr Cys Gln Gln Ser Tyr Ser Thr Pro Tyr Thr Phe Gly Gln Gly
        115                 120                 125

Thr Lys Val Asp Ile Lys Arg Thr
    130                 135


<210> SEQ ID NO 135
<211> LENGTH: 136
<212> TYPE: PRT
<213> ORGANISM: Artificial Sequence
<220> FEATURE:
<223> OTHER INFORMATION: CDR2_C_09

<400> SEQUENCE: 135

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Gly Gly Cys Pro Arg Ile Leu Met Arg Cys Lys Gln Asp
    50                  55                  60

Ser Asp Cys Leu Ala Gly Cys Val Cys Gly Pro Asn Gly Phe Cys Gly
65                  70                  75                  80

Ala Pro Ser Gly Val Pro Ser Arg Phe Ser Gly Ser Gly Ser Gly Thr
                85                  90                  95

Asp Phe Thr Leu Thr Ile Ser Gly Leu Gln Pro Glu Asp Phe Gly Thr
            100                 105                 110

Tyr Tyr Cys Gln Gln Ser Tyr Ser Thr Pro Leu Thr Phe Gly Gly Gly
        115                 120                 125

Thr Lys Leu Glu Ile Lys Arg Thr
    130                 135
```

<210> SEQ ID NO 136
<211> LENGTH: 136
<212> TYPE: PRT
<213> ORGANISM: Artificial Sequence
<220> FEATURE:
<223> OTHER INFORMATION: CDR2_E_08

<400> SEQUENCE: 136

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Gly Val Cys Pro Arg Ile Leu Met Arg Cys Lys Gln Asp
    50                  55                  60

Ser Asp Cys Leu Ala Gly Cys Val Cys Gly Pro Asn Gly Phe Cys Gly
65                  70                  75                  80

Ser Arg Ser Gly Val Pro Ser Arg Phe Ser Gly Ser Gly Ser Gly Thr
                85                  90                  95

Asp Phe Thr Leu Thr Ile Ser Ser Leu Gln Pro Glu Asp Phe Ala Thr
            100                 105                 110

Tyr Tyr Cys Gln Gln Gly Ala Ser Pro Pro Tyr Thr Phe Gly Gln Gly
        115                 120                 125

Thr Lys Val Glu Ile Lys Arg Thr
    130                 135
```

<210> SEQ ID NO 137
<211> LENGTH: 136
<212> TYPE: PRT
<213> ORGANISM: Artificial Sequence
<220> FEATURE:
<223> OTHER INFORMATION: CDR2_G_11

<400> SEQUENCE: 137

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Gly Arg Cys Pro Arg Ile Leu Met Arg Cys Lys Gln Asp
    50                  55                  60

Ser Asp Cys Leu Ala Gly Cys Val Cys Gly Pro Asn Gly Phe Cys Gly
65                  70                  75                  80

Gly His Ser Gly Val Pro Ser Arg Phe Ser Gly Ser Gly Ser Gly Thr
                85                  90                  95

Asp Phe Thr Leu Thr Ile Ser Ser Leu Gln Pro Glu Asp Phe Ala Thr
            100                 105                 110

Tyr Tyr Cys Gln Gln Ser Tyr Ser Thr Pro Pro Thr Phe Gly Gln Gly
        115                 120                 125

Thr Lys Leu Glu Ile Lys Arg Thr
    130                 135
```

<210> SEQ ID NO 138
<211> LENGTH: 136
<212> TYPE: PRT

<213> ORGANISM: Artificial Sequence
<220> FEATURE:
<223> OTHER INFORMATION: CDR2_B_03

<400> SEQUENCE: 138

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Gly Tyr
20 25 30

Leu Asn Trp Tyr Gln Gln Lys Pro Gly Lys Ala Pro Lys Leu Leu Ile
35 40 45

Tyr Ala Ala Glu Val Cys Pro Arg Ile Leu Met Arg Cys Lys Gln Asp
50 55 60

Ser Asp Cys Leu Ala Gly Cys Val Cys Gly Pro Asn Gly Phe Cys Gly
65 70 75 80

Gly Thr Ser Gly Val Pro Ser Arg Phe Ser Gly Ser Arg Ser Gly Thr
85 90 95

Glu Phe Thr Leu Thr Ile Ser Ser Leu Gln Pro Glu Asp Phe Ala Thr
100 105 110

Tyr Tyr Cys Gln Lys Val Asp Asp Tyr Pro Leu Thr Phe Gly Gly Gly
115 120 125

Thr Lys Val Glu Ile Lys Arg Thr
130 135

<210> SEQ ID NO 139
<211> LENGTH: 136
<212> TYPE: PRT
<213> ORGANISM: Artificial Sequence
<220> FEATURE:
<223> OTHER INFORMATION: CDR2_H_02

<400> SEQUENCE: 139

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Ala Ala Glu Ile Cys Pro Arg Ile Leu Met Arg Cys Lys Gln Asp
50 55 60

Ser Asp Cys Leu Ala Gly Cys Val Cys Gly Pro Asn Gly Phe Cys Gly
65 70 75 80

Pro Ser Ser Gly Ile Pro Ala Arg Phe Ser Gly Ser Gly Tyr Gly Thr
85 90 95

Asp Phe Thr Leu Thr Ile Asn Asn Ile Glu Ser Glu Asp Ala Ala Tyr
100 105 110

Tyr Phe Cys Leu Gln His Asp Asn Phe Pro Tyr Thr Phe Gly Gln Gly
115 120 125

Thr Lys Val Glu Ile Lys Arg Thr
130 135

<210> SEQ ID NO 140
<211> LENGTH: 4
<212> TYPE: PRT
<213> ORGANISM: Artificial Sequence
<220> FEATURE:
<223> OTHER INFORMATION: CDR1_C_12

<400> SEQUENCE: 140

Gly Arg Ala Met
1

<210> SEQ ID NO 141
<211> LENGTH: 4
<212> TYPE: PRT
<213> ORGANISM: Artificial Sequence
<220> FEATURE:
<223> OTHER INFORMATION: CDR1_F_02

<400> SEQUENCE: 141

Gly Ser Arg Pro
1

<210> SEQ ID NO 142
<211> LENGTH: 4
<212> TYPE: PRT
<213> ORGANISM: Artificial Sequence
<220> FEATURE:
<223> OTHER INFORMATION: CDR1_F_10

<400> SEQUENCE: 142

Gly Glu Arg Pro
1

<210> SEQ ID NO 143
<211> LENGTH: 12
<212> TYPE: PRT
<213> ORGANISM: Artificial Sequence
<220> FEATURE:
<223> OTHER INFORMATION: KB_Tr_F03

<400> SEQUENCE: 143

His Ala Ala Asn Trp Glu Glu Pro Gly Phe Asp Pro
1 5 10

<210> SEQ ID NO 144
<211> LENGTH: 12
<212> TYPE: PRT
<213> ORGANISM: Artificial Sequence
<220> FEATURE:
<223> OTHER INFORMATION: KB_Tr_E05

<400> SEQUENCE: 144

Arg Ser Ser Ala Gly Asp Gly Ala Tyr Phe Asp Tyr
1 5 10

<210> SEQ ID NO 145
<211> LENGTH: 15
<212> TYPE: PRT
<213> ORGANISM: Artificial Sequence
<220> FEATURE:
<223> OTHER INFORMATION: KB_Tr_E02

<400> SEQUENCE: 145

Asp Arg Gly Leu Gly Thr Ser Thr Tyr Tyr Tyr Gly Met Asp Val
1 5 10 15

<210> SEQ ID NO 146
<211> LENGTH: 12
<212> TYPE: PRT
<213> ORGANISM: Artificial Sequence
<220> FEATURE:
<223> OTHER INFORMATION: KB_Tr_D10

<400> SEQUENCE: 146

Ser Gln Ser Gly Val Gly Gly Thr Gly Phe Asp Pro
1 5 10

<210> SEQ ID NO 147
<211> LENGTH: 8
<212> TYPE: PRT
<213> ORGANISM: Artificial Sequence
<220> FEATURE:
<223> OTHER INFORMATION: KB_TR_A08

<400> SEQUENCE: 147

Gln Leu Gly Gly Thr Phe Asp Val
1 5

<210> SEQ ID NO 148
<211> LENGTH: 20
<212> TYPE: PRT
<213> ORGANISM: Artificial Sequence
<220> FEATURE:
<223> OTHER INFORMATION: KB_Tr_E10

<400> SEQUENCE: 148

Ala Leu Asp Gly Ala Trp Thr Asp Tyr Gly Asp Ser His Glu Ala Tyr
1 5 10 15

Gly Met Asp Val
20

<210> SEQ ID NO 149
<211> LENGTH: 10
<212> TYPE: PRT
<213> ORGANISM: Artificial Sequence
<220> FEATURE:
<223> OTHER INFORMATION: KB_Tr_B08

<400> SEQUENCE: 149

Ser Phe Asp Tyr Gly Asp Pro Phe Asp Tyr
1 5 10

<210> SEQ ID NO 150
<211> LENGTH: 12
<212> TYPE: PRT
<213> ORGANISM: Artificial Sequence
<220> FEATURE:
<223> OTHER INFORMATION: KB_Tr_C12

<400> SEQUENCE: 150

Ser Gly Ala Val Gly Ala Arg Asp Ala Phe Asp Ile
1 5 10

<210> SEQ ID NO 151
<211> LENGTH: 11
<212> TYPE: PRT
<213> ORGANISM: Artificial Sequence
<220> FEATURE:
<223> OTHER INFORMATION: KB_Tr_F01

<400> SEQUENCE: 151

Asp Arg Ile Gly Glu Gly Ile Pro Met Asp Val
1 5 10

<210> SEQ ID NO 152
<211> LENGTH: 13
<212> TYPE: PRT
<213> ORGANISM: Artificial Sequence
<220> FEATURE:
<223> OTHER INFORMATION: KB_Tr_A10

<400> SEQUENCE: 152

Gly Gly Ile Val Gly Ala Thr Asn Asp Ala Phe Asp Ile
1 5 10

<210> SEQ ID NO 153
<211> LENGTH: 10
<212> TYPE: PRT
<213> ORGANISM: Artificial Sequence
<220> FEATURE:
<223> OTHER INFORMATION: KB_Tr_B02

<400> SEQUENCE: 153

Ala Gly Ala Gly Glu Gly Gly Met Asp Val
1 5 10

<210> SEQ ID NO 154
<211> LENGTH: 9
<212> TYPE: PRT
<213> ORGANISM: Artificial Sequence
<220> FEATURE:
<223> OTHER INFORMATION: KB_Tr_H03

<400> SEQUENCE: 154

Asp Asn Pro Leu Arg Gly Met Asp Val
1 5

<210> SEQ ID NO 155
<211> LENGTH: 13
<212> TYPE: PRT
<213> ORGANISM: Artificial Sequence
<220> FEATURE:
<223> OTHER INFORMATION: KB_Tr_A07

<400> SEQUENCE: 155

Glu Ser Gly Gly Thr Asn Gly Trp Asp Ala Phe Asp Met
1 5 10

<210> SEQ ID NO 156
<211> LENGTH: 14
<212> TYPE: PRT
<213> ORGANISM: Artificial Sequence
<220> FEATURE:
<223> OTHER INFORMATION: KB_Tr_B07

<400> SEQUENCE: 156

Gly Glu Arg Pro Asp Tyr Tyr Tyr Tyr Tyr Gly Met Asp Val
1 5 10

<210> SEQ ID NO 157
<211> LENGTH: 10
<212> TYPE: PRT
<213> ORGANISM: Artificial Sequence
<220> FEATURE:
<223> OTHER INFORMATION: KB_Tr_C04

<400> SEQUENCE: 157

Glu Pro Gly Gly Asp Ser Tyr Phe Asp Tyr
1 5 10

<210> SEQ ID NO 158
<211> LENGTH: 10
<212> TYPE: PRT
<213> ORGANISM: Artificial Sequence
<220> FEATURE:
<223> OTHER INFORMATION: KB_Tr_D05

<400> SEQUENCE: 158

Met Arg Gly Tyr Asn Gly Gly Phe Asp Leu
1 5 10

<210> SEQ ID NO 159
<211> LENGTH: 13
<212> TYPE: PRT
<213> ORGANISM: Artificial Sequence
<220> FEATURE:
<223> OTHER INFORMATION: KB_Tr_D01

<400> SEQUENCE: 159

Ser Gly Gly Glu Gly Val Arg Ala Tyr Gly Met Asp Val
1 5 10

<210> SEQ ID NO 160
<211> LENGTH: 9
<212> TYPE: PRT
<213> ORGANISM: Artificial Sequence
<220> FEATURE:
<223> OTHER INFORMATION: KB_Tr_B03

<400> SEQUENCE: 160

Asp Gly Asn Val Arg Gly Met Asp Val
1 5

<210> SEQ ID NO 161
<211> LENGTH: 9
<212> TYPE: PRT
<213> ORGANISM: Artificial Sequence
<220> FEATURE:
<223> OTHER INFORMATION: KB_Tr_D03

<400> SEQUENCE: 161

Gly Gly Ser Asp Tyr Tyr Met Asp Val
1 5

<210> SEQ ID NO 162
<211> LENGTH: 11
<212> TYPE: PRT
<213> ORGANISM: Artificial Sequence
<220> FEATURE:
<223> OTHER INFORMATION: KB_Tr_H07

<400> SEQUENCE: 162

Gly Asp Ser Ser Gly Tyr Gly Ser Phe Asp Ile
1 5 10

<210> SEQ ID NO 163
<211> LENGTH: 10
<212> TYPE: PRT
<213> ORGANISM: Artificial Sequence
<220> FEATURE:
<223> OTHER INFORMATION: KB_Tr_G09

<400> SEQUENCE: 163

Ser Gly Gly Leu Gly Asp Ala Phe Asp Ile
1 5 10

<210> SEQ ID NO 164
<211> LENGTH: 12
<212> TYPE: PRT
<213> ORGANISM: Artificial Sequence
<220> FEATURE:
<223> OTHER INFORMATION: KB_Tr_D07

<400> SEQUENCE: 164

Val Ser Thr Tyr Ser Gly Ser Gln Pro Phe Asp Tyr
1 5 10

<210> SEQ ID NO 165
<211> LENGTH: 9
<212> TYPE: PRT
<213> ORGANISM: Artificial Sequence
<220> FEATURE:
<223> OTHER INFORMATION: KB_Tr_D09

<400> SEQUENCE: 165

Gly Ala Gly Glu Gly Tyr Phe Asp Tyr
1 5

<210> SEQ ID NO 166
<211> LENGTH: 42
<212> TYPE: DNA
<213> ORGANISM: Artificial Sequence
<220> FEATURE:
<223> OTHER INFORMATION: Huwen_A07 Fwd

<400> SEQUENCE: 166
tatgctgcag gggtcgagtg cctggaaatc ttcaaggcct gc 42

<210> SEQ ID NO 167
<211> LENGTH: 42
<212> TYPE: DNA
<213> ORGANISM: Artificial Sequence
<220> FEATURE:
<223> OTHER INFORMATION: Huwen_A07 Rev

<400> SEQUENCE: 167
tgggactccg gagcggctga tctggtactt gcaccaccgg gt 42

<210> SEQ ID NO 168
<211> LENGTH: 42
<212> TYPE: DNA
<213> ORGANISM: Artificial Sequence
<220> FEATURE:
<223> OTHER INFORMATION: ProTx-II A07 Rev

<400> SEQUENCE: 168
tgggactccg gagcggctcc acagcttttt cttgcaccac ag 42

<210> SEQ ID NO 169
<211> LENGTH: 41
<212> TYPE: DNA
<213> ORGANISM: Artificial Sequence
<220> FEATURE:
<223> OTHER INFORMATION: ProTx_II A07 Fwd

<400> SEQUENCE: 169
tatgctgcag gggtctactg ccagaaatgg atgtggacct g 41

<210> SEQ ID NO 170
<211> LENGTH: 42
<212> TYPE: DNA
<213> ORGANISM: Artificial Sequence
<220> FEATURE:
<223> OTHER INFORMATION: Ssm6_A07 Fwd

<400> SEQUENCE: 170
tatgctgcag gggtcgccga caacaagtgc gagaacagcc tg 42

<210> SEQ ID NO 171
<211> LENGTH: 42

<212> TYPE: DNA
<213> ORGANISM: Artificial Sequence
<220> FEATURE:
<223> OTHER INFORMATION: SSm6_A07 Rev

<400> SEQUENCE: 171
tgggactccg gagcggctgt gcagcaggtc ctggcacttc tt 42

<210> SEQ ID NO 172
<211> LENGTH: 51
<212> TYPE: DNA
<213> ORGANISM: Artificial Sequence
<220> FEATURE:
<223> OTHER INFORMATION: Ssm6_GGS_A07 Fwd

<400> SEQUENCE: 172
tatgctgcag gggtcggcgg tagcgccgac aacaagtgcg agaacagcct g 51

<210> SEQ ID NO 173
<211> LENGTH: 51
<212> TYPE: DNA
<213> ORGANISM: Artificial Sequence
<220> FEATURE:
<223> OTHER INFORMATION: Ssm6_GGs_A07 Rev

<400> SEQUENCE: 173
gactccggag cggctaccgc cgctgtgcag caggtcctgg cacttcttga a 51

<210> SEQ ID NO 174
<211> LENGTH: 42
<212> TYPE: DNA
<213> ORGANISM: Artificial Sequence
<220> FEATURE:
<223> OTHER INFORMATION: Kalio_A07_Fwd_B

<400> SEQUENCE: 174
atctatgctg caggggtcgg tgtggaaatt aacgtgaagt gt 42

<210> SEQ ID NO 175
<211> LENGTH: 42
<212> TYPE: DNA
<213> ORGANISM: Artificial Sequence
<220> FEATURE:
<223> OTHER INFORMATION: Kalio_A07 Rev

<400> SEQUENCE: 175
tgggactccg gagcggctct tcggcgtgca gtggcattta cg 42

<210> SEQ ID NO 176
<211> LENGTH: 42
<212> TYPE: DNA
<213> ORGANISM: Artificial Sequence
<220> FEATURE:
<223> OTHER INFORMATION: Moka-1 A07 Fwd

<400> SEQUENCE: 176
tatgctgcag gggtcatcaa cgtgaagtgc agcctgcccc ag 42

<210> SEQ ID NO 177
<211> LENGTH: 42
<212> TYPE: DNA
<213> ORGANISM: Artificial Sequence
<220> FEATURE:
<223> OTHER INFORMATION: Moka-1 A07 Rev

<400> SEQUENCE: 177
tgggactccg gagcggctgc tgtagcaccg gcatttcttg tt 42

<210> SEQ ID NO 178
<211> LENGTH: 43
<212> TYPE: DNA
<213> ORGANISM: Artificial Sequence
<220> FEATURE:
<223> OTHER INFORMATION: Shk_A07 Fwd

<400> SEQUENCE: 178
tatgctgcag gggtcagaag ctgcatcgac accatcccca aga 43

<210> SEQ ID NO 179
<211> LENGTH: 42
<212> TYPE: DNA
<213> ORGANISM: Artificial Sequence
<220> FEATURE:
<223> OTHER INFORMATION: Shk_A07_Rev

<400> SEQUENCE: 179
tgggactccg gagcggctac aggtgccgca ggtctttcta ca 42

<210> SEQ ID NO 180
<211> LENGTH: 42
<212> TYPE: DNA
<213> ORGANISM: Artificial Sequence
<220> FEATURE:
<223> OTHER INFORMATION: PcTx-I A07 Fwd

<400> SEQUENCE: 180
tatgctgcag gggtcgagga ctgcatcccc aagtggaagg gc 42

<210> SEQ ID NO 181
<211> LENGTH: 42
<212> TYPE: DNA
<213> ORGANISM: Artificial Sequence
<220> FEATURE:
<223> OTHER INFORMATION: PcTx-I A07 Rev

<400> SEQUENCE: 181
tgggactccg gagcggctgg tcttaggggt cttgggcacg ca 42

<210> SEQ ID NO 182
<211> LENGTH: 45
<212> TYPE: DNA
<213> ORGANISM: Artificial Sequence
<220> FEATURE:
<223> OTHER INFORMATION: Huwen A12 Rev

<400> SEQUENCE: 182
gactccggag ttggcgatct ggtacttgca ccaccgggtc tttct 45

<210> SEQ ID NO 183
<211> LENGTH: 42
<212> TYPE: DNA
<213> ORGANISM: Artificial Sequence
<220> FEATURE:
<223> OTHER INFORMATION: Huwen_A12 Fwd

<400> SEQUENCE: 183
tatgctgcag ggagggagtg cctggaaatc ttcaaggcct gc 42

<210> SEQ ID NO 184
<211> LENGTH: 42
<212> TYPE: DNA
<213> ORGANISM: Artificial Sequence

```
<220> FEATURE:
<223> OTHER INFORMATION: ProTx-II A12 fwd

<400> SEQUENCE: 184

tatgctgcag ggaggtactg ccagaaatgg atgtggacct gc                         42


<210> SEQ ID NO 185
<211> LENGTH: 42
<212> TYPE: DNA
<213> ORGANISM: Artificial Sequence
<220> FEATURE:
<223> OTHER INFORMATION: ProTx-II A12 Rev

<400> SEQUENCE: 185

gactccggag ttggcccaca gctttttctt gcaccacagc cg                         42


<210> SEQ ID NO 186
<211> LENGTH: 42
<212> TYPE: DNA
<213> ORGANISM: Artificial Sequence
<220> FEATURE:
<223> OTHER INFORMATION: Ssm6a_A12 Fwd

<400> SEQUENCE: 186

tatgctgcag ggagggccga caacaagtgc gagaacagcc tg                         42


<210> SEQ ID NO 187
<211> LENGTH: 43
<212> TYPE: DNA
<213> ORGANISM: Artificial Sequence
<220> FEATURE:
<223> OTHER INFORMATION: Ssm6a_A12 Rev

<400> SEQUENCE: 187

gactccggag ttggcgtgca gcaggtcctg gcacttcttg aag                        43


<210> SEQ ID NO 188
<211> LENGTH: 51
<212> TYPE: DNA
<213> ORGANISM: Artificial Sequence
<220> FEATURE:
<223> OTHER INFORMATION: Ssm6a_GGS_A12 Fwd

<400> SEQUENCE: 188

tatgctgcag ggaggggcgg tagcgccgac aacaagtgcg agaacagcct g              51


<210> SEQ ID NO 189
<211> LENGTH: 51
<212> TYPE: DNA
<213> ORGANISM: Artificial Sequence
<220> FEATURE:
<223> OTHER INFORMATION: Ssm6a_GGS_A12 Rev

<400> SEQUENCE: 189

actccggagt tggcaccgcc gctgtgcagc aggtcctggc acttcttgaa g              51


<210> SEQ ID NO 190
<211> LENGTH: 42
<212> TYPE: DNA
<213> ORGANISM: Artificial Sequence
<220> FEATURE:
<223> OTHER INFORMATION: Kalio_A12 Fwd B

<400> SEQUENCE: 190

atctatgctg cagggagggg tgtggaaatt aacgtgaagt gt                         42
```

<210> SEQ ID NO 191
<211> LENGTH: 41
<212> TYPE: DNA
<213> ORGANISM: Artificial Sequence
<220> FEATURE:
<223> OTHER INFORMATION: Kalio_A12 Rev

<400> SEQUENCE: 191
gagactccgg agttggcctt cggcgtgcag tggcatttac g 41

<210> SEQ ID NO 192
<211> LENGTH: 42
<212> TYPE: DNA
<213> ORGANISM: Artificial Sequence
<220> FEATURE:
<223> OTHER INFORMATION: Moka1 A12 Fwd

<400> SEQUENCE: 192
tatgctgcag ggaggatcaa cgtgaagtgc agcctgcccc ag 42

<210> SEQ ID NO 193
<211> LENGTH: 42
<212> TYPE: DNA
<213> ORGANISM: Artificial Sequence
<220> FEATURE:
<223> OTHER INFORMATION: Moka1_A12 Rev

<400> SEQUENCE: 193
gactccggag ttggcgctgt agcaccggca tttcttgttc at 42

<210> SEQ ID NO 194
<211> LENGTH: 42
<212> TYPE: DNA
<213> ORGANISM: Artificial Sequence
<220> FEATURE:
<223> OTHER INFORMATION: Shk_A12 Fwd

<400> SEQUENCE: 194
tatgctgcag ggaggagaag ctgcatcgac accatcccca ag 42

<210> SEQ ID NO 195
<211> LENGTH: 43
<212> TYPE: DNA
<213> ORGANISM: Artificial Sequence
<220> FEATURE:
<223> OTHER INFORMATION: Shk_A12 rev

<400> SEQUENCE: 195
gactccggag ttggcacagg tgccgcaggt ctttctacag aag 43

<210> SEQ ID NO 196
<211> LENGTH: 42
<212> TYPE: DNA
<213> ORGANISM: Artificial Sequence
<220> FEATURE:
<223> OTHER INFORMATION: PcTx-1 A12 Fwd

<400> SEQUENCE: 196
tatgctgcag ggagggagga ctgcatcccc aagtggaagg gc 42

<210> SEQ ID NO 197
<211> LENGTH: 42
<212> TYPE: DNA
<213> ORGANISM: Artificial Sequence
<220> FEATURE:
<223> OTHER INFORMATION: PcTX-1 A12 Rev

<400> SEQUENCE: 197
gactccggag ttggcggtct taggggtctt gggcacgcac ac 42

<210> SEQ ID NO 198
<211> LENGTH: 309
<212> TYPE: DNA
<213> ORGANISM: Artificial Sequence
<220> FEATURE:
<223> OTHER INFORMATION: Ad#LOX1#A

<400> SEQUENCE: 198
gctacaggcg tgcgggctgt gcccggcaat gagaacagcc tggaaatcga ggaactggcc 60
agattcgccg tggacgagca caacaagaaa gagaacgccc tgctggaatt cgtgcgggtc 120
gtgaaggcca aagagcagtg gagcgaggcc gacaacgact ggcacaccat gtactacctg 180
accctggaag ccaaggacgg cggcaagaag aagctgtacg aggccaaagt gtgggtcaag 240
ctggacctgg aaacctggca gcacttcaac ttcaaagagc tccaggaatt caagcccgtg 300
ggcgacgct 309

<210> SEQ ID NO 199
<211> LENGTH: 315
<212> TYPE: DNA
<213> ORGANISM: Artificial Sequence
<220> FEATURE:
<223> OTHER INFORMATION: Ad#LOX1#B

<400> SEQUENCE: 199
gctacaggcg tgcgggctgt gcccggcaat gagaacagcc tggaaatcga ggaactggcc 60
agattcgccg tggacgagca caacaagaaa gagaacgccc tgctggaatt cgtgcgggtc 120
gtgaaggcca aagagcagga acagcccatc ggcgagcacc ccgtgaacga caccatgtac 180
tacctgaccc tggaagccaa ggacggcggc aagaagaagc tgtacgaggc caaagtgtgg 240
gtcaagcggt ggctgcggtt caccgagatc tacaacttca aagagctcca ggaattcaag 300
cccgtgggcg acgct 315

<210> SEQ ID NO 200
<211> LENGTH: 45
<212> TYPE: DNA
<213> ORGANISM: Artificial Sequence
<220> FEATURE:
<223> OTHER INFORMATION: Ad_SUMO_10 A07 Fwd

<400> SEQUENCE: 200
atctatgctg caggggtcgc tacaggcgtg cgggctgtgc ccggc 45

<210> SEQ ID NO 201
<211> LENGTH: 45
<212> TYPE: DNA
<213> ORGANISM: Artificial Sequence
<220> FEATURE:
<223> OTHER INFORMATION: Ad_SUMO_10_A07 Rev

<400> SEQUENCE: 201
gggactccgg agcggcttgc gtcgcccacg ggcttgaatt cctgg 45

<210> SEQ ID NO 202
<211> LENGTH: 45
<212> TYPE: DNA
<213> ORGANISM: Artificial Sequence
<220> FEATURE:

<223> OTHER INFORMATION: Ad_SUMO_10 A12 Fwd

<400> SEQUENCE: 202
atctatgctg cagggagggc tacaggcgtg cgggctgtgc ccggc 45

<210> SEQ ID NO 203
<211> LENGTH: 45
<212> TYPE: DNA
<213> ORGANISM: Artificial Sequence
<220> FEATURE:
<223> OTHER INFORMATION: Ad_SUMO10_A12 Rev

<400> SEQUENCE: 203
gagactccgg agttggcggc gtcgcccacg ggcttgaatt cctgg 45

<210> SEQ ID NO 204
<211> LENGTH: 10
<212> TYPE: DNA
<213> ORGANISM: Artificial Sequence
<220> FEATURE:
<223> OTHER INFORMATION: KB_A07 (Gly4Ser)2

<400> SEQUENCE: 204 ggggsggggs 10

<210> SEQ ID NO 205
<211> LENGTH: 432
<212> TYPE: DNA
<213> ORGANISM: Artificial Sequence
<220> FEATURE:
<223> OTHER INFORMATION: KB_A07

<400> SEQUENCE: 205
ggtggcgcta gcgacataca aatgacccaa tcacctagct ctcttagtgc ctctgttggg 60
gatcgggtca ccatcacttg tagagcgagc cagagtatct catcatactt gaactggtac 120
cagcagaagc cagggaaggc ccccaagctg ttgatttacg cggctggggt ctgcccgcgc 180
atcttgatga ggtgcaaaca agactcagac tgcctggctg gatgtgtttg cggaccaaat 240
ggtttctgcg gaagccgctc aggcgtgcca tcaagattta gtggttcagg aagtggtacg 300
gacttcacgc tgacgatttc atctcttcaa cccgaagatt tcgccacgta ctactgtcaa 360
cagggtgctt ctccacctta tactttcggt cagggtacca aggttgagat taagcgcacc 420
gcggccgcaa tc 432

<210> SEQ ID NO 206
<211> LENGTH: 480
<212> TYPE: DNA
<213> ORGANISM: Artificial Sequence
<220> FEATURE:
<223> OTHER INFORMATION: KB_A07 Gly4Ser

<400> SEQUENCE: 206
ggtggcgcta gcgacataca aatgacccaa agtccgagct ccttgagtgc ctccgtaggt 60
gatagggtca ctattacttg cagagcgtct cagtccatct cctcctattt gaattggtac 120
caacagaaac cggggaaagc ccctaagctc ctgatctacg ccgctggggg aggcgggagt 180 gggggggcg ggtcctgtcc gcgcatcctt atgcggtgta aacaggacag tgattgcctt 240
gctggttgtg tctgcggccc caatggtttt tgcgggggtg gggggggcag cggtgggggc 300
ggttcctccg ggtgccatc tcgctttagc ggttcaggta gtggaacgga ctttacactg 360
acaatatcat ctttgcaacc agaggatttc gccacgtact actgtcagca aggtgcctct 420
ccaccttaca cgtttggaca aggcaccaaa gtagagatta agcggaccgc ggccgcaatc 480

<210> SEQ ID NO 207
<211> LENGTH: 450
<212> TYPE: DNA
<213> ORGANISM: Artificial Sequence
<220> FEATURE:
<223> OTHER INFORMATION: KB_A07 (Gly4Ser)2

<400> SEQUENCE: 207
ggtggcgcta gcgacataca aatgacccaa tcacctagct ctcttagtgc ctctgttggg 60
gatcgggtca ccatcacttg tagagcgagc cagagtatct catcatactt gaactggtac 120
cagcagaagc cagggaaggc ccccaagctg ttgatttacg cggctggcgg aggagggtcc 180
tgcccgcgca tcttgatgag gtgcaaacaa gactcagact gcctggctgg atgtgtttgc 240
ggaccaaatg gtttctgcgg aggaggcgga ggttcctcag gcgtgccatc aagatttagt 300
ggttcaggaa gtggtacgga cttcacgctg acgatttcat ctcttcaacc cgaagatttc 360
gccacgtact actgtcaaca gggtgcttct ccaccttata ctttcggtca gggtaccaag 420
gttgagatta agcgcaccgc ggccgcaatc 450

<210> SEQ ID NO 208
<211> LENGTH: 444
<212> TYPE: DNA
<213> ORGANISM: Artificial Sequence
<220> FEATURE:
<223> OTHER INFORMATION: KB_A12

<400> SEQUENCE: 208
ggtggcgcta gccagagtgt cttgacgcag ccaccttctg tcagcgaggc cccacgccag 60
agggttacca taacatgttc cggtccagc tctaacatag ggaataacgc ggtaaactgg 120
tatcagcaat tgcccggcaa agcaccgaaa ctcttgatct atgcagcggg gaggtgtcct 180
cgaatactga tgcgatgtaa acaggactcc gattgtcttg cgggatgtgt gtgtggtccg 240
aatgggtttt gcggcgccaa cagcggcgta agtgatcgat tctcagcggc gaaatccggc 300
acatccgcct cactggcgat caacggattg cgaagtgagg acgaagctga ctattattgc 360
gcggcctggg atgattcctt gaacgggtat gtatttggca caggaacgaa gctgactgtg 420
ctgggacaac ccgcggccgc aatc 444

<210> SEQ ID NO 209
<211> LENGTH: 492
<212> TYPE: DNA
<213> ORGANISM: Artificial Sequence
<220> FEATURE:
<223> OTHER INFORMATION: KB_A12 Gly4Ser

<400> SEQUENCE: 209
ggtggcgcta gccagagcgt actgacgcag ccgccttctg ttagcgaggc tccccgacag 60
cgagtaacga taacgtgcag cggttcaagc agtaatatcg ggaataatgc agtaaattgg 120
tatcagcaac tgcctggaaa agcgcccaag ctgctcatat atgcggccgg gggcgggggt 180
agcggcggag ggggaagctg cccaagaatc ttgatgcggt gtaaacaaga ttcagactgt 240
ttggccggtt gcgtatgcgg tccaaatggg ttctgcggag gtggtggtgg gtccggtgga 300
ggaggtagta gcggggttag tgatcgattc tccgcggcga agtccggcac cagtgcaagt 360
ctcgctataa acgggctcag gtcagaagat gaggcagatt attactgtgc cgcatgggac 420
gacagtttga acggctatgt cttcggaacg gggactaaac ttaccgtact tggacagccc 480
gcggccgcaa tc 492

<210> SEQ ID NO 210
<211> LENGTH: 462
<212> TYPE: DNA
<213> ORGANISM: Artificial Sequence
<220> FEATURE:
<223> OTHER INFORMATION: KB_A12 (Gly4Ser)2

<400> SEQUENCE: 210
ggtggcgcta gccagagtgt cttgacgcag ccaccttctg tcagcgaggc cccacgccag 60
agggttacca taacatgttc cgggtccagc tctaacatag ggaataacgc ggtaaactgg 120
tatcagcaat tgcccggcaa agcaccgaaa ctcttgatct atgcagcggg agggggaggc 180
tcttgtcctc gaatactgat gcgatgtaaa caggactccg attgtcttgc gggatgtgtg 240
tgtggtccga atgggttttg cggcggtggg ggcggctcta gcggcgtaag tgatcgattc 300
tcagcggcga aatccggcac atccgcctca ctggcgatca acggattgcg aagtgaggac 360
gaagctgact attattgcgc ggcctgggat gattccttga acgggtatgt atttggcaca 420
ggaacgaagc tgactgtgct gggacaaccc gcggccgcaa tc 462

<210> SEQ ID NO 211
<211> LENGTH: 10
<212> TYPE: PRT
<213> ORGANISM: Artificial Sequence
<220> FEATURE:
<223> OTHER INFORMATION: KB_A12_cMET_H01

<400> SEQUENCE: 211

Cys His Arg Met Ser Gly Thr Gly Arg Cys
1 5 10

<210> SEQ ID NO 212
<211> LENGTH: 11
<212> TYPE: PRT
<213> ORGANISM: Artificial Sequence
<220> FEATURE:
<223> OTHER INFORMATION: KB_A12_cMET_F05

<400> SEQUENCE: 212

Cys Lys Arg Leu Met Ser Gly Ala Gly Arg Cys
1 5 10

<210> SEQ ID NO 213
<211> LENGTH: 10
<212> TYPE: PRT
<213> ORGANISM: Artificial Sequence
<220> FEATURE:
<223> OTHER INFORMATION: KB_A12_cMET_G01

<400> SEQUENCE: 213

Cys Gln Arg Gln Ser Gly Thr Gly Arg Cys
1 5 10

<210> SEQ ID NO 214
<211> LENGTH: 10
<212> TYPE: PRT
<213> ORGANISM: Artificial Sequence
<220> FEATURE:
<223> OTHER INFORMATION: KB_A12_cMET_G07

<400> SEQUENCE: 214

Cys Arg Ala Ser Ser Gly Thr Gly Arg Cys
1 5 10

<210> SEQ ID NO 215
<211> LENGTH: 11
<212> TYPE: PRT
<213> ORGANISM: Artificial Sequence
<220> FEATURE:
<223> OTHER INFORMATION: KB_A12_cMET_E07

<400> SEQUENCE: 215

Cys Pro Lys Arg His Thr Gly Thr Gly Arg Cys
1 5 10

<210> SEQ ID NO 216
<211> LENGTH: 10
<212> TYPE: PRT
<213> ORGANISM: Artificial Sequence
<220> FEATURE:
<223> OTHER INFORMATION: KB_A12_cMET_E04

<400> SEQUENCE: 216

Cys Gly His Leu Ser Gly Thr Gly Arg Cys
1 5 10

<210> SEQ ID NO 217
<211> LENGTH: 10
<212> TYPE: PRT
<213> ORGANISM: Artificial Sequence
<220> FEATURE:
<223> OTHER INFORMATION: KB_A12_cMET_F02

<400> SEQUENCE: 217

Cys Gly Arg Ala Ser Gly Thr Gly Arg Cys
1 5 10

<210> SEQ ID NO 218
<211> LENGTH: 10
<212> TYPE: PRT
<213> ORGANISM: Artificial Sequence
<220> FEATURE:
<223> OTHER INFORMATION: KB_A12_cMET_H05

<400> SEQUENCE: 218

Cys Asn Arg Ala Ser Gly Ala Gly Arg Cys
1 5 10

<210> SEQ ID NO 219
<211> LENGTH: 10
<212> TYPE: PRT
<213> ORGANISM: Artificial Sequence
<220> FEATURE:
<223> OTHER INFORMATION: KB_A12_cMET_H03

<400> SEQUENCE: 219

Cys Arg Gly Met Thr Gly Val Gly Arg Cys
1 5 10

<210> SEQ ID NO 220
<211> LENGTH: 11
<212> TYPE: PRT
<213> ORGANISM: Artificial Sequence
<220> FEATURE:
<223> OTHER INFORMATION: KB_A12_cMET_H08

<400> SEQUENCE: 220

Cys Gln Thr Gly Arg Ser Gly Thr Gly Arg Cys 1               5                   10

<210> SEQ ID NO 221
<211> LENGTH: 10
<212> TYPE: PRT
<213> ORGANISM: Artificial Sequence
<220> FEATURE:
<223> OTHER INFORMATION: KB_A12_cMET_E05

<400> SEQUENCE: 221

Cys Asp Arg Lys Ala Gly Thr Gly Arg Cys
1               5                   10

<210> SEQ ID NO 222
<211> LENGTH: 10
<212> TYPE: PRT
<213> ORGANISM: Artificial Sequence
<220> FEATURE:
<223> OTHER INFORMATION: KB_A12_cMET_E11

<400> SEQUENCE: 222

Cys Ala Lys Lys Ser Gly Thr Gly Arg Cys
1               5                   10

<210> SEQ ID NO 223
<211> LENGTH: 10
<212> TYPE: PRT
<213> ORGANISM: Artificial Sequence
<220> FEATURE:
<223> OTHER INFORMATION: KB_A12_cMET_E12

<400> SEQUENCE: 223

Cys Ala Lys Arg Ser Gly Thr Gly Arg Cys
1               5                   10

<210> SEQ ID NO 224
<211> LENGTH: 10
<212> TYPE: PRT
<213> ORGANISM: Artificial Sequence
<220> FEATURE:
<223> OTHER INFORMATION: KB_A12_cMET_H04

<400> SEQUENCE: 224

Cys Pro Gln Met Thr Gly Thr Gly Arg Cys
1               5                   10

<210> SEQ ID NO 225
<211> LENGTH: 10
<212> TYPE: PRT
<213> ORGANISM: Artificial Sequence
<220> FEATURE:
<223> OTHER INFORMATION: KB_A12_cMET_E01

<400> SEQUENCE: 225

Cys Asn Leu Thr Ser Gly Thr Gly Arg Cys
1               5                   10

<210> SEQ ID NO 226
<211> LENGTH: 10
<212> TYPE: PRT
<213> ORGANISM: Artificial Sequence
<220> FEATURE:
<223> OTHER INFORMATION: KB_A12_cMET_G10

<400> SEQUENCE: 226

Cys Glu Lys His Ser Gly Thr Gly Arg Cys
1               5                   10

<210> SEQ ID NO 227
<211> LENGTH: 10
<212> TYPE: PRT
<213> ORGANISM: Artificial Sequence
<220> FEATURE:
<223> OTHER INFORMATION: KB_A12_cMET_H02

<400> SEQUENCE: 227

Cys Ala Lys Arg Thr Gly Thr Gly Arg Cys
1 5 10

<210> SEQ ID NO 228
<211> LENGTH: 10
<212> TYPE: PRT
<213> ORGANISM: Artificial Sequence
<220> FEATURE:
<223> OTHER INFORMATION: KB_A12_cMET_F06

<400> SEQUENCE: 228

Cys Pro His Gln Thr Gly Thr Gly Arg Cys
1 5 10

<210> SEQ ID NO 229
<211> LENGTH: 11
<212> TYPE: PRT
<213> ORGANISM: Artificial Sequence
<220> FEATURE:
<223> OTHER INFORMATION: KB_A12_cMET_F10

<400> SEQUENCE: 229

Cys Arg Ser Leu Met Ser Gly Thr Gly Arg Cys
1 5 10

<210> SEQ ID NO 230
<211> LENGTH: 10
<212> TYPE: PRT
<213> ORGANISM: Artificial Sequence
<220> FEATURE:
<223> OTHER INFORMATION: KB_A12_cMET_F12

<400> SEQUENCE: 230

Cys Lys Ala Gln Ser Gly Ser Gly Arg Cys
1 5 10

<210> SEQ ID NO 231
<211> LENGTH: 10
<212> TYPE: PRT
<213> ORGANISM: Artificial Sequence
<220> FEATURE:
<223> OTHER INFORMATION: KB_A12_cMET_G06

<400> SEQUENCE: 231

Cys Asn Lys Ser Gly Gly Thr Gly Arg Cys
1 5 10

<210> SEQ ID NO 232
<211> LENGTH: 10
<212> TYPE: PRT
<213> ORGANISM: Artificial Sequence
<220> FEATURE:
<223> OTHER INFORMATION: KB_A12_cMET_E02

<400> SEQUENCE: 232

Cys Arg Lys Lys Ser Gly Ala Asn Arg Cys
1 5 10

<210> SEQ ID NO 233
<211> LENGTH: 10
<212> TYPE: PRT
<213> ORGANISM: Artificial Sequence
<220> FEATURE:
<223> OTHER INFORMATION: KB_A12_cMET_G08

<400> SEQUENCE: 233

Cys Ala Arg Leu Ser Gly Ser Gly Arg Cys
1 5 10

<210> SEQ ID NO 234
<211> LENGTH: 11
<212> TYPE: PRT
<213> ORGANISM: Artificial Sequence
<220> FEATURE:
<223> OTHER INFORMATION: KB_A12_B-gal_F02

<400> SEQUENCE: 234

Cys Arg Thr Thr Ser Thr Ile Arg Arg Arg Cys
1 5 10

<210> SEQ ID NO 235
<211> LENGTH: 11
<212> TYPE: PRT
<213> ORGANISM: Artificial Sequence
<220> FEATURE:
<223> OTHER INFORMATION: KB_A12_B-gal_G05

<400> SEQUENCE: 235

Cys Leu Asp Thr Val Asn Leu Arg Arg Arg Cys
1 5 10

<210> SEQ ID NO 236
<211> LENGTH: 11
<212> TYPE: PRT
<213> ORGANISM: Artificial Sequence
<220> FEATURE:
<223> OTHER INFORMATION: KB_A12_B-gal_H03

<400> SEQUENCE: 236

Cys Asn Gln Thr Met Ser Ile Arg Arg Pro Cys
1 5 10

<210> SEQ ID NO 237
<211> LENGTH: 11
<212> TYPE: PRT
<213> ORGANISM: Artificial Sequence
<220> FEATURE:
<223> OTHER INFORMATION: KB_A12_B-gal_E04

<400> SEQUENCE: 237

Cys Leu Ala Thr Thr Ser Ile Arg Arg Pro Cys
1 5 10

<210> SEQ ID NO 238
<211> LENGTH: 11
<212> TYPE: PRT
<213> ORGANISM: Artificial Sequence
<220> FEATURE:
<223> OTHER INFORMATION: KB_A12_B-gal_E05

<400> SEQUENCE: 238

Cys Arg Glu Thr Ser Ser Leu Arg Arg Pro Cys
1 5 10

<210> SEQ ID NO 239
<211> LENGTH: 11
<212> TYPE: PRT
<213> ORGANISM: Artificial Sequence
<220> FEATURE:
<223> OTHER INFORMATION: KB_A12_B-gal_F09

<400> SEQUENCE: 239

Cys Ile Ala Thr Ser His Ile Arg Arg His Cys
1               5                   10

<210> SEQ ID NO 240
<211> LENGTH: 11
<212> TYPE: PRT
<213> ORGANISM: Artificial Sequence
<220> FEATURE:
<223> OTHER INFORMATION: KB_A12_B-gal_F11

<400> SEQUENCE: 240

Cys His Glu Thr Ala Gln Ile Arg Arg Arg Cys
1               5                   10

<210> SEQ ID NO 241
<211> LENGTH: 11
<212> TYPE: PRT
<213> ORGANISM: Artificial Sequence
<220> FEATURE:
<223> OTHER INFORMATION: KB_A12_B-gal_H07

<400> SEQUENCE: 241

Cys Thr Gln Thr Ala Leu Ile Arg Arg Arg Cys
1               5                   10

<210> SEQ ID NO 242
<211> LENGTH: 11
<212> TYPE: PRT
<213> ORGANISM: Artificial Sequence
<220> FEATURE:
<223> OTHER INFORMATION: KB_A12_B-gal_H02

<400> SEQUENCE: 242

Cys Glu Gln Thr Ser Val Ile Arg Arg His Cys
1               5                   10

<210> SEQ ID NO 243
<211> LENGTH: 11
<212> TYPE: PRT
<213> ORGANISM: Artificial Sequence
<220> FEATURE:
<223> OTHER INFORMATION: KB_A12_B-gal_F03

<400> SEQUENCE: 243

Cys Leu Ala Thr Thr Ser Ile Arg Arg His Cys
1               5                   10

<210> SEQ ID NO 244
<211> LENGTH: 11
<212> TYPE: PRT
<213> ORGANISM: Artificial Sequence
<220> FEATURE:
<223> OTHER INFORMATION: KB_A12_B-gal_F07

<400> SEQUENCE: 244

Cys Arg Thr Thr Ala Asn Val Arg Arg His Cys
1               5                   10

<210> SEQ ID NO 245

<211> LENGTH: 67
<212> TYPE: DNA
<213> ORGANISM: Artificial Sequence
<220> FEATURE:
<223> OTHER INFORMATION: A12_ L1 (6)
<220> FEATURE:
<221> NAME/KEY: misc_feature
<222> LOCATION: (26)..(26)
<223> OTHER INFORMATION: S=C or G
<220> FEATURE:
<221> NAME/KEY: misc_feature
<222> LOCATION: (27)..(27)
<223> OTHER INFORMATION: N=A, C, G or T
<220> FEATURE:
<221> NAME/KEY: misc_feature
<222> LOCATION: (28)..(28)
<223> OTHER INFORMATION: B=T, G or C
<220> FEATURE:
<221> NAME/KEY: misc_feature
<222> LOCATION: (29)..(29)
<223> OTHER INFORMATION: S=C or G
<220> FEATURE:
<221> NAME/KEY: misc_feature
<222> LOCATION: (30)..(30)
<223> OTHER INFORMATION: N=A, C, G or T
<220> FEATURE:
<221> NAME/KEY: misc_feature
<222> LOCATION: (31)..(31)
<223> OTHER INFORMATION: B=T, G or C
<220> FEATURE:
<221> NAME/KEY: misc_feature
<222> LOCATION: (32)..(32)
<223> OTHER INFORMATION: S=C or G
<220> FEATURE:
<221> NAME/KEY: misc_feature
<222> LOCATION: (33)..(33)
<223> OTHER INFORMATION: N=A, C, G or T
<220> FEATURE:
<221> NAME/KEY: misc_feature
<222> LOCATION: (34)..(34)
<223> OTHER INFORMATION: B=T, G or C
<220> FEATURE:
<221> NAME/KEY: misc_feature
<222> LOCATION: (35)..(35)
<223> OTHER INFORMATION: S=C or G
<220> FEATURE:
<221> NAME/KEY: misc_feature
<222> LOCATION: (36)..(26)
<223> OTHER INFORMATION: N=A, C, G or T
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (37)..(37)
<223> OTHER INFORMATION: B=T, G or C
<220> FEATURE:
<221> NAME/KEY: misc_feature
<222> LOCATION: (38)..(38)
<223> OTHER INFORMATION: S=C or G
<220> FEATURE:
<221> NAME/KEY: misc_feature
<222> LOCATION: (39)..(39)
<223> OTHER INFORMATION: N=A, C, G or T
<220> FEATURE:
<221> NAME/KEY: misc_feature
<222> LOCATION: (40)..(40)
<223> OTHER INFORMATION: B=T, G or C
<220> FEATURE:
<221> NAME/KEY: misc_feature
<222> LOCATION: (41)..(41)
<223> OTHER INFORMATION: S=C or G
<220> FEATURE:
<221> NAME/KEY: misc_feature
<222> LOCATION: (42)..(42)
<223> OTHER INFORMATION: N=A, C, G or T
<220> FEATURE:
<221> NAME/KEY: misc_feature
<222> LOCATION: (43)..(43)
<223> OTHER INFORMATION: B=T, G or C

<400> SEQUENCE: 245
acaggcagtc tgagtcctgt ttgcasnbsn bsnbsnbsnb snbgcacctc cctgcagcat 60
agatcag 67

<210> SEQ ID NO 246
<211> LENGTH: 72
<212> TYPE: DNA
<213> ORGANISM: Artificial Sequence
<220> FEATURE:
<223> OTHER INFORMATION: A12_L1 (8)
<220> FEATURE:
<221> NAME/KEY: misc_feature
<222> LOCATION: (25)..(25)
<223> OTHER INFORMATION: S= C or G
<220> FEATURE:
<221> NAME/KEY: misc_feature
<222> LOCATION: (26)..(26)
<223> OTHER INFORMATION: N=A, C, G or T
<220> FEATURE:
<221> NAME/KEY: misc_feature
<222> LOCATION: (27)..(27)
<223> OTHER INFORMATION: B=T, G or C
<220> FEATURE:
<221> NAME/KEY: misc_feature
<222> LOCATION: (28)..(28)
<223> OTHER INFORMATION: S= C or G
<220> FEATURE:
<221> NAME/KEY: misc_feature
<222> LOCATION: (29)..(29)
<223> OTHER INFORMATION: N=A, C, G or T
<220> FEATURE:
<221> NAME/KEY: misc_feature
<222> LOCATION: (30)..(30)
<223> OTHER INFORMATION: B=T, G or C
<220> FEATURE:
<221> NAME/KEY: misc_feature
<222> LOCATION: (31)..(31)
<223> OTHER INFORMATION: S= C or G
<220> FEATURE:
<221> NAME/KEY: misc_feature
<222> LOCATION: (32)..(32)
<223> OTHER INFORMATION: N=A, C, G or T
<220> FEATURE:
<221> NAME/KEY: misc_feature
<222> LOCATION: (33)..(33)
<223> OTHER INFORMATION: B=T, G or C
<220> FEATURE:
<221> NAME/KEY: misc_feature
<222> LOCATION: (34)..(34)
<223> OTHER INFORMATION: S= C or G
<220> FEATURE:
<221> NAME/KEY: misc_feature
<222> LOCATION: (35)..(35)
<223> OTHER INFORMATION: N=A, C, G or T
<220> FEATURE:
<221> NAME/KEY: misc_feature
<222> LOCATION: (36)..(36)
<223> OTHER INFORMATION: B=T, G or C
<220> FEATURE:
<221> NAME/KEY: misc_feature
<222> LOCATION: (37)..(37)
<223> OTHER INFORMATION: S= C or G
<220> FEATURE:
<221> NAME/KEY: misc_feature
<222> LOCATION: (38)..(38)
<223> OTHER INFORMATION: N=A, C, G or T
<220> FEATURE:
<221> NAME/KEY: misc_feature
<222> LOCATION: (39)..(39)
<223> OTHER INFORMATION: B=T, G or C
<220> FEATURE:
<221> NAME/KEY: misc_feature
<222> LOCATION: (40)..(40)

<223> OTHER INFORMATION: S= C or G
<220> FEATURE:
<221> NAME/KEY: misc_feature
<222> LOCATION: (41)..(41)
<223> OTHER INFORMATION: N=A, C, G or T
<220> FEATURE:
<221> NAME/KEY: misc_feature
<222> LOCATION: (42)..(42)
<223> OTHER INFORMATION: B=T, G or C
<220> FEATURE:
<221> NAME/KEY: misc_feature
<222> LOCATION: (43)..(43)
<223> OTHER INFORMATION: S= C or G
<220> FEATURE:
<221> NAME/KEY: misc_feature
<222> LOCATION: (44)..(44)
<223> OTHER INFORMATION: N=A, C, G or T
<220> FEATURE:
<221> NAME/KEY: misc_feature
<222> LOCATION: (45)..(45)
<223> OTHER INFORMATION: B=T, G or C
<220> FEATURE:
<221> NAME/KEY: misc_feature
<222> LOCATION: (46)..(46)
<223> OTHER INFORMATION: S= C or G
<220> FEATURE:
<221> NAME/KEY: misc_feature
<222> LOCATION: (47)..(47)
<223> OTHER INFORMATION: N=A, C, G or T
<220> FEATURE:
<221> NAME/KEY: misc_feature
<222> LOCATION: (48)..(48)
<223> OTHER INFORMATION: B=T, G or C

<400> SEQUENCE: 246
caggcagtct gagtcctgtt tgcasnbsnb snbsnbsnbs nbsnbsnbgc acctccctgc 60
agcatagatc ag 72

<210> SEQ ID NO 247
<211> LENGTH: 75
<212> TYPE: DNA
<213> ORGANISM: Artificial Sequence
<220> FEATURE:
<223> OTHER INFORMATION: A12_L1 (9)
<220> FEATURE:
<221> NAME/KEY: misc_feature
<222> LOCATION: (25)..(25)
<223> OTHER INFORMATION: S=C or G
<220> FEATURE:
<221> NAME/KEY: misc_feature
<222> LOCATION: (26)..(26)
<223> OTHER INFORMATION: N=A, C, G or T
<220> FEATURE:
<221> NAME/KEY: misc_feature
<222> LOCATION: (27)..(27)
<223> OTHER INFORMATION: B=T, G or C
<220> FEATURE:
<221> NAME/KEY: misc_feature
<222> LOCATION: (28)..(28)
<223> OTHER INFORMATION: S=C or G
<220> FEATURE:
<221> NAME/KEY: misc_feature
<222> LOCATION: (29)..(29)
<223> OTHER INFORMATION: N=A, C, G or T
<220> FEATURE:
<221> NAME/KEY: misc_feature
<222> LOCATION: (30)..(30)
<223> OTHER INFORMATION: B=T, G or C
<220> FEATURE:
<221> NAME/KEY: misc_feature
<222> LOCATION: (31)..(31)
<223> OTHER INFORMATION: S=C or G
<220> FEATURE:
<221> NAME/KEY: misc_feature
<222> LOCATION: (32)..(32)
<223> OTHER INFORMATION: N=A, C, G or T
<220> FEATURE:
<221> NAME/KEY: misc_feature
<222> LOCATION: (33)..(33)
<223> OTHER INFORMATION: B=T, G or C
<220> FEATURE:
<221> NAME/KEY: misc_feature
<222> LOCATION: (34)..(34)
<223> OTHER INFORMATION: S=C or G
<220> FEATURE:
<221> NAME/KEY: misc_feature
<222> LOCATION: (35)..(35)
<223> OTHER INFORMATION: N=A, C, G or T
<220> FEATURE:
<221> NAME/KEY: misc_feature
<222> LOCATION: (36)..(36)
<223> OTHER INFORMATION: B=T, G or C
<220> FEATURE:
<221> NAME/KEY: misc_feature
<222> LOCATION: (37)..(37)
<223> OTHER INFORMATION: S=C or G
<220> FEATURE:
<221> NAME/KEY: misc_feature
<222> LOCATION: (38)..(38)
<223> OTHER INFORMATION: N=A, C, G or T
<220> FEATURE:
<221> NAME/KEY: misc_feature
<222> LOCATION: (39)..(39)
<223> OTHER INFORMATION: B=T, G or C
<220> FEATURE:
<221> NAME/KEY: misc_feature
<222> LOCATION: (40)..(40)
<223> OTHER INFORMATION: S=C or G
<220> FEATURE:
<221> NAME/KEY: misc_feature
<222> LOCATION: (41)..(41)
<223> OTHER INFORMATION: N=A, C, G or T
<220> FEATURE:
<221> NAME/KEY: misc_feature
<222> LOCATION: (42)..(42)
<223> OTHER INFORMATION: B=T, G or C
<220> FEATURE:
<221> NAME/KEY: misc_feature
<222> LOCATION: (43)..(43)
<223> OTHER INFORMATION: S=C or G
<220> FEATURE:
<221> NAME/KEY: misc_feature
<222> LOCATION: (44)..(44)
<223> OTHER INFORMATION: N=A, C, G or T
<220> FEATURE:
<221> NAME/KEY: misc_feature
<222> LOCATION: (45)..(45)
<223> OTHER INFORMATION: B=T, G or C
<220> FEATURE:
<221> NAME/KEY: misc_feature
<222> LOCATION: (46)..(46)
<223> OTHER INFORMATION: S=C or G
<220> FEATURE:
<221> NAME/KEY: misc_feature
<222> LOCATION: (47)..(47)
<223> OTHER INFORMATION: N=A, C, G or T
<220> FEATURE:
<221> NAME/KEY: misc_feature
<222> LOCATION: (48)..(48)
<223> OTHER INFORMATION: B=T, G or C
<220> FEATURE:
<221> NAME/KEY: misc_feature
<222> LOCATION: (49)..(49)
<223> OTHER INFORMATION: S=C or G
<220> FEATURE:
<221> NAME/KEY: misc_feature
<222> LOCATION: (50)..(50)
<223> OTHER INFORMATION: N=A, C, G or T
<220> FEATURE:
<221> NAME/KEY: misc_feature
<222> LOCATION: (51)..(51)
<223> OTHER INFORMATION: B=T, G or C

<400> SEQUENCE: 247
caggcagtct gagtcctgtt tgcasnbsnb snbsnbsnbs nbsnbsnbsn bgcacctccc 60
tgcagcatag atcag 75

<210> SEQ ID NO 248
<211> LENGTH: 78
<212> TYPE: DNA
<213> ORGANISM: Artificial Sequence
<220> FEATURE:
<223> OTHER INFORMATION: A12_L1 (10)
<220> FEATURE:
<221> NAME/KEY: misc_feature
<222> LOCATION: (25)..(25)
<223> OTHER INFORMATION: S=C or G
<220> FEATURE:
<221> NAME/KEY: misc_feature
<222> LOCATION: (26)..(26)
<223> OTHER INFORMATION: N=A, C, G or T
<220> FEATURE:
<221> NAME/KEY: misc_feature
<222> LOCATION: (27)..(27)
<223> OTHER INFORMATION: B=T, G or C
<220> FEATURE:
<221> NAME/KEY: misc_feature
<222> LOCATION: (28)..(28)
<223> OTHER INFORMATION: S=C or G
<220> FEATURE:
<221> NAME/KEY: misc_feature
<222> LOCATION: (29)..(29)
<223> OTHER INFORMATION: N=A, C, G or T
<220> FEATURE:
<221> NAME/KEY: misc_feature
<222> LOCATION: (30)..(30)
<223> OTHER INFORMATION: B=T, G or C
<220> FEATURE:
<221> NAME/KEY: misc_feature
<222> LOCATION: (31)..(31)
<223> OTHER INFORMATION: S=C or G
<220> FEATURE:
<221> NAME/KEY: misc_feature
<222> LOCATION: (32)..(32)
<223> OTHER INFORMATION: N=A, C, G or T
<220> FEATURE:
<221> NAME/KEY: misc_feature
<222> LOCATION: (33)..(33)
<223> OTHER INFORMATION: B=T, G or C
<220> FEATURE:
<221> NAME/KEY: misc_feature
<222> LOCATION: (34)..(34)
<223> OTHER INFORMATION: S=C or G
<220> FEATURE:
<221> NAME/KEY: misc_feature
<222> LOCATION: (35)..(35)
<223> OTHER INFORMATION: N=A, C, G or T
<220> FEATURE:
<221> NAME/KEY: misc_feature
<222> LOCATION: (36)..(36)
<223> OTHER INFORMATION: B=T, G or C
<220> FEATURE:
<221> NAME/KEY: misc_feature
<222> LOCATION: (37)..(37)
<223> OTHER INFORMATION: S=C or G
<220> FEATURE:
<221> NAME/KEY: misc_feature
<222> LOCATION: (38)..(38)
<223> OTHER INFORMATION: N=A, C, G or T
<220> FEATURE:
<221> NAME/KEY: misc_feature
<222> LOCATION: (39)..(39)
<223> OTHER INFORMATION: B=T, G or C
<220> FEATURE:
<221> NAME/KEY: misc_feature
<222> LOCATION: (40)..(40)
<223> OTHER INFORMATION: S=C or G
<220> FEATURE:
<221> NAME/KEY: misc_feature
<222> LOCATION: (41)..(41)
<223> OTHER INFORMATION: N=A, C, G or T
<220> FEATURE:
<221> NAME/KEY: misc_feature
<222> LOCATION: (42)..(42)
<223> OTHER INFORMATION: B=T, G or C
<220> FEATURE:
<221> NAME/KEY: misc_feature
<222> LOCATION: (43)..(43)
<223> OTHER INFORMATION: S=C or G
<220> FEATURE:
<221> NAME/KEY: misc_feature
<222> LOCATION: (44)..(44)
<223> OTHER INFORMATION: N=A, C, G or T
<220> FEATURE:
<221> NAME/KEY: misc_feature
<222> LOCATION: (45)..(45)
<223> OTHER INFORMATION: B=T, G or C
<220> FEATURE:
<221> NAME/KEY: misc_feature
<222> LOCATION: (46)..(46)
<223> OTHER INFORMATION: S=C or G
<220> FEATURE:
<221> NAME/KEY: misc_feature
<222> LOCATION: (47)..(47)
<223> OTHER INFORMATION: N=A, C, G or T
<220> FEATURE:
<221> NAME/KEY: misc_feature
<222> LOCATION: (48)..(48)
<223> OTHER INFORMATION: B=T, G or C
<220> FEATURE:
<221> NAME/KEY: misc_feature
<222> LOCATION: (49)..(49)
<223> OTHER INFORMATION: S=C or G
<220> FEATURE:
<221> NAME/KEY: misc_feature
<222> LOCATION: (50)..(50)
<223> OTHER INFORMATION: N=A, C, G or T
<220> FEATURE:
<221> NAME/KEY: misc_feature
<222> LOCATION: (51)..(51)
<223> OTHER INFORMATION: B=T, G or C
<220> FEATURE:
<221> NAME/KEY: misc_feature
<222> LOCATION: (52)..(52)
<223> OTHER INFORMATION: S=C or G
<220> FEATURE:
<221> NAME/KEY: misc_feature
<222> LOCATION: (53)..(53)
<223> OTHER INFORMATION: N=A, C, G or T
<220> FEATURE:
<221> NAME/KEY: misc_feature
<222> LOCATION: (54)..(54)
<223> OTHER INFORMATION: B=T, G or C

<400> SEQUENCE: 248
caggcagtct gagtcctgtt tgcasnbsnb snbsnbsnbs nbsnbsnbsn bsnbgcacct 60
ccctgcagca tagatcag 78

<210> SEQ ID NO 249
<211> LENGTH: 125
<212> TYPE: PRT
<213> ORGANISM: Artificial Sequence
<220> FEATURE:
<223> OTHER INFORMATION: KB_TFR_B05

<400> SEQUENCE: 249

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Ala Ile Ser Trp Val Arg Gln Ala Pro Gly Gln Gly Leu Glu Trp Met
35 40 45

Gly Arg Asn Ile Pro Ile Leu Gly Ile Ala Asn Tyr Ala Gln Lys Ser

```
    50                  55                  60

Arg Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Ala Pro Tyr Ser Ser Gly Trp Ala Asn Val Asp Ala Phe
            100                 105                 110

Asp Ile Trp Gly Gln Gly Thr Leu Val Thr Val Ser Ser
        115                 120                 125


<210> SEQ ID NO 250
<211> LENGTH: 122
<212> TYPE: PRT
<213> ORGANISM: Artificial Sequence
<220> FEATURE:
<223> OTHER INFORMATION: KB_TFR_B07

<400> SEQUENCE: 250

Gln Val Gln Leu Val Gln Ser Glu Pro Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Arg Ile Ile Pro Ile Phe Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Gly Ile Thr Gly Thr Asn Gly Pro His Asp Ala Phe Asp Ile Trp
            100                 105                 110

Gly Gln Gly Thr Met Val Thr Val Ser Ser
        115                 120


<210> SEQ ID NO 251
<211> LENGTH: 125
<212> TYPE: PRT
<213> ORGANISM: Artificial Sequence
<220> FEATURE:
<223> OTHER INFORMATION: KB_TFR_B09

<400> SEQUENCE: 251

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Thr Ile Ser Trp Val Arg Gln Ala Pro Gly Gln Gly Leu Glu Trp Met
        35                  40                  45

Gly Arg Ile Ile Pro Ile Leu Ser Ile Ala Asn Tyr Ala Gln Lys Phe
    50                  55                  60

Gln Ser Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Arg Pro Tyr Tyr Asp Ser Ser Ala Asp Leu Asp Ala Phe
            100                 105                 110
```

Asp Ile Trp Gly Gln Gly Thr Met Val Thr Val Ser Ser
115 120 125

<210> SEQ ID NO 252
<211> LENGTH: 116
<212> TYPE: PRT
<213> ORGANISM: Artificial Sequence
<220> FEATURE:
<223> OTHER INFORMATION: KB_TFR_B11

<400> SEQUENCE: 252

Glu Val Gln Leu Val Gln Phe Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Arg Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Glu Asp Thr Ala Val Tyr Tyr Cys
85 90 95

Ala Arg Gly Arg Gly Pro Leu Ser Tyr Trp Gly Gln Gly Thr Leu Val
100 105 110

Thr Val Ser Ser
115

<210> SEQ ID NO 253
<211> LENGTH: 121
<212> TYPE: PRT
<213> ORGANISM: Artificial Sequence
<220> FEATURE:
<223> OTHER INFORMATION: KB_TFR_C01

<400> SEQUENCE: 253

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Tyr Ser Ser Asn
20 25 30

Thr Phe Thr Trp Val Arg Gln Ala Pro Gly Gln Gly Leu Glu Trp Met
35 40 45

Gly Arg Ile Ile Pro Val Leu Asp Leu Thr Asn Ser Ala Val Asn Phe
50 55 60

Gln Asp Arg Val Thr Ile Thr Ala Asp Glu Ser Thr Ser Thr Val Tyr
65 70 75 80

Met Glu Leu Ser Ser Leu Arg Ser Glu Asp Thr Ala Val Tyr Tyr Cys
85 90 95

Ala Ser Thr Thr Ala Met Val Pro Thr Asp Ala Phe Asp Ile Trp Gly
100 105 110

Gln Gly Thr Met Val Thr Val Ser Ser
115 120

<210> SEQ ID NO 254
<211> LENGTH: 129
<212> TYPE: PRT
<213> ORGANISM: Artificial Sequence
<220> FEATURE:
<223> OTHER INFORMATION: KB_TFR_C03

<400> SEQUENCE: 254

Glu Val Gln Leu Val Glu Ser Gly Ala Glu Val Lys Lys Pro Gly Ser
1               5                   10                  15

Ser Val Lys Val Ser Cys Lys Ala Ser Gly Gly Thr Val Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Leu Phe Gln Arg Ser Gly Ser Tyr Pro Tyr Tyr Tyr Tyr
            100                 105                 110

Tyr Tyr Gly Met Asp Val Trp Gly Gln Gly Thr Met Val Thr Val Ser
        115                 120                 125

Ser

<210> SEQ ID NO 255
<211> LENGTH: 125
<212> TYPE: PRT
<213> ORGANISM: Artificial Sequence
<220> FEATURE:
<223> OTHER INFORMATION: KB_TFR_C05

<400> SEQUENCE: 255

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Tyr Ser Ser Asn
            20                  25                  30

Thr Phe Thr Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Val Leu Ser Ser Leu Arg Ser Glu Asp Thr Ala Val Tyr Tyr Cys
                85                  90                  95

Ala Arg Val Arg Pro Tyr Tyr Asp Ser Ser Ala Asp Leu Asp Ala Phe
            100                 105                 110

Asp Ile Trp Gly Gln Gly Thr Leu Val Thr Val Ser Ser
        115                 120                 125

<210> SEQ ID NO 256
<211> LENGTH: 124
<212> TYPE: PRT
<213> ORGANISM: Artificial Sequence
<220> FEATURE:
<223> OTHER INFORMATION: KB_TFR_C06

<400> SEQUENCE: 256

Gln Val Gln Leu Val Glu Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met

```
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ile Ala Leu Arg Asp Ser Ser Gly Tyr Tyr Thr Asp Ala Leu Asp
            100                 105                 110

Ile Trp Gly Gln Gly Thr Leu Val Thr Val Ser Ser
        115                 120


<210> SEQ ID NO 257
<211> LENGTH: 127
<212> TYPE: PRT
<213> ORGANISM: Artificial Sequence
<220> FEATURE:
<223> OTHER INFORMATION: KB_TFR_C07

<400> SEQUENCE: 257

Gln Met Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Gly Thr Ala Tyr
65                  70                  75                  80

Met Glu Leu Ser Ser Leu Arg Ser Glu Asp Thr Ala Val Tyr Tyr Cys
                85                  90                  95

Ala Gly Pro Gly Gly Tyr Tyr Asp Ile Leu Thr Gly Tyr Pro Thr Asp
            100                 105                 110

Ala Phe Asp Ile Trp Gly Gln Gly Thr Met Val Thr Val Ser Ser
        115                 120                 125


<210> SEQ ID NO 258
<211> LENGTH: 900
<212> TYPE: DNA
<213> ORGANISM: Artificial Sequence
<220> FEATURE:
<223> OTHER INFORMATION: EETI-II Cow ULVC-Ab

<400> SEQUENCE: 258

cagccggcca tggcccaagt gcaacttcgc gaaagcgggc cttccttggt taaaccatcg      60

cagaccctga gtcttacgtg cacggccagc ggtttttccc tgtccgataa agcagtaggg     120

tgggtgcgcc aagcgccggg aaaggcatta gagtggcttg gttccattga tacggggggg     180

aacacaggat acaatcccgg cttgaagtct cgcctttcaa tcaccaaaga caactcaaag     240

tctcaagtct ccctgagcgt ctcatcggtt accaccgagg actcagccac gtactactgc     300

acatccgttc atcaggagac caaaaaatac caatcttgtc cccgcatcct gatgcgttgt     360

aaacaagaca gcgactgcct ggcaggttgt gtatgcggtc ctaatgggtt ttgtggatta     420

accactctgc cagtctcata ttcttacact tataattatg agtggcatgt tgatgtctgg     480

gggcaggggc ttcttgtcac ggtctcgagt ggtggaggcg gttcaggcgg aggtggctct     540
```

ggcggtggcg ctagccaggc tgttttaaac caacccagct cggttagtgg atcgttgggg 600
cagcgcgtct caatcacttg ttccggctcc tcctcgaatg ttggtaatgg atatgtttcc 660
tggtaccagc ttatccccgg tagcgctcct cgcaccttaa tttatggtga cacgtcccgt 720
gccagcggtg tccctgatcg tttctctggg agccgttccg ggaacaccgc cacacttaca 780
attagtagcc ttcaagctga ggacgaagcg gactattttt gtgcctctgc agaggattca 840
tcctctaacg ctgtgtttgg cagtggcacc acccttactg tgttaggggc ggccgcagat 900

<210> SEQ ID NO 259
<211> LENGTH: 75
<212> TYPE: DNA
<213> ORGANISM: Artificial Sequence
<220> FEATURE:
<223> OTHER INFORMATION: Primer 2979

<400> SEQUENCE: 259
ctaagctcct gatctatgct gcaggggtct gcccgcgtat cctgatgcgt tgcaaacagg 60
actcagactg cctgg 75

<210> SEQ ID NO 260
<211> LENGTH: 81
<212> TYPE: DNA
<213> ORGANISM: Artificial Sequence
<220> FEATURE:
<223> OTHER INFORMATION: Primer 2980

<400> SEQUENCE: 260
gaaccttgat gggactccgg agcggctccc gcagaagccg ttcggaccgc atacgcagcc 60
ggccaggcag tctgagtcct g 81

<210> SEQ ID NO 261
<211> LENGTH: 75
<212> TYPE: DNA
<213> ORGANISM: Artificial Sequence
<220> FEATURE:
<223> OTHER INFORMATION: Primer 2983

<400> SEQUENCE: 261
ctaagctcct gatctatgct gcagggaggt gcccgcgtat cctgatgcgt tgcaaacagg 60
actcagactg cctgg 75

<210> SEQ ID NO 262
<211> LENGTH: 81
<212> TYPE: DNA
<213> ORGANISM: Artificial Sequence
<220> FEATURE:
<223> OTHER INFORMATION: Primer 2984

<400> SEQUENCE: 262
gaatcggtca gagactccgg agttggcccc gcagaagccg ttcggaccgc atacgcagcc 60
ggccaggcag tctgagtcct g 81

<210> SEQ ID NO 263
<211> LENGTH: 26
<212> TYPE: DNA
<213> ORGANISM: Artificial Sequence
<220> FEATURE:
<223> OTHER INFORMATION: Primer 2985

<400> SEQUENCE: 263 tttttccat ggctgaagtc caactg 26

<210> SEQ ID NO 264
<211> LENGTH: 24
<212> TYPE: DNA
<213> ORGANISM: Artificial Sequence
<220> FEATURE:
<223> OTHER INFORMATION: Primer 2995

<400> SEQUENCE: 264 tttttgcgg ccgcggtacg tttg 24

<210> SEQ ID NO 265
<211> LENGTH: 23
<212> TYPE: DNA
<213> ORGANISM: Artificial Sequence
<220> FEATURE:
<223> OTHER INFORMATION: Primer 2999

<400> SEQUENCE: 265
tgcagcatag atcaggagct tag 23

<210> SEQ ID NO 266
<211> LENGTH: 21
<212> TYPE: DNA
<213> ORGANISM: Artificial Sequence
<220> FEATURE:
<223> OTHER INFORMATION: Primer 3000

<400> SEQUENCE: 266
tccggagtcc catcaaggtt c 21

<210> SEQ ID NO 267
<211> LENGTH: 26
<212> TYPE: DNA
<213> ORGANISM: Artificial Sequence
<220> FEATURE:
<223> OTHER INFORMATION: Primer 3002

<400> SEQUENCE: 267 tttttgcgg ccgcaggctg acctag 26

<210> SEQ ID NO 268
<211> LENGTH: 23
<212> TYPE: DNA
<213> ORGANISM: Artificial Sequence
<220> FEATURE:
<223> OTHER INFORMATION: Primer 3003

<400> SEQUENCE: 268
tgcagcatag atcaggagct tag 23

<210> SEQ ID NO 269
<211> LENGTH: 21
<212> TYPE: DNA
<213> ORGANISM: Artificial Sequence
<220> FEATURE:
<223> OTHER INFORMATION: Primer 3004

<400> SEQUENCE: 269
tccggagtct ctgaccgatt c 21

<210> SEQ ID NO 270
<211> LENGTH: 245
<212> TYPE: PRT
<213> ORGANISM: Artificial Sequence
<220> FEATURE:

```
<223> OTHER INFORMATION: Amino acid sequence of the parental anti-TACE
      D1A12 scFv101

<400> SEQUENCE: 270

Glu Val Gln Leu Val Glu Ser Gly Gly Gly Leu Val Arg Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Thr Lys Asn Ser Leu Tyr
65                  70                  75                  80

Leu Gln Met Thr Ser Leu Arg Ala Asp Asp Thr Ala Phe Tyr Tyr Cys
                85                  90                  95

Val Asp Phe Gly Pro Gly Tyr Gly Thr Gly Trp Phe Asp Tyr Trp Gly
            100                 105                 110

Pro Gly Thr Leu Val Thr Val Ser Ser Gly Gly Gly Gly Ser Gly Gly
        115                 120                 125

Gly Gly Ser Gly Gly Gly Ala Ser Asp Ile Gln Met Thr Gln Ser Pro
    130                 135                 140

Ser Ser Leu Ser Ala Ser Val Gly Asp Arg Val Thr Ile Thr Cys Arg
145                 150                 155                 160

Ala Ser Gln Ser Ile Ser Ser Tyr Leu Asn Trp Tyr Gln Gln Lys Pro
                165                 170                 175

Gly Lys Ala Pro Lys Leu Leu Ile His Asp Ala Ser Ser Leu Gln Ser
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Phe Ala Thr Tyr Tyr Cys
    210                 215                 220

Gln Gln Ser Phe Ser Ile Pro Leu Thr Phe Gly Gly Gly Thr Lys Met
225                 230                 235                 240

Asp Ile Lys Arg Thr
                245


<210> SEQ ID NO 271
<211> LENGTH: 74
<212> TYPE: DNA
<213> ORGANISM: Artificial Sequence
<220> FEATURE:
<223> OTHER INFORMATION: Primer 2965
<220> FEATURE:
<221> NAME/KEY: misc_feature
<222> LOCATION: (22)..(22)
<223> OTHER INFORMATION: V=A, C or G
<220> FEATURE:
<221> NAME/KEY: misc_feature
<222> LOCATION: (23)..(23)
<223> OTHER INFORMATION: N=A, C, G or T
<220> FEATURE:
<221> NAME/KEY: misc_feature
<222> LOCATION: (24)..(24)
<223> OTHER INFORMATION: S=C or G
<220> FEATURE:
<221> NAME/KEY: misc_feature
<222> LOCATION: (25)..(25)
<223> OTHER INFORMATION: V=A, C or G
<220> FEATURE:
<221> NAME/KEY: misc_feature
<222> LOCATION: (26)..(26)
```

<223> OTHER INFORMATION: N=A, C, G or T
<220> FEATURE:
<221> NAME/KEY: misc_feature
<222> LOCATION: (27)..(27)
<223> OTHER INFORMATION: S=C or G

<400> SEQUENCE: 271
gcgtcgggtt ttacctttag cvnsvnstgt ccccggatac ttatgagatg taagcaagat 60
agtgattgcc tcgc 74

<210> SEQ ID NO 272
<211> LENGTH: 79
<212> TYPE: DNA
<213> ORGANISM: Artificial Sequence
<220> FEATURE:
<223> OTHER INFORMATION: Primer 2966
<220> FEATURE:
<221> NAME/KEY: misc_feature
<222> LOCATION: (19)..(19)
<223> OTHER INFORMATION: S=C or G
<220> FEATURE:
<221> NAME/KEY: misc_feature
<222> LOCATION: (20)..(20)
<223> OTHER INFORMATION: N=A, C, G or T
<220> FEATURE:
<221> NAME/KEY: misc_feature
<222> LOCATION: (21)..(21)
<223> OTHER INFORMATION: B=T, G or C
<220> FEATURE:
<221> NAME/KEY: misc_feature
<222> LOCATION: (22)..(22)
<223> OTHER INFORMATION: S=C or G
<220> FEATURE:
<221> NAME/KEY: misc_feature
<222> LOCATION: (23)..(23)
<223> OTHER INFORMATION: N=A, C, G or T
<220> FEATURE:
<221> NAME/KEY: misc_feature
<222> LOCATION: (24)..(24)
<223> OTHER INFORMATION: B=T, G or C

<400> SEQUENCE: 272
cggagcctga cgaacccasn bsnbgccaca aaacccgttg ggaccacaga cacatccggc 60
gaggcaatca ctatcttgc 79

<210> SEQ ID NO 273
<211> LENGTH: 76
<212> TYPE: DNA
<213> ORGANISM: Artificial Sequence
<220> FEATURE:
<223> OTHER INFORMATION: Primer 2967
<220> FEATURE:
<221> NAME/KEY: misc_feature
<222> LOCATION: (24)..(24)
<223> OTHER INFORMATION: V=A, C or G
<220> FEATURE:
<221> NAME/KEY: misc_feature
<222> LOCATION: (25)..(25)
<223> OTHER INFORMATION: N=A, C, G or T
<220> FEATURE:
<221> NAME/KEY: misc_feature
<222> LOCATION: (26)..(26)
<223> OTHER INFORMATION: S=C or G
<220> FEATURE:
<221> NAME/KEY: misc_feature
<222> LOCATION: (27)..(27)
<223> OTHER INFORMATION: V=A, C or G
<220> FEATURE:
<221> NAME/KEY: misc_feature
<222> LOCATION: (28)..(28)
<223> OTHER INFORMATION: N=A, C, G or T
<220> FEATURE:
<221> NAME/KEY: misc_feature
<222> LOCATION: (29)..(29)
<223> OTHER INFORMATION: S=C or G

<400> SEQUENCE: 273
gtaaaggcct ggaatgggtc tccvnsvnst gtccccggat acttatgaga tgtaagcaag 60
atagtgattg cctcgc 76

<210> SEQ ID NO 274
<211> LENGTH: 82
<212> TYPE: DNA
<213> ORGANISM: Artificial Sequence
<220> FEATURE:
<223> OTHER INFORMATION: Primer 2968
<220> FEATURE:
<221> NAME/KEY: misc_feature
<222> LOCATION: (22)..(22)
<223> OTHER INFORMATION: S=C or G
<220> FEATURE:
<221> NAME/KEY: misc_feature
<222> LOCATION: (23)..(23)
<223> OTHER INFORMATION: N=A, C, G or T
<220> FEATURE:
<221> NAME/KEY: misc_feature
<222> LOCATION: (24)..(24)
<223> OTHER INFORMATION: B=T, G or C
<220> FEATURE:
<221> NAME/KEY: misc_feature
<222> LOCATION: (25)..(25)
<223> OTHER INFORMATION: S=C or G
<220> FEATURE:
<221> NAME/KEY: misc_feature
<222> LOCATION: (26)..(26)
<223> OTHER INFORMATION: N=A, C, G or T
<220> FEATURE:
<221> NAME/KEY: misc_feature
<222> LOCATION: (27)..(27)
<223> OTHER INFORMATION: B=T, G or C

<400> SEQUENCE: 274
gtcgcgagag atggtgaaac gsnbsnbgcc acaaaacccg ttgggaccac agacacatcc 60
ggcgaggcaa tcactatctt gc 82

<210> SEQ ID NO 275
<211> LENGTH: 78
<212> TYPE: DNA
<213> ORGANISM: Artificial Sequence
<220> FEATURE:
<223> OTHER INFORMATION: Primer 2969
<220> FEATURE:
<221> NAME/KEY: misc_feature
<222> LOCATION: (26)..(26)
<223> OTHER INFORMATION: V=A, C or G
<220> FEATURE:
<221> NAME/KEY: misc_feature
<222> LOCATION: (27)..(27)
<223> OTHER INFORMATION: N=A, C, G or T
<220> FEATURE:
<221> NAME/KEY: misc_feature
<222> LOCATION: (28)..(28)
<223> OTHER INFORMATION: S=C or G
<220> FEATURE:
<221> NAME/KEY: misc_feature
<222> LOCATION: (29)..(29)
<223> OTHER INFORMATION: V=A, C or G
<220> FEATURE:
<221> NAME/KEY: misc_feature
<222> LOCATION: (30)..(30)
<223> OTHER INFORMATION: N=A, C, G or T
<220> FEATURE:
<221> NAME/KEY: misc_feature
<222> LOCATION: (31)..(31)
<223> OTHER INFORMATION: S=C or G

<400> SEQUENCE: 275
cacggctttt tattactgcg ttgatvnsvn stgtccccgg atacttatga gatgtaagca 60
agatagtgat tgcctcgc 78

<210> SEQ ID NO 276
<211> LENGTH: 79
<212> TYPE: DNA
<213> ORGANISM: Artificial Sequence
<220> FEATURE:
<223> OTHER INFORMATION: Primer 2970
<220> FEATURE:
<221> NAME/KEY: misc_feature
<222> LOCATION: (19)..(19)
<223> OTHER INFORMATION: S=C or G
<220> FEATURE:
<221> NAME/KEY: misc_feature
<222> LOCATION: (20)..(20)
<223> OTHER INFORMATION: N=A, C, G or T
<220> FEATURE:
<221> NAME/KEY: misc_feature
<222> LOCATION: (21)..(21)
<223> OTHER INFORMATION: B=T, G or C
<220> FEATURE:
<221> NAME/KEY: misc_feature
<222> LOCATION: (22)..(22)
<223> OTHER INFORMATION: S=C or G
<220> FEATURE:
<221> NAME/KEY: misc_feature
<222> LOCATION: (23)..(23)
<223> OTHER INFORMATION: N=A, C, G or T
<220> FEATURE:
<221> NAME/KEY: misc_feature
<222> LOCATION: (24)..(24)
<223> OTHER INFORMATION: B=T, G or C

<400> SEQUENCE: 276
cagggtgccc ggaccccasn bsnbgccaca aaacccgttg ggaccacaga cacatccggc 60
gaggcaatca ctatcttgc 79

<210> SEQ ID NO 277
<211> LENGTH: 76
<212> TYPE: DNA
<213> ORGANISM: Artificial Sequence
<220> FEATURE:
<223> OTHER INFORMATION: Primer 2971
<220> FEATURE:
<221> NAME/KEY: misc_feature
<222> LOCATION: (24)..(24)
<223> OTHER INFORMATION: V=A, C or G
<220> FEATURE:
<221> NAME/KEY: misc_feature
<222> LOCATION: (25)..(25)
<223> OTHER INFORMATION: N=A, C, G or T
<220> FEATURE:
<221> NAME/KEY: misc_feature
<222> LOCATION: (26)..(26)
<223> OTHER INFORMATION: S=C or G
<220> FEATURE:
<221> NAME/KEY: misc_feature
<222> LOCATION: (27)..(27)
<223> OTHER INFORMATION: V=A, C or G
<220> FEATURE:
<221> NAME/KEY: misc_feature
<222> LOCATION: (28)..(28)
<223> OTHER INFORMATION: N=A, C, G or T
<220> FEATURE:
<221> NAME/KEY: misc_feature
<222> LOCATION: (29)..(29)
<223> OTHER INFORMATION: S=C or G

<400> SEQUENCE: 277
gagacagagt caccatcact tgcvnsvnst gtccccggat acttatgaga tgtaagcaag 60
atagtgattg cctcgc 76

<210> SEQ ID NO 278
<211> LENGTH: 81
<212> TYPE: DNA
<213> ORGANISM: Artificial Sequence
<220> FEATURE:
<223> OTHER INFORMATION: Primer 2972
<220> FEATURE:
<221> NAME/KEY: misc_feature
<222> LOCATION: (21)..(21)
<223> OTHER INFORMATION: S=C or G
<220> FEATURE:
<221> NAME/KEY: misc_feature
<222> LOCATION: (22)..(22)
<223> OTHER INFORMATION: N=A, C, G or T
<220> FEATURE:
<221> NAME/KEY: misc_feature
<222> LOCATION: (23)..(23)
<223> OTHER INFORMATION: B=T, G or C
<220> FEATURE:
<221> NAME/KEY: misc_feature
<222> LOCATION: (24)..(24)
<223> OTHER INFORMATION: S=C or G
<220> FEATURE:
<221> NAME/KEY: misc_feature
<222> LOCATION: (25)..(25)
<223> OTHER INFORMATION: N=A, C, G or T
<220> FEATURE:
<221> NAME/KEY: misc_feature
<222> LOCATION: (26)..(26)
<223> OTHER INFORMATION: B=T, G or C

<400> SEQUENCE: 278
cctggcttct gctgatacca snbsnbgcca caaaacccgt tgggaccaca gacacatccg 60
gcgaggcaat cactatcttg c 81

<210> SEQ ID NO 279
<211> LENGTH: 75
<212> TYPE: DNA
<213> ORGANISM: Artificial Sequence
<220> FEATURE:
<223> OTHER INFORMATION: Primer 2973
<220> FEATURE:
<221> NAME/KEY: misc_feature
<222> LOCATION: (23)..(23)
<223> OTHER INFORMATION: V=A, C or G
<220> FEATURE:
<221> NAME/KEY: misc_feature
<222> LOCATION: (24)..(24)
<223> OTHER INFORMATION: N=A, C, G or T
<220> FEATURE:
<221> NAME/KEY: misc_feature
<222> LOCATION: (25)..(25)
<223> OTHER INFORMATION: S=C or G
<220> FEATURE:
<221> NAME/KEY: misc_feature
<222> LOCATION: (26)..(26)
<223> OTHER INFORMATION: V=A, C or G
<220> FEATURE:
<221> NAME/KEY: misc_feature
<222> LOCATION: (27)..(27)
<223> OTHER INFORMATION: N=A, C, G or T
<220> FEATURE:
<221> NAME/KEY: misc_feature
<222> LOCATION: (28)..(28)
<223> OTHER INFORMATION: S=C or G

<400> SEQUENCE: 279
ccctaagctc ctgatccatg atvnsvnstg tccccggata cttatgagat gtaagcaaga 60
tagtgattgc ctcgc 75

<210> SEQ ID NO 280
<211> LENGTH: 81
<212> TYPE: DNA
<213> ORGANISM: Artificial Sequence
<220> FEATURE:
<223> OTHER INFORMATION: Primer 2974
<220> FEATURE:
<221> NAME/KEY: misc_feature
<222> LOCATION: (21)..(21)
<223> OTHER INFORMATION: S= C or G
<220> FEATURE:
<221> NAME/KEY: misc_feature
<222> LOCATION: (22)..(22)
<223> OTHER INFORMATION: N=A, C, G or T
<220> FEATURE:
<221> NAME/KEY: misc_feature
<222> LOCATION: (23)..(23)
<223> OTHER INFORMATION: B=T, G or C
<220> FEATURE:
<221> NAME/KEY: misc_feature
<222> LOCATION: (24)..(24)
<223> OTHER INFORMATION: S= C or G
<220> FEATURE:
<221> NAME/KEY: misc_feature
<222> LOCATION: (25)..(25)
<223> OTHER INFORMATION: N=A, C, G or T
<220> FEATURE:
<221> NAME/KEY: misc_feature
<222> LOCATION: (26)..(26)
<223> OTHER INFORMATION: B=T, G or C

<400> SEQUENCE: 280
ctgaaccttg atgggacccc snbsnbgcca caaaacccgt tgggaccaca gacacatccg 60
gcgaggcaat cactatcttg c 81

<210> SEQ ID NO 281
<211> LENGTH: 80
<212> TYPE: DNA
<213> ORGANISM: Artificial Sequence
<220> FEATURE:
<223> OTHER INFORMATION: Primer 2975
<220> FEATURE:
<221> NAME/KEY: misc_feature
<222> LOCATION: (28)..(28)
<223> OTHER INFORMATION: V=A, C or G
<220> FEATURE:
<221> NAME/KEY: misc_feature
<222> LOCATION: (29)..(29)
<223> OTHER INFORMATION: N=A, C, G or T
<220> FEATURE:
<221> NAME/KEY: misc_feature
<222> LOCATION: (30)..(30)
<223> OTHER INFORMATION: S=C or G
<220> FEATURE:
<221> NAME/KEY: misc_feature
<222> LOCATION: (31)..(31)
<223> OTHER INFORMATION: V=A, C or G
<220> FEATURE:
<221> NAME/KEY: misc_feature
<222> LOCATION: (32)..(32)
<223> OTHER INFORMATION: N=A, C, G or T
<220> FEATURE:
<221> NAME/KEY: misc_feature
<222> LOCATION: (33)..(33)
<223> OTHER INFORMATION: S=C or G

<400> SEQUENCE: 281
cctgaagatt ttgcaactta ctactgtvns vnstgtcccc ggatacttat gagatgtaag 60
caagatagtg attgcctcgc 80

<210> SEQ ID NO 282
<211> LENGTH: 82

<212> TYPE: DNA
<213> ORGANISM: Artificial Sequence
<220> FEATURE:
<223> OTHER INFORMATION: Primer 2976
<220> FEATURE:
<221> NAME/KEY: misc_feature
<222> LOCATION: (22)..(22)
<223> OTHER INFORMATION: S=C or G
<220> FEATURE:
<221> NAME/KEY: misc_feature
<222> LOCATION: (23)..(23)
<223> OTHER INFORMATION: N=A, C, G or T
<220> FEATURE:
<221> NAME/KEY: misc_feature
<222> LOCATION: (24)..(24)
<223> OTHER INFORMATION: B=T, G or C
<220> FEATURE:
<221> NAME/KEY: misc_feature
<222> LOCATION: (25)..(25)
<223> OTHER INFORMATION: S=C or G
<220> FEATURE:
<221> NAME/KEY: misc_feature
<222> LOCATION: (26)..(26)
<223> OTHER INFORMATION: N=A, C, G or T
<220> FEATURE:
<221> NAME/KEY: misc_feature
<222> LOCATION: (27)..(27)
<223> OTHER INFORMATION: B=T, G or C

<400> SEQUENCE: 282
cattttggtc cctccgccga asnbsnbgcc acaaaacccg ttgggaccac agacacatcc 60
ggcgaggcaa tcactatctt gc 82

<210> SEQ ID NO 283
<211> LENGTH: 75
<212> TYPE: DNA
<213> ORGANISM: Artificial Sequence
<220> FEATURE:
<223> OTHER INFORMATION: Primer 2977
<220> FEATURE:
<221> NAME/KEY: misc_feature
<222> LOCATION: (24)..(24)
<223> OTHER INFORMATION: V=A, C or G
<220> FEATURE:
<221> NAME/KEY: misc_feature
<222> LOCATION: (25)..(25)
<223> OTHER INFORMATION: N=A, C, G or T
<220> FEATURE:
<221> NAME/KEY: misc_feature
<222> LOCATION: (26)..(26)
<223> OTHER INFORMATION: S=C or G
<220> FEATURE:
<221> NAME/KEY: misc_feature
<222> LOCATION: (27)..(27)
<223> OTHER INFORMATION: V=A, C or G
<220> FEATURE:
<221> NAME/KEY: misc_feature
<222> LOCATION: (28)..(28)
<223> OTHER INFORMATION: N=A, C, G or T
<220> FEATURE:
<221> NAME/KEY: misc_feature
<222> LOCATION: (29)..(29)
<223> OTHER INFORMATION: S=C or G

<400> SEQUENCE: 283
ctaagctcct gatctatgct gcavnsvnst gcccgcgtat cctgatgcgt tgcaaacagg 60
actcagactg cctgg 75

<210> SEQ ID NO 284
<211> LENGTH: 81
<212> TYPE: DNA
<213> ORGANISM: Artificial Sequence
<220> FEATURE:

<223> OTHER INFORMATION: Primer 2978
<220> FEATURE:
<221> NAME/KEY: misc_feature
<222> LOCATION: (22)..(22)
<223> OTHER INFORMATION: S=C or G
<220> FEATURE:
<221> NAME/KEY: misc_feature
<222> LOCATION: (23)..(23)
<223> OTHER INFORMATION: N=A, C, G or T
<220> FEATURE:
<221> NAME/KEY: misc_feature
<222> LOCATION: (24)..(24)
<223> OTHER INFORMATION: B=T, G or C
<220> FEATURE:
<221> NAME/KEY: misc_feature
<222> LOCATION: (25)..(25)
<223> OTHER INFORMATION: S=C or G
<220> FEATURE:
<221> NAME/KEY: misc_feature
<222> LOCATION: (26)..(26)
<223> OTHER INFORMATION: N=A, C, G or T
<220> FEATURE:
<221> NAME/KEY: misc_feature
<222> LOCATION: (27)..(27)
<223> OTHER INFORMATION: B=T, G or C

<400> SEQUENCE: 284
gaaccttgat gggactccgg asnbsnbccc gcagaagccg ttcggaccgc atacgcagcc 60
ggccaggcag tctgagtcct g 81

<210> SEQ ID NO 285
<211> LENGTH: 75
<212> TYPE: DNA
<213> ORGANISM: Artificial Sequence
<220> FEATURE:
<223> OTHER INFORMATION: Primer 2981
<220> FEATURE:
<221> NAME/KEY: misc_feature
<222> LOCATION: (24)..(24)
<223> OTHER INFORMATION: V=A, C or G
<220> FEATURE:
<221> NAME/KEY: misc_feature
<222> LOCATION: (25)..(25)
<223> OTHER INFORMATION: N=A, C, G or T
<220> FEATURE:
<221> NAME/KEY: misc_feature
<222> LOCATION: (26)..(26)
<223> OTHER INFORMATION: S=C or G
<220> FEATURE:
<221> NAME/KEY: misc_feature
<222> LOCATION: (27)..(27)
<223> OTHER INFORMATION: V=A, C or G
<220> FEATURE:
<221> NAME/KEY: misc_feature
<222> LOCATION: (28)..(28)
<223> OTHER INFORMATION: N=A, C, G or T
<220> FEATURE:
<221> NAME/KEY: misc_feature
<222> LOCATION: (29)..(29)
<223> OTHER INFORMATION: S=C or G

<400> SEQUENCE: 285
ctaagctcct gatctatgct gcavnsvnst gcccgcgtat cctgatgcgt tgcaaacagg 60
actcagactg cctgg 75

<210> SEQ ID NO 286
<211> LENGTH: 81
<212> TYPE: DNA
<213> ORGANISM: Artificial Sequence
<220> FEATURE:
<223> OTHER INFORMATION: Primer 2982

<400> SEQUENCE: 286
gaatcggtca gagactccgg agttggcccc gcagaagccg ttcggaccgc atacgcagcc 60
ggccaggcag tctgagtcct g 81

<210> SEQ ID NO 287
<211> LENGTH: 21
<212> TYPE: DNA
<213> ORGANISM: Artificial Sequence
<220> FEATURE:
<223> OTHER INFORMATION: Primer 2986

<400> SEQUENCE: 287
gctaaaggta aaacccgacg c 21

<210> SEQ ID NO 288
<211> LENGTH: 18
<212> TYPE: DNA
<213> ORGANISM: Artificial Sequence
<220> FEATURE:
<223> OTHER INFORMATION: Primer 2987

<400> SEQUENCE: 288
tgggttcgtc aggctccg 18

<210> SEQ ID NO 289
<211> LENGTH: 24
<212> TYPE: DNA
<213> ORGANISM: Artificial Sequence
<220> FEATURE:
<223> OTHER INFORMATION: Primer 2988

<400> SEQUENCE: 289
ttttttctcg agacggtcac cagg 24

<210> SEQ ID NO 290
<211> LENGTH: 23
<212> TYPE: DNA
<213> ORGANISM: Artificial Sequence
<220> FEATURE:
<223> OTHER INFORMATION: Primer 2989

<400> SEQUENCE: 290
ggagacccat tccaggcctt tac 23

<210> SEQ ID NO 291
<211> LENGTH: 21
<212> TYPE: DNA
<213> ORGANISM: Artificial Sequence
<220> FEATURE:
<223> OTHER INFORMATION: Primer 2990

<400> SEQUENCE: 291
cgtttcacca tctctcgcga c 21

<210> SEQ ID NO 292
<211> LENGTH: 25
<212> TYPE: DNA
<213> ORGANISM: Artificial Sequence
<220> FEATURE:
<223> OTHER INFORMATION: Primer 2991

<400> SEQUENCE: 292
atcaacgcag taataaaaag ccgtg 25

<210> SEQ ID NO 293

<211> LENGTH: 27
<212> TYPE: DNA
<213> ORGANISM: Artificial Sequence
<220> FEATURE:
<223> OTHER INFORMATION: Primer 2992

<400> SEQUENCE: 293 tttttgcta gcgacatcca gatgacc 27

<210> SEQ ID NO 294
<211> LENGTH: 23
<212> TYPE: DNA
<213> ORGANISM: Artificial Sequence
<220> FEATURE:
<223> OTHER INFORMATION: Primer 2993

<400> SEQUENCE: 294
gcaagtgatg gtgactctgt ctc 23

<210> SEQ ID NO 295
<211> LENGTH: 20
<212> TYPE: DNA
<213> ORGANISM: Artificial Sequence
<220> FEATURE:
<223> OTHER INFORMATION: Primer 2994

<400> SEQUENCE: 295
tggtatcagc agaagccagg 20

<210> SEQ ID NO 296
<211> LENGTH: 22
<212> TYPE: DNA
<213> ORGANISM: Artificial Sequence
<220> FEATURE:
<223> OTHER INFORMATION: Primer 2996

<400> SEQUENCE: 296
atcatggatc aggagcttag gg 22

<210> SEQ ID NO 297
<211> LENGTH: 20
<212> TYPE: DNA
<213> ORGANISM: Artificial Sequence
<220> FEATURE:
<223> OTHER INFORMATION: Primer 2997

<400> SEQUENCE: 297
ggggtcccat caaggttcag 20

<210> SEQ ID NO 298
<211> LENGTH: 27
<212> TYPE: DNA
<213> ORGANISM: Artificial Sequence
<220> FEATURE:
<223> OTHER INFORMATION: Primer 2998

<400> SEQUENCE: 298
acagtagtaa gttgcaaaat cttcagg 27

<210> SEQ ID NO 299
<211> LENGTH: 26
<212> TYPE: DNA
<213> ORGANISM: Artificial Sequence
<220> FEATURE:
<223> OTHER INFORMATION: Primer 3001

<400> SEQUENCE: 299 tttttgcta gccagtctgt gctgac 26

<210> SEQ ID NO 300
<211> LENGTH: 39
<212> TYPE: DNA
<213> ORGANISM: Artificial Sequence
<220> FEATURE:
<223> OTHER INFORMATION: Primer 3005

<400> SEQUENCE: 300
aaatttactc gagacggtca ccagggtgcc cggacccca 39

<210> SEQ ID NO 301
<211> LENGTH: 18
<212> TYPE: DNA
<213> ORGANISM: Artificial Sequence
<220> FEATURE:
<223> OTHER INFORMATION: Primer 3012

<400> SEQUENCE: 301
tggggtccgg gcaccctg 18

<210> SEQ ID NO 302
<211> LENGTH: 26
<212> TYPE: PRT
<213> ORGANISM: Artificial Sequence
<220> FEATURE:
<223> OTHER INFORMATION: EET 1-5

<400> SEQUENCE: 302

Cys Pro Arg Ile Leu Met Arg Cys Lys Gln Asp Ser Asp Cys Leu Ala
1 5 10 15

Gly Cys Val Cys Gly Pro Asn Gly Phe Cys
20 25

<210> SEQ ID NO 303
<211> LENGTH: 28
<212> TYPE: PRT
<213> ORGANISM: Artificial Sequence
<220> FEATURE:
<223> OTHER INFORMATION: EET 2-6

<400> SEQUENCE: 303

Cys Lys Gln Asp Ser Asp Cys Leu Ala Gly Cys Val Cys Gly Pro Asn
1 5 10 15

Gly Phe Cys Gly Ser Gly Ser Asp Gly Gly Val Cys
20 25

<210> SEQ ID NO 304
<211> LENGTH: 29
<212> TYPE: PRT
<213> ORGANISM: Artificial Sequence
<220> FEATURE:
<223> OTHER INFORMATION: EET 3-1

<400> SEQUENCE: 304

Cys Leu Ala Gly Cys Val Cys Gly Pro Asn Gly Phe Cys Gly Ser Gly
1 5 10 15

Ser Asp Gly Gly Val Cys Pro Arg Ile Leu Met Arg Cys
20 25

<210> SEQ ID NO 305
<211> LENGTH: 31
<212> TYPE: PRT

<213> ORGANISM: Artificial Sequence
<220> FEATURE:
<223> OTHER INFORMATION: EET 4-2

<400> SEQUENCE: 305

Cys Val Cys Gly Pro Asn Gly Phe Cys Gly Ser Gly Ser Asp Gly Gly
1 5 10 15

Val Cys Pro Arg Ile Leu Met Arg Cys Lys Gln Asp Ser Asp Cys
20 25 30

<210> SEQ ID NO 306
<211> LENGTH: 33
<212> TYPE: PRT
<213> ORGANISM: Artificial Sequence
<220> FEATURE:
<223> OTHER INFORMATION: EET 5-3

<400> SEQUENCE: 306

Cys Gly Pro Asn Gly Phe Cys Gly Ser Gly Ser Asp Gly Gly Val Cys
1 5 10 15

Pro Arg Ile Leu Met Arg Cys Lys Gln Asp Ser Asp Cys Leu Ala Gly
20 25 30

Cys

<210> SEQ ID NO 307
<211> LENGTH: 29
<212> TYPE: PRT
<213> ORGANISM: Artificial Sequence
<220> FEATURE:
<223> OTHER INFORMATION: EET 6-4

<400> SEQUENCE: 307

Cys Gly Ser Gly Ser Asp Gly Gly Val Cys Pro Arg Ile Leu Met Arg
1 5 10 15

Cys Lys Gln Asp Ser Asp Cys Leu Ala Gly Cys Val Cys
20 25

<210> SEQ ID NO 308
<211> LENGTH: 140
<212> TYPE: PRT
<213> ORGANISM: Artificial Sequence
<220> FEATURE:
<223> OTHER INFORMATION: C09 (9820)

<400> SEQUENCE: 308

Gln Ser Val Leu Thr Gln Pro Pro Ser Val Ser Glu Ala Pro Arg Gln
1 5 10 15

Arg Val Thr Ile Thr Cys Gly Gly Lys Arg Cys Gly Pro Asn Gly Phe
20 25 30

Cys Gly Ser Gly Ser Asp Gly Gly Val Cys Pro Arg Ile Leu Met Arg
35 40 45

Cys Lys Gln Asp Ser Asp Cys Leu Ala Gly Cys Thr Ser Asn Trp Tyr
50 55 60

Gln Gln Lys Pro Gly Gln Ala Pro Val Leu Val Val Gln Asp Asp Ser
65 70 75 80

Val Arg Pro Ser Gly Ile Pro Glu Arg Phe Ser Gly Ser Asn Ser Gly
85 90 95

Asn Thr Ala Thr Leu Thr Ile Ser Arg Val Glu Ala Gly Asp Gly Ala
100 105 110

Asp Tyr Tyr Cys Gln Val Trp Asp Ile Ser Ser Asp Leu Gly Val Phe
115 120 125

```
Gly Gly Gly Thr Lys Leu Thr Val Leu Gly Gln Pro
    130                 135                 140


<210> SEQ ID NO 309
<211> LENGTH: 147
<212> TYPE: PRT
<213> ORGANISM: Artificial Sequence
<220> FEATURE:
<223> OTHER INFORMATION: E01 (127988)

<400> SEQUENCE: 309

Gln Ser Val Leu Thr Gln Pro Pro Ser Val Ser Glu Ala Pro Arg Gln
1               5                   10                  15

Arg Val Thr Ile Thr Cys Ser Gly Ser Ser Ser Asn Ile Gly Asn Asn
            20                  25                  30

Ala Val Asn Trp Tyr Gln Gln Leu Pro Gly Lys Ala Pro Lys Leu Leu
        35                  40                  45

Ile Tyr Ala Ala Gly Gly Cys Gly Pro Asn Gly Phe Cys Gly Ser Gly
    50                  55                  60

Ser Asp Gly Gly Val Cys Pro Arg Ile Leu Met Arg Cys Lys Gln Asp
65                  70                  75                  80

Ser Asp Cys Leu Ala Gly Cys Gly Ile His Ser Gly Val Ser Asp Arg
                85                  90                  95

Phe Ser Asp Ser Lys Ser Gly Thr Ser Ala Ser Leu Ala Ile Ser Gly
            100                 105                 110

Leu Gln Ser Glu Asp Glu Ala Asp Tyr Tyr Cys Ala Ala Trp Asp Asp
        115                 120                 125

Ser Leu Asn Gly Tyr Val Phe Gly Thr Gly Thr Lys Leu Thr Val Leu
    130                 135                 140

Gly Gln Pro
145


<210> SEQ ID NO 310
<211> LENGTH: 147
<212> TYPE: PRT
<213> ORGANISM: Artificial Sequence
<220> FEATURE:
<223> OTHER INFORMATION: E08 (121047)

<400> SEQUENCE: 310

Gln Ser Val Leu Thr Gln Pro Pro Ser Val Ser Glu Ala Pro Arg Gln
1               5                   10                  15

Arg Val Thr Ile Thr Cys Ser Gly Ser Ser Ser Asn Ile Gly Asn Asn
            20                  25                  30

Ala Val Asn Trp Tyr Gln Gln Leu Pro Gly Lys Ala Pro Lys Leu Leu
        35                  40                  45

Ile Tyr Ala Ala Gly Gly Cys Gly Pro Asn Gly Phe Cys Gly Ser Gly
    50                  55                  60

Ser Asp Gly Gly Val Cys Pro Arg Ile Leu Met Arg Cys Lys Gln Asp
65                  70                  75                  80

Ser Asp Cys Leu Ala Gly Cys Gly Ile Gln Ser Gly Ile Pro Glu Arg
                85                  90                  95

Phe Ser Gly Ser Lys Ser Gly Thr Ser Ala Ser Leu Ala Ile Ser Gly
            100                 105                 110

Leu Arg Ser Glu Asp Glu Ala Asp Tyr Tyr Cys Ala Ala Trp Asp Asp
        115                 120                 125

Asn Leu Ser Gly Tyr Val Phe Gly Thr Gly Thr Lys Leu Thr Val Leu
```

```
    130                 135                 140

Gly Gln Pro
145


<210> SEQ ID NO 311
<211> LENGTH: 147
<212> TYPE: PRT
<213> ORGANISM: Artificial Sequence
<220> FEATURE:
<223> OTHER INFORMATION: E05 (118631)

<400> SEQUENCE: 311

Gln Ser Val Leu Thr Gln Pro Pro Ser Val Ser Glu Ala Pro Arg Gln
1               5                   10                  15

Arg Val Thr Ile Thr Cys Ser Gly Ser Ser Ser Asn Ile Gly Asn Asn
            20                  25                  30

Ala Val Asn Trp Tyr Gln Gln Leu Pro Gly Lys Ala Pro Lys Leu Leu
        35                  40                  45

Ile Tyr Ala Ala Gly Gly Cys Gly Pro Asn Gly Phe Cys Gly Ser Gly
    50                  55                  60

Ser Asp Gly Gly Val Cys Pro Arg Ile Leu Met Arg Cys Lys Gln Asp
65                  70                  75                  80

Ser Asp Cys Leu Ala Gly Cys Gly Ala Gln Ser Gly Ile Pro Glu Arg
                85                  90                  95

Phe Ser Gly Ser Lys Ser Gly Thr Ser Ala Ser Leu Ala Ile Ser Gly
            100                 105                 110

Leu Gln Ser Glu Asp Glu Ala His Tyr Tyr Cys Ala Ala Trp Asp Asp
        115                 120                 125

Ser Leu Asn Gly Tyr Val Phe Gly Thr Gly Thr Lys Val Thr Val Leu
    130                 135                 140

Gly Gln Pro
145


<210> SEQ ID NO 312
<211> LENGTH: 143
<212> TYPE: PRT
<213> ORGANISM: Artificial Sequence
<220> FEATURE:
<223> OTHER INFORMATION: F01 (101798)

<400> SEQUENCE: 312

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Asp Ala Ala Gly Glu Cys Gly Pro Asn Gly Phe Cys Gly Ser Gly Ser
    50                  55                  60

Asp Gly Gly Val Cys Pro Arg Ile Asn Met Arg Cys Lys Gln Asp Ser
65                  70                  75                  80

Asp Cys Leu Ala Gly Cys Gly Arg Asp Ser Gly Val Pro Ser Arg Phe
                85                  90                  95

Ser Gly Ser Gly Ser Gly Thr Asp Phe Thr Leu Thr Ile Ser Ser Leu
            100                 105                 110

Gln Pro Glu Asp Phe Ala Thr Tyr Tyr Cys Gln Gln Ser Tyr Ser Thr
        115                 120                 125
```

Pro Trp Thr Phe Gly Gln Gly Thr Lys Val Glu Ile Lys Arg Thr
    130                 135                 140

<210> SEQ ID NO 313
<211> LENGTH: 147
<212> TYPE: PRT
<213> ORGANISM: Artificial Sequence
<220> FEATURE:
<223> OTHER INFORMATION: E03 (82495)

<400> SEQUENCE: 313

Gln Ser Val Leu Thr Gln Pro Pro Ser Val Ser Glu Ala Pro Arg Gln
1               5                   10                  15

Arg Val Thr Ile Thr Cys Ser Gly Ser Ser Ser Asn Ile Gly Asn Asn
            20                  25                  30

Ala Val Asn Trp Tyr Gln Gln Leu Pro Gly Lys Ala Pro Lys Leu Leu
        35                  40                  45

Ile Tyr Ala Ala Gly Gly Cys Gly Pro Asn Gly Phe Cys Gly Ser Gly
    50                  55                  60

Ser Asp Gly Gly Val Cys Pro Arg Ile Leu Met Arg Cys Lys Gln Asp
65                  70                  75                  80

Ser Asp Cys Leu Ala Gly Cys Gly Arg Asn Ser Gly Ile Pro Glu Arg
                85                  90                  95

Phe Ser Gly Ser Lys Ser Gly His Thr Ala Thr Leu Thr Ile Ser Arg
            100                 105                 110

Val Glu Ala Gly Asp Glu Ala Asp Tyr Tyr Cys Gln Val Trp Asp Ser
        115                 120                 125

Ser Ser Asp His Val Leu Phe Gly Gly Gly Thr Lys Leu Thr Val Leu
    130                 135                 140

Gly Gln Pro
145

<210> SEQ ID NO 314
<211> LENGTH: 147
<212> TYPE: PRT
<213> ORGANISM: Artificial Sequence
<220> FEATURE:
<223> OTHER INFORMATION: F07 (72824)

<400> SEQUENCE: 314

Gln Ser Val Leu Thr Gln Pro Pro Ser Val Ser Glu Ala Pro Arg Gln
1               5                   10                  15

Arg Val Thr Ile Thr Cys Ser Gly Ser Ser Ser Asn Ile Gly Asn Asn
            20                  25                  30

Ala Val Asn Trp Tyr Gln Gln Leu Pro Gly Lys Ala Pro Lys Leu Leu
        35                  40                  45

Ile Tyr Ala Ala Gly Gly Cys Gly Pro Asn Gly Phe Cys Gly Ser Gly
    50                  55                  60

Ser Asp Gly Gly Val Cys Pro Arg Ile Leu Met Arg Cys Lys Gln Asp
65                  70                  75                  80

Ser Asp Cys Leu Ala Gly Cys Gly Gly Gln Ser Gly Val Pro Asp Arg
                85                  90                  95

Phe Ser Gly Ser Lys Ser Gly Thr Ser Ala Ser Leu Ala Ile Ser Arg
            100                 105                 110

Leu Gln Ser Glu Asp Glu Ala Asp Tyr Tyr Cys Ala Ala Trp Asp Asp
        115                 120                 125

Ser Leu Asn Ala Tyr Val Phe Gly Thr Gly Thr Lys Val Thr Val Leu
    130                 135                 140

Gly Gln Pro
145

<210> SEQ ID NO 315
<211> LENGTH: 147
<212> TYPE: PRT
<213> ORGANISM: Artificial Sequence
<220> FEATURE:
<223> OTHER INFORMATION: E09 (70274)

<400> SEQUENCE: 315

Gln Ser Val Leu Thr Gln Pro Pro Ser Val Ser Glu Ala Pro Arg Gln
1 5 10 15

Arg Val Thr Ile Thr Cys Ser Gly Ser Ser Ser Asn Ile Gly Asn Asn
20 25 30

Ala Val Asn Trp Tyr Gln Gln Leu Pro Gly Lys Ala Pro Lys Leu Leu
35 40 45

Ile Tyr Ala Ala Gly Gly Cys Gly Pro Asn Gly Phe Cys Gly Ser Gly
50 55 60

Ser Asp Gly Gly Val Cys Pro Arg Ile Leu Met Arg Cys Lys Gln Asp
65 70 75 80

Ser Asp Cys Leu Ala Gly Cys Gly Thr Gln Ser Gly Ile Pro Glu Arg
85 90 95

Phe Ser Gly Ser Lys Ser Gly Thr Ser Ala Ser Leu Ala Ile Ser Gly
100 105 110

Leu Arg Ser Glu Asp Glu Ala Asp Tyr Tyr Cys Ala Ala Trp Asp Asp
115 120 125

Ser Leu Arg Ala Tyr Val Phe Gly Thr Gly Thr Gln Leu Thr Val Leu
130 135 140

Gly Gln Pro
145

<210> SEQ ID NO 316
<211> LENGTH: 147
<212> TYPE: PRT
<213> ORGANISM: Artificial Sequence
<220> FEATURE:
<223> OTHER INFORMATION: F03 (67972)

<400> SEQUENCE: 316

Gln Ser Val Leu Thr Gln Pro Pro Ser Val Ser Glu Ala Pro Arg Gln
1 5 10 15

Arg Val Thr Ile Thr Cys Ser Gly Ser Ser Ser Asn Ile Gly Asn Asn
20 25 30

Ala Val Asn Trp Tyr Gln Gln Leu Pro Gly Arg Ala Pro Lys Leu Leu
35 40 45

Ile Tyr Ala Ala Gly Gly Cys Gly Pro Asn Gly Phe Cys Gly Ser Gly
50 55 60

Gly Asp Gly Gly Val Cys Pro Arg Ile Leu Met Arg Cys Lys Gln Asp
65 70 75 80

Ser Asp Cys Leu Ala Gly Cys Gly Ala His Ser Gly Ile Pro Glu Arg
85 90 95

Phe Ser Gly Ser Lys Ser Gly Thr Ser Ala Ser Leu Ala Ile Ser Gly
100 105 110

Leu Arg Ser Glu Asp Glu Ala Asp Tyr Tyr Cys Ala Ala Trp Asp Asp
115 120 125

Ser Leu Asn Gly Trp Val Phe Gly Gly Gly Thr Lys Val Thr Val Leu

```
    130                 135                 140

Gly Gln Pro
145


<210> SEQ ID NO 317
<211> LENGTH: 147
<212> TYPE: PRT
<213> ORGANISM: Artificial Sequence
<220> FEATURE:
<223> OTHER INFORMATION: G11 (27650)

<400> SEQUENCE: 317

Gln Ser Val Leu Thr Gln Pro Pro Ser Val Ser Glu Ala Pro Arg Gln
1               5                   10                  15

Arg Val Thr Ile Thr Cys Ser Gly Ser Ser Ser Asn Ile Gly Asn Asn
            20                  25                  30

Ala Val Asn Trp Tyr Gln Gln Leu Pro Gly Lys Ala Pro Lys Leu Leu
        35                  40                  45

Ile Tyr Ala Ala Gly Gly Cys Gly Pro Asn Gly Phe Cys Gly Ser Gly
    50                  55                  60

Ser Asp Gly Gly Val Cys Pro Arg Ile Leu Met Arg Cys Lys Gln Asp
65                  70                  75                  80

Ser Asp Cys Leu Ala Gly Cys Gly Gln Ser Ser Gly Val Ser Asp Arg
                85                  90                  95

Phe Ser Gly Ser Lys Ser Gly Thr Ser Ala Thr Leu Asp Ile Thr Gly
            100                 105                 110

Leu Gln Thr Gly Asp Glu Ala Asp Tyr Tyr Cys Gly Thr Trp Asp Asn
        115                 120                 125

Ser Leu Ser Val Gly Val Phe Gly Gly Gly Thr Lys Val Thr Val Leu
    130                 135                 140

Gly Gln Pro
145


<210> SEQ ID NO 318
<211> LENGTH: 50
<212> TYPE: DNA
<213> ORGANISM: Artificial Sequence
<220> FEATURE:
<223> OTHER INFORMATION: Primer 3006

<400> SEQUENCE: 318

tttttgcgg ccgcggtacg tttgatatcc attttggtcc ctccgccgaa                50


<210> SEQ ID NO 319
<211> LENGTH: 219
<212> TYPE: DNA
<213> ORGANISM: Artificial Sequence
<220> FEATURE:
<223> OTHER INFORMATION: CDR1 of IGLV1-36
<220> FEATURE:
<221> NAME/KEY: misc_feature
<222> LOCATION: (73)..(73)
<223> OTHER INFORMATION: V=A, C or G
<220> FEATURE:
<221> NAME/KEY: misc_feature
<222> LOCATION: (74)..(74)
<223> OTHER INFORMATION: N=A, C, G or T
<220> FEATURE:
<221> NAME/KEY: misc_feature
<222> LOCATION: (75)..(75)
<223> OTHER INFORMATION: S=C or G
<220> FEATURE:
<221> NAME/KEY: misc_feature
<222> LOCATION: (76)..(76)
```

<223> OTHER INFORMATION: V=A, C or G
<220> FEATURE:
<221> NAME/KEY: misc_feature
<222> LOCATION: (77)..(77)
<223> OTHER INFORMATION: N=A, C, G or T
<220> FEATURE:
<221> NAME/KEY: misc_feature
<222> LOCATION: (78)..(78)
<223> OTHER INFORMATION: S=C or G
<220> FEATURE:
<221> NAME/KEY: misc_feature
<222> LOCATION: (79)..(79)
<223> OTHER INFORMATION: V=A, C or G
<220> FEATURE:
<221> NAME/KEY: misc_feature
<222> LOCATION: (80)..(80)
<223> OTHER INFORMATION: N=A, C, G or T
<220> FEATURE:
<221> NAME/KEY: misc_feature
<222> LOCATION: (81)..(81)
<223> OTHER INFORMATION: S=C or G
<220> FEATURE:
<221> NAME/KEY: misc_feature
<222> LOCATION: (163)..(163)
<223> OTHER INFORMATION: V=A, C or G
<220> FEATURE:
<221> NAME/KEY: misc_feature
<222> LOCATION: (164)..(164)
<223> OTHER INFORMATION: N=A, C, G or T
<220> FEATURE:
<221> NAME/KEY: misc_feature
<222> LOCATION: (165)..(165)
<223> OTHER INFORMATION: S=C or G
<220> FEATURE:
<221> NAME/KEY: misc_feature
<222> LOCATION: (166)..(166)
<223> OTHER INFORMATION: V=A, C or G
<220> FEATURE:
<221> NAME/KEY: misc_feature
<222> LOCATION: (167)..(167)
<223> OTHER INFORMATION: N=A, C, G or T

<400> SEQUENCE: 319
gctagccagt ctgtgctgac tcagccaccc tcggtgtctg aagcccccag gcagagggtc 60
accatcacgt gtvnsvnsvn stgcccgcgt atcctgatgc gttgcaaaca ggactcagac 120
tgcctggccg gctgcgtatg cggtccgaac ggcttctgcg ggvnsvncaa ttggtaccag 180
cagctcccag gaaccgtcct aggtcagccc gcggccgca 219

<210> SEQ ID NO 320
<211> LENGTH: 73
<212> TYPE: PRT
<213> ORGANISM: Artificial Sequence
<220> FEATURE:
<223> OTHER INFORMATION: CDR1 of IGLV1-36
<220> FEATURE:
<221> NAME/KEY: MISC_FEATURE
<222> LOCATION: (25)..(27)
<223> OTHER INFORMATION: Xaa = any amino acide except for Cys, Tyr, Trp
or Phe
<220> FEATURE:
<221> NAME/KEY: MISC_FEATURE
<222> LOCATION: (55)..(55)
<223> OTHER INFORMATION: Xaa = any amino acide except for Cys, Tyr, Trp
or Phe
<220> FEATURE:
<221> NAME/KEY: MISC_FEATURE
<222> LOCATION: (56)..(56)
<223> OTHER INFORMATION: Xaa = one of the 12 amino acids encoded by
codon VNC where N=A,C, G or T and V= A, C or G.

<400> SEQUENCE: 320

Ala Ser Gln Ser Val Leu Thr Gln Pro Pro Ser Val Ser Glu Ala Pro
1 5 10 15

```
Arg Gln Arg Val Thr Ile Thr Cys Xaa Xaa Xaa Cys Pro Arg Ile Leu
            20                  25                  30

Met Arg Cys Lys Gln Asp Ser Asp Cys Leu Ala Gly Cys Val Cys Gly
        35                  40                  45

Pro Asn Gly Phe Cys Gly Xaa Xaa Asn Trp Tyr Gln Gln Leu Pro Gly
    50                  55                  60

Thr Val Leu Gly Gln Pro Ala Ala Ala
65                  70


<210> SEQ ID NO 321
<211> LENGTH: 215
<212> TYPE: DNA
<213> ORGANISM: Artificial Sequence
<220> FEATURE:
<223> OTHER INFORMATION: CDR1 of IGKV1D-39
<220> FEATURE:
<221> NAME/KEY: misc_feature
<222> LOCATION: (76)..(76)
<223> OTHER INFORMATION: V=A, C or G
<220> FEATURE:
<221> NAME/KEY: misc_feature
<222> LOCATION: (77)..(77)
<223> OTHER INFORMATION: N=A, C, G or T
<220> FEATURE:
<221> NAME/KEY: misc_feature
<222> LOCATION: (78)..(78)
<223> OTHER INFORMATION: S=C or G
<220> FEATURE:
<221> NAME/KEY: misc_feature
<222> LOCATION: (79)..(79)
<223> OTHER INFORMATION: V=A, C or G
<220> FEATURE:
<221> NAME/KEY: misc_feature
<222> LOCATION: (80)..(80)
<223> OTHER INFORMATION: N=A, C, G or T
<220> FEATURE:
<221> NAME/KEY: misc_feature
<222> LOCATION: (81)..(81)
<223> OTHER INFORMATION: S=C or G
<220> FEATURE:
<221> NAME/KEY: misc_feature
<222> LOCATION: (82)..(82)
<223> OTHER INFORMATION: V=A, C or G
<220> FEATURE:
<221> NAME/KEY: misc_feature
<222> LOCATION: (83)..(83)
<223> OTHER INFORMATION: N=A, C, G or T
<220> FEATURE:
<221> NAME/KEY: misc_feature
<222> LOCATION: (84)..(84)
<223> OTHER INFORMATION: S=C or G
<220> FEATURE:
<221> NAME/KEY: misc_feature
<222> LOCATION: (166)..(166)
<223> OTHER INFORMATION: V=A, C or G
<220> FEATURE:
<221> NAME/KEY: misc_feature
<222> LOCATION: (167)..(167)
<223> OTHER INFORMATION: N=A, C, G or T
<220> FEATURE:
<221> NAME/KEY: misc_feature
<222> LOCATION: (168)..(168)
<223> OTHER INFORMATION: S=C or G
<220> FEATURE:
<221> NAME/KEY: misc_feature
<222> LOCATION: (169)..(169)
<223> OTHER INFORMATION: V=A, C or G
<220> FEATURE:
<221> NAME/KEY: misc_feature
<222> LOCATION: (170)..(170)
<223> OTHER INFORMATION: N=A, C, G or T

<400> SEQUENCE: 321
```

```
gctagcgaca tccagatgac ccagtctcca tcctccctgt ctgcatctgt aggagacaga     60

gtcaccatca cgtgtvnsvn svnstgcccg cgtatcctga tgcgttgcaa acaggactca    120

gactgcctgg ccggctgcgt atgcggtccg aacggcttct gcgggvnsvn caattggtat    180

cagcagaaac caggatcaaa cgtaccgcgg ccgca                               215
```

<210> SEQ ID NO 322
<211> LENGTH: 71
<212> TYPE: PRT
<213> ORGANISM: Artificial Sequence
<220> FEATURE:
<223> OTHER INFORMATION: CDR1 of IGKV1D-39
<220> FEATURE:
<221> NAME/KEY: MISC_FEATURE
<222> LOCATION: (26)..(28)
<223> OTHER INFORMATION: Xaa = any amino acide except for Cys, Tyr, Trp or Phe
<220> FEATURE:
<221> NAME/KEY: MISC_FEATURE
<222> LOCATION: (56)..(56)
<223> OTHER INFORMATION: Xaa = any amino acide except for Cys, Tyr, Trp or Phe
<220> FEATURE:
<221> NAME/KEY: MISC_FEATURE
<222> LOCATION: (57)..(57)
<223> OTHER INFORMATION: Xaa = one of the 12 amino acids encoded by codon VNC where N=A,C, G or T and V= A, C or G.

<400> SEQUENCE: 322

```
Ala Ser Asp Ile Gln Met Thr Gln Ser Pro Ser Ser Leu Ser Ala Ser
1               5                   10                  15

Val Gly Asp Arg Val Thr Ile Thr Cys Xaa Xaa Xaa Cys Pro Arg Ile
            20                  25                  30

Leu Met Arg Cys Lys Gln Asp Ser Asp Cys Leu Ala Gly Cys Val Cys
        35                  40                  45

Gly Pro Asn Gly Phe Cys Gly Xaa Xaa Asn Trp Tyr Gln Gln Lys Pro
    50                  55                  60

Ile Lys Arg Thr Ala Ala Ala
65                  70
```

<210> SEQ ID NO 323
<211> LENGTH: 312
<212> TYPE: DNA
<213> ORGANISM: Artificial Sequence
<220> FEATURE:
<223> OTHER INFORMATION: CDR2 of IGLV1-36
<220> FEATURE:
<221> NAME/KEY: misc_feature
<222> LOCATION: (164)..(164)
<223> OTHER INFORMATION: N=A, C, G or T
<220> FEATURE:
<221> NAME/KEY: misc_feature
<222> LOCATION: (165)..(165)
<223> OTHER INFORMATION: S=C or G
<220> FEATURE:
<221> NAME/KEY: misc_feature
<222> LOCATION: (166)..(166)
<223> OTHER INFORMATION: V=A, C or G
<220> FEATURE:
<221> NAME/KEY: misc_feature
<222> LOCATION: (167)..(167)
<223> OTHER INFORMATION: N=A, C, G or T
<220> FEATURE:
<221> NAME/KEY: misc_feature
<222> LOCATION: (168)..(168)
<223> OTHER INFORMATION: S=C or G
<220> FEATURE:
<221> NAME/KEY: misc_feature
<222> LOCATION: (250)..(250)
<223> OTHER INFORMATION: V=A, C or G

```
<220> FEATURE:
<221> NAME/KEY: misc_feature
<222> LOCATION: (251)..(251)
<223> OTHER INFORMATION: N=A, C, G or T
<220> FEATURE:
<221> NAME/KEY: misc_feature
<222> LOCATION: (252)..(252)
<223> OTHER INFORMATION: S=C or G
<220> FEATURE:
<221> NAME/KEY: misc_feature
<222> LOCATION: (253)..(253)
<223> OTHER INFORMATION: V=A, C or G
<220> FEATURE:
<221> NAME/KEY: misc_feature
<222> LOCATION: (254)..(254)
<223> OTHER INFORMATION: N=A, C, G or T
<220> FEATURE:
<221> NAME/KEY: misc_feature
<222> LOCATION: (255)..(255)
<223> OTHER INFORMATION: S=C or G

<400> SEQUENCE: 323

gctagccagt ctgtgctgac tcagccaccc tcggtgtctg aagcccccag gcagagggtc      60

accatcacgt gttctggaag cagctccaac atcggaaata atgctgtaaa ctggtaccag     120

cagctcccag ggaaagcccc taagctcctg atctatgctg cagnsvnstg cccgcgtatc     180

ctgatgcgtt gcaaacagga ctcagactgc ctggccggct gcgtatgcgg tccgaacggc     240

ttctgcgggv nsvnstccgg agtctctgac cgattctctg gctccaccgt cctaggtcag     300

cccgcggccg ca                                                         312


<210> SEQ ID NO 324
<211> LENGTH: 104
<212> TYPE: PRT
<213> ORGANISM: Artificial Sequence
<220> FEATURE:
<223> OTHER INFORMATION: CDR2 of IGLV1-36
<220> FEATURE:
<221> NAME/KEY: MISC_FEATURE
<222> LOCATION: (55)..(55)
<223> OTHER INFORMATION: Xaa = any aminno acid selected from Val, Ala,
      As or Gly
<220> FEATURE:
<221> NAME/KEY: MISC_FEATURE
<222> LOCATION: (56)..(56)
<223> OTHER INFORMATION: Xaa = any aminno acid except for Cys, Tyr, Trp
      or Phe
<220> FEATURE:
<221> NAME/KEY: MISC_FEATURE
<222> LOCATION: (84)..(85)
<223> OTHER INFORMATION: Xaa = any aminno acid except for Cys, Tyr, Trp
      or Phe

<400> SEQUENCE: 324

Ala Ser Gln Ser Val Leu Thr Gln Pro Pro Ser Val Ser Glu Ala Pro
1               5                   10                  15

Arg Gln Arg Val Thr Ile Thr Cys Ser Gly Ser Ser Ser Asn Ile Gly
            20                  25                  30

Asn Asn Ala Val Asn Trp Tyr Gln Gln Leu Pro Gly Lys Ala Pro Lys
        35                  40                  45

Leu Leu Ile Tyr Ala Ala Xaa Xaa Cys Pro Arg Ile Leu Met Arg Cys
    50                  55                  60

Lys Gln Asp Ser Asp Cys Leu Ala Gly Cys Val Cys Gly Pro Asn Gly
65                  70                  75                  80

Phe Cys Gly Xaa Xaa Ser Gly Val Ser Asp Arg Phe Ser Gly Ser Thr
                85                  90                  95

Val Leu Gly Gln Pro Ala Ala Ala
```

100

<210> SEQ ID NO 325
<211> LENGTH: 303
<212> TYPE: DNA
<213> ORGANISM: Artificial Sequence
<220> FEATURE:
<223> OTHER INFORMATION: CDR2 of IGKV1D-39
<220> FEATURE:
<221> NAME/KEY: misc_feature
<222> LOCATION: (161)..(161)
<223> OTHER INFORMATION: N=A, C, G or T
<220> FEATURE:
<221> NAME/KEY: misc_feature
<222> LOCATION: (162)..(162)
<223> OTHER INFORMATION: S=C or G
<220> FEATURE:
<221> NAME/KEY: misc_feature
<222> LOCATION: (163)..(163)
<223> OTHER INFORMATION: V=A, C or G
<220> FEATURE:
<221> NAME/KEY: misc_feature
<222> LOCATION: (164)..(164)
<223> OTHER INFORMATION: N=A, C, G or T
<220> FEATURE:
<221> NAME/KEY: misc_feature
<222> LOCATION: (165)..(165)
<223> OTHER INFORMATION: S=C or G
<220> FEATURE:
<221> NAME/KEY: misc_feature
<222> LOCATION: (247)..(247)
<223> OTHER INFORMATION: V=A, C or G
<220> FEATURE:
<221> NAME/KEY: misc_feature
<222> LOCATION: (248)..(248)
<223> OTHER INFORMATION: N=A, C, G or T
<220> FEATURE:
<221> NAME/KEY: misc_feature
<222> LOCATION: (249)..(249)
<223> OTHER INFORMATION: S=C or G
<220> FEATURE:
<221> NAME/KEY: misc_feature
<222> LOCATION: (250)..(250)
<223> OTHER INFORMATION: V=A, C or G
<220> FEATURE:
<221> NAME/KEY: misc_feature
<222> LOCATION: (251)..(251)
<223> OTHER INFORMATION: N=A, C, G or T
<220> FEATURE:
<221> NAME/KEY: misc_feature
<222> LOCATION: (252)..(252)
<223> OTHER INFORMATION: S=C or G

<400> SEQUENCE: 325
gctagcgaca tccagatgac ccagtctcca tcctccctgt ctgcatctgt aggagacaga 60
gtcaccatca cgtgccgggc aagtcagagc attagcagct atttaaattg gtatcagcag 120
aaaccaggga aagcccctaa gctcctgatc tatgctgcag nsvnstgccc gcgtatcctg 180
atgcgttgca aacaggactc agactgcctg gccggctgcg tatgcggtcc gaacggcttc 240
tgcgggvnsv nstccggagt cccatcaagg ttcagtggca gtatcaaacg taccgcggcc 300
gca 303

<210> SEQ ID NO 326
<211> LENGTH: 101
<212> TYPE: PRT
<213> ORGANISM: Artificial Sequence
<220> FEATURE:
<223> OTHER INFORMATION: CDR2 of IGKV1D-39
<220> FEATURE:
<221> NAME/KEY: MISC_FEATURE
<222> LOCATION: (54)..(54)
<223> OTHER INFORMATION: Xaa = any amino acid selected from Val, Ala, Asp or Gly
<220> FEATURE:
<221> NAME/KEY: MISC_FEATURE
<222> LOCATION: (55)..(55)
<223> OTHER INFORMATION: Xaa = any amino acid except for Cys, Tyr, Trp or Phe
<220> FEATURE:
<221> NAME/KEY: MISC_FEATURE
<222> LOCATION: (83)..(84)
<223> OTHER INFORMATION: Xaa = any amino acid except for Cys, Tyr, Trp or Phe

<400> SEQUENCE: 326

```
Ala Ser Asp Ile Gln Met Thr Gln Ser Pro Ser Ser Leu Ser Ala Ser
1               5                   10                  15

Val Gly Asp Arg Val Thr Ile Thr Cys Arg Ala Ser Gln Ser Ile Ser
            20                  25                  30

Ser Tyr Leu Asn Trp Tyr Gln Gln Lys Pro Gly Lys Ala Pro Lys Leu
        35                  40                  45

Leu Ile Tyr Ala Ala Xaa Xaa Cys Pro Arg Ile Leu Met Arg Cys Lys
    50                  55                  60

Gln Asp Ser Asp Cys Leu Ala Gly Cys Val Cys Gly Pro Asn Gly Phe
65                  70                  75                  80

Cys Gly Xaa Xaa Ser Gly Val Pro Ser Arg Phe Ser Gly Ser Ile Lys
                85                  90                  95

Arg Thr Ala Ala Ala
            100
```

<210> SEQ ID NO 327
<211> LENGTH: 23
<212> TYPE: PRT
<213> ORGANISM: Artificial Sequence
<220> FEATURE:
<223> OTHER INFORMATION: insertion of EETI-II donor knottin into VH CDR1

<400> SEQUENCE: 327

```
Cys Ala Ala Ser Gly Phe Thr Phe Ser Ser Tyr Ala Met Ser Trp Val
1               5                   10                  15

Arg Gln Ala Pro Gly Lys Gly
            20
```

<210> SEQ ID NO 328
<211> LENGTH: 49
<212> TYPE: PRT
<213> ORGANISM: Artificial Sequence
<220> FEATURE:
<223> OTHER INFORMATION: insertion of EETI-II donor knottin into VH CDR1
<220> FEATURE:
<221> NAME/KEY: MISC_FEATURE
<222> LOCATION: (10)..(11)
<223> OTHER INFORMATION: Xaa = randomising residue
<220> FEATURE:
<221> NAME/KEY: MISC_FEATURE
<222> LOCATION: (39)..(40)
<223> OTHER INFORMATION: Xaa = randomising residue

<400> SEQUENCE: 328

```
Cys Ala Ala Ser Gly Phe Thr Phe Ser Xaa Xaa Cys Pro Arg Ile Leu
1               5                   10                  15

Met Arg Cys Lys Gln Asp Ser Asp Cys Leu Ala Gly Cys Val Cys Gly
            20                  25                  30

Pro Asn Gly Phe Cys Gly Xaa Xaa Trp Val Arg Gln Ala Pro Gly Lys
        35                  40                  45

Gly
```

<210> SEQ ID NO 329
<211> LENGTH: 35
<212> TYPE: PRT
<213> ORGANISM: Artificial Sequence
<220> FEATURE:
<223> OTHER INFORMATION: insertion of EETI-II donor knottin into VH CDR2

<400> SEQUENCE: 329

Pro Gly Lys Gly Leu Glu Trp Val Ser Ala Ile Ser Gly Ser Gly Gly
1 5 10 15

Ser Thr Tyr Tyr Ala Asp Ser Val Lys Gly Arg Phe Thr Ile Ser Arg
20 25 30

Asp Asn Thr
35

<210> SEQ ID NO 330
<211> LENGTH: 49
<212> TYPE: PRT
<213> ORGANISM: Artificial Sequence
<220> FEATURE:
<223> OTHER INFORMATION: insertion of EETI-II donor knottin into VH CDR2
<220> FEATURE:
<221> NAME/KEY: MISC_FEATURE
<222> LOCATION: (10)..(11)
<223> OTHER INFORMATION: Xaa = randomising residue
<220> FEATURE:
<221> NAME/KEY: MISC_FEATURE
<222> LOCATION: (39)..(40)
<223> OTHER INFORMATION: Xaa = randomising residue

<400> SEQUENCE: 330

Pro Gly Lys Gly Leu Glu Trp Val Ser Xaa Xaa Cys Pro Arg Ile Leu
1 5 10 15

Met Arg Cys Lys Gln Asp Ser Asp Cys Leu Ala Gly Cys Val Cys Gly
20 25 30

Pro Asn Gly Phe Cys Gly Xaa Xaa Arg Phe Thr Ile Ser Arg Asp Asn
35 40 45

Thr

<210> SEQ ID NO 331
<211> LENGTH: 30
<212> TYPE: PRT
<213> ORGANISM: Artificial Sequence
<220> FEATURE:
<223> OTHER INFORMATION: insertion of EETI-II donor knottin into VH CDR3

<400> SEQUENCE: 331

Asp Thr Ala Phe Tyr Tyr Cys Val Asp Phe Gly Pro Gly Tyr Gly Thr
1 5 10 15

Gly Trp Phe Asp Tyr Trp Gly Pro Gly Thr Leu Val Thr Val
20 25 30

<210> SEQ ID NO 332
<211> LENGTH: 49
<212> TYPE: PRT
<213> ORGANISM: Artificial Sequence
<220> FEATURE:
<223> OTHER INFORMATION: insertion of EETI-II donor knottin into VH CDR3
<220> FEATURE:
<221> NAME/KEY: MISC_FEATURE
<222> LOCATION: (10)..(11)
<223> OTHER INFORMATION: Xaa = randomising residue
<220> FEATURE:
<221> NAME/KEY: MISC_FEATURE
<222> LOCATION: (39)..(40)

<223> OTHER INFORMATION: Xaa = randomising residue

<400> SEQUENCE: 332

Asp Thr Ala Phe Tyr Tyr Cys Val Asp Xaa Xaa Cys Pro Arg Ile Leu
1               5                   10                  15

Met Arg Cys Lys Gln Asp Ser Asp Cys Leu Ala Gly Cys Val Cys Gly
            20                  25                  30

Pro Asn Gly Phe Cys Gly Xaa Xaa Trp Gly Pro Gly Thr Leu Val Thr
        35                  40                  45

Val

<210> SEQ ID NO 333
<211> LENGTH: 29
<212> TYPE: PRT
<213> ORGANISM: Artificial Sequence
<220> FEATURE:
<223> OTHER INFORMATION: insertion of EETI-II donor knottin into VL CDR1

<400> SEQUENCE: 333

Val Gly Asp Arg Val Thr Ile Thr Cys Arg Ala Ser Gln Ser Ile Ser
1               5                   10                  15

Ser Tyr Leu Asn Trp Tyr Gln Gln Lys Pro Gly Lys Ala
            20                  25

<210> SEQ ID NO 334
<211> LENGTH: 49
<212> TYPE: PRT
<213> ORGANISM: Artificial Sequence
<220> FEATURE:
<223> OTHER INFORMATION: insertion of EETI-II donor knottin into VL CDR1
<220> FEATURE:
<221> NAME/KEY: MISC_FEATURE
<222> LOCATION: (10)..(11)
<223> OTHER INFORMATION: Xaa = randomising residue
<220> FEATURE:
<221> NAME/KEY: MISC_FEATURE
<222> LOCATION: (39)..(40)
<223> OTHER INFORMATION: Xaa = randomising residue

<400> SEQUENCE: 334

Val Gly Asp Arg Val Thr Ile Thr Cys Xaa Xaa Cys Pro Arg Ile Leu
1               5                   10                  15

Met Arg Cys Lys Gln Asp Ser Asp Cys Leu Ala Gly Cys Val Cys Gly
            20                  25                  30

Pro Asn Gly Phe Cys Gly Xaa Xaa Trp Tyr Gln Gln Lys Pro Gly Lys
        35                  40                  45

Ala

<210> SEQ ID NO 335
<211> LENGTH: 24
<212> TYPE: PRT
<213> ORGANISM: Artificial Sequence
<220> FEATURE:
<223> OTHER INFORMATION: insertion of EETI-II donor knottin into VL CDR2

<400> SEQUENCE: 335

Lys Ala Pro Lys Leu Leu Ile His Asp Ala Ser Ser Leu Gln Ser Gly
1               5                   10                  15

Val Pro Ser Arg Phe Ser Gly Ser
            20

<210> SEQ ID NO 336
<211> LENGTH: 49

<212> TYPE: PRT
<213> ORGANISM: Artificial Sequence
<220> FEATURE:
<223> OTHER INFORMATION: insertion of EETI-II donor knottin into VL CDR2
<220> FEATURE:
<221> NAME/KEY: MISC_FEATURE
<222> LOCATION: (10)..(11)
<223> OTHER INFORMATION: Xaa = randomising residue
<220> FEATURE:
<221> NAME/KEY: MISC_FEATURE
<222> LOCATION: (39)..(40)
<223> OTHER INFORMATION: Xaa = randomising residue

<400> SEQUENCE: 336

Lys Ala Pro Lys Leu Leu Ile His Asp Xaa Xaa Cys Pro Arg Ile Leu
1               5                   10                  15

Met Arg Cys Lys Gln Asp Ser Asp Cys Leu Ala Gly Cys Val Cys Gly
            20                  25                  30

Pro Asn Gly Phe Cys Gly Xaa Xaa Gly Val Pro Ser Arg Phe Ser Gly
        35                  40                  45

Ser

<210> SEQ ID NO 337
<211> LENGTH: 27
<212> TYPE: PRT
<213> ORGANISM: Artificial Sequence
<220> FEATURE:
<223> OTHER INFORMATION: insertion of EETI-II donor knottin into VL CDR3

<400> SEQUENCE: 337

Pro Glu Asp Phe Ala Thr Tyr Tyr Cys Gln Gln Ser Phe Ser Ile Pro
1               5                   10                  15

Leu Thr Phe Gly Gly Gly Thr Lys Met Asp Ile
            20                  25

<210> SEQ ID NO 338
<211> LENGTH: 49
<212> TYPE: PRT
<213> ORGANISM: Artificial Sequence
<220> FEATURE:
<223> OTHER INFORMATION: insertion of EETI-II donor knottin into VL CDR3
<220> FEATURE:
<221> NAME/KEY: MISC_FEATURE
<222> LOCATION: (10)..(11)
<223> OTHER INFORMATION: Xaa = randomising residue
<220> FEATURE:
<221> NAME/KEY: MISC_FEATURE
<222> LOCATION: (39)..(40)
<223> OTHER INFORMATION: Xaa = randomising residue

<400> SEQUENCE: 338

Pro Glu Asp Phe Ala Thr Tyr Tyr Cys Xaa Xaa Cys Pro Arg Ile Leu
1               5                   10                  15

Met Arg Cys Lys Gln Asp Ser Asp Cys Leu Ala Gly Cys Val Cys Gly
            20                  25                  30

Pro Asn Gly Phe Cys Gly Xaa Xaa Phe Gly Gly Gly Thr Lys Met Asp
        35                  40                  45

Ile

<210> SEQ ID NO 339
<211> LENGTH: 48
<212> TYPE: PRT
<213> ORGANISM: Artificial Sequence
<220> FEATURE:
<223> OTHER INFORMATION: insertion of EETI-II donor knottin into VL CDR2

<400> SEQUENCE: 339

Ala Pro Lys Leu Leu Ile Tyr Ala Ala Gly Val Cys Pro Arg Ile Leu
1 5 10 15

Met Arg Cys Lys Gln Asp Ser Asp Cys Leu Ala Gly Cys Val Cys Gly
20 25 30

Pro Asn Gly Phe Cys Gly Ser Arg Ser Gly Val Pro Ser Arg Phe Ser
35 40 45

<210> SEQ ID NO 340
<211> LENGTH: 48
<212> TYPE: PRT
<213> ORGANISM: Artificial Sequence
<220> FEATURE:
<223> OTHER INFORMATION: insertion of EETI-II donor knottin into VL CDR2
<220> FEATURE:
<221> NAME/KEY: MISC_FEATURE
<222> LOCATION: (10)..(11)
<223> OTHER INFORMATION: Xaa = randomising residue
<220> FEATURE:
<221> NAME/KEY: MISC_FEATURE
<222> LOCATION: (39)..(40)
<223> OTHER INFORMATION: Xaa = randomising residue

<400> SEQUENCE: 340

Ala Pro Lys Leu Leu Ile Tyr Ala Ala Xaa Xaa Cys Pro Arg Ile Leu
1 5 10 15

Met Arg Cys Lys Gln Asp Ser Asp Cys Leu Ala Gly Cys Val Cys Gly
20 25 30

Pro Asn Gly Phe Cys Gly Xaa Xaa Ser Gly Val Pro Ser Arg Phe Ser
35 40 45

<210> SEQ ID NO 341
<211> LENGTH: 99
<212> TYPE: DNA
<213> ORGANISM: Artificial Sequence
<220> FEATURE:
<223> OTHER INFORMATION: knottin construct EET 5-3

<400> SEQUENCE: 341
tgcggtccga acggcttctg cggaagcggc agcgatggcg gtgtgtgccc gcgtatcctg 60
atgcgttgca aacaggactc agactgcctg gccggctgc 99

<210> SEQ ID NO 342
<211> LENGTH: 33
<212> TYPE: PRT
<213> ORGANISM: Artificial Sequence
<220> FEATURE:
<223> OTHER INFORMATION: knottin construct EET 5-3

<400> SEQUENCE: 342

Cys Gly Pro Asn Gly Phe Cys Gly Ser Gly Ser Asp Gly Gly Val Cys
1 5 10 15

Pro Arg Ile Leu Met Arg Cys Lys Gln Asp Ser Asp Cys Leu Ala Gly
20 25 30

Cys

<210> SEQ ID NO 343
<211> LENGTH: 25
<212> TYPE: PRT
<213> ORGANISM: Artificial Sequence
<220> FEATURE:
<223> OTHER INFORMATION: V lambda recipient domain at CDR1 before
insertion of the knottin

<400> SEQUENCE: 343

Arg Val Thr Ile Thr Cys Ser Gly Ser Ser Ser Asn Ile Gly Asn Asn
1 5 10 15

Ala Val Asn Trp Tyr Gln Gln Leu Pro
20 25

<210> SEQ ID NO 344
<211> LENGTH: 51
<212> TYPE: PRT
<213> ORGANISM: Artificial Sequence
<220> FEATURE:
<223> OTHER INFORMATION: V lambda recipient domain at CDR1 after insertion of the 5-3 EETI-II donor
<220> FEATURE:
<221> NAME/KEY: misc_feature
<222> LOCATION: (7)..(9)
<223> OTHER INFORMATION: Xaa can be any naturally occurring amino acid
<220> FEATURE:
<221> NAME/KEY: MISC_FEATURE
<222> LOCATION: (43)..(43)
<223> OTHER INFORMATION: Xaa represents the amino acids encoded by the codon VNC (encoding 12 amino acids) or VNS encoding 16 amino acids in total. (V=A, C or G and S=C or G)
<220> FEATURE:
<221> NAME/KEY: misc_feature
<222> LOCATION: (44)..(44)
<223> OTHER INFORMATION: Xaa can be any naturally occurring amino acid

<400> SEQUENCE: 344

Arg Val Thr Ile Thr Cys Xaa Xaa Xaa Cys Gly Pro Asn Gly Phe Cys
1 5 10 15

Gly Ser Gly Ser Asp Gly Gly Val Cys Pro Arg Ile Leu Met Arg Cys
20 25 30

Lys Gln Asp Ser Asp Cys Leu Ala Gly Cys Xaa Xaa Asn Trp Tyr Gln
35 40 45

Gln Leu Pro
50

<210> SEQ ID NO 345
<211> LENGTH: 52
<212> TYPE: PRT
<213> ORGANISM: Artificial Sequence
<220> FEATURE:
<223> OTHER INFORMATION: V lambda recipient domain at CDR1after insertion of the 5-3 EETI-II donor.
<220> FEATURE:
<221> NAME/KEY: MISC_FEATURE
<222> LOCATION: (8)..(9)
<223> OTHER INFORMATION: Xaa = any naturally occurring amino acid
<220> FEATURE:
<221> NAME/KEY: MISC_FEATURE
<222> LOCATION: (10)..(10)
<223> OTHER INFORMATION: Xaa represents the amino acids encoded by the codon VNC (encoding 12 amino acids) or VNS encoding 16 amino acids in total. (V=A, C or G and S=C or G)
<220> FEATURE:
<221> NAME/KEY: MISC_FEATURE
<222> LOCATION: (44)..(44)
<223> OTHER INFORMATION: Xaa represents the amino acids encoded by the codon VNC (encoding 12 amino acids) or VNS encoding 16 amino acids in total. (V=A, C or G and S=C or G)
<220> FEATURE:
<221> NAME/KEY: MISC_FEATURE
<222> LOCATION: (45)..(45)
<223> OTHER INFORMATION: Xaa = any naturally occurring amino acid

<400> SEQUENCE: 345

Arg Val Thr Ile Thr Cys Gly Xaa Xaa Xaa Cys Gly Pro Asn Gly Phe
1 5 10 15

Cys Gly Ser Gly Ser Asp Gly Gly Val Cys Pro Arg Ile Leu Met Arg
            20                  25                  30

Cys Lys Gln Asp Ser Asp Cys Leu Ala Gly Cys Xaa Xaa Asn Trp Tyr
        35                  40                  45

Gln Gln Leu Pro
    50

<210> SEQ ID NO 346
<211> LENGTH: 19
<212> TYPE: PRT
<213> ORGANISM: Artificial Sequence
<220> FEATURE:
<223> OTHER INFORMATION: V lambda recipient domain at CDR2 before donor insertion

<400> SEQUENCE: 346

Lys Leu Leu Ile Tyr Tyr Asp Asp Leu Leu Pro Ser Gly Val Ser Asp
1               5                   10                  15

Arg Phe Ser

<210> SEQ ID NO 347
<211> LENGTH: 53
<212> TYPE: PRT
<213> ORGANISM: Artificial Sequence
<220> FEATURE:
<223> OTHER INFORMATION: V lambda recipient domain at CDR2 after insertion of the EETI-II donor
<220> FEATURE:
<221> NAME/KEY: MISC_FEATURE
<222> LOCATION: (8)..(8)
<223> OTHER INFORMATION: Xaa means any amino acid from Val, Ala, Asp, Gly or Glu
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (44)..(45)
<223> OTHER INFORMATION: Xaa can be any naturally occurring amino acid

<400> SEQUENCE: 347

Lys Leu Leu Ile Tyr Ala Ala Glx Xaa Cys Gly Pro Asn Gly Phe Cys
1               5                   10                  15

Gly Ser Gly Ser Asp Gly Gly Val Cys Pro Arg Ile Leu Met Arg Cys
            20                  25                  30

Lys Gln Asp Ser Asp Cys Leu Ala Gly Cys Gly Xaa Xaa Ser Gly Val
        35                  40                  45

Ser Asp Arg Phe Ser
    50

<210> SEQ ID NO 348
<211> LENGTH: 218
<212> TYPE: DNA
<213> ORGANISM: Artificial Sequence
<220> FEATURE:
<223> OTHER INFORMATION: sequence of the construct arising from insertion of the 5-3 EETI-II knottin donor into either CDR1
<220> FEATURE:
<221> NAME/KEY: misc_feature
<222> LOCATION: (73)..(73)
<223> OTHER INFORMATION: V=A, C or G
<220> FEATURE:
<221> NAME/KEY: misc_feature
<222> LOCATION: (74)..(74)
<223> OTHER INFORMATION: N=A, C, G or T
<220> FEATURE:
<221> NAME/KEY: misc_feature
<222> LOCATION: (75)..(75)
<223> OTHER INFORMATION: S=C or G
<220> FEATURE:
<221> NAME/KEY: misc_feature
<222> LOCATION: (76)..(76)
<223> OTHER INFORMATION: V=A, C or G
<220> FEATURE:
<221> NAME/KEY: misc_feature
<222> LOCATION: (77)..(77)
<223> OTHER INFORMATION: N=A, C, G or T
<220> FEATURE:
<221> NAME/KEY: misc_feature
<222> LOCATION: (78)..(78)
<223> OTHER INFORMATION: S=C or G
<220> FEATURE:
<221> NAME/KEY: misc_feature
<222> LOCATION: (79)..(79)
<223> OTHER INFORMATION: V=A, C or G
<220> FEATURE:
<221> NAME/KEY: misc_feature
<222> LOCATION: (80)..(80)
<223> OTHER INFORMATION: N=A, C, G or T
<220> FEATURE:
<221> NAME/KEY: misc_feature
<222> LOCATION: (81)..(81)
<223> OTHER INFORMATION: S=C or G
<220> FEATURE:
<221> NAME/KEY: misc_feature
<222> LOCATION: (181)..(181)
<223> OTHER INFORMATION: V=A, C or G
<220> FEATURE:
<221> NAME/KEY: misc_feature
<222> LOCATION: (182)..(182)
<223> OTHER INFORMATION: N=A, C, G or T
<220> FEATURE:
<221> NAME/KEY: misc_feature
<222> LOCATION: (183)..(183)
<223> OTHER INFORMATION: S=C or G
<220> FEATURE:
<221> NAME/KEY: misc_feature
<222> LOCATION: (184)..(184)
<223> OTHER INFORMATION: V=A, C or G
<220> FEATURE:
<221> NAME/KEY: misc_feature
<222> LOCATION: (185)..(185)
<223> OTHER INFORMATION: N=A, C, G or T

<400> SEQUENCE: 348
gctagccagt ctgtgctgac tcagccaccc tcggtgtctg aagcccccag gcagagggtc 60
accatcacgt gtvnsvnsvn stgcggtccg aacggcttct gcggaagcgg cagcgatggc 120
ggtgtgtgcc cgcgtatcct gatgcgttgc aaacaggact cagactgcct ggccggctgc 180
vnsvncaatt ggtaccagca gctcccagga gcggccgc 218

<210> SEQ ID NO 349
<211> LENGTH: 70
<212> TYPE: PRT
<213> ORGANISM: Artificial Sequence
<220> FEATURE:
<223> OTHER INFORMATION: sequence of the construct arising from
insertion of the 5-3 EETI-II knottin donor into either CDR1
<220> FEATURE:
<221> NAME/KEY: MISC_FEATURE
<222> LOCATION: (25)..(27)
<223> OTHER INFORMATION: Xaa = any amino acid except for Cys, Tyr, Trp
or Phe
<220> FEATURE:
<221> NAME/KEY: MISC_FEATURE
<222> LOCATION: (61)..(61)
<223> OTHER INFORMATION: Xaa = any amino acid except for Cys, Tyr, Trp
or Phe
<220> FEATURE:
<221> NAME/KEY: MISC_FEATURE
<222> LOCATION: (62)..(62)
<223> OTHER INFORMATION: Xaa = one of the 12 amino acids encoded by codon VNC (where V=A, C or G and N=A, C, G or T)

<400> SEQUENCE: 349

```
Ala Ser Gln Ser Val Leu Thr Gln Pro Pro Ser Val Ser Glu Ala Pro
1               5                   10                  15

Arg Gln Arg Val Thr Ile Thr Cys Xaa Xaa Xaa Cys Gly Pro Asn Gly
            20                  25                  30

Phe Cys Gly Ser Gly Ser Asp Gly Gly Val Cys Pro Arg Ile Leu Met
        35                  40                  45

Arg Cys Lys Gln Asp Ser Asp Cys Leu Ala Gly Cys Xaa Xaa Asn Trp
    50                  55                  60

Tyr Gln Gln Leu Pro Gly
65                  70
```

<210> SEQ ID NO 350
<211> LENGTH: 332
<212> TYPE: DNA
<213> ORGANISM: Artificial Sequence
<220> FEATURE:
<223> OTHER INFORMATION: sequence of the construct arising from insertion of the 5-3 EETI-II knottin donor into either CDR2 of IGLV1-36
<220> FEATURE:
<221> NAME/KEY: misc_feature
<222> LOCATION: (164)..(164)
<223> OTHER INFORMATION: N=A, C, G or T
<220> FEATURE:
<221> NAME/KEY: misc_feature
<222> LOCATION: (165)..(165)
<223> OTHER INFORMATION: S=C or G
<220> FEATURE:
<221> NAME/KEY: misc_feature
<222> LOCATION: (166)..(166)
<223> OTHER INFORMATION: V=A, C or G
<220> FEATURE:
<221> NAME/KEY: misc_feature
<222> LOCATION: (167)..(167)
<223> OTHER INFORMATION: N=A, C, G or T
<220> FEATURE:
<221> NAME/KEY: misc_feature
<222> LOCATION: (168)..(168)
<223> OTHER INFORMATION: S=C or G
<220> FEATURE:
<221> NAME/KEY: misc_feature
<222> LOCATION: (271)..(271)
<223> OTHER INFORMATION: V=A, C or G
<220> FEATURE:
<221> NAME/KEY: misc_feature
<222> LOCATION: (272)..(272)
<223> OTHER INFORMATION: N=A, C, G or T
<220> FEATURE:
<221> NAME/KEY: misc_feature
<222> LOCATION: (273)..(273)
<223> OTHER INFORMATION: S=C or G
<220> FEATURE:
<221> NAME/KEY: misc_feature
<222> LOCATION: (274)..(274)
<223> OTHER INFORMATION: V=A, C or G
<220> FEATURE:
<221> NAME/KEY: misc_feature
<222> LOCATION: (275)..(275)
<223> OTHER INFORMATION: N=A, C, G or T
<220> FEATURE:
<221> NAME/KEY: misc_feature
<222> LOCATION: (276)..(276)
<223> OTHER INFORMATION: S=C or G

<400> SEQUENCE: 350

```
gctagccagt ctgtgctgac tcagccaccc tcggtgtctg aagcccccag gcagagggtc     60

accatcacgt gttctggaag cagctccaac atcggaaata atgctgtaaa ctggtaccag    120
```

```
cagctcccag ggaaagcccc taagctcctg atctatgctg cagnsvnstg cggtccgaac    180

ggcttctgcg gaagcggcag cgatggcggt gtgtgcccgc gtatcctgat gcgttgcaaa    240

caggactcag actgcctggc cggctgcggg vnsvnstccg gagtctctga ccgattctct    300

ggctccaccg tcctaggtca gcccgcggcc gc                                  332
```

```
<210> SEQ ID NO 351
<211> LENGTH: 108
<212> TYPE: PRT
<213> ORGANISM: Artificial Sequence
<220> FEATURE:
<223> OTHER INFORMATION: sequence of the construct arising from
      insertion of the 5-3 EETI-II knottin donor into CDR2 of IGLV1-36
<220> FEATURE:
<221> NAME/KEY: MISC_FEATURE
<222> LOCATION: (55)..(55)
<223> OTHER INFORMATION: Glx = any amino acid selected from Val, Ala,
      Asp, Gly or Glu
<220> FEATURE:
<221> NAME/KEY: MISC_FEATURE
<222> LOCATION: (56)..(56)
<223> OTHER INFORMATION: Xaa = any amino acid except for Cys, Tyr, Trp
      or Phe
<220> FEATURE:
<221> NAME/KEY: MISC_FEATURE
<222> LOCATION: (91)..(92)
<223> OTHER INFORMATION: Xaa = any amino acid except for Cys, Tyr, Trp
      or Phe

<400> SEQUENCE: 351

Ala Ser Gln Ser Val Leu Thr Gln Pro Pro Ser Val Ser Glu Ala Pro
1               5                   10                  15

Arg Gln Arg Val Thr Ile Thr Cys Ser Gly Ser Ser Ser Asn Ile Gly
            20                  25                  30

Asn Asn Ala Val Asn Trp Tyr Gln Gln Leu Pro Gly Lys Ala Pro Lys
        35                  40                  45

Leu Leu Ile Tyr Ala Ala Glx Xaa Cys Gly Pro Asn Gly Phe Cys Gly
    50                  55                  60

Ser Gly Ser Asp Gly Gly Val Cys Pro Arg Ile Leu Met Arg Cys Lys
65                  70                  75                  80

Gln Asp Ser Asp Cys Leu Ala Gly Cys Gly Xaa Xaa Ser Gly Val Ser
                85                  90                  95

Asp Arg Phe Ser Gly Ser Thr Val Leu Gly Gln Pro
            100                 105
```

```
<210> SEQ ID NO 352
<211> LENGTH: 593
<212> TYPE: DNA
<213> ORGANISM: Artificial Sequence
<220> FEATURE:
<223> OTHER INFORMATION: sequence of synthetic single chain Fv genes
      used in KnotBody construction

<400> SEQUENCE: 352

gccatggctg aagtccaact ggtcgaaagc ggtggtggtc tggtgcgtcc gggcggctcc     60

ctgcgtctgt cgtgtgcggc gtcgggtttt acctttagct cttatgcgat gagctgggtt    120

cgtcaggctc cgggtaaagg cctggaatgg gtctccgcaa ttagtggttc cggcggttcg    180

acgtattacg ctgatagcgt gaaaggccgt ttcaccatct ctcgcgacaa cacgaaaaat    240

agtctgtacc tgcaaatgac ctctctgcgc gcagatgaca cggcttttta ttactgcgtt    300

gatttcggtc cgggctatgg taccggctgg tttgactact ggggtccggg caccctggtg    360

accgtctcga gtggtggagg cggttcaggc ggaggtggct ctggcggtgg cgctagccag    420
```

tctgtgctga ctcagccacc ctcggtgtct gaagccccca ggcagagggt caccatcacg 480
tgttctggaa gcagctccaa catcggaaat aatgctgtaa actggtacca gcagctccca 540
gggaaagccc ctaagctcct gatctatgct gcaggtgtgc tgggtgcggc cgc 593

<210> SEQ ID NO 353
<211> LENGTH: 194
<212> TYPE: PRT
<213> ORGANISM: Artificial Sequence
<220> FEATURE:
<223> OTHER INFORMATION: sequence of synthetic single chain Fv genes used in KnotBody construction

<400> SEQUENCE: 353

Ala Met Ala Glu Val Gln Leu Val Glu Ser Gly Gly Gly Leu Val Arg
1 5 10 15

Pro Gly Gly Ser Leu Arg Leu Ser Cys Ala Ala Ser Gly Phe Thr Phe
20 25 30

Ser Ser Tyr Ala Met Ser Trp Val Arg Gln Ala Pro Gly Lys Gly Leu
35 40 45

Glu Trp Val Ser Ala Ile Ser Gly Ser Gly Gly Ser Thr Tyr Tyr Ala
50 55 60

Asp Ser Val Lys Gly Arg Phe Thr Ile Ser Arg Asp Asn Thr Lys Asn
65 70 75 80

Ser Leu Tyr Leu Gln Met Thr Ser Leu Arg Ala Asp Asp Thr Ala Phe
85 90 95

Tyr Tyr Cys Val Asp Phe Gly Pro Gly Tyr Gly Thr Gly Trp Phe Asp
100 105 110

Tyr Trp Gly Pro Gly Thr Leu Val Thr Val Ser Ser Gly Gly Gly Gly
115 120 125

Ser Gly Gly Gly Gly Ser Gly Gly Gly Ala Ser Gln Ser Val Leu Thr
130 135 140

Gln Pro Pro Ser Val Ser Glu Ala Pro Arg Gln Arg Val Thr Ile Thr
145 150 155 160

Cys Ser Gly Ser Ser Ser Asn Ile Gly Asn Asn Ala Val Asn Trp Tyr
165 170 175

Gln Gln Leu Pro Gly Lys Ala Pro Lys Leu Leu Ile Tyr Ala Ala Gly
180 185 190

Ala Ala

<210> SEQ ID NO 354
<211> LENGTH: 590
<212> TYPE: DNA
<213> ORGANISM: Artificial Sequence
<220> FEATURE:
<223> OTHER INFORMATION: sequence of synthetic single chain Fv genes used in KnotBody construction

<400> SEQUENCE: 354
gccatggctg aagtccaact ggtcgaaagc ggtggtggtc tggtgcgtcc gggcggctcc 60
ctgcgtctgt cgtgtgcggc gtcgggtttt acctttagct cttatgcgat gagctgggtt 120
cgtcaggctc cgggtaaagg cctggaatgg gtctccgcaa ttagtggttc cggcggttcg 180
acgtattacg ctgatagcgt gaaaggccgt ttcaccatct ctcgcgacaa cacgaaaaat 240
agtctgtacc tgcaaatgac ctctctgcgc gcagatgaca cggcttttta ttactgcgtt 300
gatttcggtc cgggctatgg taccggctgg tttgactact ggggtccggg caccctggtg 360
accgtctcga gtggtggagg cggttcaggc ggaggtggct ctggcggtgg cgctagcgac 420
atccagatga cccagtctcc atcctccctg tctgcatctg taggagacag agtcaccatc 480
acgtgccggg caagtcagag cattagcagc tatttaaatt ggtatcagca gaaaccaggg 540
aaagccccta agctcctgat ctatgctgca ggtgtgctgg gtgcggccgc 590

<210> SEQ ID NO 355
<211> LENGTH: 196
<212> TYPE: PRT
<213> ORGANISM: Artificial Sequence
<220> FEATURE:
<223> OTHER INFORMATION: sequence of synthetic single chain Fv genes used in KnotBody construction

<400> SEQUENCE: 355

Ala Met Ala Glu Val Gln Leu Val Glu Ser Gly Gly Gly Leu Val Arg
1 5 10 15

Pro Gly Gly Ser Leu Arg Leu Ser Cys Ala Ala Ser Gly Phe Thr Phe
20 25 30

Ser Ser Tyr Ala Met Ser Trp Val Arg Gln Ala Pro Gly Lys Gly Leu
35 40 45

Glu Trp Val Ser Ala Ile Ser Gly Ser Gly Gly Ser Thr Tyr Tyr Ala
50 55 60

Asp Ser Val Lys Gly Arg Phe Thr Ile Ser Arg Asp Asn Thr Lys Asn
65 70 75 80

Ser Leu Tyr Leu Gln Met Thr Ser Leu Arg Ala Asp Asp Thr Ala Phe
85 90 95

Tyr Tyr Cys Val Asp Phe Gly Pro Gly Tyr Gly Thr Gly Trp Phe Asp
100 105 110

Tyr Trp Gly Pro Gly Thr Leu Val Thr Val Ser Ser Gly Gly Gly Gly
115 120 125

Ser Gly Gly Gly Gly Ser Gly Gly Gly Ala Ser Asp Ile Gln Met Thr
130 135 140

Gln Ser Pro Ser Ser Leu Ser Ala Ser Val Gly Asp Arg Val Thr Ile
145 150 155 160

Thr Cys Arg Ala Ser Gln Ser Ile Ser Ser Tyr Leu Asn Trp Tyr Gln
165 170 175

Gln Lys Pro Gly Lys Ala Pro Lys Leu Leu Ile Tyr Ala Ala Gly Val
180 185 190

Leu Gly Ala Ala
195

<210> SEQ ID NO 356
<211> LENGTH: 84
<212> TYPE: DNA
<213> ORGANISM: Artificial Sequence
<220> FEATURE:
<223> OTHER INFORMATION: sequence of knottin donor EETI-II

<400> SEQUENCE: 356
ggctgcccgc gtatcctgat gcgttgcaaa caggactcag actgcctggc cggctgcgta 60
tgcggtccga acggcttctg cggg 84

<210> SEQ ID NO 357
<211> LENGTH: 28
<212> TYPE: PRT
<213> ORGANISM: Artificial Sequence
<220> FEATURE:
<223> OTHER INFORMATION: sequence of knottin donor EETI-II

<400> SEQUENCE: 357

Gly Cys Pro Arg Ile Leu Met Arg Cys Lys Gln Asp Ser Asp Cys Leu
1 5 10 15

Ala Gly Cys Val Cys Gly Pro Asn Gly Phe Cys Gly
20 25

<210> SEQ ID NO 358
<211> LENGTH: 27
<212> TYPE: PRT
<213> ORGANISM: Artificial Sequence
<220> FEATURE:
<223> OTHER INFORMATION: a representation of the insertion of EETI-II donor into CDR1 or CDR2 of the lambda germline gene IGLV1-36

<400> SEQUENCE: 358

Arg Gln Arg Val Thr Ile Thr Cys Ser Gly Ser Ser Ser Asn Ile Gly
1 5 10 15

Asn Asn Ala Val Asn Trp Tyr Gln Gln Leu Pro
20 25

<210> SEQ ID NO 359
<211> LENGTH: 47
<212> TYPE: PRT
<213> ORGANISM: Artificial Sequence
<220> FEATURE:
<223> OTHER INFORMATION: a representation of the insertion of EETI-II donor into CDR1 or CDR2 of the lambda germline gene IGLV1-36
<220> FEATURE:
<221> NAME/KEY: MISC_FEATURE
<222> LOCATION: (9)..(9)
<223> OTHER INFORMATION: x is a randomising residue
<220> FEATURE:
<221> NAME/KEY: MISC_FEATURE
<222> LOCATION: (10)..(10)
<223> OTHER INFORMATION: Xaa is a randomising residue
<220> FEATURE:
<221> NAME/KEY: MISC_FEATURE
<222> LOCATION: (11)..(11)
<223> OTHER INFORMATION: Xaa is a randomising residue
<220> FEATURE:
<221> NAME/KEY: MISC_FEATURE
<222> LOCATION: (39)..(39)
<223> OTHER INFORMATION: Xaa represents the amino acids encoded by the codon VNC (encoding 12 amino acids) or VNS encoding 16 amino acids in total. (V=A, C or G, N=A, C, G or T and S=C or G)
<220> FEATURE:
<221> NAME/KEY: MISC_FEATURE
<222> LOCATION: (40)..(40)
<223> OTHER INFORMATION: Xaa is a randomising residue

<400> SEQUENCE: 359

Arg Gln Arg Val Thr Ile Thr Cys Xaa Xaa Xaa Cys Pro Arg Ile Leu
1 5 10 15

Met Arg Cys Lys Gln Asp Ser Asp Cys Leu Ala Gly Cys Val Cys Gly
20 25 30

Pro Asn Gly Phe Cys Gly Xaa Xaa Asn Trp Tyr Gln Gln Leu Pro
35 40 45

<210> SEQ ID NO 360
<211> LENGTH: 48
<212> TYPE: PRT
<213> ORGANISM: Artificial Sequence
<220> FEATURE:
<223> OTHER INFORMATION: shows a representation of the insertion of EETI-II donor into CDR1 or CDR2 of the lambda germline gene IGLV1-36
<220> FEATURE:
<221> NAME/KEY: MISC_FEATURE
<222> LOCATION: (10)..(12)
<223> OTHER INFORMATION: Xaa is a randomising residue
<220> FEATURE:
<221> NAME/KEY: MISC_FEATURE
<222> LOCATION: (40)..(40)
<223> OTHER INFORMATION: Xaa represents the amino acids encoded by the codon VNC (encoding 12 amino acids) or VNS encoding 16 amino acids in total.
<220> FEATURE:
<221> NAME/KEY: MISC_FEATURE
<222> LOCATION: (41)..(41)
<223> OTHER INFORMATION: Xaa is a randomising residue

<400> SEQUENCE: 360

```
Arg Gln Arg Val Thr Ile Thr Cys Gly Xaa Xaa Xaa Cys Pro Arg Ile
1               5                   10                  15

Leu Met Arg Cys Lys Gln Asp Ser Asp Cys Leu Ala Gly Cys Val Cys
            20                  25                  30

Gly Pro Asn Gly Phe Cys Gly Xaa Xaa Asn Trp Tyr Gln Gln Leu Pro
        35                  40                  45
```

<210> SEQ ID NO 361
<211> LENGTH: 22
<212> TYPE: PRT
<213> ORGANISM: Artificial Sequence
<220> FEATURE:
<223> OTHER INFORMATION: a representation of the insertion of EETI-II donor into CDR1 or CDR2 of the lambda germline gene IGLV1-36

<400> SEQUENCE: 361

```
Lys Ala Pro Lys Leu Leu Ile Tyr Tyr Asp Asp Leu Leu Pro Ser Gly
1               5                   10                  15

Val Ser Asp Arg Phe Ser
            20
```

<210> SEQ ID NO 362
<211> LENGTH: 49
<212> TYPE: PRT
<213> ORGANISM: Artificial Sequence
<220> FEATURE:
<223> OTHER INFORMATION: a representation of the insertion of EETI-II donor into CDR1 or CDR2 of the lambda germline gene IGLV1-36
<220> FEATURE:
<221> NAME/KEY: MISC_FEATURE
<222> LOCATION: (11)..(11)
<223> OTHER INFORMATION: Glx means any amino acid from Val, Ala, Asp or Gly
<220> FEATURE:
<221> NAME/KEY: MISC_FEATURE
<222> LOCATION: (12)..(12)
<223> OTHER INFORMATION: Xaa is a randomising residue
<220> FEATURE:
<221> NAME/KEY: MISC_FEATURE
<222> LOCATION: (40)..(40)
<223> OTHER INFORMATION: Xaa is a randomising residue
<220> FEATURE:
<221> NAME/KEY: MISC_FEATURE
<222> LOCATION: (41)..(41)
<223> OTHER INFORMATION: Xaa is a randomising residue

<400> SEQUENCE: 362

```
Lys Ala Pro Lys Leu Leu Ile Tyr Ala Ala Glx Xaa Cys Pro Arg Ile
1               5                   10                  15

Leu Met Arg Cys Lys Gln Asp Ser Asp Cys Leu Ala Gly Cys Val Cys
            20                  25                  30

Gly Pro Asn Gly Phe Cys Gly Xaa Xaa Ser Gly Val Ser Asp Arg Phe
        35                  40                  45

Ser
```

```
<210> SEQ ID NO 363
<211> LENGTH: 7
<212> TYPE: PRT
<213> ORGANISM: Artificial Sequence
<220> FEATURE:
<223> OTHER INFORMATION: peptide
<220> FEATURE:
<221> NAME/KEY: misc_feature
<222> LOCATION: (5)..(6)
<223> OTHER INFORMATION: Xaa can be any naturally occurring amino acid

<400> SEQUENCE: 363

Arg Gly Asp Leu Xaa Xaa Leu
1               5
```